US012024500B2

(12) United States Patent
Lian et al.

(10) Patent No.: US 12,024,500 B2
(45) Date of Patent: Jul. 2, 2024

(54) FIVE-MEMBERED RING-SUBSTITUTED PYRIDAZINOL COMPOUNDS AND DERIVATIVES, PREPARATION METHODS, HERBICIDAL COMPOSITIONS AND APPLICATIONS THEREOF

(71) Applicant: Qingdao Kingagroot Chemical Compound Co., Ltd., Qingdao (CN)

(72) Inventors: Lei Lian, Qingdao (CN); Yurong Zheng, Qingdao (CN); Rongbao Hua, Qingdao (CN); Jianfeng Wang, Qingdao (CN); Xuegang Peng, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 1004 days.

(21) Appl. No.: 16/966,704

(22) PCT Filed: Sep. 13, 2018

(86) PCT No.: PCT/CN2018/105408
§ 371 (c)(1),
(2) Date: Jul. 31, 2020

(87) PCT Pub. No.: WO2019/148851
PCT Pub. Date: Aug. 8, 2019

(65) Prior Publication Data

US 2021/0032222 A1 Feb. 4, 2021

(30) Foreign Application Priority Data

Feb. 2, 2018 (CN) ......................... 201810104963.4
Sep. 6, 2018 (CN) ......................... 201811035457.0

(51) Int. Cl.

| | |
|---|---|
| ***C07D 403/04*** | (2006.01) |
| ***A01N 43/58*** | (2006.01) |
| ***A01N 43/82*** | (2006.01) |
| ***A01N 43/84*** | (2006.01) |
| ***C07D 401/14*** | (2006.01) |
| ***C07D 403/14*** | (2006.01) |
| ***C07D 409/04*** | (2006.01) |
| ***C07D 409/14*** | (2006.01) |
| ***C07D 413/04*** | (2006.01) |
| ***C07D 417/04*** | (2006.01) |
| ***C07D 487/04*** | (2006.01) |

(52) U.S. Cl.
CPC ........... *C07D 403/04* (2013.01); *A01N 43/58* (2013.01); *A01N 43/82* (2013.01); *A01N 43/84* (2013.01); *C07D 401/14* (2013.01); *C07D 403/14* (2013.01); *C07D 409/04* (2013.01); *C07D 409/14* (2013.01); *C07D 413/04* (2013.01); *C07D 417/04* (2013.01); *C07D 487/04* (2013.01)

(58) Field of Classification Search
None
See application file for complete search history.

(56) References Cited

U.S. PATENT DOCUMENTS

| | | | | |
|---|---|---|---|---|
| 5,013,659 | A | 5/1991 | Bedbrook et al. | |
| 5,362,708 | A | 11/1994 | Kores et al. | |
| 2009/0215625 | A1* | 8/2009 | McElroy ................ | A01N 47/38 504/107 |
| 2016/0081337 | A1* | 3/2016 | Bereznak .............. | A01N 43/56 546/256 |

FOREIGN PATENT DOCUMENTS

| | | | |
|---|---|---|---|
| AT | 356966 | B | 6/1980 |
| CN | 1543455 | A | 11/2004 |
| CN | 101041639 | A | 9/2007 |
| CN | 103910672 | | 7/2014 |
| CN | 105121411 | A | 12/2015 |
| CN | 105451558 | A | 3/2016 |
| DE | 4013734 | A1 | 10/1991 |
| EP | 0131624 | A | 1/1985 |
| EP | 0142924 | A | 5/1985 |
| EP | 0193259 | A | 9/1986 |
| EP | 0221044 | A | 5/1987 |
| EP | 0242236 | A | 10/1987 |
| EP | 0242246 | A | 10/1987 |
| EP | 0257993 | A | 3/1988 |

(Continued)

OTHER PUBLICATIONS

Christou P, Transformation Technology, *Trends in Plant Science*, 1:423-431 (1996).

(Continued)

*Primary Examiner* — David J Blanchard
*Assistant Examiner* — Edwin Coleman Mitchell
(74) *Attorney, Agent, or Firm* — FINNEGAN, HENDERSON, FARABOW, GARRETT & DUNNER LLP

(57) ABSTRACT

The present disclosure provides an herbicidal compound according to Formula I, which is a five-membered ring-substituted pyridazinol compound, as well as derivatives of the compound, an herbicidal composition comprising the compound, preparation methods thereof, and applications thereof.

I

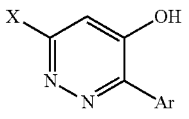

15 Claims, No Drawings

(56) References Cited

FOREIGN PATENT DOCUMENTS

| | | | |
|---|---|---|---|
| WO | WO91/13972 | 9/1991 | |
| WO | WO91/19806 | 12/1991 | |
| WO | WO92/00377 | 1/1992 | |
| WO | WO92/11376 | 7/1992 | |
| WO | WO92/14827 | 9/1992 | |
| WO | WO2017148787 A1 | 9/2017 | |
| WO | WO-2017148787 A1 * | 9/2017 | ........... A61K 31/501 |

OTHER PUBLICATIONS

Braun et al., The General Mitochondrial Processing Peptidase from Potato Is an Integral Part of Cytochrome C Reductase of The Respiratory Chain, *EMBO J.* 11:3219-3227 (1992).

Wolter et al., Rbcs Genes in Solanum Tuberosum: Conservation of Transit Peptide and Exon Shuffling During Evolution, *Proc. Natl. Acad. Sci. USA*, 85:846-850 (1988).

Sonnewald et al., Transgenic Tobacco Plants Expressing Yeast-Derived Invertase In Either the Cytosol, Vacuole or Apoplast: A Powerful Tool for Studying Sucrose Metabolism and Sink/Source Interactions, *Plant J.* 1:95-106 (1991).

International Patent Application No. PCT/CN2018/105408: International Search Report mailed Jun. 5, 2019.

* cited by examiner

FIVE-MEMBERED RING-SUBSTITUTED PYRIDAZINOL COMPOUNDS AND DERIVATIVES, PREPARATION METHODS, HERBICIDAL COMPOSITIONS AND APPLICATIONS THEREOF

This application is a national stage filing under 35 U.S.C. § 371 of International Application No. PCT/CN2018/105408, filed Sep. 13, 2018, and claims the priority to and benefits of Chinese Patent Application No. 201810104963.4, filed Feb. 2, 2018, and Chinese Patent Application No. 201811035457.0, filed Sep. 6, 2018, which are incorporated herein by reference in their entireties.

TECHNICAL FIELD

The invention belongs to the technical field of agricultural chemicals, and in particular relates to a five-membered ring-substituted pyridazinol compound and a derivatives thereof, preparation method, herbicidal composition and application thereof.

BACKGROUND ART

Weed control is a vital part in achieving high-efficiency agriculture. At present, various herbicides are available in the market, such as pyridazine herbicides pyridate

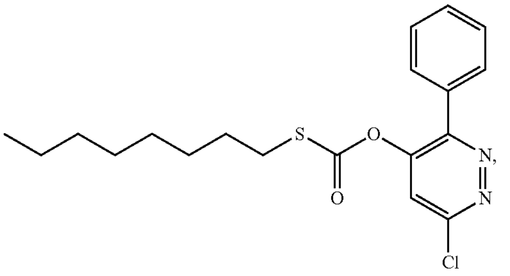 [SMILES: CCCCCCCCSC(=O)Oc1cc(Cl)nnc1-c1ccccc1]

pyridazinol

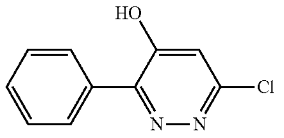 [SMILES: Oc1cc(Cl)nnc1-c1ccccc1]

and the like, which are photosystem II inhibitors that inhibit photosynthesis by blocking electron transport and conversion of light energy.

Since the continuous expansion of the market, the resistance of weeds, the service life of herbicides and the economical efficiency of herbicides as well as the increasing attention on environmental protection, it is in great demand of constantly research of scientists for developing new herbicides with high-efficiency, safety, economical efficiency and different mechanism of action.

CONTENTS OF THE INVENTION

In order to solve the above problems in the prior art, the present invention provides a five-membered ring-substituted pyridazinol compound and a derivative, preparation method, herbicidal composition and use thereof. The compound and the derivative, as well as the composition thereof have very high herbicidal activity and good selectivity, and are safe for crops.

The technical solution adopted by the present invention is as follows:

A five-membered ring-substituted pyridazinol compound of Formula I or a derivative thereof:

I

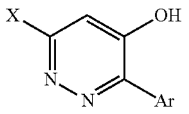

wherein, X is halogen, cyano, alkyl, halogenated alkyl, alkoxy, halogenated alkoxy, $R_1R_2N-(C{=}O)-$, $R_1R_2N-$, hydroxy, or unsubstituted or substituted aryl;

Ar is

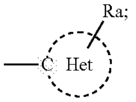

Het is a 5-membered unsaturated ring, the ring contains, besides the 1-C atom, 0 to 4 atoms or radicals follows to form the ring: O, $NR_b$, S;

$R_a$ is one or more groups selected from: hydrogen, halogen, cyano, nitro, azido, a halogen-containing or not containing group selected from alkyl, alkenyl, alkynyl, cycloalkyl, cycloalkenyl, and cycloalkylalkyl, a group selected from aryl, arylalkyl, heteroaryl, and heteroarylalkyl, which is unsubstituted or substituted, $R-O-(CH_2)_n-$, $R-O-(CH_2)_p-O-(CH_2)_q-$, $R-O-(CH_2)_p-S-(CH_2)_q-$, $R-S-(CH_2)_n-$, $R-S-(CH_2)_p-O-(CH_2)_q-$, $R-S-(CH_2)_p-S-(CH_2)_q-$, $R-O-(CH_2)_n-(C{=}O)-(CH_2)_q-(O)_m-$, $R-S-(CH_2)_n-(C{=}S)-(CH_2)_q-(S)_m-$, $R-O-(CH_2)_n-(C{=}O)-(CH_2)_q-(S)_m-$, $R-O-(CH_2)_n-(C{=}S)-(CH_2)_q-(O)_m-$, $R-S-(CH_2)_n-(C{=}O)-(CH_2)_q-(O)_m-$, $R-O-(CH_2)_n-(C{=}S)-(CH_2)_q-(S)_m-$, $R-S-(CH_2)_n-(C{=}O)-(CH_2)_q-(S)_m-$, $R-S-(CH_2)_n-(C{=}S)-(CH_2)_q-(O)_m-$, $R-(C{=}O)-(CH_2)_n-$, $R-(C{=}S)-(CH_2)_n-$, $R-(C{=}O)-(CH_2)_n-O-(CH_2)_q-$, $R-(C{=}S)-(CH_2)_n-S-(CH_2)_q-$, $R-(C{=}O)-(CH_2)_n-S-(CH_2)_q-$, $R-(C{=}S)-(CH_2)-O-(CH_2)_q-$, $R-SO-(CH_2)-(O)_m-$, $R-SO-(CH_2)-(S)_m-$, $R-SO-(CH_2)_n-(NR_3)_m-$, $R-SO_2-(CH_2)_n-(O)_m$, $R-SO_2-(CH_2)_n-(S)_m-$, $R-SO_2-(CH_2)_n-(NR_3)_m-$, $R_1R_2N-(CH_2)_n-$, $R_1R_2N-(CH_2)_n-O-(CH_2)_q-(O)_m-$, $R_1R_2N-(CH_2)_n-O-(CH_2)_q-(S)_m$, $R_1R_2N-(CH_2)_n-O-(CH_2)_q-(NR_3)_m-$, $R_1R_2N-(CH_2)_n-(C{=}O)-(CH_2)_q-(O)_m-$, $R_1R_2N-(CH_2)_n-(C{=}O)-(CH_2)_q-(S)_m-$, $R_1R_2N-(CH_2)_n-(C{=}O)-(CH_2)_q-(NR_3)_m-$, $R_1R_2N-(CH_2)_n-SO_2-(CH_2)_q-(O)_m-$, $R_1R_2N-(CH_2)_n-SO_2-(CH_2)_q-(S)_m-$, $R_1R_2N-(CH_2)_n-SO_2-(CH_2)_q-(NR_3)_m$, $R_1R_2PO_3-(O)_m(CH_2)_q-$, $R_1R_2R_3SiO-(CH_2)_q-$, $R_1R_2R_3Si-(CH{=}CH)_m-(CH_2)_q-$, $R_1R_2C{=}N-(O)_m-(CH_2)_n-$, and $R_1R_2C{=}N-NH-(CH_2)_n-$; or two adjacent $R_a$ form $-OCH_2O-$, $-CH_2CH_2O-$, $-OCH_2CH_2O-$, —$OCH(CH_3)O$—, —$OC(CH_3)_2O$—, —$OCF_2O$—, —$CF_2CF_2O$—, —$OCF_2CF_2O$—, or —CH═CH—CH═CH—;

m is 0 or 1, n and q are independently an integer from 0 to 8, p is an integer from 1 to 8; wherein, m, n, q, p in the above substituents are valued independently, and these values render the substituents $R_a$ different from each other;

R is hydrogen, a halogen-containing or not containing group selected from alkyl, alkenyl, alkynyl, cycloalkyl, cycloalkenyl, and cycloalkylalkyl, or a group selected from aryl, arylalkyl, heteroaryl, and heteroarylalkyl, which is unsubstituted or substituted;

$R_b$, $R_1$, $R_2$, $R_3$ are each independently hydrogen, nitro, hydroxy, amino, a halogen-containing or not containing group selected from alkyl, alkenyl, alkynyl, cycloalkyl, cycloalkenyl, cycloalkylalkyl, alkoxy, alkenyloxy, alkynyloxy, cycloalkyloxy, alkoxyalkyl, alkoxycarbonyl, alkylsulfanylcarbonyl, alkylsulfonyl, alkylsulfonylalkyl, alkylcarbonyl, alkylcarbonylalkyl, alkylcarbonyloxy, alkylamino, alkylaminocarbonyl, alkoxyaminocarbonyl, alkoxycarbonylalkyl, alkylaminocarbonylalkyl, trialkylsilyl, and dialkylphosphonyl, or a group selected from 6-membered heterocyclyl, aryl, arylalkyl, aryloxy, arylalkyloxy, aryloxyalkyl, arylcarbonyl, arylsulfonyl, heteroaryl, heteroarylalkyl, heteroaryloxy, heteroarylalkyloxy, heteroaryloxyalkyl, heteroarylcarbonyl, and heteroarylsulfonyl, which is unsubstituted or substituted; or $R_1R_2N$— forms a 6-membered heterocyclyl; or adjacent $R_a$ and $R_b$ form —$CH_2CH_2NR_3CH_2$—.

Preferably, X is halogen, cyano, $C_{1-8}$alkyl, halogenated $C_{1-8}$alkyl, $C_{1-8}$alkoxy, halogenated $C_{1-8}$alkoxy, $R_1R_2N$—(C═O)—, $R_1R_2N$—, hydroxy, or aryl, said aryl is unsubstituted or substituted with 1~5 substituents independently selected from the group consisting of halogen, cyano, nitro, hydroxy, carboxyl, sulfhydryl, amino, and a halogen-containing or not containing group selected from $C_{1-8}$alkyl, $C_{3-8}$cycloalkyl, $C_{3-8}$cycloalkyl-$C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, $C_{1-8}$alkylsulfonyl, $C_{1-8}$alkylamino, and $C_{1-8}$alkylcarbonyloxy;

Ar is

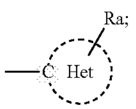

Het is a 5-membered unsaturated heterocycle, the heterocycle contains, besides the 1-C atom, 1 to 4 atoms or radicals follows to form the ring: O, $NR_b$, S;

$R_a$ is one or more substituents selected from: hydrogen, halogen, cyano, nitro, azido, a halogen-containing or not containing group selected from $C_{1-8}$alkyl, $C_{2-8}$alkenyl, $C_{2-8}$alkynyl, $C_{3-8}$cycloalkyl, $C_{5-8}$cycloalkenyl, and $C_{3-8}$cycloalkyl-$C_{1-8}$alkyl, aryl, aryl-$C_{1-8}$alkyl, heteroaryl, heteroaryl-$C_{1-8}$alkyl, each of said aryl, aryl-$C_{1-8}$alkyl, heteroaryl, or heteroaryl-$C_{1-8}$alkyl is unsubstituted or substituted with 1~5 groups independently selected from halogen, cyano, nitro, hydroxy, carboxyl, sulfhydryl, amino, and a halogen-containing or not containing group selected from $C_{1-8}$alkyl, $C_{3-8}$cycloalkyl, $C_{3-8}$cycloalkyl-$C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, $C_{1-8}$alkylsulfonyl, $C_{1-8}$alkylamino, and $C_{1-8}$alkylcarbonyloxy, R—O—$(CH_2)_n$—, R—O—$(CH_2)_p$—O—$(CH_2)_q$—, R—O—$(CH_2)_p$—S—$(CH_2)_q$—, R—S—$(CH_2)_n$—, R—S—$(CH_2)_p$—O—$(CH_2)_q$—, R—S—$(CH_2)_p$—S—$(CH_2)_q$—, R—O—$(CH_2)_n$—(C═O)—$(CH_2)_q$—, R—S—$(CH_2)_n$—(C═S)—$(CH_2)_q$—, R—O—$(CH_2)_n$—(C═S)—$(CH_2)_q$—, R—S—$(CH_2)_n$—(C═O)—$(CH_2)_q$—, R—O—(C═O)—$(CH_2)_q$—$(O)_m$—, R—S—(C═S)—$(CH_2)_q$—$(S)_m$—, R—O—(C═O)—$(CH_2)_q$—$(S)_m$—, R—O—(C═S)—$(CH_2)_q$—$(O)_m$—, R—S—(C═O)—$(CH_2)_q$—$(O)_m$—, R—O—(C═S)—$(CH_2)_q$—$(S)_m$—, R—S—(C═O)—$(CH_2)_q$—$(S)_m$—, R—S—(C═S)—$(CH_2)_q$—$(O)_m$—, R—O—$(CH_2)_n$—(C═O)—$(O)_m$—, R—S—$(CH_2)_n$—(C═S)—$(S)_m$—, R—O—$(CH_2)_n$—(C═O)—$(S)_m$—, R—O—$(CH_2)_n$—(C═S)—$(O)_m$—, R—S—$(CH_2)_n$—(C═O)—$(O)_m$—, R—O—$(CH_2)_n$—(C═S)—$(S)_m$—, R—S—$(CH_2)_n$—(C═O)—$(S)_m$—, R—S—$(CH_2)_n$—(C═S)—$(O)_m$—, R—(C═O)—, R—(C═S)—, R—(C═O)—$(CH_2)$—O—, R—(C═S)—$(CH_2)$—S—, R—(C═O)—$(CH_2)$—S—, R—(C═S)—$(CH_2)$—O—, R—(C═O)—O—$(CH_2)_q$—, R—(C═S)—S—$(CH_2)_q$—, R—(C═O)—S—$(CH_2)_q$—, R—(C═S)—O—$(CH_2)_q$—, R—SO—$(O)_m$—, R—SO—$(S)_m$—, R—SO—$(NR_3)_m$—, R—$SO_2$—$(O)_m$—, R—$SO_2$—$(S)_m$—, R—$SO_2$—$(NR_3)_m$—, R—SO—$(CH_2)_n$—, R—$SO_2$—$(CH_2)_n$—, $R_1R_2N$—, $R_1R_2N$—$(CH_2)_n$—O—$(CH_2)_q$—, $R_1R_2N$—$(CH_2)_n$—(C═O)—$(CH_2)_q$—, $R_1R_2N$—$(CH_2)_n$—$SO_2$—$(CH_2)_q$—, $R_1R_2N$—$(CH_2)$—(C═O)—$(O)_m$—, $R_1R_2N$—$(CH_2)_n$—(C═O)—$(S)_m$—, $R_1R_2N$—$(CH_2)_n$—(C═O)—$(NR_3)_m$—, $R_1R_2N$—$(CH_2)_n$—$SO_2$—$(O)_m$—, $R_1R_2N$—$(CH_2)_n$—$SO_2$—$(S)_m$—, $R_1R_2N$—$(CH_2)_n$—$SO_2$—$(NR_3)_m$—, $R_1R_2N$—(C═O)—$(CH_2)_n$—$(O)_m$—, $R_1R_2N$—(C═O)—$(CH_2)$—$(S)_m$—, $R_1R_2N$—(C═O)—$(CH_2)$—$(NR_3)_m$—, $R_1R_2N$—$SO_2$—$(CH_2)_q$—$(O)_m$, $R_1R_2N$—$SO_2$—$(CH_2)_q$—$(S)_m$, $R_1R_2N$—$SO_2$—$(CH_2)_q$—$(NR_3)_m$, $R_1R_2N$—$(CH_2)$—O—, $R_1R_2N$—O—$(CH_2)_q$—, $R_1R_2PO_3$—$(O)_m$, $R_1R_2R_3SiO$—, $R_1R_2R_3Si$—$(CH═CH)_m$, $R_1R_2C$═N—$(O)_m$, and $R_1R_2C$═N—NH—; or two adjacent $R_a$ form —$OCH_2O$—, —$CH_2CH_2O$—, —$OCH_2CH_2O$—, —$OCH(CH_3)O$—, —$OC(CH_3)_2O$—, —$OCF_2O$—, —$CF_2CF_2O$—, —$OCF_2CF_2O$—, or —CH═CH—CH═CH—;

m is 0 or 1, n and q are independently an integer from 0 to 6, p is an integer from 1 to 6; wherein, m, n, q, p in the above substituents are valued independently, and these values render the substituents $R_a$ different from each other;

R is hydrogen, a halogen-containing or not containing group selected from $C_{1-8}$alkyl, $C_{2-8}$alkenyl, $C_{2-8}$alkynyl, $C_{3-8}$cycloalkyl, $C_{5-8}$cycloalkenyl, and $C_{3-8}$cycloalkyl-$C_{1-8}$alkyl, aryl, aryl-$C_{1-8}$alkyl, heteroaryl, or heteroaryl-$C_{1-8}$alkyl, each of said aryl, aryl-$C_{1-8}$alkyl, heteroaryl, or heteroaryl-$C_{1-8}$alkyl is unsubstituted or substituted with 1~5 groups substituents independently selected from halogen, cyano, nitro, hydroxy, carboxyl, sulfhydryl, amino, and a halogen-containing or not containing group selected from $C_{1-8}$alkyl, $C_{3-8}$cycloalkyl, $C_{3-8}$cycloalkyl-$C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, $C_{1-8}$alkylsulfonyl, $C_{1-8}$alkylamino, and $C_{1-8}$alkylcarbonyloxy;

$R_b$, $R_1$, $R_2$, $R_3$ are each independently hydrogen, nitro, hydroxy, amino, a halogen-containing or not containing group selected from $C_{1-8}$alkyl, $C_{2-8}$alkenyl, $C_{2-8}$alkynyl, $C_{3-8}$cycloalkyl, $C_{5-8}$cycloalkenyl, $C_{3-8}$cycloalkyl-$C_{1-8}$alkyl, $C_{1-8}$alkoxy, $C_{2-8}$alkenyloxy, $C_{2-8}$alkynyloxy, $C_{3-8}$cycloalkyloxy, $C_{1-8}$alkoxy-$C_{1-8}$alkyl, $C_{1-8}$alkoxycarbonyl, $C_{1-8}$alkylcarbonyl-$C_{1-8}$alkyl, $C_{1-8}$alkylsulfanylcarbonyl, $C_{1-8}$alkylsulfonyl, $C_{1-8}$alkylsulfonyl-$C_{1-8}$alkyl, $C_{1-8}$alkylcarbonyl, $C_{1-8}$alkylcarbonyloxy, $C_{1-8}$alkylamino, $C_{1-8}$alkylaminocarbonyl, $C_{1-8}$alkoxyaminocarbonyl, $C_{1-8}$alkoxycarbonyl-$C_{1-8}$alkyl, $C_{1-8}$alkylaminocarbonyl-$C_{1-8}$alkyl, tri$C_{1-8}$alkylsilyl, and di$C_{1-8}$alkylphosphonyl, 6-membered heterocyclyl, aryl, aryl-$C_{1-8}$alkyl, aryloxy, aryl-$C_{1-8}$alkyloxy, aryloxy-$C_{1-8}$alkyl, arylcarbonyl, arylsulfonyl, heteroaryl, heteroaryl-$C_{1-8}$alkyl, heteroaryloxy, heteroaryl-$C_{1-8}$alkyloxy, heteroaryloxy-$C_{1-8}$alkyl, heteroarylcarbonyl, or heteroarylsulfonyl, each of said 6-membered heterocyclyl, aryl, aryl-$C_{1-8}$alkyl, aryloxy, aryl-$C_{1-8}$alkyloxy, aryloxy-$C_{1-8}$alkyl, arylcarbonyl, arylsulfonyl, heteroaryl, heteroaryl-$C_{1-8}$alkyl, heteroaryloxy, heteroaryl-$C_{1-8}$alkyloxy, heteroaryloxy-$C_{1-8}$alkyl, heteroarylcarbonyl, or heteroarylsulfonyl is unsubstituted or substituted with 1~5 groups independently selected from halogen, cyano, nitro, hydroxy, carboxyl, sulfhydryl, amino, and a halogen-containing or not containing group selected from $C_{1-8}$alkyl, $C_{3-8}$cycloalkyl, $C_{3-8}$cycloalkyl-$C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, $C_{1-8}$alkylsulfonyl, $C_{1-8}$alkylamino, and $C_{1-8}$alkylcarbonyloxy; or $R_1R_2N$— forms a 6-membered heterocyclyl containing or not containing other hetero atoms; or adjacent $R_a$ and $R_b$ form —$CH_2CH_2NR_3CH_2$—.

More preferably, X is fluorine, chlorine, bromine, iodine, cyano, $C_{1-6}$alkyl, halogenated $C_{1-6}$alkyl, $C_{1-6}$alkoxy, halogenated $C_{1-6}$alkoxy, $R_1R_2N$—(C═O)—, $R_1R_2N$—, hydroxy, or phenyl, said phenyl is unsubstituted or substituted with 1~5 substituents independently selected from the group consisting of halogen, cyano, nitro, hydroxy, carboxyl, sulfhydryl, amino, and a halogen-containing or not containing group selected from $C_{1-6}$alkyl, $C_{3-6}$cycloalkyl, $C_{3-6}$cycloalkyl-$C_{1-6}$alkyl, $C_{2-6}$alkenyl, $C_{2-6}$alkynyl, $C_{1-6}$alkoxy, $C_{1-6}$alkylcarbonyl, $C_{1-6}$alkoxycarbonyl, $C_{1-6}$alkylsulfonyl, $C_{1-6}$alkylamino, and $C_{1-6}$alkylcarbonyloxy;

Ar is

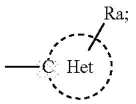

Het is a 5-membered unsaturated heterocycle, the heterocycle contains, besides the 1-C atom, 2, 3, or 4 atoms or radicals follows to form the ring: O, $NR_b$, S;

$R_a$ is one or more substituents selected from: hydrogen, fluorine, chlorine, bromine, cyano, nitro, azido, a fluoro-, chloro-, or bromo-containing or not containing group selected from $C_{1-6}$alkyl, $C_{2-6}$alkenyl, $C_{2-6}$alkynyl, $C_{3-6}$cycloalkyl, $C_{5-6}$cycloalkenyl, and $C_{3-6}$cycloalkyl-$C_{1-6}$alkyl, aryl, aryl-$C_{1-6}$alkyl, heteroaryl, heteroaryl-$C_{1-6}$alkyl, each of said aryl, aryl-$C_{1-6}$alkyl, heteroaryl, or heteroaryl-$C_{1-6}$alkyl is unsubstituted or substituted with 1~3 groups independently selected from fluorine, chlorine, bromine, cyano, nitro, hydroxy, carboxyl, sulfhydryl, amino, and a fluoro-, chloro-, or bromo-containing or not containing group selected from $C_{1-6}$alkyl, $C_{3-6}$cycloalkyl, $C_{3-6}$cycloalkyl-$C_{1-6}$alkyl, $C_{2-6}$alkenyl, $C_{2-6}$alkynyl, $C_{1-6}$alkoxy, $C_{1-6}$alkylcarbonyl, $C_{1-6}$alkoxycarbonyl, $C_{1-6}$alkylsulfonyl, $C_{1-6}$alkylamino, and $C_{1-6}$alkylcarbonyloxy, R—O—, R—O—$(CH_2)_p$—O—, R—O—$(CH_2)_p$—S—, R—S—, R—S—$(CH_2)_p$—O—, R—S—$(CH_2)_p$—S—, R—O—(C═O)—$(O)_m$—, R—S—(C═S)—$(S)_m$—, R—O—(C═O)—$(S)_m$—, R—O—(C═S)—$(O)_m$—, R—S—(C═O)—$(O)_m$—, R—O—(C═S)—$(S)_m$, R—S—(C═O)—$(S)_m$—, R—S—(C═S)—$(O)_m$—, R—O—(C═O)—$(CH_2)_q$—, R—S—(C═S)—$(CH_2)_q$—, R—O—(C═S)—$(CH_2)_q$—, R—S—(C═O)—$(CH_2)_q$—, R—O—$(CH_2)_n$—(C═O)—, R—S—$(CH_2)_n$—(C═S)—, R—O—$(CH_2)_n$—(C═S)—, R—S—$(CH_2)_n$—(C═O)—, R—(C═O)—, R—(C═S)—, R—(C═O)—O—, R—(C═S)—S—, R—(C═O)—S—, R—(C═S)—O—, R—SO—, R—$SO_2$—, $R_1R_2N$—, $R_1R_2N$—O—, $R_1R_2N$—(C═O)—$(CH_2)_p$—, $R_1R_2N$—(C═O)—$(O)_m$—, $R_1R_2N$—(C═O)—$(S)_m$—, $R_1R_2N$—(C═O)—$(NR_3)_m$—, $R_1R_2N$—$SO_2$—$(CH_2)_p$—, R—, $R_1R_2N$—$(CH_2)_p$—(C═O)—, $R_1R_2N$—$(CH_2)_p$—$SO_2$—, $R_1R_2N$—$(CH_2)_p$—O—, $R_1R_2N$—O—$(CH_2)_p$—, $R_1R_2PO_3$—, $R_1R_2R_3SiO$—, $R_1R_2R_3Si$—, $R_1R_2R_3Si$—CH═CH—, $R_1R_2C$═N—, $R_1R_2C$═N—O—, and $R_1R_2C$═N—NH—; or two adjacent $R_a$ form —CH═CH—CH═CH—;

m is 0 or 1, n and q are each independently 0, 1, 2, 3 or 4, p is 1, 2, 3 or 4; wherein, m, n, q, p in the above substituents are valued independently, and these values render the substituents $R_a$ different from each other;

R is hydrogen, a fluoro-, chloro-, or bromo-containing or not containing group selected from $C_{1-6}$alkyl, $C_{2-6}$alkenyl, $C_{2-6}$alkynyl, $C_{3-6}$cycloalkyl, $C_{5-6}$cycloalkenyl, and $C_{3-6}$cycloalkyl-$C_{1-6}$alkyl, aryl, aryl-$C_{1-6}$alkyl, heteroaryl, or heteroaryl-$C_{1-6}$alkyl, each of said aryl, aryl-$C_{1-6}$alkyl, heteroaryl, or heteroaryl-$C_{1-6}$alkyl is unsubstituted or substituted with 1~3 substituents independently selected from the group consisting of fluorine, chlorine, bromine, cyano, nitro, hydroxy, carboxyl, sulfhydryl, amino, and a fluoro-, chloro-, or bromo-containing or not containing group selected from $C_{1-6}$alkyl, $C_{3-6}$cycloalkyl, $C_{3-6}$cycloalkyl-$C_{1-6}$alkyl, $C_{2-6}$alkenyl, $C_{2-6}$alkynyl, $C_{1-6}$alkoxy, $C_{1-6}$alkylcarbonyl, $C_{1-6}$alkoxycarbonyl, $C_{1-6}$alkylsulfonyl, $C_{1-6}$alkylamino, and $C_{1-6}$alkylcarbonyloxy;

$R_b$, $R_1$, $R_2$, $R_3$ are each independently hydrogen, nitro, hydroxy, amino, a fluoro-, chloro-, or bromo-containing or not containing group selected from $C_{1-6}$alkyl, $C_{2-6}$alkenyl, $C_{2-6}$alkynyl, $C_{3-6}$cycloalkyl, $C_{5-6}$cycloalkenyl, $C_{3-6}$cycloalkyl-$C_{1-6}$alkyl, $C_{1-6}$alkoxy, $C_{2-6}$ alkenyloxy, $C_{2-6}$ alkynyloxy, $C_{3-6}$ cycloalkyloxy, $C_{1-6}$ alkoxy-$C_{1-6}$ alkyl, $C_{1-6}$ alkoxycarbonyl, $C_{1-6}$ alkylsulfanylcarbonyl, $C_{1-6}$ alkylsulfonyl, $C_{1-6}$ alkylsulfonyl-$C_{1-6}$ alkyl, $C_{1-6}$ alkylcarbonyl, $C_{1-6}$ alkylcarbonyl-$C_{1-6}$ alkyl, $C_{1-6}$ alkylcarbonyloxy, $C_{1-6}$ alkylamino, $C_{1-6}$ alkylaminocarbonyl, $C_{1-6}$ alkoxyaminocarbonyl, $C_{1-6}$ alkoxycarbonyl-$C_{1-6}$ alkyl, $C_{1-6}$ alkylaminocarbonyl-$C_{1-6}$ alkyl, tri$C_{1-6}$ alkylsilyl, and di$C_{1-6}$ alkylphosphonyl,

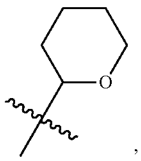,
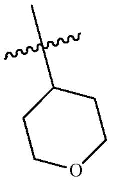,
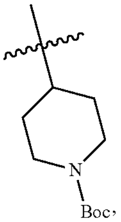

aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl, each of said

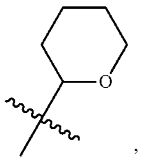,
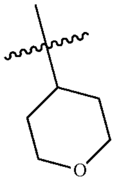,
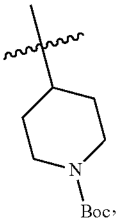

aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl is unsubstituted or substituted with 1~3 groups independently selected from fluorine, chlorine, bromine, cyano, nitro, hydroxy, carboxyl, sulfhydryl, amino, and a fluoro-, chloro-, or bromo-containing or not containing group selected from $C_{1-6}$ alkyl, $C_{3-6}$ cycloalkyl, $C_{3-6}$ cycloalkyl-$C_{1-6}$ alkyl, $C_{2-6}$ alkenyl, $C_{2-6}$ alkynyl, $C_{1-6}$ alkoxy, $C_{1-6}$ alkylcarbonyl, $C_{1-6}$ alkoxycarbonyl, $C_{1-8}$alkylsulfonyl, $C_{1-6}$alkylamino, and $C_{1-6}$ alkylcarbonyloxy; or $R_1R_2N$— is

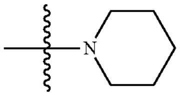,
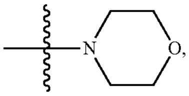, or
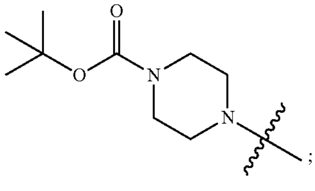;

or adjacent $R_a$ and $R_b$ form —$CH_2CH_2N(Boc)CH_2$—; the aryl is selected from

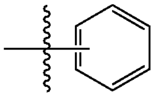,
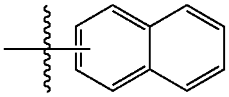,
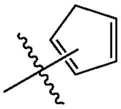,
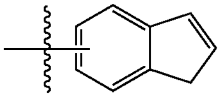,

-continued

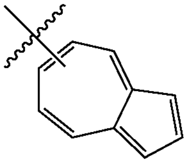,
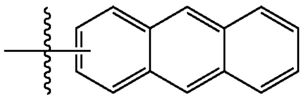,
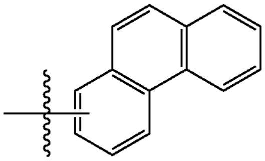, and
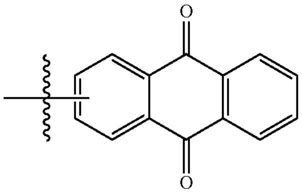;

the heteroaryl is selected from

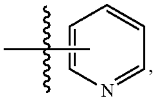,
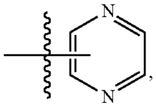,
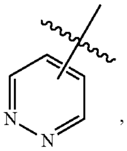,
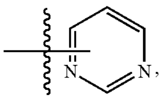,
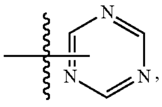,
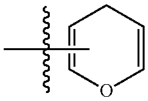,
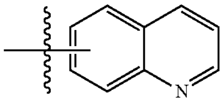,
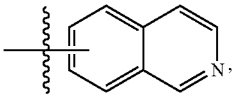,
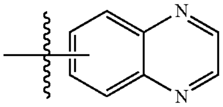,
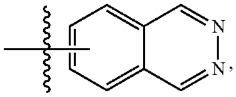,
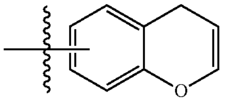,
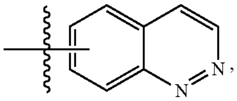,
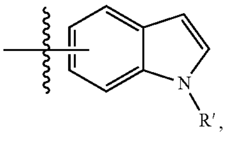,
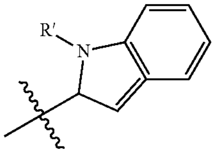,
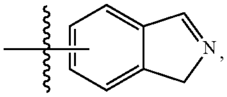,
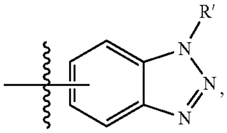,
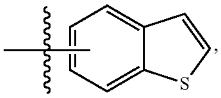,
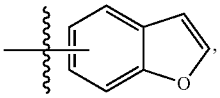,
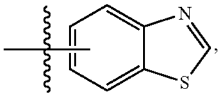,
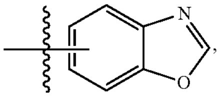, -continued

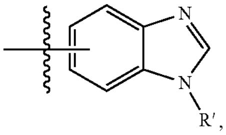,
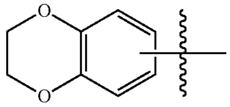,
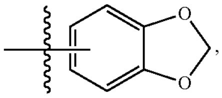,
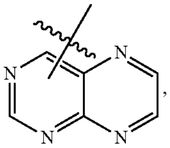,
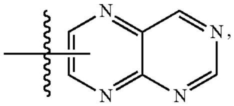,
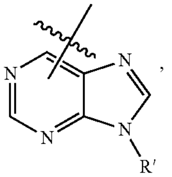,
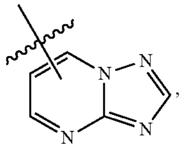,
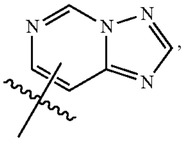,
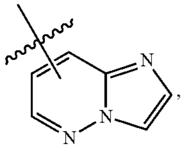,
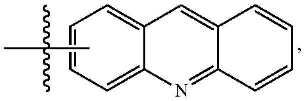,
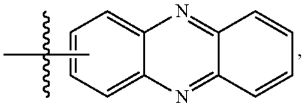,
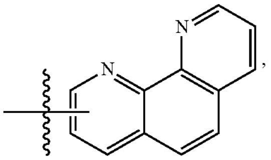,
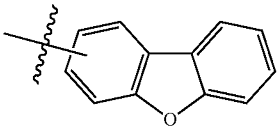,
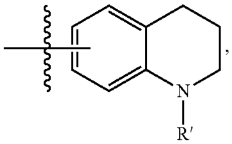,
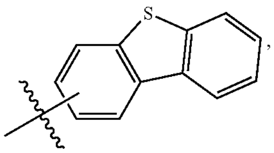,
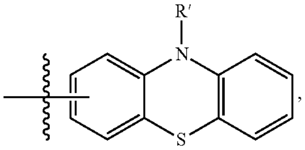,
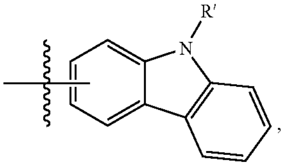,
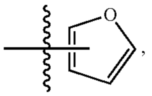, -continued

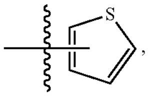,
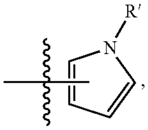,
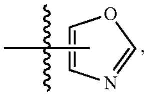,
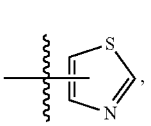,
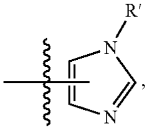,
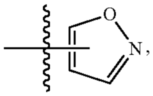,
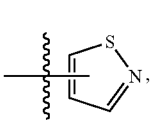,
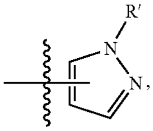,
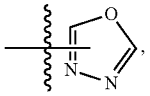,
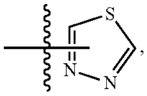,
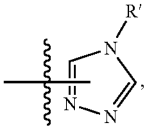,
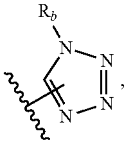,
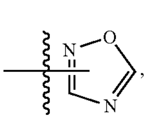,
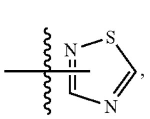,
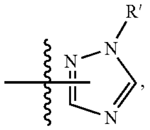,
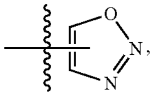,
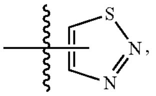,
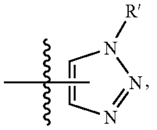
and
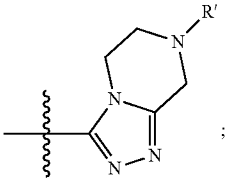
;

R' is hydrogen, nitro, hydroxy, amino, a fluoro-, chloro-, or bromo-containing or not containing group selected from $C_{1-6}$ alkyl, $C_{2-6}$ alkenyl, $C_{2-6}$ alkynyl, $C_{3-6}$ cycloalkyl, $C_{5-6}$ cycloalkenyl, $C_{3-6}$ cycloalkyl-$C_{1-6}$ alkyl, $C_{1-6}$ alkoxy, $C_{2-6}$ alkenyloxy, $C_{2-6}$ alkynyloxy, $C_{3-6}$ cycloalkyloxy, $C_{1-6}$ alkoxy-$C_{1-6}$ alkyl, $C_{1-6}$ alkoxycarbonyl, $C_{1-6}$ alkylsulfanylcarbonyl, $C_{1-6}$ alkylsulfonyl, $C_{1-6}$ alkylsulfonyl-$C_{1-6}$ alkyl, $C_{1-6}$ alkylcarbonyl, $C_{1-6}$ alkylcarbonyl-$C_{1-6}$ alkyl, $C_{1-6}$ alkylcarbonyloxy, $C_{1-6}$ alkylamino, $C_{1-6}$ alkylaminocarbonyl, $C_{1-6}$ alkoxyaminocarbonyl, $C_{1-6}$ alkoxycarbonyl-$C_{1-6}$ alkyl, $C_{1-6}$alkylaminocarbonyl-$C_{1-6}$ alkyl, tri$C_{1-6}$ alkylsilyl, and di$C_{1-6}$ alkylphosphonyl,

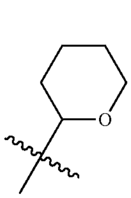,
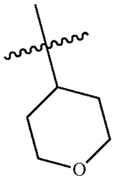,
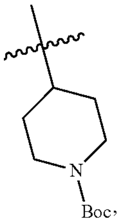

aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl, each of said

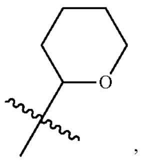, 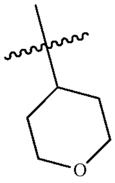, 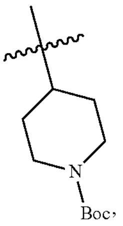, aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl is unsubstituted or substituted with 1~3 groups independently selected from fluorine, chlorine, bromine, cyano, nitro, hydroxy, carboxyl, sulfhydryl, amino, and a fluoro-, chloro-, or bromo-containing or not containing group selected from $C_{1-6}$ alkyl, $C_{3-6}$ cycloalkyl, $C_{3-6}$ cycloalkyl-$C_{1-6}$ alkyl, $C_{2-6}$ alkenyl, $C_{2-6}$ alkynyl, $C_{1-6}$ alkoxy, $C_{1-6}$ alkylcarbonyl, $C_{1-6}$ alkoxycarbonyl, $C_{1-6}$ alkylsulfonyl, $C_{1-6}$ alkylamino, and $C_{1-6}$ alkylcarbonyloxy.

More preferably, X represents fluorine, chlorine, bromine, iodine, cyano, methyl, ethyl, trifluoromethyl, pentafluoroethyl, difluoromethyl, monofluoromethyl, methoxy, ethoxy, trifluoromethoxy, or pentafluoroethoxy;

Het is

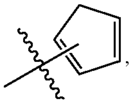, 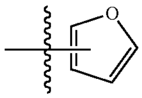, 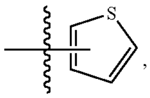,

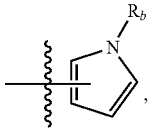, 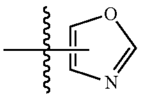, 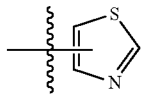,

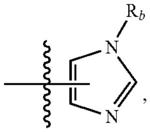, 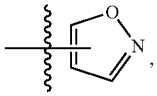, 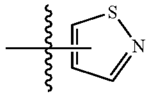,

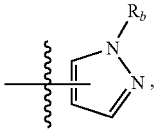, 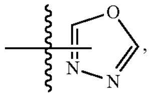, 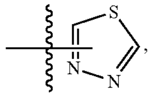,

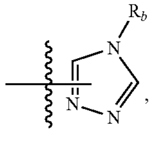, 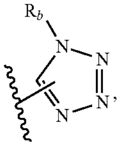, 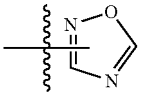,

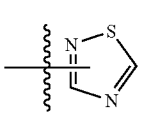, 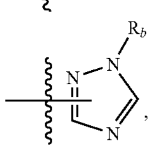, 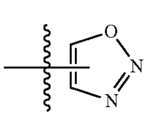,

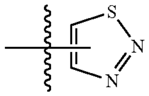, or 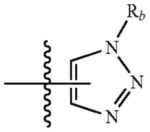;

$R_a$ is selected from one or more of the following groups: hydrogen, methyl, ethyl, cyano, cyclopropyl, phenyl, fluorine, chlorine, bromine, iodine, cyano, nitro, difluoromethyl, 2,2,2,-trifluoroethyl, trifluoromethyl, methoxy, ethoxy, benzyloxy, —COOEt, amino, methylamino, dimethylamino, acetyl amino,

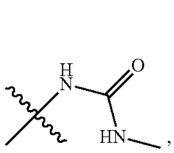, 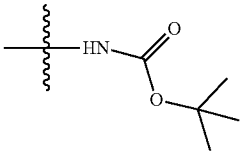,

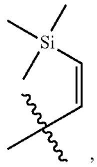, 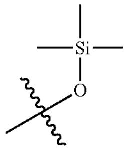, 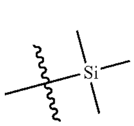,

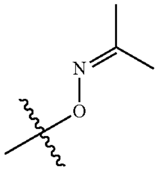, 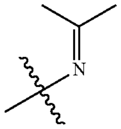, and 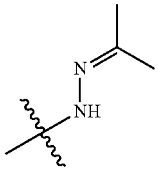;

or Ar is

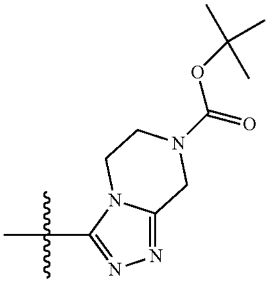, 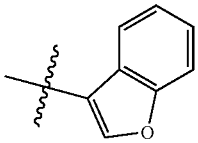,

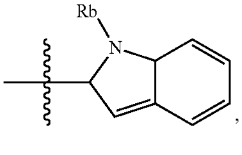, 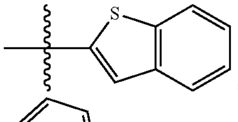, or

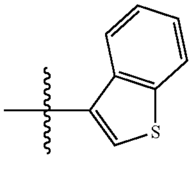;

$R_b$ represents hydrogen, methyl, ethyl, n-propyl, isopropyl, difluoromethyl, 2,2,2-trifluoromethyl, acetyl, phenyl, benzyl,

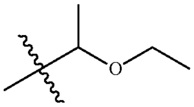, 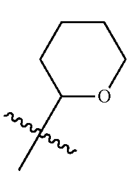, 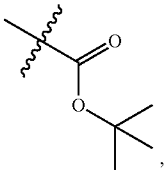,

-continued

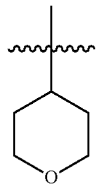
,
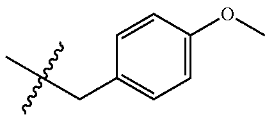
,
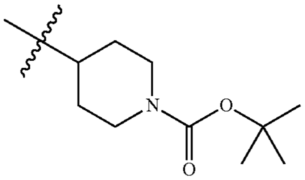
,
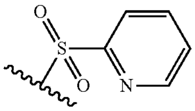
, or triphenylmethyl.

In the present invention, the derivative

I-1

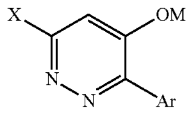

refers to an agriculturally acceptable derivative of the 4-hydroxy of the pyridazine ring of Formula I, including a salt, an ester, a hydrazine, a hydroxylamine, an ether thereof, and the like.

The salt derivative is a salt commonly used in agricultural chemicals, for example, the pyridazaine compound or the derivative may be processed into an alkali metal salt, an alkaline earth metal salt or an amine salt, or, when a basic moiety is present in the molecule, it can be processed into, for example, a sulfate, a hydrochloride, a nitrate, a phosphate, etc. When these salts are used as herbicides in agriculture or horticulture, they are also included in the present invention. In the present invention, the "alkali metal salt" may be, for example, a sodium salt, a potassium salt or a lithium salt, preferably a sodium salt or a potassium salt. In the present invention, the "alkaline earth metal salt" may be, for example, a calcium salt or a magnesium salt, preferably a calcium salt. In the present invention, the "amine salt" may be, for example, a secondary alkylamine salt, a tertiary alkylamine salt or a quaternary alkylammonium salt; a primary alkanolamine salt, a secondary alkanolamine salt, a tertiary alkanolamine salt or a quaternary alkanoammonium salt; a primary alkylalkanolamine salt, a secondary alkylalkanolamine salt, a tertiary alkylalkanolamine salt or a quaternary alkylalkanolammonium salt; or a primary alkoxyalkanolamine salt, a secondary alkoxyalkanolamine salt, a tertiary alkoxyalkanolamine salt or a quaternary alkoxyalkanolammonium salt, preferably, wherein the alkyl, alkanol and alkoxy are independently saturated and independently contain 1~4 carbon atoms, more preferably, ethanolamine salt, dimethylethanolamine salt, triethanolamine salt, dimethylamine salt, triethylamine salt, isopropylamine salt, choline salt or diglycolamine salt.

Solvates of the compounds of the invention are also included in the invention.

The compound of the present invention may also have a chiral carbon atom. In this case, the present invention also includes an optical isomer and a mixture of optical isomers in any ratio.

The ester derivative refers to a compound formed by bonding an acyl group (including carbonyl, thiocarbonyl, sulfinyl, sulfonyl, phosphoryl, thiophosphoryl, etc.) to the 4-hydroxy of the pyridazine ring, for example, (thio)formyl, C1~C18 alkyl(thio)carbonyl, wherein the (thio)formyl, or C1~C18 alkyl(thio)carbonyl is optionally substituted by a substituent [the substituent is one or more same or different substituents selected from halogen, amino, C3~C8 cycloalkyl, C1~C8 alkoxy, C1~C8 alkylsulfanyl, C1~C8 alkoxycarbonyl, C1~C8 alkylcarbonyloxy, C1~C8 alkylcarbonyl, C2~C8 alkenyloxycarbonyl optionally substituted by a substituent {the substituent is 1~3 same or different substituents selected from C3~C8 cycloalkyl, cyano, and benzoyl optionally substituted by a substituent (the substituent is 1~3 same or different substituents selected from halogen, C1~C8 alkyl, C1~C8 halogenated alkyl, C1~C8 alkoxycarbonyl, nitro and C1~C8 alkylsulfonyl)}, hydroxy(methyl)phosphinyl, C3~C8 cycloalkenyloxycarbonyl optionally substituted by a substituent {the substituent is 1~2 same or different substituents selected from oxo and benzoyl optionally substituted by a substituent (the substituent is 1~3 same or different substituents selected from halogen atom, C1~C8 alkyl, C1~C8 halogenated alkyl, C1~C8 alkoxycarbonyl, nitro and C1~C8 alkylsulfonyl)}, 5- or 6-membered heterocyclyloxycarbonyl optionally substituted by a substituent {the ring of the heterocyclyl contains one nitrogen atom, oxygen atom or sulfur atom, and may further contain one or two nitrogen atoms, the substituent is 1~3 same or different substituents selected from halogen, a C1~C8 alkyl, phenoxy optionally substituted by a substituent (the substituent is 1~3 same or different substituents selected from halogen, C1~C8 alkyl, C1~C8 halogenated alkyl, C3~C8 cycloalkyl and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, C1~C8 halogenated alkyl, C1~C8 alkoxycarbonyl, nitro and C1~C8 alkylsulfonyl)}, phenyl, phenoxy, benzyloxy, phenylsulfanyl, benzylsulfanyl, wherein the phenyl, phenoxy, benzyloxy, phenylsulfanyl, or benzylsulfanyl is optionally substituted by a substituent (the substituent is 1~3 same or different substituents selected from halogen, C1~C8 alkyl, C1~C8 alkoxy, C1~C8 halogenated alkyl, and C1~C8 alkoxycarbonyl), and C1~C8 alkylsulfanyl], C3~C8 cycloalkyl(thio)carbonyl, adamantyl (thio)carbonyl, C2~C8 alkenyl(thio)carbonyl optionally substituted by a substituent {the substituent is one or more same or different substituents selected from halogen, C1~C8 alkoxy, phenyl, phenylsulfanyl, and phenoxy, wherein the phenyl, phenylsulfanyl, or phenoxy is optionally substituted by a substituent (the substituent is 1~3 same or different substituents selected from halogen, C1~C8 alkyl, C1~C8 alkoxy, C1~C8 halogenated alkyl, and C1~C8 alkoxycarbonyl)}, C2~C8 alkynyl(thio)carbonyl, (thio)benzoyl, (thio) naphthoyl, wherein the (thio)benzoyl or (thio)naphthoyl is optionally substituted by a substitutent [the substituent is 1~3 same or different substituents selected from halogen atom, C1~C8 alkyl optionally substituted by a substituent (the substituent is one or more same or different substituents selected from halogen and phenyl), cyano, hydroxy, C1~C8 alkylcarbonyl, C1~C8 alkoxycarbonyl, C1~C8 alkylcarbonyloxy, C1~C8 alkylcarbonylamino, amino optionally substituted by a substituent (the substituent is 1~3 same or different substituents selected from C1~C8 alkyl, C1~C8 alkoxy, C1~C8 alkylcarbonyl, halogenated C1~C8 alkyl and phenyl), C2~C8 alkenyloxycarbonyl optionally substituted by a substituent {the substituent is 1~3 same or different substituents selected from C1~C8 cycloalkyl, cyano, and benzoyl optionally substituted by a substituent (the substituent is 1~3 same or different substituents selected from halogen, C1~C8 alkyl, C1~C8 halogenated alkyl, C1~C8 alkoxycarbonyl, nitro, and C1~C8 alkylsulfonyl)}, C3~C8 cycloalkenyloxycarbonyl optionally substituted by a substituent {the substituent is 1~2 same or different substituents selected from oxo, and benzoyl optionally substituted by a substituent (the substituent is 1~3 same or different substituents selected from halogen, C1~C8 alkyl, halogenated C1~C8 alkyl, C1~C8 alkoxycarbonyl, nitro, and C1~C8 alkylsulfonyl)}, phenyl, nitro, C1~C8 alkoxy optionally substituted by a substituent (the substituent is 1~3 same or different substituents selected from halogen and phenyl), phenoxy, 5- or 6-membered heterocyclyloxycarbonyl optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen, C1~C8 alkyl, halogenated C1~C8 alkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, halogenated C1~C8 alkyl, C1~C8 alkoxycarbonyl, nitro, and C1~C8 alkylsulfonyl)}, and 5- or 6-membered heterocyclyloxysulfonyl optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen, C1~C8 alkyl, phenoxy optionally substituted by a substituent (the substituent is 1~3 same or different substituents selected from halogen, C1~C8 alkyl, halogenated C1~C8 alkyl, C3~C8cycloalkyl, and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, C1~C8 halogenated alkyl, C1~C8 alkoxycarbonyl, nitro, and C1~C8 alkylsulfonyl)}], halogen-substituted sulfhydryl formyl, 3- to 8-membered heterocyclyl(thio)carbonyl optionally substituted by a substituent {the ring of the heterocyclyl contains 1 nitrogen atom, oxygen atom or sulfur atom, and may further contain 1 to 2 nitrogen atoms, or may form a 5- to 6-membered spiro ring having 1 to 2 oxygen atoms in the heterocyclyl, the substituent is 1~3 same or different substituents selected from halogen, C1~C8 alkyl optionally substituted by a substituent (the substituent is one or more same or different substituents selected from halogen and phenyl), C1~C8 alkylcarbonyl, C1~C8 alkoxycarbonyl, phenyl optionally substituted by a substituent (the substituent is 1~3 same or different halogen), nitro, hydroxy, C1~C8 alkoxy, phenoxy, C1~C8 alkylsulfanyl, C2~C8 alkenylsulfanyl, and phenylsulfanyl}, fused 5- to 14-membered bicyclic or tricyclic heterocyclyl (thio)carbonyl optionally substituted by a substituent (the ring of the heterocyclyl contains 1 nitrogen atom, oxygen atom or sulfur atom, and may further contain 1 to 2 nitrogen atoms or oxygen atoms; the substituent is 1~3 same or different substituents selected from halogen atom and C1~C8 alkyl), 5- or 6-membered heterocyclyl(thio)carbonyl (thio)carbonyl (the ring of the heterocyclyl contains one nitrogen atom, oxygen atom or sulfur atom, and may further contain one or two nitrogen atoms), C1~C18 alkoxy(thio) carbonyl, C1~C18 alkylthio(thio)carbonyl, wherein the C1~C18 alkoxy(thio)carbonyl or C1~C18 alkylthio(thio) carbonyl is optionally substituted by a substituent (the substituent is one or more same or different substituents selected from halogen atom, C1~C8 alkoxy and phenyl), C2~C8 alkenyloxy(thio)carbonyl, C2~C8 alkenylsulfanyl (thio)carbonyl, C2~C8 chain alkynyloxy(thio)carbonyl, C2~C8 chain alkynylsulfanyl(thio)carbonyl, C3~C8 cycloalkyloxy(thio)carbonyl, C3~C8 cycloalkylsulfanyl(thio)carbonyl, phenoxy(thio)carbonyl, phenylsulfanyl(thio) carbonyl, phenyl C1~C8 alkyloxy(thio)carbonyl, phenyl C1~C8 alkylthio(thio)carbonyl, wherein the phenoxy(thio) carbonyl, phenylsulfanyl(thio)carbonyl, phenyl C1~C8 alkyloxy(thio)carbonyl or phenyl C1~C8 alkylthio(thio)carbonyl is optionally substituted by a substituent (the substituent is 1~3 same or different substituents selected from halogen, C1~C8 alkyl, cyano, C1~C8 alkylcarbonyl, C1~C8 alkoxycarbonyl, nitro, and C1~C8 alkoxy), fused polycyclicoxy (thio)carbonyl, fused polycyclicsulfanyl(thio)carbonyl, a group selected from 5- or 6-membered heterocyclyloxy(thio)carbonyl and 5- or 6-membered heterocyclylsulfanyl(thio)carbonyl, which is optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, C1~C8 halogenated alkyl, C1~C8 alkoxycarbonyl, nitro, and C1~C8 alkylsulfonyl)}, amino(thio)formyl optionally substituted by a substituent {the substituent is 1~3 same or different substituents selected from C1~C8 alkyl optionally substituted by a substituent (the substituent is one or more same or different substituents selected from halogen, C1~C8 alkoxycarbonyl, cyano, phenyl, and C1~C8 alkoxy), C2~C8 alkenyl, phenyl, C1~C8 alkylcarbonyl, C1~C8 alkoxycarbonyl, and C1~C8 alkoxy},

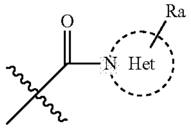

(Het is a 5- to 6-membered heterocyclyl, the heterocyclyl contains, besides C atoms and the 1-N, 0 to 3 atoms or radicals follows to form the ring: O, $NR_b$, C═O, $R_a$ and $R_b$ independently are hydrogen or C1~C8 alkyl), C1~C8 alkylsulfoxide, C1~C8 alkylsulfonyl, C2~C8 alkenylsulfonyl, C3~C8 cycloalkylsulfonyl, wherein the C1~C8 alkylsulfoxide, C1~C8 alkylsulfonyl, C2~C8 alkenylsulfonyl, or C3~C8 cycloalkylsulfonyl is optionally substituted by a substituent (the substituent is one or more same or different substituents selected from halogen and C1~C8 alkylsulfonyl), phenylsulfonyl, benzylsulfonyl, naphthylsulfonyl, wherein the phenylsulfonyl, benzylsulfonyl, or naphthylsulfonyl is optionally substituted by a substituent [the substituent is 1~3 same or different substituents selected from halogen, C1~C8 alkyl, halogenated C1~C8 alkyl, cyano, C1~C8 alkylcarbonyl, C1~C8 alkoxycarbonyl, nitro, C1~C8 alkoxy, halogenated C1~C8 alkoxy, C1~C8 alkylsulfonyl, aminoformyl optionally substituted by a substituent (the substituent is C1~C8 alkyl), phenoxy optionally substituted by a substituent (the substituent is 1~3 same or different substituents selected from halogen, C1~C8 alkyl, C1~C8 halogenated alkyl, C3~C8 cycloalkyl, and C1~C8 alkoxycarbonyl), C2~C8 alkenyloxysulfonyl optionally substituted by a substituent {the substituent is 1~3 same or different substituents selected from C3~C8 cycloalkyl, cyano, and benzoyl optionally substituted by a substituent (the substituent is 1~3 same or different substituents selected from halogen, C1~C8 alkyl, C1~C8 halogenated alkyl, C1~C8 alkoxycarbonyl, nitro, and C1~C8 alkylsulfonyl)}, C3~C8 cycloalkenyloxysulfonyl optionally substituted by a substituent {the substituent is 1~2 same or different substituents selected from oxo, and benzoyl optionally substituted by a substituent (the substituent is 1~3 same or different substituents selected from halogen, C1~C8 alkyl, C1~C8 halogenated alkyl, C1~C8 alkoxycarbonyl, nitro, and C1~C8 alkylsulfonyl)}, and 5- or 6-membered heterocyclyloxysulfonyl optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}], 5- to 10-membered heteroarylsulfonyl, 5- to 10-membered heterocyclyloxysulfonyl, wherein the 5- to 10-membered heteroarylsulfonyl or 5- to 10-membered heterocyclyloxysulfonyl is optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}, C1~C8 alkoxysulfonyl, C1~C8 alkylaminosulfonyl optionally substituted by a substituent the substituent is one or more same or different substituents selected from halogen atom),

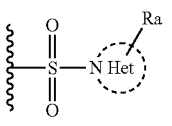

(Het is a 5- to 6-membered heterocyclyl, and contains, besides C atoms and the 1-N, 0 to 3 atoms or radicals as follows to form the ring: O, $NR_b$, and C═O, $R_a$ and $R_b$ independently are hydrogen or C1~C8 alkyl), di(C1~C8 alkyl)phosphoryl, or di(C1~C8 alkyl)thiophosphoryl.

Preferably, may be C1~C10 alkyl(thio)carbonyl optionally substituted by a substituent {the substituent is one or more same or different substituents selected from fluorine, chlorine, bromine, C1~C6 cycloalkyl, C1~C6 alkoxy, C1~C6 alkylsulfanyl, C1~C6 alkoxycarbonyl, C1~C6 alkylcarbonyl, C1~C6 alkylcarbonyloxy, phenyl, phenylsulfanyl, phenoxy, and benzyloxy, wherein the phenyl, phenylsulfanyl, phenoxy or benzyloxy is optionally substituted by a substituent (the substituent is 1~3 same or different substituents selected from fluorine, chlorine, bromine, C1~C6 alkyl, and C1~C6 alkoxy)}, C1~C6 cycloalkyl(thio)carbonyl, C1~C6 alkenyl(thio)carbonyl optionally substituted by a substituent {the substituent is one or more same or different substituents selected from fluorine, chlorine, bromine, C1~C6 alkoxy, phenyl, phenylthio, and phenoxy, wherein the phenyl, phenylthio or phenoxy is optionally substituted by a substituent (the substituent is 1~3 same or different substituents selected from fluoride, chlorine, bromine, C1~C6 alkyl, and C1~C6 alkoxy)}, (thio)benzoyl, (thio) naphthoyl, wherein the (thio)benzoyl or (thio)naphthoyl is optionally substituted by a substituent {the substituent is 1~3 same or different substituents selected from fluorine, chlorine, bromine, C1~C6 alkyl, C1~C6 alkoxy, wherein the C1~C6 alkyl or C1~C6 alkoxy is optionally substituted by a substituent (the substituent is 1~3 same or different substituents selected from fluorine, chlorine, bromine, and phenyl), cyano, hydroxy, C1~C6 alkylcarbonyl, C1~C6 alkoxycarbonyl, C1~C6 alkylcarbonyloxy, C1~C6 alkylcarbonylamino, amino optionally substituted by a substituent (the substituent is 1~3 same or different substituents selected from C1~C6 alkyl, C1~C6 alkoxy, C1~C6 alkylcarbonyl, halogenated C1~C6 alkyl, and phenyl), phenyl, nitro, and phenoxy, 3- to 8-membered heterocyclyl(thio)carbonyl optionally substituted by a substituent {the heterocyclyl is

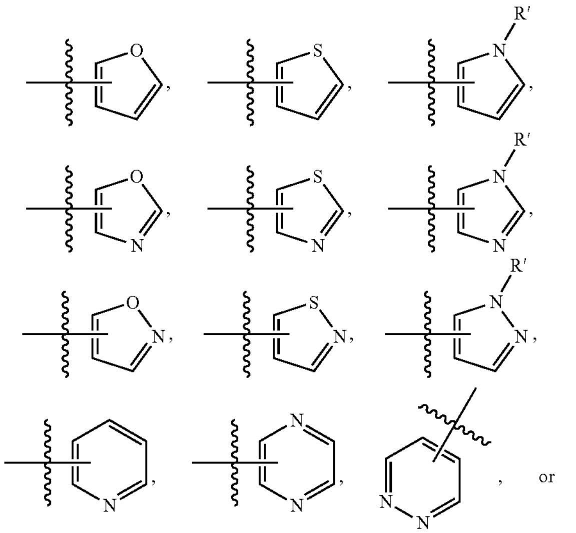

or

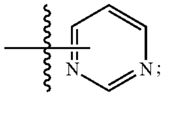

the substituent is 1~3 same or different substituents selected from fluorine, chlorine, bromine, C1~C6 alkyl optionally substituted by a substituent (the substituent is one or more same or different substituents selected from fluorine, chlorine, bromine, and phenyl), C1~C6 alkylcarbonyl, C1~C6 alkoxycarbonyl, phenyl optionally substituted by a substituent (the substituent is 1~3 same or different substituents selected from fluorine, chlorine, and bromine), nitro, hydroxy, C1~C6 alkoxy, phenoxy, C1~C6 alkylsulfanyl, C1~C6 alkenylsulfanyl, and phenylsulfanyl}, fused 5- to 14-membered bicyclic or tricyclic heterocyclyl(thio)carbonyl optionally substituted by a substituent (the heterocyclyl is

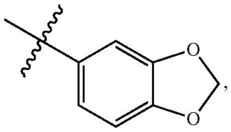, 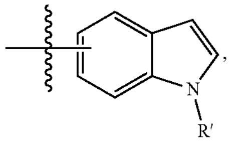, 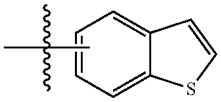, 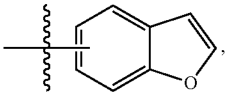, 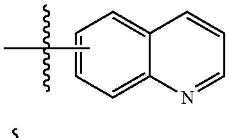, 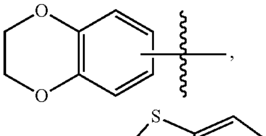, 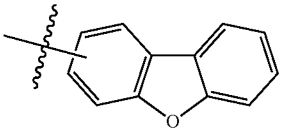, 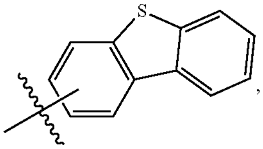, 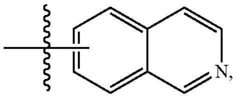, 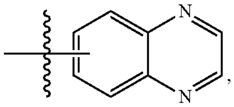, 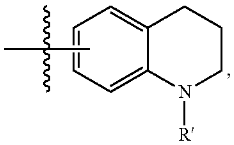, 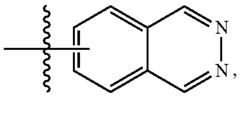, 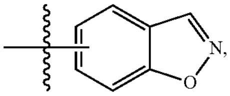, 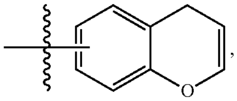, 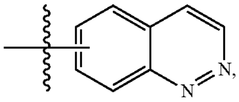, 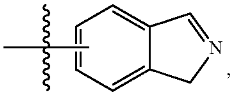, 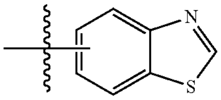, 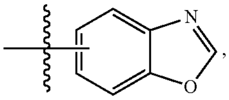, 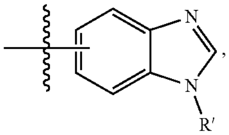, 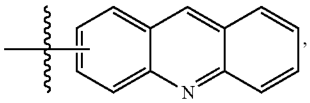, 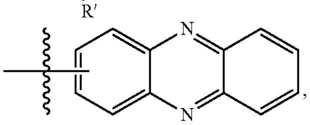, 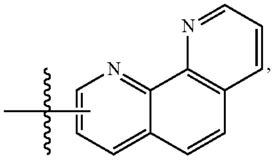, 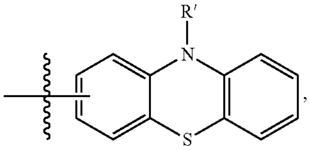, or -continued

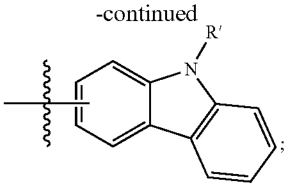;

the substituent is 1~3 same or different substituents selected from fluorine, chlorine, bromine, and C1~C6 alkyl), C1~C10 alkoxy(thio)carbonyl, C1~C10 alkylsulfanyl(thio)carbonyl, wherein the C1~C10 alkoxy(thio)carbonyl or C1~C10 alkylsulfanyl(thio)carbonyl is optionally substituted by a substituent (the substituent is one or more same or different substituents selected from fluorine, chlorine, bromine, C1~C6 alkoxy, and phenyl), C1~C6 cycloalkyloxy(thio)carbonyl, C1~C6 cycloalkylsulfanyl(thio)carbonyl, phenoxy(thio)carbonyl, phenylsulfanyl(thio)carbonyl, phenyl-C1~C6 alkyloxy(thio)carbonyl, phenyl-C1~C6 alkylthio(thio)carbonyl, wherein the phenoxy(thio)carbonyl, phenylsulfanyl(thio)carbonyl, phenyl-C1~C6 alkyloxy(thio)carbonyl or phenyl-C1~C6 alkylthio(thio)carbonyl is optionally substituted by a substituent (the substituent is 1~3 same or different substituents selected from fluorine, chlorine, bromine, C1~C6 alkyl, cyano, C1~C6 alkylcarbonyl, C1~C6 alkoxycarbonyl, nitro, and C1~C6 alkoxy), amino(thio)formyl optionally substituted by a substituent {the substituent is 1~3 same or different substituents selected from C1~C6 alkyl optionally substituted by a substituent (the substituent is one or more same or different substituents selected from fluorine, chlorine, and bromine), C1~C6 alkenyl, phenyl, C1~C6 alkylcarbonyl C1~C6 alkoxycarbonyl, and C1~C6 alkoxy)},

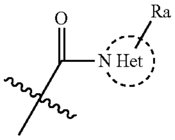

(Het is

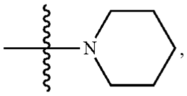, 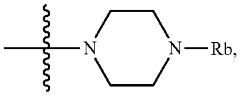, 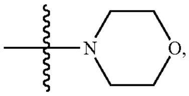, or 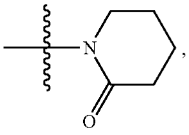, $R_a$ and $R_b$ independently are hydrogen or C1~C6 alkyl), C1~C6 alkylsulfoxide, C1~C6 alkylsulfonyl, C1~C6 alkenylsulfonyl, C1~C6 cycloalkylsulfonyl, wherein the C1~C6 alkylsulfoxide, C1~C6 alkylsulfonyl, C1~C6 alkenylsulfonyl or C1~C6 cycloalkylsulfonyl is optionally substituted by a substituent (the substituent is one or more same or different substituents selected from fluorine, chlorine, bromine, and C1~C6 alkylsulfonyl), phenylsulfonyl, benzylsulfonyl, naphthylsulfonyl, wherein the phenylsulfonyl, benzylsulfonyl or naphthylsulfonyl is optionally substituted by a substituent {the substituent is 1~3 same or different substituents selected from fluorine, chlorine, bromine, C1~C6 alkyl, halogenated C1~C6 alkyl, cyano, C1~C6 alkanocarbonyl, C1~C6 alkoxycarbonyl, nitro, C1~C6 alkoxy, halogenated C1~C6 alkoxy, C1~C6 alkylsulfonyl, aminoformyl optionally substituted by a substituent (the substituent is C1~C6 alkyl), and phenoxy optionally substituted by a substituent (the substituent is 1~3 same or different substituents selected from fluorine, chlorine, bromine, C1~C6 alkyl, C1~C8 halogenated alkyl, C1~C6 cycloalkyl, and C1~C6 alkoxycarbonyl)}, 5- to 10-membered heteroarylsulfonyl optionally substituted by a substituent {the heterocyclyl is

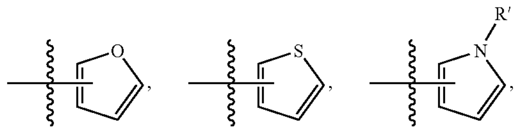

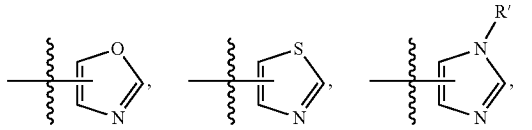

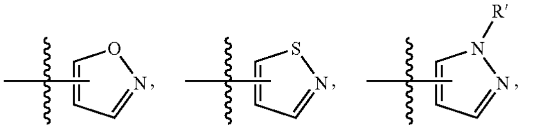

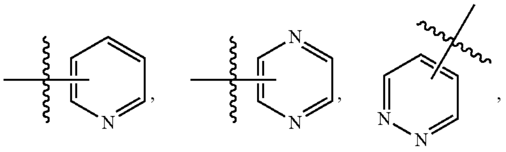

, or

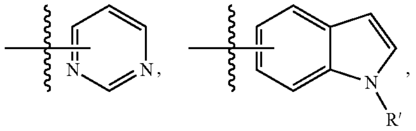

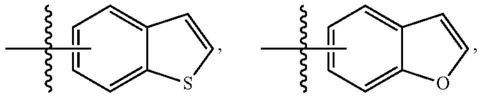

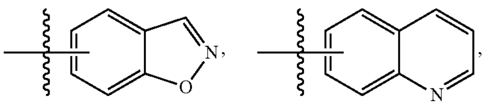

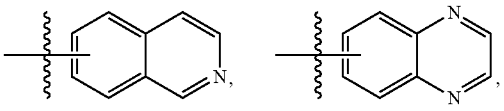

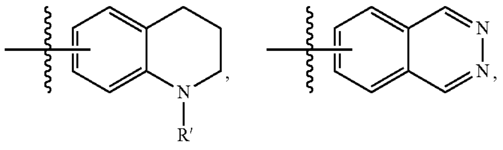

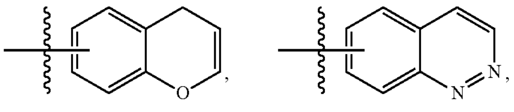

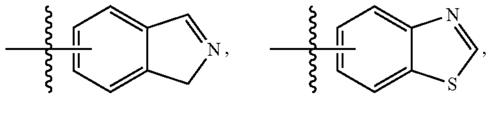

-continued

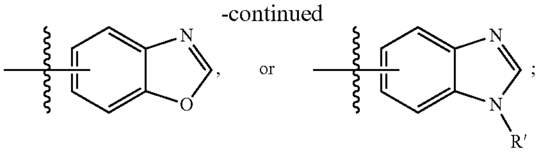

the substituent is 1~3 same or different substituents selected from fluorine, chlorine, bromine, C1~C6 alkyl, and phenoxy optionally substituted by a substituent (the substituent is 1~3 same or different substituents selected from fluorine, chlorine, bromine, C1~C6 alkyl, C1~C6 halogenated alkyl, C1~C6 cycloalkyl, and C1~C6 alkoxycarbonyl)}, C1~C6 alkylaminosulfonyl optionally substituted by a substituent (the substituent is one or more same or different substituents selected from fluorine, chlorine, and bromine),

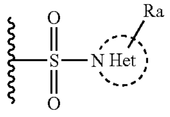

(Het is

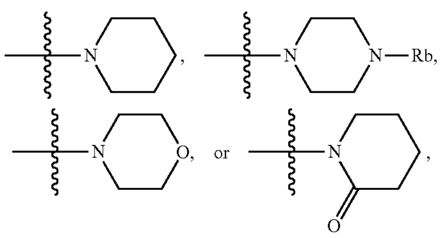

$R_a$ and $R_b$ independently are hydrogen or C1~C6 alkyl), di(C1~C6 alkyl)phosphoryl, or di(C1~C6 alkyl)thiophosphoryl.

The oxime derivative refers to a compound having an oximido group of

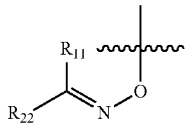

formed on the 4-hydroxy of the pyridazine ring of Formula I, for example, $R_1$, $R_{22}$ independently are hydrogen, C1~C18 alkyl, C1~C18 alkenyl, wherein the C1~C18 alkyl or C1~C18 alkenyl is optionally substituted with a substituent (the substituent is one or more same or different substituents selected from halogen atom, C1~C8 alkoxy, C1~C8 alkylsulfanyl, and C1~C8 alkylamino), phenyl, phenylcarbonyl, 5- to 6-membered heteroaryl, wherein the phenyl, phenylcarbonyl or 5- to 6-membered heteroaryl is optionally substituted with a substituent (the substituent is 1~3 same or different substituents selected from halogen atom, C1~C8 alkyl, C2~C8 alkenyl, C2~C8 alkynyl, C3~C8 cycloalkyl, C1~C8 halogenated alkyl, C1~C8 alkylcarbonyl, C1~C8 alkoxy, C1~C8 alkoxycarbonyl, C1~C8 alkylamino, hydroxy, carboxyl, sulfhydryl, amino, cyano, nitro, and C1~C8 alkylsulfonyl, the heteroaryl contains at least one oxygen, sulfur, or nitrogen, or other heteroatoms), or $R_1$, $R_{22}$ form a 5- to 6-membered saturated carbocyclic ring or 5- to 6-membered heterocyclic ring (containing at least one heteroatom such as oxygen, sulfur, nitrogen, etc.).

Preferably, $R_{11}$, $R_{22}$ independently may be hydrogen, C1~C10 alkyl, C1~C10 alkenyl, the C1~C10 alkyl or C1~C10 alkenyl is optionally substituted with a substituent (the substituent is one or more same or different substituents selected from fluorine, chlorine, bromine, C1~C6 alkoxy, C1~C6 alkylsulfanyl, and C1~C6 alkylamino), phenyl, benzoyl, 5- to 6-membered heteroaryl, wherein the phenyl, benzoyl or 5- to 6-membered heteroaryl is optionally substituted with a substituent (the heteroaryl is

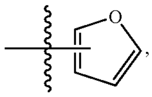, 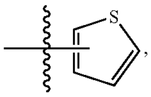, 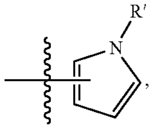, 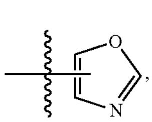, 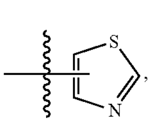, 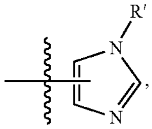, 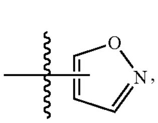, 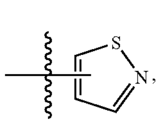, 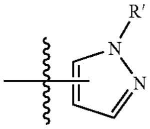, 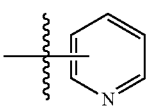, 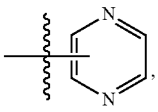, 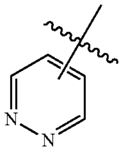, or 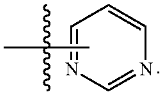.

the substituent is 1~3 same or different substituents selected from fluorine, chlorine, bromine, C1~C6 alkyl, C1~C6 cycloalkyl, C1~C6 halogenated alkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl), or $R_{11}$ and $R_{22}$ form a 5- to 6-membered saturated carbocyclic ring or a 5- to 6-membered heterocyclic ring (containing at least one heteroatom such as oxygen, sulfur, nitrogen, etc.).

The hydroxylamine derivative refers to a compound having a hydroxylamine moiety of

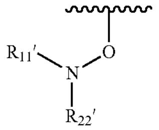

formed on the 4-hydroxy of the pyridazine ring of Formula I, for example, $R_{11}'$, $R_{22}'$ independently may be hydrogen, C1~C18 alkyl, C1~C18 alkenyl, wherein the C1~C18 alkyl or C1~C18 alkenyl is optionally substituent with a substituent (the substituent is one or more same or different substituents selected from halogen atom, C1~C8 alkoxy, C1~C8 alkylsulfanyl, and C1~C8 alkylamino), phenyl optionally substituent with a substituent (the substituent is 1~3 same or different substituents selected from halogen atom, C1~C8 alkyl, C2~C8 alkenyl, C2~C8 alkynyl, C3~C8 cycloalkyl, C1~C8 halogenated alkyl, C1~C8 alkylcarbonyl, C1~C8 alkoxy, C1~C8 alkoxycarbonyl, C1~C8 alkylamino, hydroxy, carboxyl, sulfhydryl, amino, cyano, nitro, and C1~C8 alkylsulfonyl), C1~C18 alkoxycarbonyl, or benzoyl optionally substituent with a substituent [the substituent is 1~3 same or different substituents selected from halogen atom, C1~C8 alkyl, C2~C8 alkenyl, C2~C8 alkynyl, C3~C8 cycloalkyl, wherein the C1~C8 alkyl, C2~C8 alkenyl, C2~C8 alkynyl or C3~C8 cycloalkyl is optionally substituent with a substituent (the substituent is 1~3 same or different substituents selected from halogen and phenyl), cyano, C1~C8 alkylcarbonyl, C1~C8 alkoxycarbonyl, C1~C8 alkylsulfonyl, C2~C8 alkenyloxycarbonyl optionally substituent with a substituent {the substituent is 1~3 same or different substituents selected from C3~C8 cycloalkyl, cyano, and benzoyl optionally substituent with a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}, C3~C8 cycloalkenyloxycarbonyl optionally substituent with a substituent {the substituent is 1~2 same or different substituents selected from oxo, and benzoyl optionally substituent with a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}, hydroxy, carboxyl, sulfhydryl, amino, phenyl, nitro, C1~C8 alkoxy, C1~C8 alkylamino, C1~C8 alkylsulfanyl, wherein the C1~C8 alkoxy, C1~C8 alkylamino or C1~C8 alkylsulfanyl is optionally substituent with a substituent (the substituent is 1~3 same or different substituents selected from halogen and phenyl), phenoxy, 5- or 6-membered heterocyclyloxycarbonyl optionally substituent with a substituent {the ring of the heterocyclyl contains one nitrogen atom, oxygen atom or sulfur atom, may further contain 1 to 2 nitrogen atoms; the substituent is 1~3 same or different substituents selected from halogen atom, C1~C8 alkyl, phenoxy optionally substituent with a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituent with a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}, and 5- or 6-membered heterocyclyloxysulfonyl optionally substituent with a substituent {the ring in the heterocyclyl contains one nitrogen atom, oxygen atom or sulfur atom, and may further contain 1 or 2 nitrogen atoms; the substituent is 1~3 same or different substituents selected from halogen atom, C1~C8 alkyl, phenoxy optionally substituent with a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxyl, and benzoyl optionally substituent with a substituent (the substituent is 1~3 same or different substitutions selected from halogen atom, C1~C8 alkyl, C1~C8 halogenated alkyl, C1~C8 alkoxycarbonyl, nitro, and C1~C8 alkylsulfonyl)}].

Preferably, $R_{11}'$, $R_{22}'$ may independently be hydrogen, C1~C10 alkyl, C1~C10 alkenyl, wherein the C1~C10 alkyl or C1~C10 alkenyl is optionally substituent with a substituent (the substituent is one or more same or different substituents selected from fluorine, chlorine, bromine), C1~C10 alkoxycarbonyl, phenyl, or benzoyl, wherein the phenyl or benzoyl optionally substituent with a substituent (the substituent is 1~3 same or different substituents selected from fluorine, chlorine, bromine, C1~C6 alkyl, C1~C6 alkenyl, C1~C6 alkynyl, C1~C6 cycloalkyl, C1~C6 halogenated alkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl).

The ether derivative refers to a compound formed by bonding the oxygen atom of the 4-hydroxy of the pyridazine ring with a group as follows:

C1~C18 alkyl, C1~C18 alkenyl, wherein the C1~C18 alkyl or C1~C18 alkenyl is optionally substituted with a substituent (the substituent is one or more same or different substituents selected from halogen atom, C1~C8 alkoxy, C1~C8 alkylsulfanyl, C1~C8 alkylamino, di(C1~C8 alkyl) amino, C1~C8 alkoxycarbonyl, and C1~C8 alkoxycarbonyloxy), phenyl, benzyl, or benzoyl-C1~C8 alkyl, wherein the phenyl, benzyl or benzoyl-C1~C8 alkyl is optionally substituent with a substituent [the substituent is 1~3 same or different substituents selected from halogen atom, C1~C8 alkyl, C2~C8 alkenyl, C2~C8 alkynyl, C3~C8 cycloalkyl, wherein the C1~C8 alkyl, C2~C8 alkenyl, C2~C8 alkynyl or C3~C8 cycloalkyl is optionally substituent with a substituent (the substituent is 1~3 same or different substituents selected from halogen and phenyl), cyano, C1~C8 alkylcarbonyl, C1~C8 alkoxycarbonyl, C1~C8 alkylsulfonyl, C2~C8 alkenyloxycarbonyl optionally substituent with a substituent {the substituent is 1~3 same or different substituents selected from C3~C8 cycloalkyl, cyano, and benzoyl optionally substituent with a substituent (the substituent is 1~3 same or different substitutions selected from halogen atom, C1~C8 alkyl, C1~C8 halogenated alkyl, C1~C8 alkoxycarbonyl, nitro, and C1~C8 alkylsulfonyl)}, C3~C8 cycloalkenyloxycarbonyl optionally substituent with a substituent {the substituent is 1~2 same or different substituents selected from oxo, and benzoyl optionally substituent with a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}, hydroxy, carboxyl, sulfhydryl, amino, phenyl, nitro, C1~C8 alkoxy, C1~C8 alkylamino, C1~C8 alkylsufanyl, wherein the C1~C8 alkoxy, C1~C8 alkylamino or C1~C8 alkylsufanyl is optionally substituent with a substituent (the substituent is 1~3 same or different substituents selected from halogen and phenyl), phenoxy, 5- or 6-membered heterocyclyloxycarbonyl optionally substituent with a substituent {the ring of the heterocyclyl contains one nitrogen atom, oxygen atom or sulfur atom, and may further contain 1 to 2 nitrogen atoms; the substituent is 1~3 same or different substituents selected from halogen atom, C1~C8 alkyl, phenoxy optionally substituent with a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituent with a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}, and 5- or 6-membered heterocyclyloxysulfonyl optionally substituent with a substituent {the ring of the heterocyclyl contains one nitrogen atom, oxygen atom or sulfur atom, and may further contain 1 to 2 nitrogen atoms; the substituent is 1~3 same or different substituents selected from halogen atom, C1~C8 alkyl, phenoxy optionally substituent with a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituent with a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}]; wherein, in Formula I-1, when X is cyano and Ar is

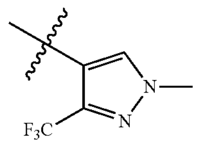

in Formula I-1, the M group is not methyl.

Preferably, may be C1~C18 alkyl, C1~C18 alkenyl, C1~C10 alkyl, C2~C10 alkenyl, wherein the C1~C10 alkyl or C2~C10 alkenyl is substituent with a substituent {the substituent is one or more same or different substituents selected from fluorine, chlorine, bromine, C1~C6 alkoxy, C1~C6 alkylsulfanyl, C1~C6 alkylamino, C1~C6 alkoxycarbonyl, and C1~C6 alkoxycarbonyloxy}, phenyl, benzyl, or benzoyl-C1~C6 alkyl, wherein the phenyl, benzyl or benzoyl-C1~C6 alkyl is optionally substituent with a substituent (the substituent is 1~3 same or different substituents selected from fluorine, chlorine, bromine, C1~C6 alkyl, C1~C6 alkenyl, C1~C6 alkynyl, C1~C6 cycloalkyl, C1~C6 halogenated alkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl).

A method for preparing the five-membered ring-substituted pyridazinol compound, comprising the steps of:

(1) subjecting a compound of Formula II and a compound of Formula III to Suzuki reaction to obtain a compound of Formula IV;

(2) subjecting a compound of Formula IV to halogenating reaction to obtain a compound of Formula V;

(3) subjecting a compound of Formula V to hydrolysis reaction to obtain a compound of Formula I;

wherein the reaction route is as follows:

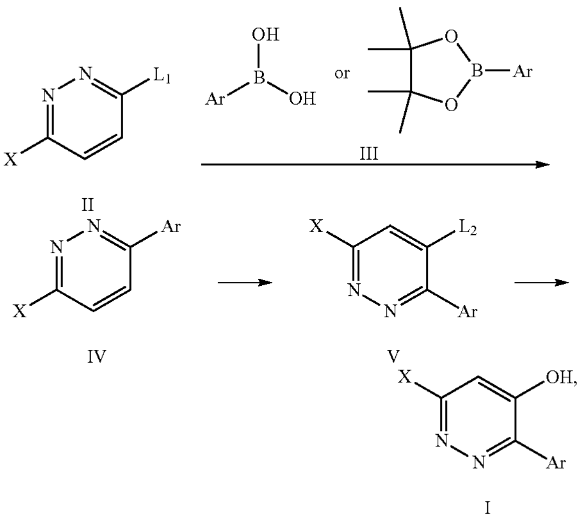

$L_1$, $L_2$ each independently represent halogen, preferably chlorine, bromine, or iodine.

The reactions are carried out in the range of 20 to 150° C., preferably 50 to 130° C.

Step (1) is carried out in the presence of a catalyst, a base and a solvent, wherein the catalyst is $Pd(dppf)Cl_2CH_2Cl_2$, $Pd(dba)_2$, $Pd_2(dba)_3$, $Pd(PPh_3)_4$, $PdCl_2$, $Pd(OAc)_2$, $Pd(dppf)Cl_2$, $Pd(PPh_3)_2Cl_2$, or $Ni(dppf)Cl_2$, the base is one or more selected from $Et_3N$, $NaHCO_3$, KOAc, $K_2CO_3$, $K_3PO_4$, $Na_2CO_3$, CsF, $Cs_2CO_3$, t-BuONa, EtONa, KOH, and NaOH, the solvent is THF/water, toluene/water, DMF/water, 1,4-dioxane/water, toluene/ethanol/water, acetonitrile/water, THF, toluene, 1,4-dioxane, acetonitrile, or DMF system; step (2) is carried out in the presence of a halogenated reagent, a catalyst and a solvent, wherein the halogenated reagent is N-chloro succinimide, N-bromo succinimide or N-iodo succinimide, the catalyst is benzoyl peroxide, and the solvent is acetonitrile; step (3) is carried out in the presence of a base and a solvent or in the presence of a solution of boron tribromide, a solution of hydrobromic acid in acetic acid, a solution of hydrochloric acid in methanol or a solution of hydrochloric acid in ethyl acetate, the base is preferably selected from NaOH, KOH, potassium acetate, and sodium acetate, the solvent is preferably water or DMSO.

The reaction route for preparing an ester or ether derivative is as follows:

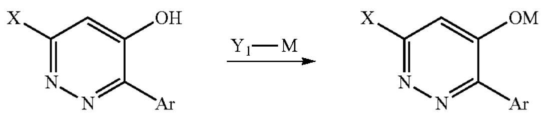

I I-1 wherein, $Y_1$ is a halogen, preferably chlorine or bromine;

The reaction route for preparing an oxime or hydroxylamine derivative is as follows:

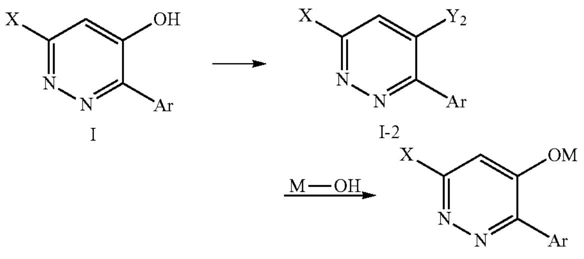

I I-2 I-1 wherein, $Y_2$ is a halogen, preferably chlorine or fluorine.

Reactions for preparing the ester or ether derivatives and the second step for preparing the oxime or hydroxylamine derivatives are carried out in the presence of a base and a solvent, the base is one or more selected from the group consisting of sodium hydroxide, potassium hydroxide, sodium carbonate, potassium carbonate, sodium hydrogen carbonate, cesium carbonate, triethylamine and diisopropylethylamine; the solvent is THF, 1,4-dioxane, toluene, 1,2-dichloroethane, ethyl acetate, acetonitrile, DMF, acetone, dichloromethane, or chloroform; the first step for preparing the oxime or hydroxylamine derivative is carried out in the presence of a halogenation reagent and a solvent, wherein the halogenation reagent is Phenofluor/cesium fluoride or $POCl_3$, and the solvent is one or more selected from the group consisting of toluene, 1,2-dichloroethane, and DMF; the reaction temperature is in the range of 0 to 120° C., preferably 20 to 80° C.

The compound of the present invention may exist in the form of one or more stereoisomers. The various isomers include enantiomers, diastereomers, and geometric isomers. These isomers and mixtures thereof are all within the scope of the invention.

A herbicidal composition, comprising component (i) the five-membered ring-substituted pyridazinol compound of Formula I or the derivative thereof.

Preferably, further comprising component (ii) one or more additional herbicides and/or safeners.

More preferably, further comprising component (iii) an agriculturally acceptable formulation auxiliary.

The additional herbicide is selected from one of an HPPD inhibitor, a hormone herbicide, and a PDS inhibitor; preferably, the HPPD inhibitor is selected from the group consisting of Sulcotrione, Mesotrione, Topramezone, Tembotrione, Bicyclopyrone, Tefuryltrione, Benzobicyclon, Lancotrione, Shuangzuocaotong, Huanbifucaotong, Sanzuohuangcaotong, Benzuofucaotong, Pyrasulfotole, Pyrazolate, Benzofenap, Tolpyralate, Fenquinotrione, and Isoxaflutole; the hormone herbicide is selected from the group consisting of Fluroxypyr, Halauxifen-methyl, Florpyrauxifen-benzyl, Quinclorac, Quinmerac, 2-methyl-4-chlorophenoxy acetic acid, 2-methyl-4-chlorophenoxypropionic acid, MCPB, 2,4-D, Dichlorprop, 2,4-DB, Dicamba, Picloram, Trichlopyr, Clopyralid, Triclopyr and derivatives thereof, the PDS inhibitor is selected from the group consisting of Flurochloridone, Flurtamone, Diflufenican, Picolinafen, Beflubutamid, Norflurazon and Fluridone.

Wherein, the Fluroxypyr derivative include, but are not limited to: Fluroxypyr-mepthyl; 2-methyl-4-chlorophenoxy acetic acid, 2-methyl 4-chlorophenoxypropionic acid, MCPB derivatives include but are not limited to: sodium salts, potassium salts, dimethylammonium salts, isopropylamine salts, etc., and methyl esters, ethyl esters, isooctyl esters, ethylthio esters, etc.; the derivatives of 2,4-D, Dichlorprop and 2,4-DB derivatives include but are not limited to: salts such as sodium salts, potassium salts, dimethylammonium salts, triethanolammonium salts, isopropylamine salts, cholines, etc., and esters such as methyl esters, ethyl esters, butyl esters, isooctyl esters, etc.

A method for controlling a harmful plant, comprising applying a herbicidally effective amount of at least one of the five-membered ring-substituted pyridazinol compound or derivative thereof, or the herbicidal composition to the harmful plant or an area with the harmful plant.

Use of at least one of the five-membered ring-substituted pyridazinol compound or derivative thereof, or the herbicidal composition for controlling a harmful plant;

Preferably, at least one of the five-membered ring-substituted pyridazinol compound or derivative thereof, or the herbicidal composition is used to control a harmful plant in a useful crop.

More preferably, the useful crop is a genetically modified crop or a crop treated by genome editing technique.

The compounds of Formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species.

Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and Sorghum, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica hederifolia, Veronica persica, Viola tricolor* and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of Formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of Formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases:

- genetically engineered changes in crop plants in order to modify the starch synthesized in the plants (for example WO 92/11376, WO 92/14827, WO 91/19806);
- transgenic crop plants which are resistant to certain herbicides, for example, glufosinate (EP-A 0 242 236, EP-A 0 242 246), glyphosate-type (WO 92/00377), or sulfonylurea-type (EP-A 0 257 993, U.S. Pat. No. 5,013,659);
- transgenic crop plants, for example cotton, having the ability to produce *Bacillus thuringiensis* toxins (Bt toxins) which impart resistance to certain pests to the plants (EP-A 0 142 924, EP-A 0 193 259);
- transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of Formula I. The compounds of Formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kuhler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflchenaktive thylenoxidaddukte" [Surface-active ethylene oxide adducts], Wiss. Verlagsgesell., Stuttgart 1976; Winnacker-Kuchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with Formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of Formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

For use, Formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of Formula I required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 250 g/ha.

SPECIFIC MODE FOR CARRYING OUT THE INVENTION

The following embodiments are used to illustrate the present invention in detail and should not be taken as any limit to the present invention. The scope of the invention would be explained through the Claims.

In view of economics, variety and biological activity of a compound, we preferably synthesized several compounds, part of which are listed in the following table 1-2. The structure and information of a certain compound are shown in Table 1-2. The compounds in Table 1-2 are listed for further explication of the present invention, other than any limit therefor. The subject of the present invention should not be interpreted by those skilled in the art as being limited to the following compounds.

TABLE 1

Structure and $^1$HNMR data of Compound I

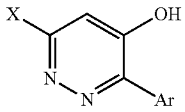

I

| No. | X | Ar | $^1$HNMR |
|---|---|---|---|
| 1 | Cl | 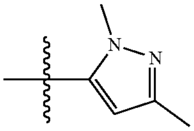 [SMILES: *c1cc(C)nn1C] | $^1$H NMR (500 MHz, DMSO-$d_6$) δ 10.21 (s, 1H), 7.37 (s, 1H), 6.59 (s, 1H), 3.88 (s, 3H), 2.39 (s, 3H). |
| 2 | Cl | 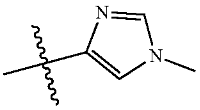 [SMILES: *c1cn(C)cn1] | $^1$H NMR (500 MHz, DMSO-$d_6$) δ 10.14 (s, 1H), 7.72 (s, 1H), 7.45 (s, 1H), 7.30 (s, 1H), 3.68 (s, 3H). |
| 3 | Cl | 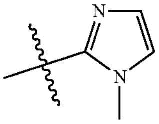 [SMILES: *c1nccn1C] | $^1$H NMR (500 MHz, DMSO-$d_6$) δ 12.92 (s, 1H), 7.39 (d, J = 2.5 Hz, 1H), 7.33 (s, 1H), 7.08 (d, J = 2.5 Hz, 1H), 3.94 (s, 3H). |
| 4 | Cl | 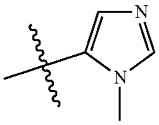 [SMILES: *c1cncn1C] | $^1$H NMR (500 MHz, DMSO-$d_6$) δ 10.21 (s, 1H), 7.74 (s, 1H), 7.56 (s, 1H), 7.38 (s, 1H), 3.79 (s, 3H). |

TABLE 1-continued

Structure and $^1$HNMR data of Compound I

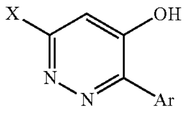

I

| No. | X | Ar | $^1$HNMR |
| --- | --- | --- | --- |
| 5 | Cl | 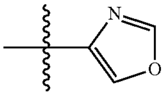 | $^1$H NMR (500 MHz, DMSO-$d_6$) δ 12.12 (s, 1H), 8.26 (s, 1H), 7.98 (s, 1H), 7.34 (s, 1H). |
| 6 | Cl | 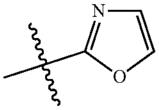 [SMILES: *c1ncco1] | $^1$H NMR (500 MHz, DMSO-$d_6$) δ 11.87 (s, 1H), 7.90 (d, J = 2.5 Hz, 1H), 7.39-7.32 (m, 2H). |
| 7 | Cl | 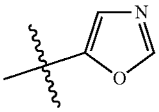 [SMILES: *c1cnco1] | $^1$H NMR (500 MHz, DMSO-$d_6$) δ 10.25 (s, 1H), 8.12 (s, 1H), 7.75 (s, 1H), 7.31 (s, 1H). |
| 8 | Cl | 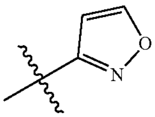 [SMILES: *c1ccon1] | $^1$H NMR (500 MHz, DMSO-$d_6$) δ 10.20 (s, 1H), 8.74 (d, J = 2.5 Hz, 1H), 7.33-7.26 (m, 2H). |
| 9 | Cl | 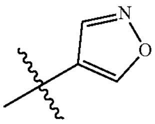 [SMILES: *c1cnoc1] | $^1$H NMR (500 MHz, DMSO-$d_6$) δ 10.23 (s, 1H), 8.36 (s, 1H), 8.17 (s, 1H), 7.31 (s, 1H). |
| 10 | Cl | 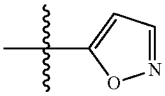 [SMILES: *c1ccno1] | $^1$H NMR (500 MHz, DMSO-$d_6$) δ 11.58 (s, 1H), 8.23 (d, J = 2.3 Hz, 1H), 7.36 (m, 2H). |
| 11 | Cl | 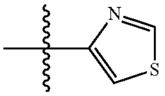 [SMILES: *c1cscn1] | $^1$H NMR (500 MHz, DMSO-$d_6$) δ 10.17 (s, 1H), 9.20 (s, 1H), 8.10 (s, 1H), 7.31 (s, 1H). |
| 12 | Cl | 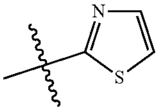 [SMILES: *c1nccs1] | $^1$H NMR (500 MHz, DMSO-$d_6$) δ 12.66 (s, 1H), 8.04 (d, J = 2.0 Hz, 1H), 7.53 (d, J = 2.0 Hz, 1H), 7.34 (s, 1H). |
| 13 | Cl | 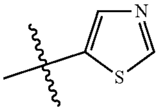 [SMILES: *c1cncs1] | $^1$H NMR (500 MHz, DMSO-$d_6$) δ 10.21 (s, 1H), 9.21 (s, 1H), 8.19 (s, 1H), 7.32 (s, 1H). |
| 14 | Cl | 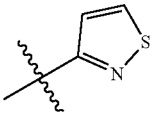 [SMILES: *c1ccsn1] | $^1$H NMR (500 MHz, DMSO-$d_6$) δ 10.04 (s, 1H), 8.72 (d, J = 2.5 Hz, 1H), 7.37 (d, J = 2.5 Hz, 1H), 7.30 (s, 1H) |
| 15 | Cl | 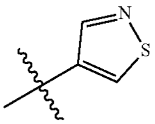 [SMILES: *c1cnsc1] | $^1$H NMR (500 MHz, DMSO-$d_6$) δ 10.19 (s, 1H), 8.72 (s, 1H), 8.00 (s, 1H), 7.31 (s, 1H). |

TABLE 1-continued

Structure and $^1$HNMR data of Compound I

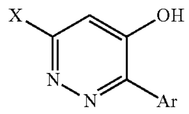

I

| No. | X | Ar | $^1$HNMR |
|---|---|---|---|
| 16 | Cl | 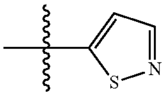 [SMILES: *c1ccns1] | $^1$H NMR (500 MHz, DMSO-$d_6$) δ 10.49 (s, 1H), 8.10 (d, J = 1.5 Hz, 1H), 7.39-7.33 (m, 2H). |
| 17 | Cl | 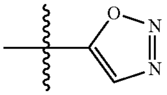 | $^1$H NMR (500 MHz, DMSO-$d_6$) δ 10.28 (s, 1H), 8.21 (s, 1H), 7.28 (s, 1H). |
| 18 | Cl | 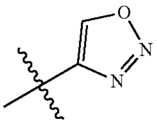 [SMILES: *c1conn1] | $^1$H NMR (500 MHz, DMSO-$d_6$) δ 10.12 (s, 1H), 8.19 (s, 1H), 7.27 (s, 1H). |
| 19 | Cl | 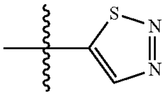 [SMILES: *c1cnns1] | $^1$H NMR (500 MHz, DMSO-$d_6$) δ 10.22 (s, 1H), 8.28 (s, 1H), 7.26 (s, 1H). |
| 20 | Cl | 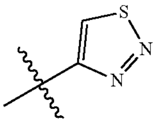 [SMILES: *c1csnn1] | $^1$H NMR (500 MHz, DMSO-$d_6$) δ 10.03 (s, 1H), 9.49 (s, 1H), 7.25 (s, 1H). |
| 21 | Cl | 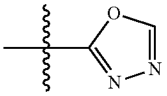 [SMILES: *c1nnco1] | $^1$H NMR (500 MHz, DMSO-$d_6$) δ 10.17 (s, 1H), 7.92 (s, 1H), 7.27 (s, 1H) |
| 22 | Cl | 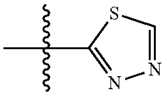 | $^1$H NMR (500 MHz, DMSO-$d_6$) δ 11.71 (s, 1H), 9.41 (s, 1H), 7.31 (s, 1H). |
| 23 | Cl | 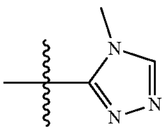 [SMILES: *c1nncn1C] | $^1$H NMR (500 MHz, DMSO-$d_6$) δ 10.11 (s, 1H), 9.11 (s, 1H), 7.33 (s, 1H), 3.78 (s, 3H). |
| 24 | Cl | 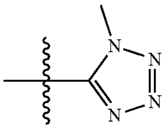 [SMILES: *c1nnnn1C] | $^1$H NMR (500 MHz, DMSO-$d_6$) δ 9.98 (s, 1H), 7.34 (s, 1H), 4.12 (s, 3H). |
| 25 | Cl | 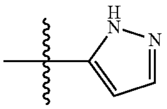 [SMILES: *c1ccn[nH]1] | $^1$H NMR (500 MHz, DMSO-$d_6$) δ 12.85 (s, 1H), 10.25 (s, 1H), 7.78-7.65 (m, 1H), 7.31 (s, 1H), 6.80-6.72 (m, 1H). |

TABLE 1-continued

Structure and $^1$HNMR data of Compound I

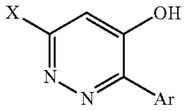

I

| No. | X | Ar | $^1$HNMR |
|---|---|---|---|
| 26 | Cl | 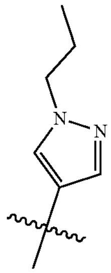 [SMILES: *c1cnn(CCC)c1] | $^1$H NMR (500 MHz, DMSO-$d_6$) δ 10.17 (s, 1H), 7.85 (s, 1H), 7.33 (s, 1H), 7.01 (s, 1H), 4.33 (t, J = 5.1 Hz, 2H), 1.91 (qt, J = 8.0, 4.9 Hz, 2H), 0.93 (t, J = 7.9 Hz, 3H). |
| 27 | Cl | 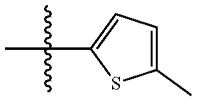 | $^1$H NMR (500 MHz, DMSO-$d_6$) δ 10.19 (s, 1H), 7.62 (d, J = 2.5 Hz, 1H), 7.31 (s, 1H), 7.11 (d, J = 2.5 Hz, 1H), 2.38 (s, 3H). |
| 28 | Cl | 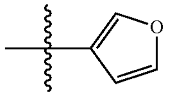 | $^1$H NMR (500 MHz, DMSO-$d_6$) δ 10.22 (s, 1H), 7.86 (s, 1H), 7.48 (d, J = 2.5 Hz, 1H), 7.31 (s, 1H), 6.65 (d, J = 2.5, Hz, 1H). |
| 29 | Cl | 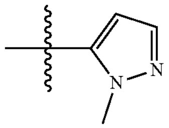 [SMILES: *c1ccnn1C] | $^1$H NMR (500 MHz, DMSO-$d_6$) δ 10.21 (s, 1H), 7.60 (d, J = 2.0 Hz, 1H), 7.31 (s, 1H), 6.74 (d, J = 2.0 Hz, 1H), 3.90 (s, 3H). |
| 30 | Cl | 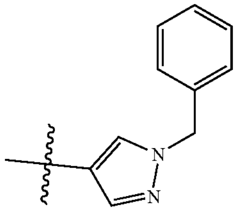 [SMILES: *c1cnn(Cc2ccccc2)c1] | $^1$H NMR (500 MHz, DMSO-$d_6$) δ 10.21 (s, 1H), 7.93 (s, 1H), 7.40-7.31 (m, 3H), 7.28-7.17 (m, 3H), 7.21 (s, 1H), 5.45 (s, 2H). |
| 31 | Cl | 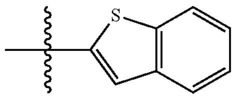 [SMILES: *c1cc2ccccc2s1] | $^1$H NMR (500 MHz, DMSO-$d_6$) δ 10.88 (s, 1H), 8.04-8.01 (m, 1H), 7.98-7.90 (m, 2H), 7.48-7.35 (m, 1H), 7.45 (s, 1H), 7.32-7.22 (m, 1H). |
| 32 | Cl | 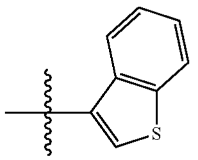 [SMILES: *c1csc2ccccc12] | $^1$H NMR (500 MHz, DMSO-$d_6$) δ 10.43 (s, 1H), 8.22 (s, 1H), 8.10-8.00 (m, 2H), 7.56-7.49 (m, 2H), 7.47 (s, 1H). |
| 33 | Cl | 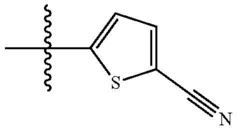 [SMILES: *c1ccc(C#N)s1] | $^1$H NMR (500 MHz, DMSO-$d_6$) δ 10.79 (s, 1H), 7.85 (d, J = 2.5 Hz, 1H), 7.80 (d, J = 2.5 Hz, 1H), 7.37 (s, 1H). |
| 34 | Cl | 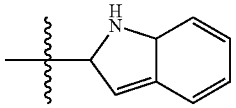 [SMILES: *C1C=C2C=CC=CC2N1] | $^1$H NMR (500 MHz, DMSO-$d_6$) δ 11.34 (s, 1H), 10.26 (s, 1H), 7.54-7.45 (m, 1H), 7.44 (s, 1H), 7.41 (s, 1H), 7.14-7.00 (m, 3H). |

TABLE 1-continued

Structure and $^1$HNMR data of Compound I

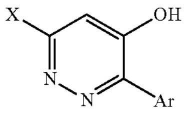

I

| No. | X | Ar | $^1$HNMR |
|---|---|---|---|
| 35 | Cl | 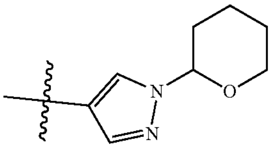 [SMILES: *c1cnn(C2CCCCO2)c1] | $^1$H NMR (500 MHz, DMSO-$d_6$) δ 10.20 (s, 1H), 7.88 (s, 1H), 7.38 (s, 1H), 7.23 (s, 1H), 6.06 (t, J = 7.0 Hz, 1H), 3.93-3.88 (m, 1H), 3.79-3.74 (m, 1H), 2.14-2.07 (m, 1H), 2.07-1.95 (m, 1H), 1.85-1.70 (m, 2H), 1.65-1.54 (m, 2H). |
| 36 | Cl | 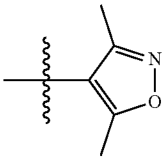 [SMILES: *c1c(C)noc1C] | $^1$H NMR (500 MHz, DMSO-$d_6$) δ 10.05 (s, 1H), 7.39 (s, 1H), 2.72 (s, 3H), 2.60 (s, 3H). |
| 37 | Br | 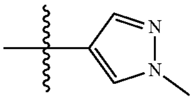 [SMILES: *c1cnn(C)c1] | $^1$H NMR (500 MHz, DMSO-$d_6$) δ 10.21 (s, 1H), 7.87 (s, 1H), 7.54 (s, 1H), 7.04 (s, 1H), 3.91 (s, 3H). |
| 38 | CN | 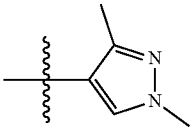 [SMILES: *c1cn(C)nc1C] | $^1$H NMR (500 MHz, DMSO-$d_6$) δ 10.18 (s, 1H), 7.85 (s, 1H), 6.87 (s, 1H), 3.92 (s, 3H), 2.39 (s, 3H). |
| 39 | Me | 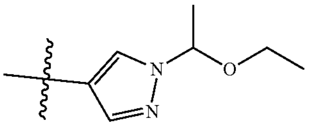 [SMILES: *c1cnn(C(C)OCC)c1] | $^1$H NMR (500 MHz, DMSO-$d_6$) δ 10.20 (s, 1H), 7.88 (s, 1H), 7.10 (s, 1H), 6.68 (s, 1H), 6.02 (q, J = 6.9 Hz, 1H), 3.66 (q, J = 8.0 Hz, 2H), 2.22 (s, 3H), 1.36 (d, J = 6.7 Hz, 3H), 1.08 (t, J = 8.0 Hz, 3H). |
| 40 | OMe | 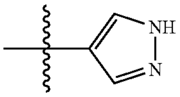 [SMILES: *c1cn[nH]c1] | $^1$H NMR (500 MHz, DMSO-$d_6$) δ 10.07 (s, 1H), 7.39 (s, 1H), 6.87 (s, 1H), 6.57 (s, 1H), 3.84 (s, 3H). |
| 41 | Et | 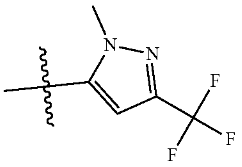 [SMILES: *c1cc(C(F)(F)F)nn1C] | $^1$H NMR (500 MHz, DMSO-$d_6$) δ 10.19 (s, 1H), 7.23 (s, 1H), 6.74 (s, 1H), 3.90 (s, 3H), 2.60 (q, J = 8.0 Hz, 2H), 1.15 (t, J = 7.9 Hz, 3H). |
| 42 | F | 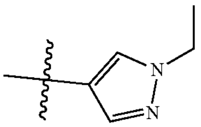 [SMILES: *c1cnn(CC)c1] | $^1$H NMR (500 MHz, DMSO-$d_6$) δ 10.06 (s, 1H), 7.81 (s, 1H), 7.16 (s, 1H), 6.98 (s, 1H), 4.29 (q, J = 8.0 Hz, 2H), 1.15 (t, J = 7.9 Hz, 3H). |
| 43 | Cl | 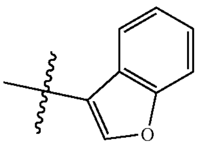 [SMILES: *c1coc2ccccc12] | $^1$H NMR (500 MHz, DMSO-$d_6$) δ 10.29 (s, 1H), 8.01 (s, 1H), 7.90-7.81 (m, 1H), 7.68-7.49 (m, 1H), 7.48 (s, 1H), 7.37-7.21 (m, 2H). |

TABLE 1-continued

Structure and $^1$HNMR data of Compound I

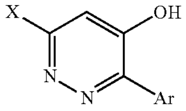

I

| No. | X | Ar | $^1$HNMR |
|---|---|---|---|
| 44 | Cl | 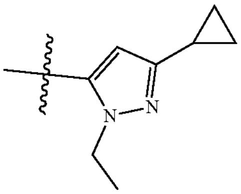 [SMILES: *c1cc(C2CC2)nn1CC] | $^1$H NMR (500 MHz, DMSO-$d_6$) δ 10.08 (s, 1H), 7.41 (s, 1H), 6.64 (s, 1H), 4.08 (q, J = 8.0 Hz, 2H), 1.90-1.84 (m, 1H), 1.15 (t, J = 7.9 Hz, 3H), 0.90-0.85 (m, 2H), 0.71-0.66 (m, 2H). |
| 45 | $CF_2CF_3$ | 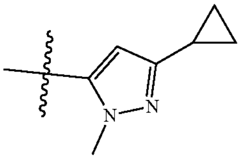 [SMILES: *c1cc(C2CC2)nn1C] | $^1$H NMR (500 MHz, DMSO-$d_6$) δ 10.08 (s, 1H), 6.63 (s, 1H), 6.37 (s, 1H), 3.76 (s, 3H), 1.90-1.84 (m, 1H), 0.90-0.85 (m, 2H), 0.71-0.66 (m, 2H). |
| 46 | $CHF_2$ | 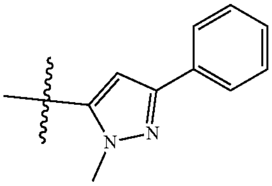 [SMILES: *c1cc(-c2ccccc2)nn1C] | $^1$H NMR (500 MHz, DMSO-$d_6$) δ 10.28 (s, 1H), 7.92-7.85 (m, 2H), 7.51-7.41 (m, 4H), 7.01 (s, 1H), 6.95 (s, 1H), 3.95 (s, 3H). |
| 47 | $CH_2F$ | 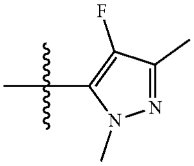 [SMILES: *c1c(F)c(C)nn1C] | $^1$H NMR (500 MHz, DMSO-$d_6$) δ 10.08 (s, 1H), 6.37 (s, 1H), 5.40 (d, J = 5.0 Hz, 2H), 3.76 (s, 3H), 2.70 (s, 3H). |
| 48 | Cl | 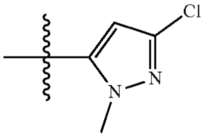 [SMILES: *c1cc(Cl)nn1C] | $^1$H NMR (500 MHz, DMSO-$d_6$) δ 10.16 (s, 1H), 7.38 (s, 1H), 6.86 (s, 1H), 3.90 (s, 3H). |
| 49 | OEt | 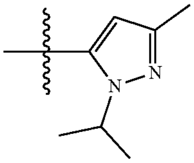 [SMILES: *c1cc(C)nn1C(C)C] | $^1$H NMR (500 MHz, DMSO-$d_6$) δ 10.31 (s, 1H), 6.82 (s, 1H), 6.57 (s, 1H), 4.61-4.56 (m, 1H), 4.39 (q, J = 6.0 Hz, 2H), 2.39 (s, 3H), 1.36 (t, J = 5.8 Hz, 3H), 1.26 (d, J = 7.0 Hz, 6H). |
| 50 | $OCF_3$ | 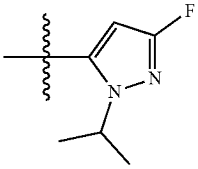 [SMILES: *c1cc(F)nn1C(C)C] | $^1$H NMR (500 MHz, DMSO-$d_6$) δ 10.08 (s, 1H), 6.84 (s, 1H), 6.20 (d, J = 8.0 Hz, 1H), 4.50-4.44 (m, 1H), 1.40 (d, J = 7.0 Hz, 6H). |

TABLE 1-continued

Structure and $^{1}$HNMR data of Compound I

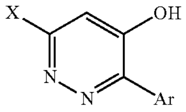

I

| No. | X | Ar | $^{1}$HNMR |
|---|---|---|---|
| 51 | $OCF_2CF_3$ | 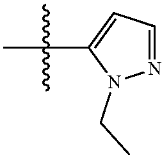 [SMILES: *c1ccnn1CC] | $^{1}$H NMR (500 MHz, DMSO-$d_6$) δ 10.21 (s, 1H), 7.60 (d, J = 2.5 Hz, 1H), 6.94 (s, 1H), 6.62 (d, J = 2.5 Hz, 1H), 4.08 (q, J = 8.0 Hz, 2H), 1.30 (t, J = 8.0 Hz, 3H). |
| 52 | Cl | 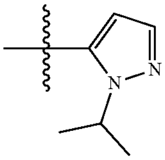 [SMILES: *c1ccnn1C(C)C] | $^{1}$H NMR (500 MHz, DMSO-$d_6$) δ 10.33 (s, 1H), 7.60 (d, J = 2.5 Hz, 1H), 7.35 (s, 1H), 6.62 (d, J = 2.5 Hz, 1H), 4.59-4.53 (m, 1H), 1.26 (d, J = 6.7 Hz, 6H). |
| 53 | Cl | 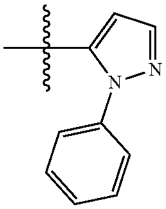 [SMILES: *c1ccnn1-c1ccccc1] | $^{1}$H NMR (500 MHz, DMSO-$d_6$) δ 10.31 (s, 1H), 7.95 (d, J = 2.5 Hz, 1H), 7.66-7.54 (m, 4H), 7.56-7.48 (m, 1H), 7.43 (s, 1H), 6.77 (d, J = 2.5 Hz, 1H). |
| 54 | Cl | 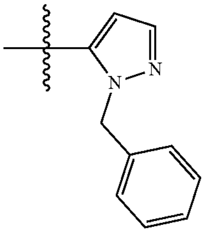 [SMILES: *c1ccnn1Cc1ccccc1] | $^{1}$H NMR (500 MHz, DMSO-$d_6$) δ 10.09 (s, 1H), 7.64 (d, J = 2.5 Hz, 1H), 7.39-7.31 (m, 3H), 7.32-7.24 (m, 1H), 7.22-7.16 (m, 2H), 6.61 (d, J = 2.5 Hz, 1H), 5.46 (s, 2H). |
| 55 | Cl | 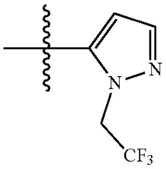 | $^{1}$H NMR (500 MHz, DMSO-$d_6$) δ 10.13 (s, 1H), 7.63 (d, J = 2.5 Hz, 1H), 7.38 (s, 1H), 6.66 (d, J = 2.5 Hz, 1H), 5.32 (q, J = 8.9 Hz, 2H). |
| 56 | Cl | 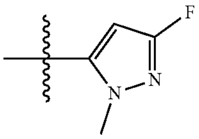 [SMILES: *c1cc(F)nn1C] | $^{1}$H NMR (500 MHz, DMSO-$d_6$) δ 10.08 (s, 1H), 7.41 (s, 1H), 6.20 (d, J = 8.0 Hz, 1H), 3.76 (s, 3H). |
| 57 | Cl | 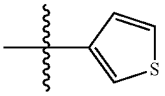 [SMILES: *c1ccsc1] | |
| 58 | Cl | 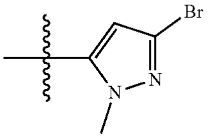 | $^{1}$H NMR (500 MHz, DMSO-$d_6$) δ 10.16 (s, 1H), 7.37 (s, 1H), 6.99 (s, 1H), 3.89 (s, 3H). |

TABLE 1-continued

Structure and $^{1}$HNMR data of Compound I

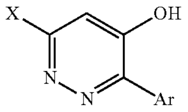

I

| No. | X | Ar | $^{1}$HNMR |
| --- | --- | --- | --- |
| 59 | Cl | 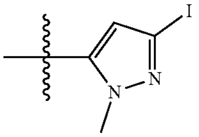 [SMILES: *c1cc(I)nn1C] | $^{1}$H NMR (500 MHz, DMSO-$d_6$) δ 10.08 (s, 1H), 7.41 (s, 1H), 6.20 (s, 1H), 3.76 (s, 3H). |
| 60 | Cl | 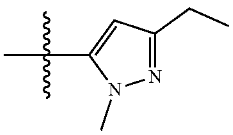 [SMILES: *c1cc(CC)nn1C] | $^{1}$H NMR (500 MHz, DMSO-$d_6$) δ 10.22 (s, 1H), 7.37 (s, 1H), 6.59 (s, 1H), 3.88 (s, 3H), 2.60 (q, J = 8.0 Hz, 2H), 1.19 (t, J = 8.0 Hz, 3H). |
| 61 | Cl | 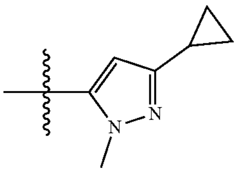 [SMILES: *c1cc(C2CC2)nn1C] | $^{1}$H NMR (500 MHz, DMSO-$d_6$) δ 10.08 (s, 1H), 7.41 (s, 1H), 6.63 (s, 1H), 3.76 (s, 3H), 1.90-1.84 (m, 1H), 0.90-0.85 (m, 2H), 0.71-0.66 (m, 2H). |
| 62 | Cl | 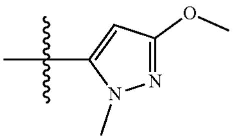 [SMILES: *c1cc(OC)nn1C] | $^{1}$H NMR (500 MHz, DMSO-$d_6$) δ 10.22 (s, 1H), 7.37 (s, 1H), 5.84 (s, 1H), 3.89 (s, 3H), 3.84 (s, 3H). |
| 63 | Cl | 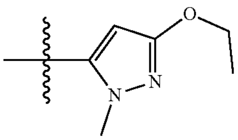 [SMILES: *c1cc(OCC)nn1C] | $^{1}$H NMR (500 MHz, DMSO-$d_6$) δ 10.22 (s, 1H), 7.37 (s, 1H), 5.84 (s, 1H), 3.89 (s, 3H), 3.84 (s, 3H). |
| 64 | Cl | 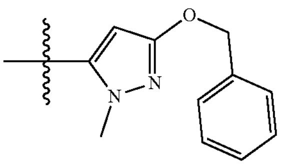 [SMILES: *c1cc(OCc2ccccc2)nn1C] | $^{1}$H NMR (500 MHz, DMSO-$d_6$) δ 10.16 (s, 1H), 7.46 (s, 1H), 7.43-7.27 (m, 5H), 5.87 (s, 1H), 5.35 (s, 2H), 3.90 (s, 3H). |
| 65 | Cl | 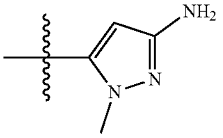 | $^{1}$H NMR (500 MHz, DMSO-$d_6$) δ 10.20 (s, 1H), 8.01 (s, 2H), 7.37 (s, 1H), 5.56 (s, 1H), 3.88 (s, 3H). |
| 66 | Cl | 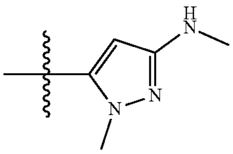 [SMILES: *c1cc(NC)nn1C] | $^{1}$H NMR (500 MHz, DMSO-$d_6$) δ 10.81 (s, 1H), 8.17 (s, 1H), 7.37 (s, 1H), 5.56 (s, 1H), 3.88 (s, 3H), 3.01 (s, 3H). |

TABLE 1-continued

Structure and $^{1}$HNMR data of Compound I

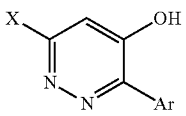

I

| No. | X | Ar | $^{1}$HNMR |
|---|---|---|---|
| 67 | Cl | 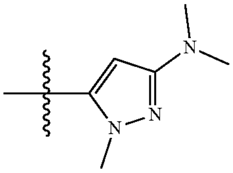 [SMILES: *c1cc(N(C)C)nn1C] | $^{1}$H NMR (500 MHz, DMSO-$d_6$) δ 10.60 (s, 1H), 7.15 (s, 1H), 5.56 (s, 1H), 3.88 (s, 3H), 3.19 (s, 6H). |
| 68 | Cl | 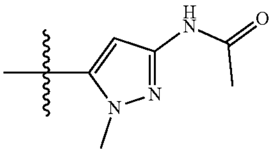 [SMILES: *c1cc(NC(C)=O)nn1C] | $^{1}$H NMR (500 MHz, DMSO-$d_6$) δ 10.82 (s, 1H), 10.38 (s, 1H), 7.36 (s, 1H), 5.56 (s, 1H), 3.92 (s, 3H), 2.13 (s, 3H). |
| 69 | Cl | 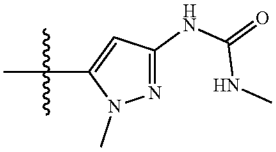 [SMILES: *c1cc(NC(=O)NC)nn1C] | $^{1}$H NMR (500 MHz, DMSO-$d_6$) δ 10.76 (s, 1H), 9.56 (s, 1H), 7.87 (s, 1H), 7.14 (s, 1H), 5.76 (s, 1H), 3.94 (s, 3H), 2.71 (s, 3H). |
| 70 | Cl | 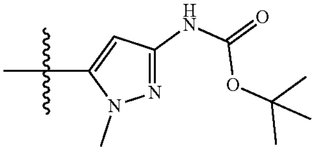 [SMILES: *c1cc(NC(=O)OC(C)(C)C)nn1C] | $^{1}$H NMR (500 MHz, DMSO-$d_6$) δ 10.79 (s, 1H), 10.01 (s, 1H), 7.40 (s, 1H), 5.56 (s, 1H), 3.94 (s, 3H), 1.29 (s, 9H). |
| 71 | Cl | 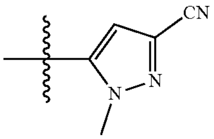 [SMILES: *c1cc(C#N)nn1C] | $^{1}$H NMR (500 MHz, DMSO-$d_6$) δ 10.62 (s, 1H), 7.38 (s, 1H), 7.01 (s, 1H), 3.92 (s, 3H). |
| 72 | Cl | 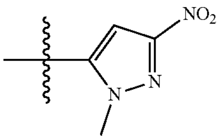 [SMILES: *c1cc([N+](=O)[O-])nn1C] | $^{1}$H NMR (500 MHz, DMSO-$d_6$) δ 10.54 (s, 1H), 7.55 (s, 1H), 7.38 (s, 1H), 3.92 (s, 3H). |
| 73 | Cl | 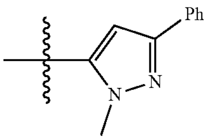 [SMILES: *c1cc(-c2ccccc2)nn1C] | $^{1}$H NMR (500 MHz, Chloroform-d) δ 7.90-7.82 (m, 2H), 7.42-7.28 (m, 3H), 7.34 (s, 1H), 7.29 (s, 1H), 5.85 (s, 1H), 4.07 (s, 3H). |
| 74 | Cl | 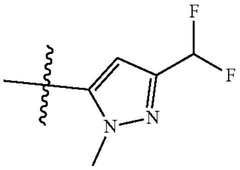 [SMILES: *c1cc(C(F)F)nn1C] | $^{1}$H NMR (500 MHz, DMSO-$d_6$) δ 10.62 (s, 1H), 7.37 (s, 1H), 6.93 (t, J = 57.5 Hz, 1H), 6.83 (s, 1H), 3.89 (s, 3H). |

TABLE 1-continued
Structure and $^{1}$HNMR data of Compound I
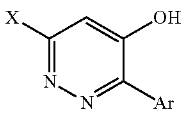
I
| No. | X | Ar | $^{1}$HNMR |
|---|---|---|---|
| 75 | Cl | 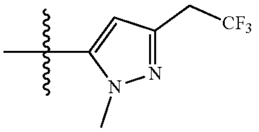 [SMILES: *c1cc(CC(F)(F)F)nn1C] | $^{1}$H NMR (500 MHz, DMSO-$d_6$) δ 10.50 (s, 1H), 7.38 (s, 1H), 6.69 (s, 1H), 3.89 (s, 3H), 3.07 (q, J = 8.9 Hz, 2H). |
| 76 | Cl | 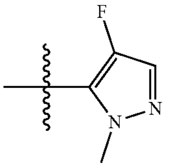 | $^{1}$H NMR (500 MHz, DMSO-$d_6$) δ 10.58 (s, 1H), 7.50 (d, J = 5.5 Hz, 1H), 7.41 (s, 1H), 3.76 (s, 3H). |
| 77 | Cl | 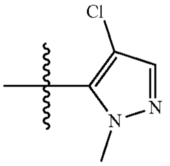 | $^{1}$H NMR (500 MHz, DMSO-$d_6$) δ 10.55 (s, 1H), 7.86 (s, 1H), 7.36 (s, 1H), 3.88 (s, 3H). |
| 78 | Cl | 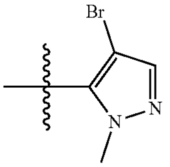 | $^{1}$H NMR (500 MHz, DMSO-$d_6$) δ 10.39 (s, 1H), 8.11 (s, 1H), 7.37 (s, 1H), 3.86 (s, 3H). |
| 79 | Cl | 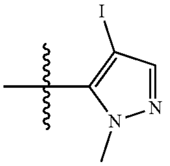 [SMILES: *c1c(I)cnn1C] | $^{1}$H NMR (500 MHz, DMSO-$d_6$) δ 10.48 (s, 1H), 7.60 (s, 1H), 6.37 (s, 1H), 3.76 (s, 3H). |
| 80 | Cl | 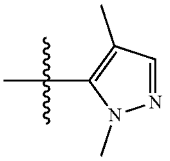 [SMILES: *c1c(C)cnn1C] | $^{1}$H NMR (500 MHz, DMSO-$d_6$) δ 10.37 (s, 1H), 7.56 (s, 1H), 7.35 (s, 1H), 3.85 (s, 3H), 2.07 (s, 3H). |
| 81 | Cl | 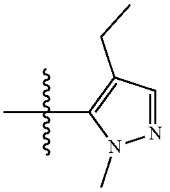 [SMILES: *c1c(CC)cnn1C] | $^{1}$H NMR (500 MHz, DMSO-$d_6$) δ 10.37 (s, 1H), 7.67 (s, 1H), 7.35 (s, 1H), 3.84 (s, 3H), 2.70 (q, J = 8.0 Hz, 2H), 1.19 (t, J = 8.0 Hz, 3H). |

TABLE 1-continued
Structure and $^1$HNMR data of Compound I
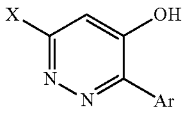
I
| No. | X | Ar | $^1$HNMR |
|---|---|---|---|
| 82 | Cl | 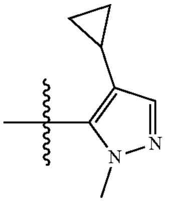 [SMILES: *c1c(C2CC2)cnn1C] | $^1$H NMR (500 MHz, DMSO-$d_6$) δ 10.38 (s, 1H), 7.76 (s, 1H), 7.41 (s, 1H), 3.76 (s, 3H), 2.41-2.36 (m, 1H), 1.12-1.02 (m, 2H), 0.82-0.72 (m, 2H). |
| 83 | Cl | 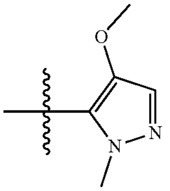 [SMILES: *c1c(OC)cnn1C] | $^1$H NMR (500 MHz, DMSO-$d_6$) δ 11.73 (s, 1H), 7.37 (s, 1H), 7.18 (s, 1H), 3.90 (s, 3H), 3.80 (s, 3H). |
| 84 | Cl | 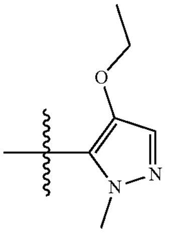 [SMILES: *c1c(OCC)cnn1C] | $^1$H NMR (500 MHz, DMSO-$d_6$) δ 11.81 (s, 1H), 7.37 (s, 1H), 7.18 (s, 1H), 4.10 (q, J = 8.0 Hz, 2H), 3.90 (s, 3H), 1.34 (t, J = 8.0 Hz, 3H). |
| 85 | Cl | 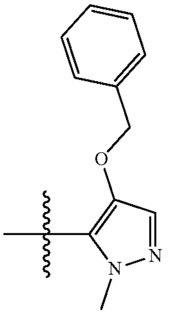 [SMILES: *c1c(OCc2ccccc2)cnn1C] | $^1$H NMR (500 MHz, DMSO-$d_6$) δ 11.73 (s, 1H), 7.68-7.16 (m, 7H), 5.15 (s, 2H), 3.91 (s, 3H). |
| 86 | Cl | 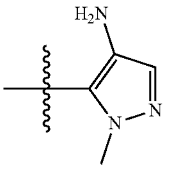 [SMILES: *c1c(N)cnn1C] | $^1$H NMR (500 MHz, DMSO-$d_6$) δ 10.99 (s, 1H), 7.69 (s, 1H), 7.33 (s, 1H), 5.83 (s, 2H), 3.89 (s, 3H). |
| 87 | $CF_2CF_3$ | 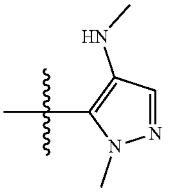 [SMILES: *c1c(NC)cnn1C] | $^1$H NMR (500 MHz, DMSO-$d_6$) δ 11.12 (s, 1H), 7.67 (s, 1H), 6.82 (s, 1H), 5.95 (s, 1H), 3.88 (s, 3H), 2.74 (s, 3H). |

TABLE 1-continued
Structure and $^1$HNMR data of Compound I
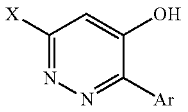
I
| No. | X | Ar | $^1$HNMR |
|---|---|---|---|
| 88 | I | 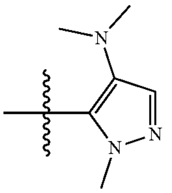 [SMILES: *c1c(N(C)C)cnn1C] | $^1$H NMR (500 MHz, DMSO-$d_6$) δ 11.28 (s, 1H), 7.69 (s, 1H), 6.29 (s, 1H), 3.87 (s, 3H), 2.85 (s, 6H). |
| 89 | Cl | 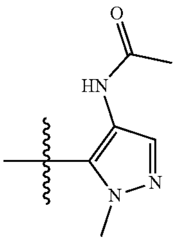 [SMILES: *c1c(NC(C)=O)cnn1C] | $^1$H NMR (500 MHz, DMSO-$d_6$) δ 10.04 (s, 1H), 9.94 (s, 1H), 7.87 (s, 1H), 7.44 (s, 1H), 3.90 (s, 3H), 2.07 (s, 3H). |
| 90 | Cl | 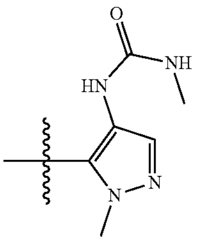 [SMILES: *c1c(NC(=O)NC)cnn1C] | $^1$H NMR (500 MHz, DMSO-$d_6$) δ 10.10 (s, 1H), 8.60 (s, 1H), 7.87 (s, 1H), 7.44 (s, 1H), 6.16 (s, 1H), 3.91 (s, 3H), 2.68 (s, 3H). |
| 91 | Cl | 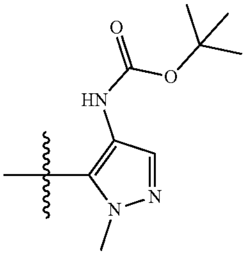 [SMILES: *c1c(NC(=O)OC(C)(C)C)cnn1C] | $^1$H NMR (500 MHz, DMSO-$d_6$) δ 10.04 (s, 1H), 9.78 (s, 1H), 7.87 (s, 1H), 7.42 (s, 1H), 3.92 (s, 3H), 1.49 (s, 9H). |
| 92 | Cl | 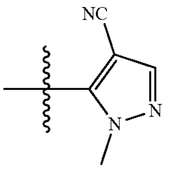 [SMILES: *c1c(C#N)cnn1C] | $^1$H NMR (500 MHz, DMSO-$d_6$) δ 10.15 (s, 1H), 7.93 (s, 1H), 7.37 (s, 1H), 3.89 (s, 3H). |
| 93 | Cl | 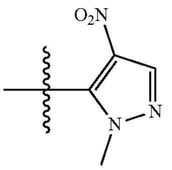 [SMILES: *c1c([N+](=O)[O-])cnn1C] | $^1$H NMR (500 MHz, DMSO-$d_6$) δ 10.27 (s, 1H), 8.22 (s, 1H), 7.60 (s, 1H), 3.86 (s, 3H). |

TABLE 1-continued
Structure and $^1$HNMR data of Compound I
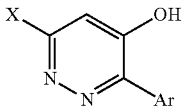
I
| No. | X | Ar | $^1$HNMR |
|---|---|---|---|
| 94 | Cl | 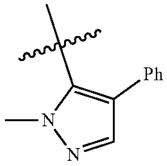 [SMILES: *c1c(-c2ccccc2)cnn1C] | |
| 95 | Br | 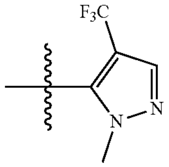 [SMILES: *c1c(C(F)(F)F)cnn1C] | $^1$H NMR (500 MHz, DMSO-$d_6$) δ 10.55 (s, 1H), 7.71 (s, 1H), 7.58 (s, 1H), 3.85 (s, 3H). |
| 96 | Cl | 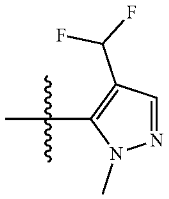 [SMILES: *c1c(C(F)F)cnn1C] | $^1$H NMR (500 MHz, DMSO-$d_6$) δ 10.48 (s, 1H), 7.88 (s, 1H), 7.36 (s, 1H), 6.69 (q, J = 57.5 Hz, 1H), 3.85 (s, 3H). |
| 97 | Cl | 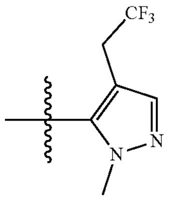 | $^1$H NMR (500 MHz, DMSO-$d_6$) δ 10.25 (s, 1H), 7.76 (s, 1H), 7.39 (s, 1H), 3.85 (s, 3H), 3.07 (q, J = 8.9 Hz, 2H). |
| 98 | Cl | 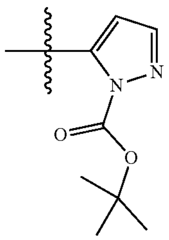 [SMILES: *c1ccnn1C(=O)OC(C)(C)C] | $^1$H NMR (500 MHz, DMSO-$d_6$) δ 9.49 (s, 1H), 8.11 (d, J = 2.5 Hz, 1H), 7.65 (s, 1H), 7.02 (d, J = 2.5 Hz, 1H), 1.61 (s, 9H). |
| 99 | Cl | 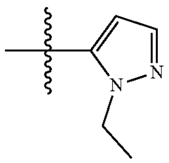 [SMILES: *c1ccnn1CC] | $^1$H NMR (500 MHz, DMSO-$d_6$) δ 10.28 (s, 1H), 7.60 (d, J = 2.5 Hz, 1H), 7.36 (s, 1H), 6.63 (d, J = 2.5 Hz, 1H), 4.08 (q, J = 8.0 Hz, 2H), 1.30 (t, J = 8.0 Hz, 3H). |
| 100 | Cl | 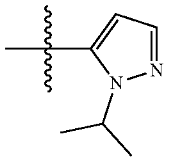 [SMILES: *c1ccnn1C(C)C] | $^1$H NMR (500 MHz, DMSO-$d_6$) δ 10.33 (s, 1H), 7.60 (d, J = 2.5 Hz, 1H), 7.35 (s, 1H), 6.62 (d, J = 2.5 Hz, 1H), 4.56 (m, 1H), 1.26 (d, J = 6.7 Hz, 6H). |

TABLE 1-continued

Structure and ¹HNMR data of Compound I

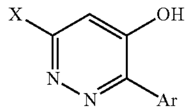

I

| No. | X | Ar | ¹HNMR |
|---|---|---|---|
| 101 | Cl | 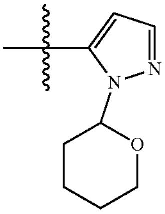 [SMILES: *c1ccnn1C1CCCCO1] | ¹H NMR (500 MHz, DMSO-$d_6$) δ 10.76 (s, 1H), 7.60 (d, J = 2.2 Hz, 1H), 7.49 (s, 1H), 6.58 (d, J = 2.5 Hz, 1H), 6.10-6.07 (m, 1H), 3.93-3.88 (m, 1H), 3.79-3.74 (m, 1H), 2.47-2.37 (m, 1H), 2.07-1.96 (m, 2H), 1.79-1.68 (m, 1H), 1.63-1.54 (m, 2H). |
| 102 | Cl | 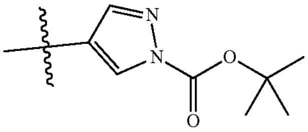 | ¹H NMR (500 MHz, DMSO-$d_6$) δ 10.04 (s, 1H), 8.40 (d, J = 1.3 Hz, 1H), 8.27 (d, J = 1.6 Hz, 1H), 7.42 (s, 1H), 1.61 (s, 9H). |
| 103 | Cl | 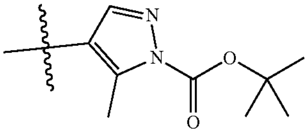 [SMILES: *c1cnn(C(=O)OC(C)(C)C)c1C] | ¹H NMR (500 MHz, DMSO-$d_6$) δ 10.23 (s, 1H), 8.18 (s, 1H), 7.38 (s, 1H), 2.74 (s, 3H), 1.61 (s, 9H). |
| 104 | Cl | 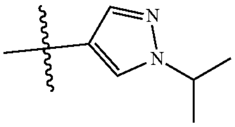 [SMILES: *c1cnn(C(C)C)c1] | ¹H NMR (500 MHz, DMSO-$d_6$) δ 10.01 (s, 1H), 7.78 (s, 1H), 7.40 (s, 1H), 6.93 (s, 1H), 4.57-4.52 (m, 1H), 1.30 (d, J = 6.7 Hz, 6H). |
| 105 | Cl | 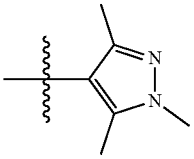 [SMILES: *c1c(C)nn(C)c1C] | ¹H NMR (500 MHz, DMSO-$d_6$) δ 10.31 (s, 1H), 7.35 (s, 1H), 3.82 (s, 3H), 2.52 (s, 3H), 2.39 (s, 3H). |
| 106 | Cl | 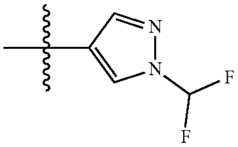 [SMILES: *c1cnn(C(F)F)c1] | ¹H NMR (500 MHz, DMSO-$d_6$) δ 9.95 (s, 4H), 7.94 (s, 1H), 7.79 (t, J = 57.5 Hz, 1H), 7.71 (s, 1H), 7.41 (s, 1H). |
| 107 | Cl | 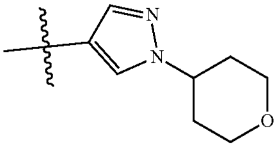 [SMILES: *c1cnn(C2CCOCC2)c1] | ¹H NMR (500 MHz, DMSO-$d_6$) δ 10.11 (s, 1H), 7.81 (s, 1H), 7.45 (s, 1H), 7.04 (s, 1H), 4.30-4.27 (m, 1H), 3.91-3.86 (m, 2H), 3.66-3.61 (m, 2H), 1.97-1.90 (m, 2H), 1.78-1.71 (m, 2H). |
| 108 | Cl | 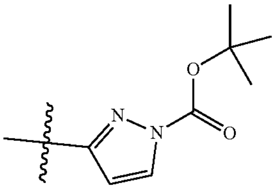 [SMILES: *c1ccn(C(=O)OC(C)(C)C)n1] | ¹H NMR (500 MHz, DMSO-$d_6$) δ 12.60 (s, 1H), 8.22 (d, J = 2.5 Hz, 1H), 7.38 (s, 1H), 7.13 (d, J = 2.5 Hz, 1H), 1.61 (s, 9H). |

TABLE 1-continued

Structure and $^1$HNMR data of Compound I

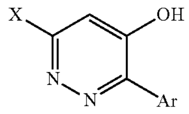

I

| No. | X | Ar | $^1$HNMR |
|---|---|---|---|
| 109 | Cl | 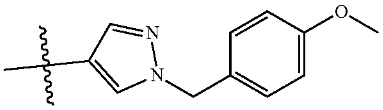 [SMILES: *c1cnn(Cc2ccc(OC)cc2)c1] | $^1$H NMR (500 MHz, DMSO-$d_6$) δ 10.04 (s, 1H), 7.81 (s, 1H), 7.45 (s, 1H), 7.32-7.26 (m, 2H), 7.03 (s, 1H), 6.95-6.89 (m, 2H), 5.45 s, 2H), 3.79 (s, 3H). |
| 110 | Cl | 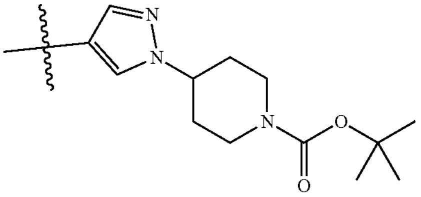 [SMILES: *c1cnn(C2CCN(C(=O)OC(C)(C)C)CC2)c1] | $^1$H NMR (500 MHz, DMSO-$d_6$) δ 10.00 (s, 1H), 7.81 (s, 1H), 7.48 (s, 1H), 7.06 (s, 1H), 4.45-4.32 (m, 1H), 3.00-2.94 (m, 4H), 1.98-1.91 (m, 2H), 1.79-1.72 (m, 2H), 1.42 (s, 9H). |
| 111 | Cl | 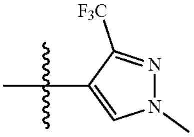 [SMILES: *c1cn(C)nc1C(F)(F)F] | $^1$H NMR (500 MHz, DMSO-$d_6$) δ 10.11 (s, 1H), 7.38 (s, 1H), 6.90 (s, 1H), 3.94 (s, 3H). |
| 112 | Cl | 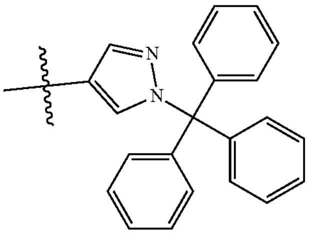 [SMILES: *c1cnn(C(c2ccccc2)(c2ccccc2)c2ccccc2)c1] | $^1$H NMR (500 MHz, DMSO-$d_6$) δ 10.03 (s, 1H), 7.87 (s, 1H), 7.77-7.71 (m, 6H), 7.43-7.31 (m, 10H), 7.24 (s, 1H). |
| 113 | Cl | 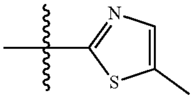 [SMILES: *c1ncc(C)s1] | $^1$H NMR (500 MHz, DMSO-$d_6$) δ 12.65 (s, 1H), 7.69 (s, 1H), 7.34 (s, 1H), 2.42 (s, 3H). |
| 114 | Cl | 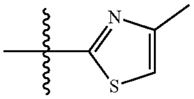 [SMILES: *c1nc(C)cs1] | $^1$H NMR (500 MHz, DMSO-$d_6$) δ 12.74 (s, 1H), 7.34 (s, 1H), 7.12 (s, 1H), 2.48 (s, 3H). |
| 115 | Cl | 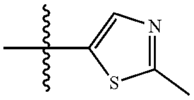 | $^1$H NMR (500 MHz, DMSO-$d_6$) δ 10.81 (s, 1H), 7.98 (s, 1H), 7.36 (s, 1H), 2.34 (s, 3H). |
| 116 | Cl | 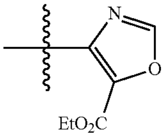 | $^1$H NMR (500 MHz, DMSO-$d_6$) δ 11.93 (s, 1H), 8.34 (s, 1H), 7.37 (s, 1H), 4.35 (q, J = 5.9 Hz, 2H), 1.32 (t, J = 5.8 Hz, 3H). |
| 117 | Cl | 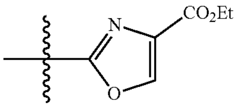 [SMILES: *c1nc(C(=O)OCC)co1] | $^1$H NMR (500 MHz, DMSO-$d_6$) δ 11.76 (s, 1H), 8.28 (s, 1H), 7.35 (s, 1H), 4.27 (q, J = 5.9 Hz, 2H), 1.30 (t, J = 5.9 Hz, 3H). |

TABLE 1-continued
Structure and $^1$HNMR data of Compound I
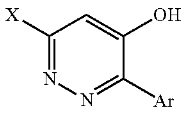
I
| No. | X | Ar | $^1$HNMR |
|---|---|---|---|
| 118 | Cl | 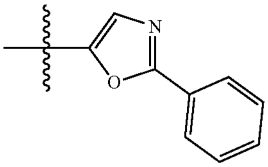 [SMILES: *c1cnc(-c2ccccc2)o1] | $^1$H NMR (500 MHz, DMSO-$d_6$) δ 11.83 (s, 1H), 8.30-8.27 (m, 2H), 7.85 (s, 1H), 7.59-7.55 (m, 3H), 7.44 (s, 1H). |
| 119 | Cl | 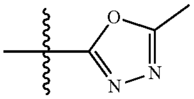 [SMILES: *c1nnc(C)o1] | $^1$H NMR (500 MHz, DMSO-$d_6$) δ 11.27 (s, 1H), 7.31 (s, 1H), 2.63 (s, 3H). |
| 120 | Cl | 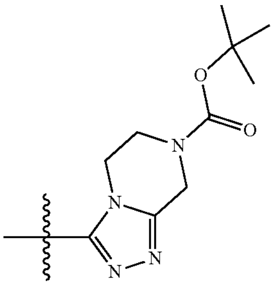 [SMILES: *c1nnc2n1CCN(C(=O)OC(C)(C)C)C2] | $^1$H NMR (500 MHz, DMSO-$d_6$) δ 12.18 (s, 1H), 7.44 (s, 1H), 4.29-4.20 (m, 4H), 3.44-3.31 (m, 2H), 1.42 (s, 9H). |
| 121 | Cl | 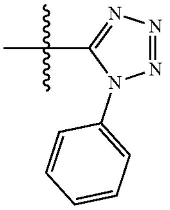 [SMILES: *c1nnnn1-c1ccccc1] | $^1$H NMR (500 MHz, DMSO-$d_6$) δ 10.92 (s, 1H), 7.68-7.61 (m, 2H), 7.60-7.52 (m, 3H), 7.46 (s, 2H). |
| 122 | Cl | 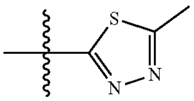 [SMILES: *c1nnc(C)s1] | $^1$H NMR (500 MHz, DMSO-$d_6$) δ 11.72 (s, 1H), 7.31 (s, 1H), 2.48 (s, 3H). |
| 123 | Cl | 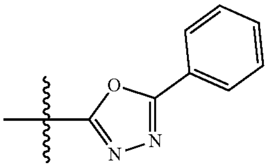 [SMILES: *c1nnc(-c2ccccc2)o1] | $^1$H NMR (500 MHz, DMSO-$d_6$) δ 11.33 (s, 1H), 7.99-7.96 (m, 2H), 7.66-7.54 (m, 3H), 7.40 (s, 1H). |
| 124 | Cl | 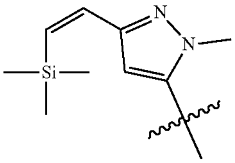 | $^1$H NMR (500 MHz, DMSO-$d_6$) δ 9.80 (s, 1H), 7.43 (s, 1H), 7.05-6.96 (m, 2H), 6.47 (s, 1H), 3.85 (s, 3H), 0.08 (s, 9H). |

TABLE 1-continued
Structure and $^{1}$HNMR data of Compound I
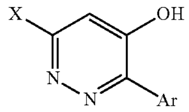
I
| No. | X | Ar | $^{1}$HNMR |
|---|---|---|---|
| 125 | Cl | 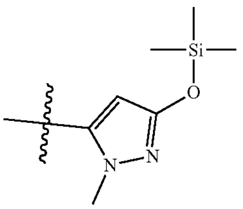 [SMILES: *c1cc(O[Si](C)(C)C)nn1C] | $^{1}$H NMR (500 MHz, DMSO-$d_6$) δ 10.08 (s, 1H), 7.39 (s, 1H), 5.88 (s, 1H), 3.89 (s, 3H), 0.21 (s, 9H). |
| 126 | Cl | 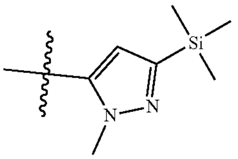 [SMILES: *c1cc([Si](C)(C)C)nn1C] | $^{1}$H NMR (500 MHz, DMSO-$d_6$) δ 10.08 (s, 1H), 7.41 (s, 1H), 6.20 (s, 1H), 3.76 (s, 3H), −0.33 (s, 9H). |
| 127 | Cl | 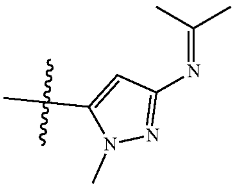 [SMILES: *c1cc(N=C(C)C)nn1C] | $^{1}$H NMR (500 MHz, DMSO-$d_6$) δ 10.23 (s, 1H), 7.37 (s, 1H), 6.82 (s, 1H), 3.89 (s, 3H), 1.97 (s, 6H). |
| 128 | Cl | 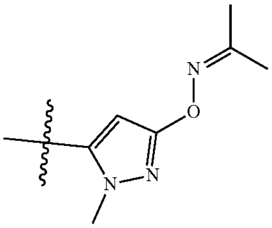 [SMILES: *c1cc(ON=C(C)C)nn1C] | $^{1}$H NMR (500 MHz, DMSO-$d_6$) δ 10.22 (s, 1H), 7.37 (s, 1H), 5.88 (s, 1H), 3.89 (s, 3H), 2.49 (s, 6H). |
| 129 | Cl | 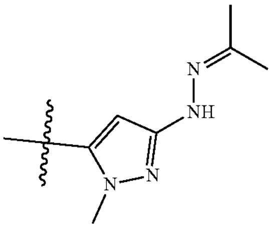 [SMILES: *c1cc(NN=C(C)C)nn1C] | $^{1}$H NMR (500 MHz, DMSO-$d_6$) δ 10.35 (s, 1H), 7.35 (s, 1H), 5.56 (s, 1H), 3.89 (s, 3H), 1.91 (s, 6H). |
| 130 | Cl | 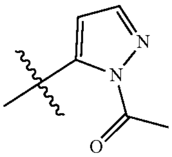 [SMILES: *c1ccnn1C(C)=O] | $^{1}$H NMR (500 MHz, DMSO-$d_6$) δ 10.10 (s, 1H), 7.98 (d, J = 2.5 Hz, 1H), 7.37 (s, 1H), 6.86 (d, J = 2.5 Hz, 1H), 2.11 (s, 3H). |

TABLE 1-continued
Structure and $^{1}$HNMR data of Compound I
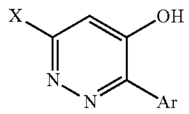
I
| No. | X | Ar | $^{1}$HNMR |
|---|---|---|---|
| 131 | Cl | 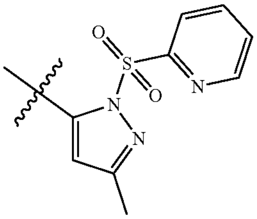 [SMILES: *c1cc(C)nn1S(=O)(=O)c1ccccn1] | $^{1}$H NMR (500 MHz, DMSO-$d_6$) δ 9.57 (s, 1H), 8.79 (dd, J = 5.1, 1.3 Hz, 1H), 7.95-7.82 (m, 3H), 7.50 (s, 1H), 6.64 (s, 1H), 2.39 (s, 3H). |
| 132 | Cl | 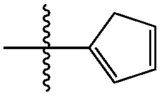 [SMILES: *C1=CC=CC1] | $^{1}$H NMR (500 MHz, DMSO-$d_6$) δ 9.54 (s, 1H), 7.21 (s, 1H), 6.67 (d, J = 6.2 Hz, 1H), 6.28 (dd, J = 10.9, 6.2 Hz, 1H), 6.11-6.02 (m, 1H), 2.90-2.81 (m, 2H). |
| 133 | CN | 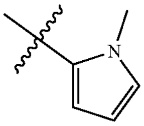 [SMILES: *c1cccn1C] | |
| 134 | $NH_2$ | 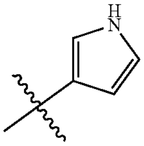 [SMILES: *c1cc[nH]c1] | |
| 135 | Ph | 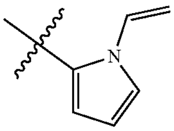 [SMILES: *c1cccn1C=C] | |
| 136 | Br | 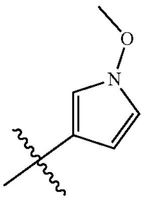 [SMILES: *c1ccn(OC)c1] | |
| 137 | Cl | 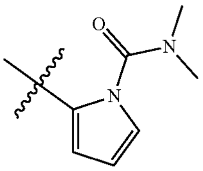 [SMILES: *c1cccn1C(=O)N(C)C] | |

TABLE 1-continued
Structure and $^1$HNMR data of Compound I
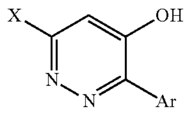
I
| No. | X | Ar | $^1$HNMR |
|---|---|---|---|
| 138 | Cl | 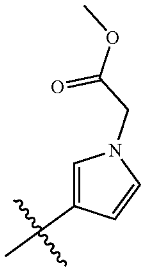 [SMILES: *c1ccn(CC(=O)OC)c1] | |
| 139 | OH | 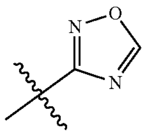 [SMILES: *c1ncon1] | |
| 140 | Cl | 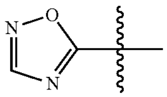 [SMILES: *c1ncno1] | |
| 141 | Cl | 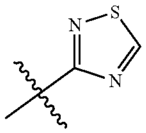 [SMILES: *c1ncsn1] | |
| 142 | Cl | 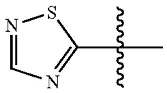 [SMILES: *c1ncns1] | |
| 143 | $CONH_2$ | 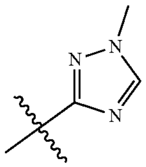 [SMILES: *c1ncn(C)n1] | |
| 144 | Cl | 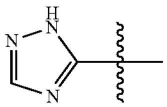 [SMILES: *c1ncn[nH]1] | |
| 145 | Cl | 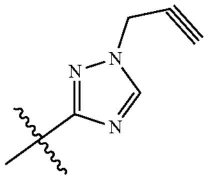 [SMILES: *c1ncn(CC#C)n1] | |

TABLE 1-continued
Structure and $^1$HNMR data of Compound I
I
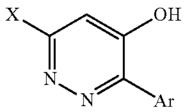
| No. | X | Ar | $^1$HNMR |
|---|---|---|---|
| 146 | Cl | 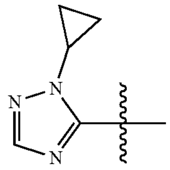 [SMILES: *c1ncnn1C1CC1] | |
| 147 | Cl | 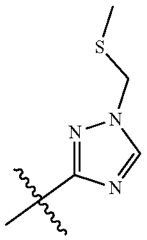 [SMILES: *c1ncn(CSC)n1] | |
| 148 | $CH_2F$ | 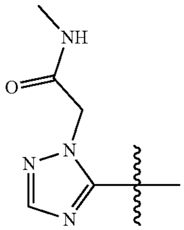 [SMILES: *c1ncnn1CC(=O)NC] | |
| 149 | Cl | 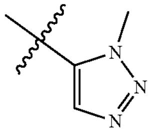 [SMILES: *c1cnnn1C] | |
| 150 | Cl | 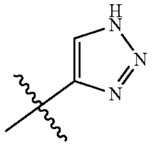 [SMILES: *c1c[nH]nn1] | |
| 151 | Cl | 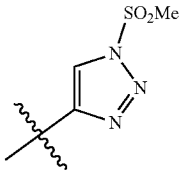 [SMILES: *c1cn(S(C)(=O)=O)nn1] | |
| 152 | Cl | 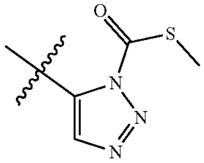 [SMILES: *c1cnnn1C(=O)SC] | |

TABLE 1-continued
Structure and ¹HNMR data of Compound I
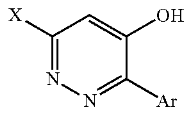
I
| No. | X | Ar | ¹HNMR |
|---|---|---|---|
| 153 | Cl | 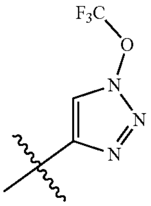 [SMILES: *c1cn(OC(F)(F)F)nn1] | |
| 154 | Cl | 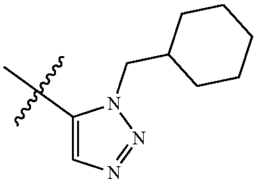 [SMILES: *c1cnnn1CC1CCCCC1] | |
| 155 | Cl | 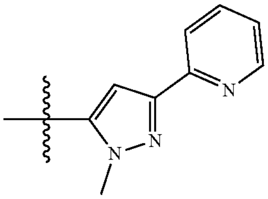 [SMILES: *c1cc(-c2ccccn2)nn1C] | |
| 156 | Cl | 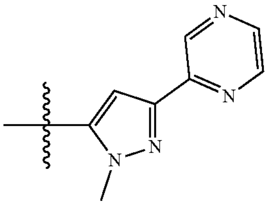 [SMILES: *c1cc(-c2cnccn2)nn1C] | |
| 157 | Cl | 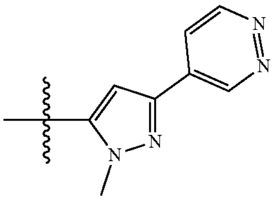 [SMILES: *c1cc(-c2ccnnc2)nn1C] | |
| 158 | Cl | 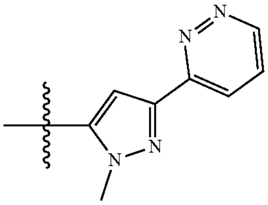 [SMILES: *c1cc(-c2cccnn2)nn1C] | |

TABLE 1-continued
Structure and $^1$HNMR data of Compound I
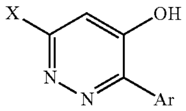
I
| No. | X | Ar | $^1$HNMR |
|---|---|---|---|
| 159 | Cl | 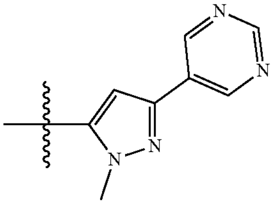 [SMILES: *c1cc(-c2cncnc2)nn1C] | |
| 160 | Cl | 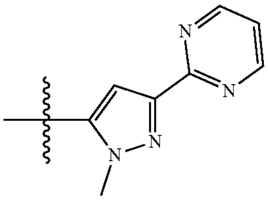 [SMILES: *c1cc(-c2ncccn2)nn1C] | |
| 161 | Cl | 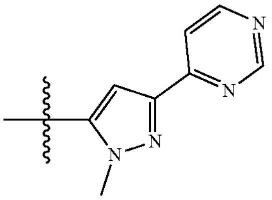 [SMILES: *c1cc(-c2ccncn2)nn1C] | |
| 162 | Cl | 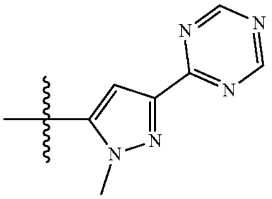 [SMILES: *c1cc(-c2ncncn2)nn1C] | |
| 163 | Cl | 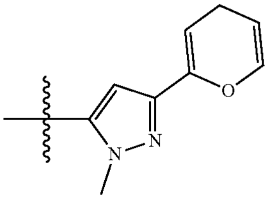 [SMILES: *c1cc(C2=CCC=CO2)nn1C] | |
| 164 | Cl | 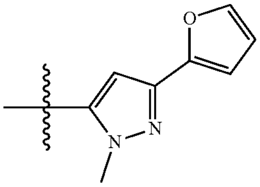 [SMILES: *c1cc(-c2ccco2)nn1C] | |

TABLE 1-continued
Structure and $^1$HNMR data of Compound I
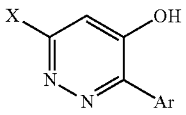
I
| No. | X | Ar | $^1$HNMR |
|---|---|---|---|
| 165 | Cl | 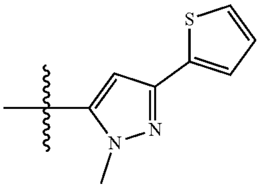 [SMILES: *c1cc(-c2cccs2)nn1C] | |
| 166 | Cl | 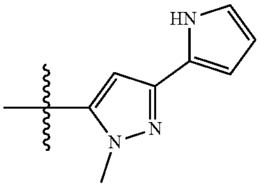 [SMILES: *c1cc(-c2ccc[nH]2)nn1C] | |
| 167 | Cl | 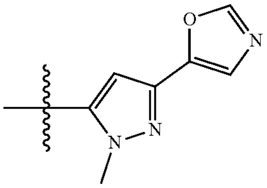 [SMILES: *c1cc(-c2cnco2)nn1C] | |
| 168 | Cl | 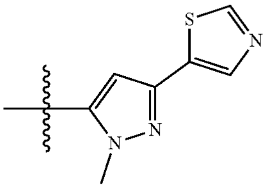 [SMILES: *c1cc(-c2cncs2)nn1C] | |
| 169 | Cl | 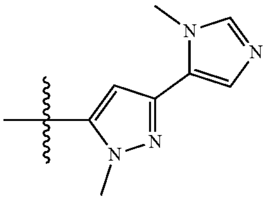 [SMILES: *c1cc(-c2cncn2C)nn1C] | |
| 170 | Cl | 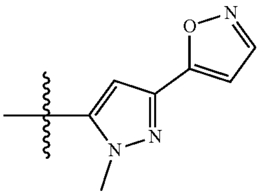 [SMILES: *c1cc(-c2ccno2)nn1C] | |
| 171 | Cl | 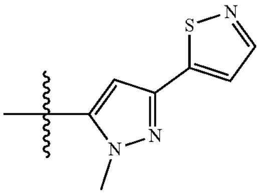 [SMILES: *c1cc(-c2ccns2)nn1C] | |

TABLE 1-continued
Structure and ¹HNMR data of Compound I
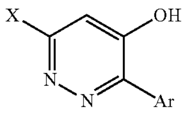
I
| No. | X | Ar | ¹HNMR |
|---|---|---|---|
| 172 | Cl | 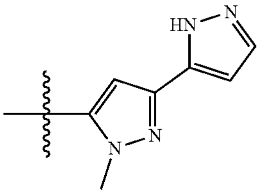 | |
| 173 | Cl | 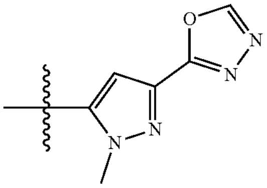 [SMILES: *c1cc(-c2nnco2)nn1C] | |
| 174 | Cl | 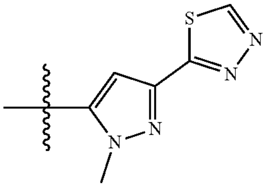 [SMILES: *c1cc(-c2nncs2)nn1C] | |
| 175 | Cl | 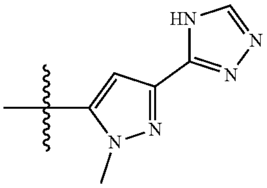 [SMILES: *c1cc(-c2nnc[nH]2)nn1C] | |
| 176 | Cl | 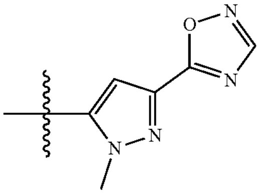 | |
| 177 | Cl | 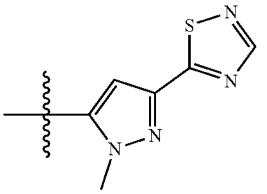 [SMILES: *c1cc(-c2ncns2)nn1C] | |

TABLE 1-continued
Structure and ¹HNMR data of Compound I
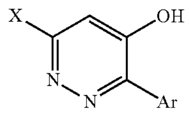
I
| No. | X | Ar | ¹HNMR |
|---|---|---|---|
| 178 | Cl | 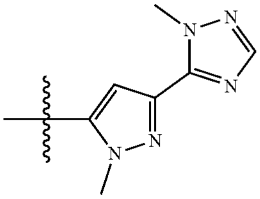 [SMILES: *c1cc(-c2ncnn2C)nn1C] | |
| 179 | Cl | 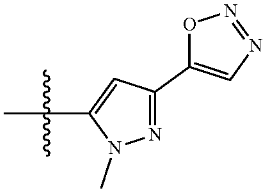 [SMILES: *c1cc(-c2cnno2)nn1C] | |
| 180 | Cl | 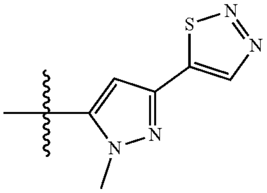 | |
| 181 | Cl | 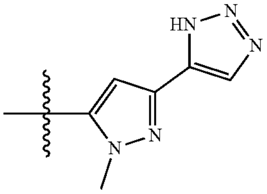 [SMILES: *c1cc(-c2cnn[nH]2)nn1C] | |
| 182 | Cl | 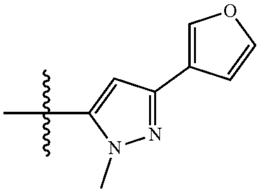 [SMILES: *c1cc(-c2ccoc2)nn1C] | |
| 183 | Cl | 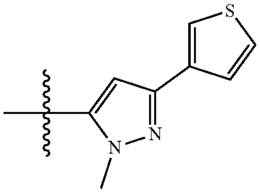 [SMILES: *c1cc(-c2ccsc2)nn1C] | |
| 184 | Cl | 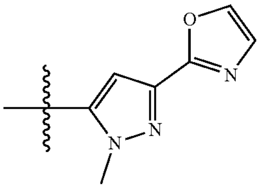 [SMILES: *c1cc(-c2ncco2)nn1C] | |

TABLE 1-continued
Structure and $^1$HNMR data of Compound I
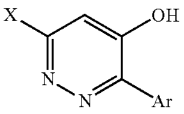
I
| No. | X | Ar | $^1$HNMR |
|---|---|---|---|
| 185 | Cl | 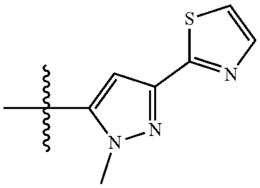 [SMILES: *c1cc(-c2nccs2)nn1C] | |
| 186 | Cl | 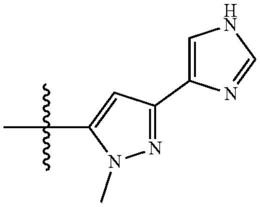 | |
| 187 | Cl | 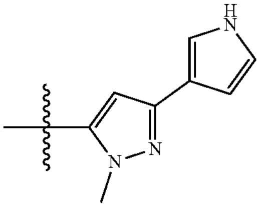 [SMILES: *c1cc(-c2cc[nH]c2)nn1C] | |
| 188 | Cl | 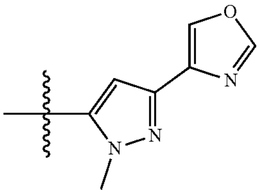 [SMILES: *c1cc(-c2cocn2)nn1C] | |
| 189 | Cl | 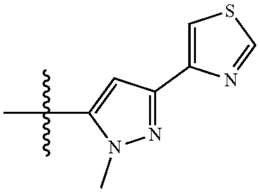 | |
| 190 | Cl | 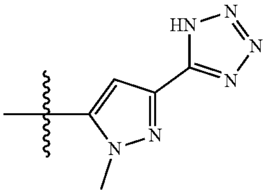 [SMILES: *c1cc(-c2nnn[nH]2)nn1C] | |

TABLE 1-continued
Structure and $^1$HNMR data of Compound I
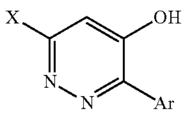
I
| No. | X | Ar | $^1$HNMR |
|---|---|---|---|
| 191 | Cl | 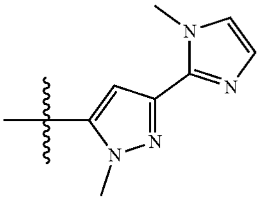 [SMILES: *c1cc(-c2nccn2C)nn1C] | |
| 192 | Cl | 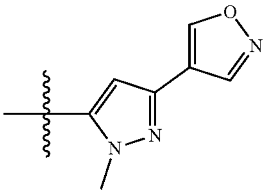 | |
| 193 | Cl | 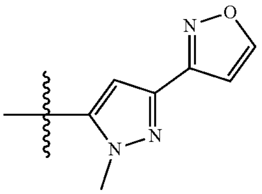 [SMILES: *c1cc(-c2ccon2)nn1C] | |
| 194 | Cl | 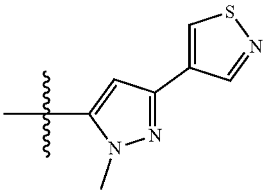 [SMILES: *c1cc(-c2cnsc2)nn1C] | |
| 195 | Cl | 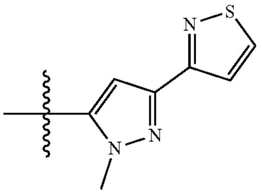 | |
| 196 | Cl | 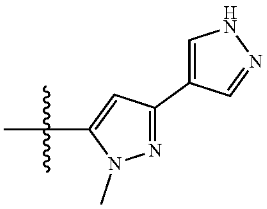 [SMILES: *c1cc(-c2cn[nH]c2)nn1C] | |

TABLE 1-continued
| Structure and $^1$HNMR data of Compound I | | | |
|---|---|---|---|
| 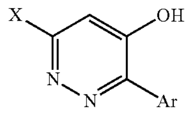 I | | | |
| No. | X | Ar | $^1$HNMR |
| 197 | Cl | 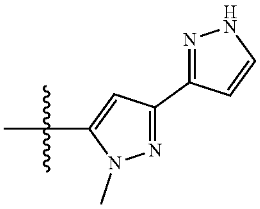 [SMILES: *c1cc(-c2cc[nH]n2)nn1C] | |
| 198 | Cl | 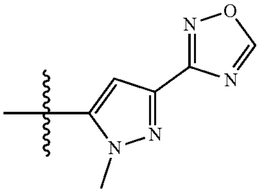 [SMILES: *c1cc(-c2ncon2)nn1C] | |
| 199 | Cl | 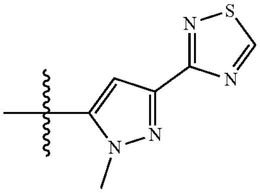 | |
| 200 | Cl | 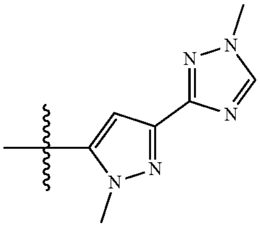 [SMILES: *c1cc(-c2ncn(C)n2)nn1C] | |
| 201 | Cl | 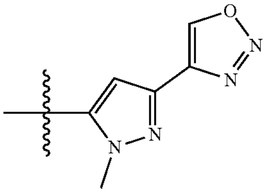 | |
| 202 | Cl | 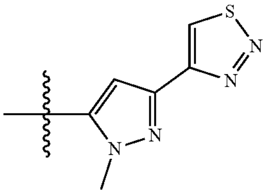 [SMILES: *c1cc(-c2csnn2)nn1C] | |

TABLE 1-continued
Structure and $^1$HNMR data of Compound I
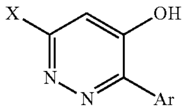
I
| No. | X | Ar | $^1$HNMR |
| --- | --- | --- | --- |
| 203 | Cl | 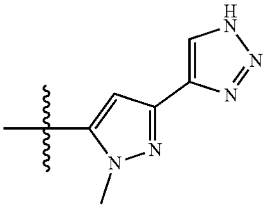 [SMILES: *c1cc(-c2c[nH]nn2)nn1C] | |
| 204 | Cl | 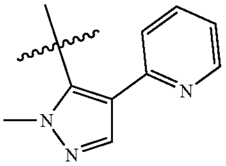 [SMILES: *c1c(-c2ccccn2)cnn1C] | |
| 205 | Cl | 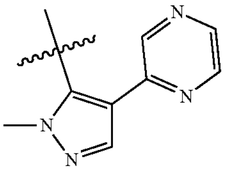 [SMILES: *c1c(-c2cnccn2)cnn1C] | |
| 206 | Cl | 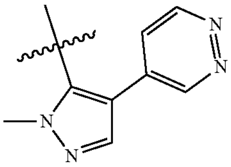 [SMILES: *c1c(-c2ccnnc2)cnn1C] | |
| 207 | Cl | 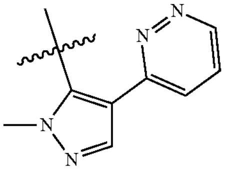 [SMILES: *c1c(-c2cccnn2)cnn1C] | |
| 208 | Cl | 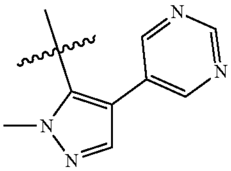 [SMILES: *c1c(-c2cncnc2)cnn1C] | |
| 209 | Cl | 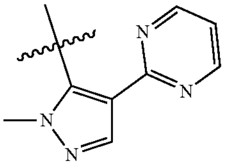 [SMILES: *c1c(-c2ncccn2)cnn1C] | |

TABLE 1-continued
Structure and $^1$HNMR data of Compound I
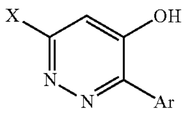
I
| No. | X | Ar | $^1$HNMR |
| --- | --- | --- | --- |
| 210 | Cl | 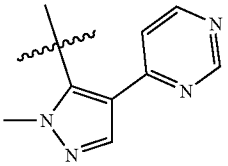 [SMILES: *c1c(-c2ccncn2)cnn1C] | |
| 211 | Cl | 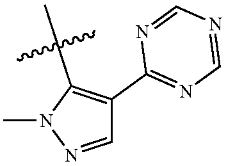 [SMILES: *c1c(-c2ncncn2)cnn1C] | |
| 212 | Cl | 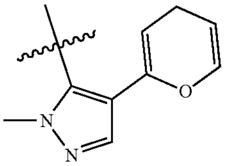 [SMILES: *c1c(C2=CCC=CO2)cnn1C] | |
| 213 | Cl | 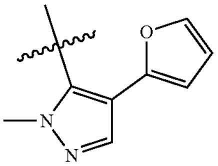 [SMILES: *c1c(-c2ccco2)cnn1C] | |
| 214 | Cl | 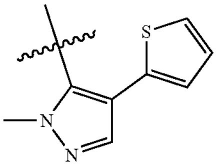 [SMILES: *c1c(-c2cccs2)cnn1C] | |
| 215 | Cl | 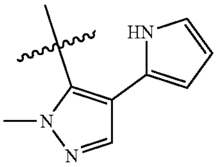 [SMILES: *c1c(-c2ccc[nH]2)cnn1C] | |
| 216 | Cl | 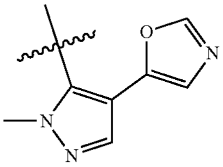 [SMILES: *c1c(-c2cnco2)cnn1C] | |
| 217 | Cl | 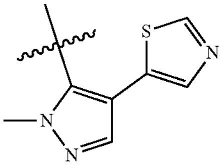 [SMILES: *c1c(-c2cncs2)cnn1C] | |

TABLE 1-continued
| Structure and $^1$HNMR data of Compound I | | | |
|---|---|---|---|
| 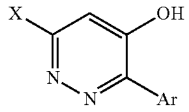 I | | | |
| No. | X | Ar | $^1$HNMR |
| 218 | Cl | 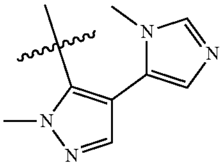 [SMILES: *c1c(-c2cncn2C)cnn1C] | |
| 219 | Cl | 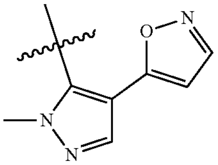 [SMILES: *c1c(-c2ccno2)cnn1C] | |
| 220 | Cl | 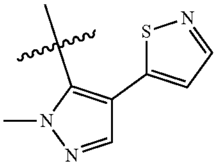 [SMILES: *c1c(-c2ccns2)cnn1C] | |
| 221 | Cl | 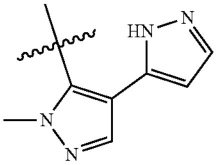 [SMILES: *c1c(-c2ccn[nH]2)cnn1C] | |
| 222 | Cl | 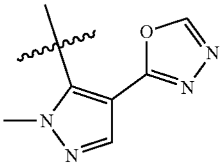 [SMILES: *c1c(-c2nnco2)cnn1C] | |
| 223 | Cl | 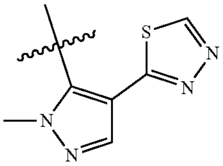 [SMILES: *c1c(-c2nncs2)cnn1C] | |
| 224 | Cl | 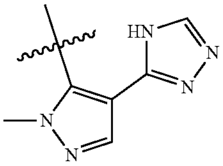 [SMILES: *c1c(-c2nnc[nH]2)cnn1C] | |

TABLE 1-continued
Structure and ¹HNMR data of Compound I
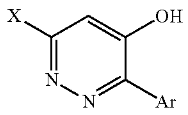
I
| No. | X | Ar | ¹HNMR |
| --- | --- | --- | --- |
| 225 | Cl | 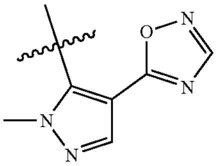 [SMILES: *c1c(-c2ncno2)cnn1C] | |
| 226 | Cl | 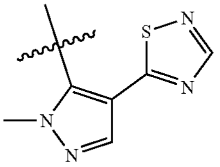 [SMILES: *c1c(-c2ncns2)cnn1C] | |
| 227 | Cl | 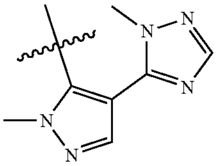 [SMILES: *c1c(-c2ncnn2C)cnn1C] | |
| 228 | Cl | 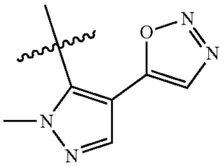 [SMILES: *c1c(-c2cnno2)cnn1C] | |
| 229 | Cl | 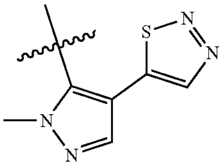 [SMILES: *c1c(-c2cnns2)cnn1C] | |
| 230 | Cl | 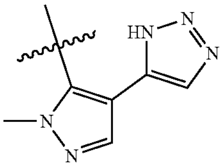 [SMILES: *c1c(-c2cnn[nH]2)cnn1C] | |
| 231 | Cl | 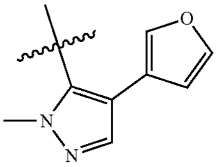 [SMILES: *c1c(-c2ccoc2)cnn1C] | |
| 232 | Cl | 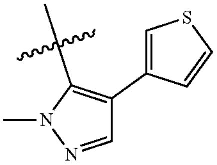 [SMILES: *c1c(-c2ccsc2)cnn1C] | |

TABLE 1-continued
Structure and $^1$HNMR data of Compound I
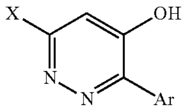
I
| No. | X | Ar | $^1$HNMR |
|---|---|---|---|
| 233 | Cl | 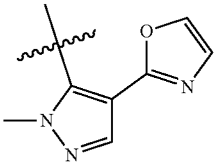 [SMILES: *c1c(-c2ncco2)cnn1C] | |
| 234 | Cl | 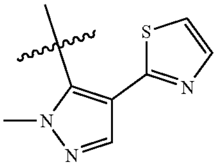 [SMILES: *c1c(-c2nccs2)cnn1C] | |
| 235 | Cl | 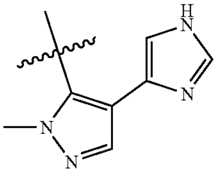 [SMILES: *c1c(-c2c[nH]cn2)cnn1C] | |
| 236 | Cl | 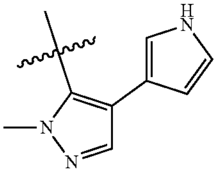 [SMILES: *c1c(-c2cc[nH]c2)cnn1C] | |
| 237 | Cl | 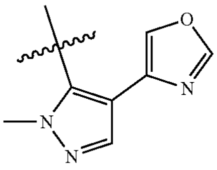 [SMILES: *c1c(-c2cocn2)cnn1C] | |
| 238 | Cl | 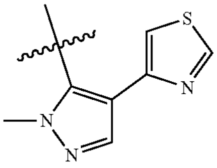 [SMILES: *c1c(-c2cscn2)cnn1C] | |
| 239 | Cl | 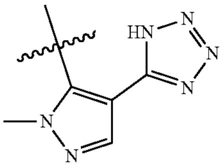 [SMILES: *c1c(-c2nnn[nH]2)cnn1C] | |

TABLE 1-continued
Structure and $^1$HNMR data of Compound I
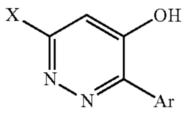
I
| No. | X | Ar | $^1$HNMR |
| --- | --- | --- | --- |
| 240 | Cl | 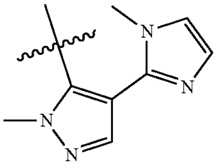 [SMILES: *c1c(-c2nccn2C)cnn1C] | |
| 241 | Cl | 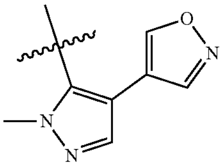 [SMILES: *c1c(-c2cnoc2)cnn1C] | |
| 242 | Cl | 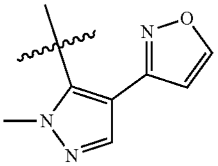 [SMILES: *c1c(-c2ccon2)cnn1C] | |
| 243 | Cl | 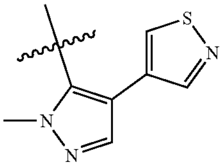 [SMILES: *c1c(-c2cnsc2)cnn1C] | |
| 244 | Cl | 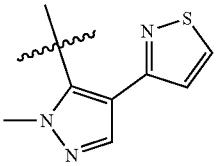 [SMILES: *c1c(-c2ccsn2)cnn1C] | |
| 245 | Cl | 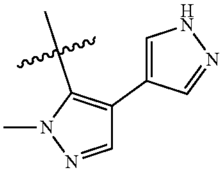 [SMILES: *c1c(-c2cn[nH]c2)cnn1C] | |
| 246 | Cl | 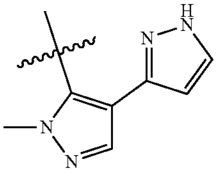 [SMILES: *c1c(-c2cc[nH]n2)cnn1C] | |

TABLE 1-continued
Structure and $^1$HNMR data of Compound I
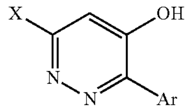
I
| No. | X | Ar | $^1$HNMR |
|---|---|---|---|
| 247 | Cl | 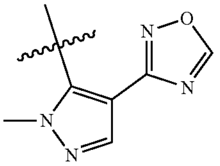 [SMILES: *c1c(-c2ncon2)cnn1C] | |
| 248 | Cl | 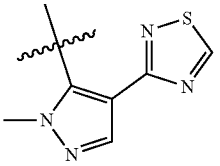 [SMILES: *c1c(-c2ncsn2)cnn1C] | |
| 249 | Cl | 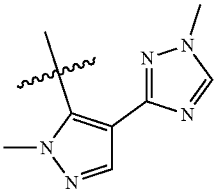 [SMILES: *c1c(-c2ncn(C)n2)cnn1C] | |
| 250 | Cl | 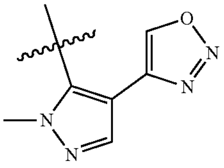 [SMILES: *c1c(-c2conn2)cnn1C] | |
| 251 | Cl | 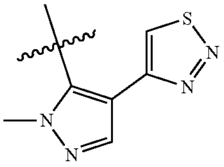 [SMILES: *c1c(-c2csnn2)cnn1C] | |
| 252 | Cl | 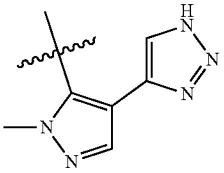 [SMILES: *c1c(-c2c[nH]nn2)cnn1C] | |
| 253 | Cl | 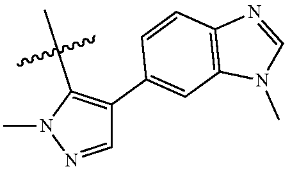 [SMILES: *c1c(-c2ccc3ncn(C)c3c2)cnn1C] | |

TABLE 1-continued
Structure and $^1$HNMR data of Compound I
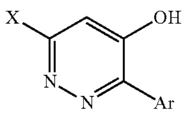
I
| No. | X | Ar | $^1$HNMR |
|---|---|---|---|
| 254 | Cl | 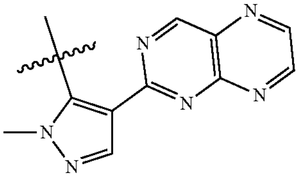 [SMILES: *c1c(-c2ncc3nccnc3n2)cnn1C] | |
| 255 | Cl | 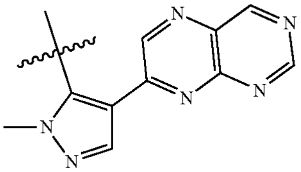 [SMILES: *c1c(-c2cnc3cncnc3n2)cnn1C] | |
| 256 | Cl | 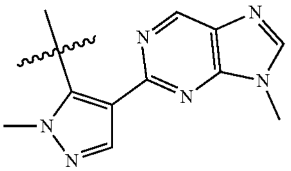 [SMILES: *c1c(-c2ncc3ncn(C)c3n2)cnn1C] | |
| 257 | Cl | 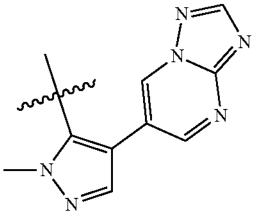 [SMILES: *c1c(-c2cnc3ncnn3c2)cnn1C] | |
| 258 | Cl | 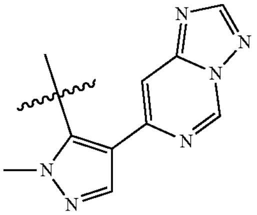 [SMILES: *c1c(-c2cc3ncnn3cn2)cnn1C] | |
| 259 | Cl | 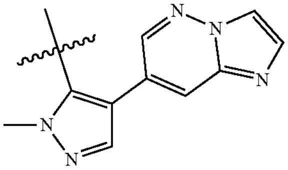 [SMILES: *c1c(-c2cnn3ccnc3c2)cnn1C] | |
| 260 | Cl | 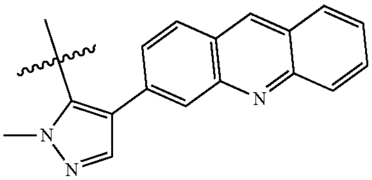 [SMILES: *c1c(-c2ccc3cc4ccccc4nc3c2)cnn1C] | |

TABLE 1-continued
Structure and $^{1}$HNMR data of Compound I
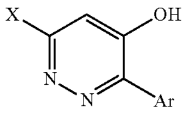
I
| No. | X | Ar | $^{1}$HNMR |
|---|---|---|---|
| 261 | Cl | 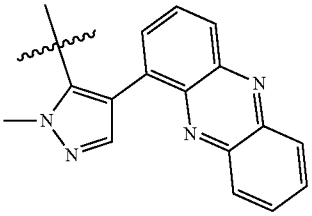 [SMILES: *c1c(-c2cccc3nc4ccccc4nc23)cnn1C] | |
| 262 | Cl | 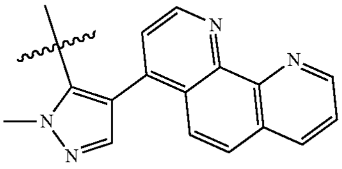 [SMILES: *c1c(-c2ccnc3c2ccc2cccnc23)cnn1C] | |
| 263 | Cl | 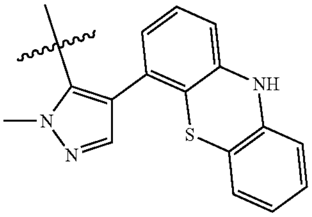 [SMILES: *c1c(-c2cccc3c2Sc2ccccc2N3)cnn1C] | |
| 264 | Cl | 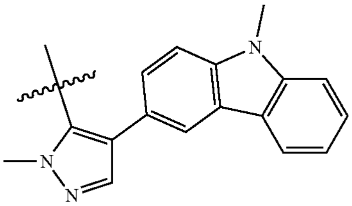 [SMILES: *c1c(-c2ccc3c(c2)c2ccccc2n3C)cnn1C] | |
| 265 | Cl | 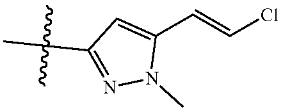 [SMILES: *c1cc(/C=C/Cl)n(C)n1] | |
| 266 | Cl | 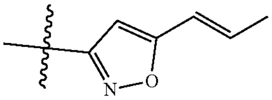 [SMILES: *c1cc(/C=C/C)on1] | |
| 267 | Cl | 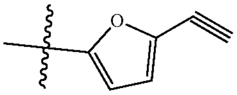 [SMILES: *c1ccc(C#C)o1] | |
| 268 | Cl | 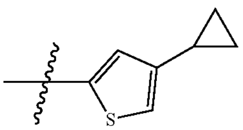 [SMILES: *c1cc(C2CC2)cs1] | |

TABLE 1-continued
Structure and $^1$HNMR data of Compound I
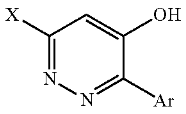
I
| No. | X | Ar | $^1$HNMR |
|---|---|---|---|
| 269 | Cl | 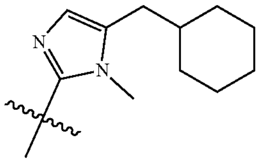 [SMILES: *c1ncc(CC2CCCCC2)n1C] | |
| 270 | Cl | 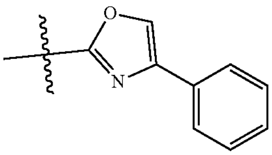 [SMILES: *c1nc(-c2ccccc2)co1] | |
| 271 | Cl | 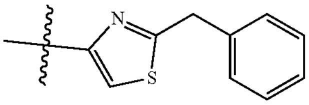 [SMILES: *c1csc(Cc2ccccc2)n1] | |
| 272 | Cl | 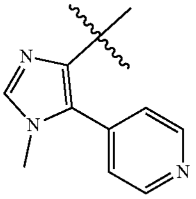 [SMILES: *c1ncn(C)c1-c1ccncc1] | |
| 273 | Cl | 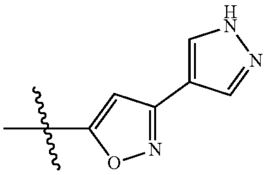 [SMILES: *c1cc(-c2cn[nH]c2)no1] | |
| 274 | Cl | 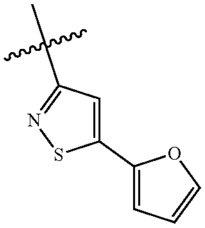 [SMILES: *c1cc(-c2ccco2)sn1] | |
| 275 | Cl | 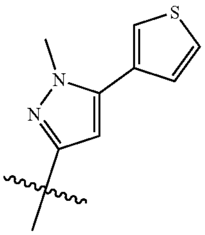 [SMILES: *c1cc(-c2ccsc2)n(C)n1] | |

TABLE 1-continued
Structure and $^1$HNMR data of Compound I
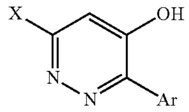
I
| No. | X | Ar | $^1$HNMR |
| --- | --- | --- | --- |
| 276 | Cl | 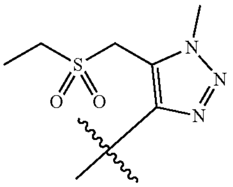 [SMILES: *c1nnn(C)c1CS(=O)(=O)CC] | |
| 277 | Cl | 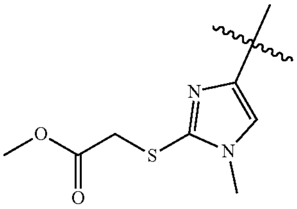 [SMILES: *c1cn(C)c(SCC(=O)OC)n1] | |
| 278 | Cl | 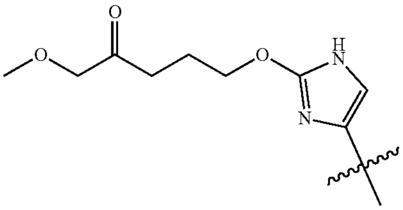 [SMILES: *c1c[nH]c(OCCCC(=O)COC)n1] | |
| 279 | Cl | 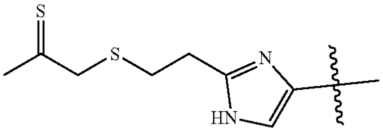 [SMILES: *c1c[nH]c(CCSCC(C)=S)n1] | |
| 280 | Cl | 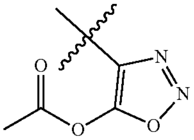 [SMILES: *c1nnoc1OC(C)=O] | |
| 281 | Cl | 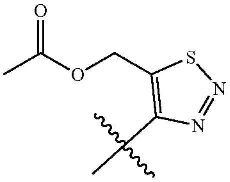 [SMILES: *c1nnsc1COC(C)=O] | |
| 282 | Cl | 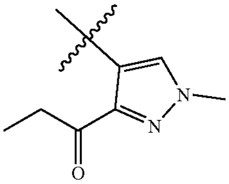 [SMILES: *c1cn(C)nc1C(=O)CC] | |

TABLE 1-continued
Structure and $^1$HNMR data of Compound I
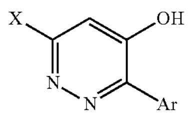
I
| No. | X | Ar | $^1$HNMR |
|---|---|---|---|
| 283 | Cl | 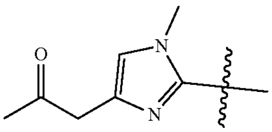 [SMILES: *c1nc(CC(C)=O)cn1C] | |
| 284 | Cl | 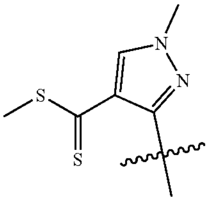 [SMILES: *c1nn(C)cc1C(=S)SC] | |
| 285 | Cl | 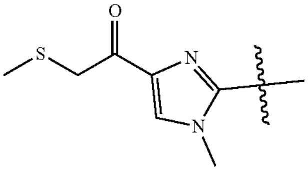 [SMILES: *c1nc(C(=O)CSC)cn1C] | |
| 286 | Cl | 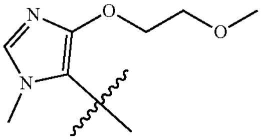 [SMILES: *c1c(OCCOC)ncn1C] | |
| 287 | Cl | 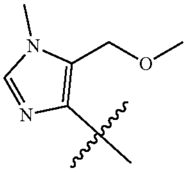 [SMILES: *c1ncn(C)c1COC] | |
| 288 | Cl | 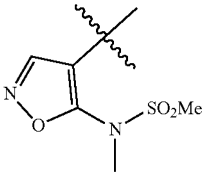 [SMILES: *c1cnoc1N(C)S(C)(=O)=O] | |
| 289 | Cl | 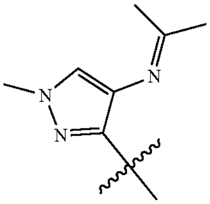 [SMILES: *c1nn(C)cc1N=C(C)C] | |

TABLE 1-continued
Structure and ¹HNMR data of Compound I
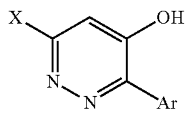
I
| No. | X | Ar | ¹HNMR |
|---|---|---|---|
| 290 | Cl | 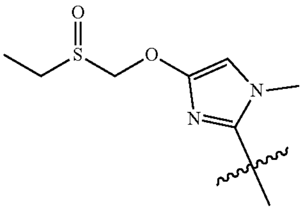 [SMILES: *c1nc(OCS(=O)CC)cn1C] | |
| 291 | Cl | 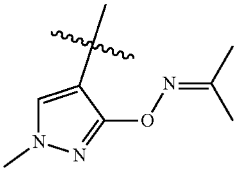 [SMILES: *c1cn(C)nc1ON=C(C)C] | |
| 292 | Cl | 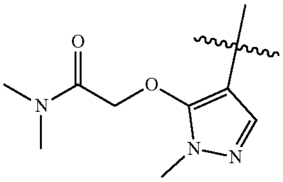 [SMILES: *c1cnn(C)c1OCC(=O)N(C)C] | |
| 293 | Cl | 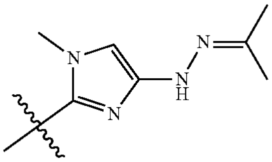 [SMILES: *c1nc(NN=C(C)C)cn1C] | |
| 294 | Cl | 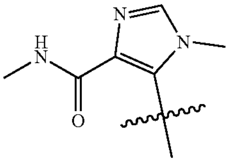 | |
| 295 | Cl | 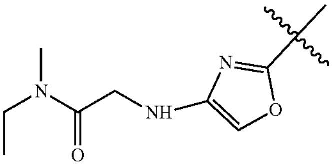 [SMILES: *c1nc(NCC(=O)N(C)CC)co1] | |
| 296 | Cl | 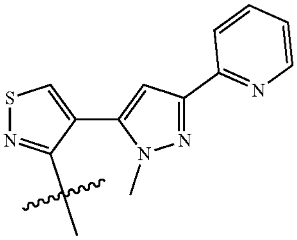 [SMILES: *c1nscc1-c1cc(-c2ccccn2)nn1C] | |

TABLE 1-continued
Structure and $^1$HNMR data of Compound I
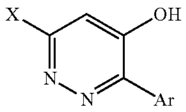
I
| No. | X | Ar | $^1$HNMR |
|---|---|---|---|
| 297 | Cl | 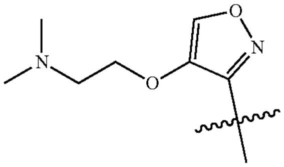 [SMILES: *c1nocc1OCCN(C)C] | |
| 298 | Cl | 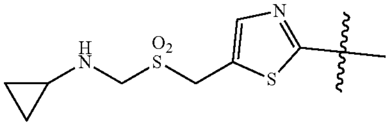 [SMILES: *c1ncc(CS(=O)(=O)CNC2CC2)s1] | |
| 299 | Cl | 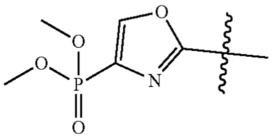 [SMILES: *c1nc(P(=O)(OC)OC)co1] | |
| 300 | Cl | 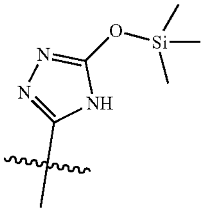 [SMILES: *c1nnc(O[Si](C)(C)C)[nH]1] | |
| 301 | Cl | 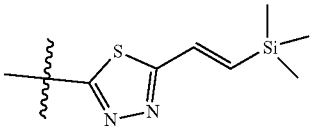 [SMILES: *c1nnc(/C=C/[Si](C)(C)C)s1] | |
| 302 | Cl | 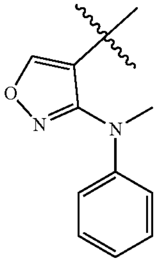 [SMILES: *c1conc1N(C)c1ccccc1] | |
| 303 | Cl | 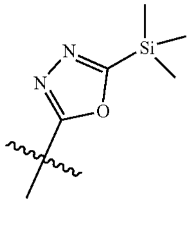 [SMILES: *c1nnc([Si](C)(C)C)o1] | |

TABLE 1-continued
Structure and $^{1}$HNMR data of Compound I
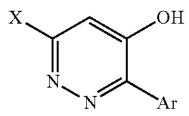
I
| No. | X | Ar | $^{1}$HNMR |
|---|---|---|---|
| 304 | Cl | 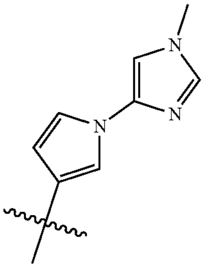 [SMILES: *c1ccn(-c2cn(C)cn2)c1] | |
| 305 | Cl | 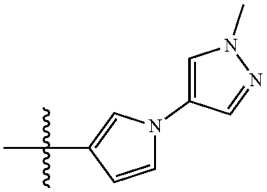 [SMILES: *c1ccn(-c2cnn(C)c2)c1] | |
| 306 | Cl | 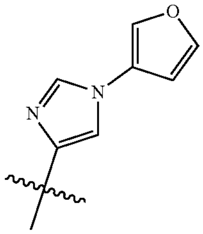 [SMILES: *c1cn(-c2ccoc2)cn1] | |
| 307 | Cl | 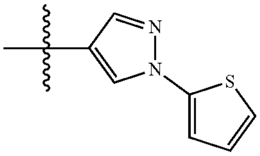 [SMILES: *c1cnn(-c2cccs2)c1] | |
| 308 | Cl | 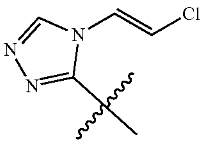 [SMILES: *c1nncn1/C=C/Cl] | |
| 309 | Cl | 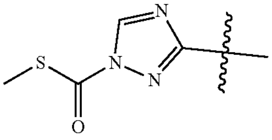 [SMILES: *c1ncn(C(=O)SC)n1] | |
| 310 | Cl | 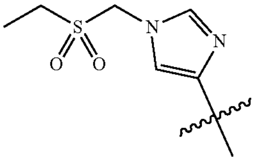 [SMILES: *c1cn(CS(=O)(=O)CC)cn1] | |

TABLE 1-continued
Structure and $^1$HNMR data of Compound I
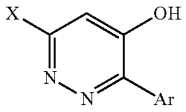
I
| No. | X | Ar | $^1$HNMR |
|---|---|---|---|
| 311 | Cl | 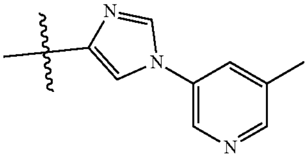 [SMILES: *c1cn(-c2cncc(C)c2)cn1] | |
| 312 | Cl | 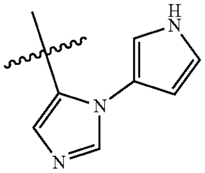 [SMILES: *c1cncn1-c1cc[nH]c1] | |
| 313 | Cl | 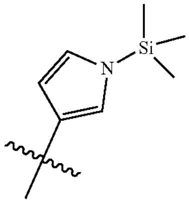 [SMILES: *c1ccn([Si](C)(C)C)c1] | |
| 314 | Cl | 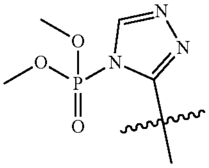 [SMILES: *c1nncn1P(=O)(OC)OC] | |
| 315 | Cl | 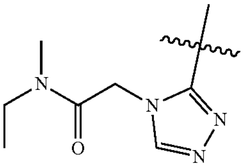 [SMILES: *c1nncn1CC(=O)N(C)CC] | |
| 316 | Cl | 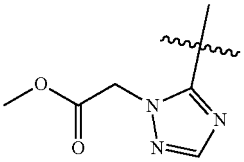 [SMILES: *c1ncnn1CC(=O)OC] | |
| 317 | Cl | 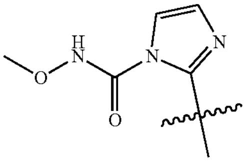 [SMILES: *c1nccn1C(=O)NOC] | |

TABLE 1-continued
Structure and $^1$HNMR data of Compound I
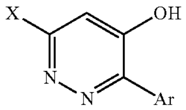
I
| No. | X | Ar | $^1$HNMR |
| --- | --- | --- | --- |
| 318 | Cl | 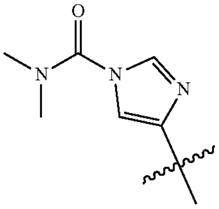 [SMILES: *c1cn(C(=O)N(C)C)cn1] | |
| 319 | Cl | 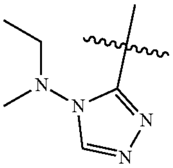 [SMILES: *c1nncn1N(C)CC] | |
| 320 | Cl | 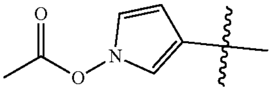 [SMILES: *c1ccn(OC(C)=O)c1] | |
| 321 | Cl | 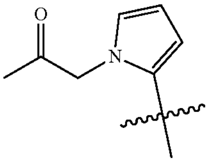 [SMILES: *c1cccn1CC(C)=O] | |
| 322 | Cl | 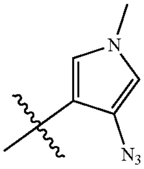 [SMILES: *c1cn(C)cc1N=[N+]=[N-]] | |
| 323 | $CF_3$ | 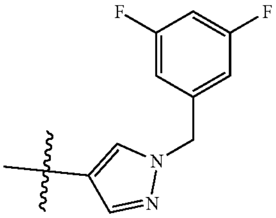 [SMILES: *c1cnn(Cc2cc(F)cc(F)c2)c1] | |
| 324 | $CF_3$ | 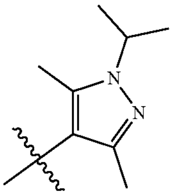 [SMILES: *c1c(C)nn(C(C)C)c1C] | |

TABLE 1-continued
Structure and ¹HNMR data of Compound I
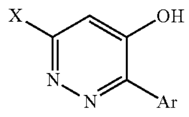
I
| No. | X | Ar | ¹HNMR |
|---|---|---|---|
| 325 | $CF_3$ | 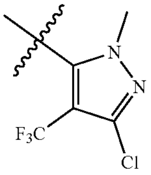 [SMILES: *c1c(C(F)(F)F)c(Cl)nn1C] | |
| 326 | $CF_3$ | 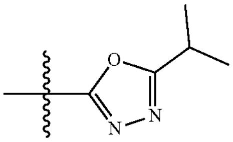 [SMILES: *c1nnc(C(C)C)o1] | |
| 327 | $CF_3$ | 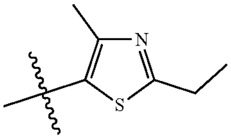 [SMILES: *c1sc(CC)nc1C] | |
| 328 | $CF_3$ | 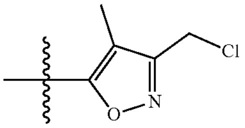 [SMILES: *c1onc(CCl)c1C] | |
| 329 | $CF_3$ | 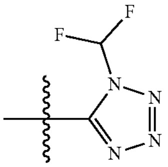 [SMILES: *c1nnnn1C(F)F] | |
| 330 | $CF_3$ | 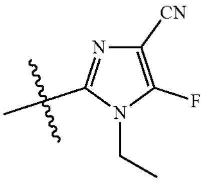 [SMILES: *c1nc(C#N)c(F)n1CC] | |
| 331 | $CF_3$ | 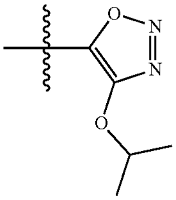 [SMILES: *c1onnc1OC(C)C] | |
| 332 | $CF_3$ | 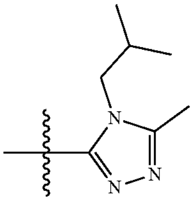 [SMILES: *c1nnc(C)n1CC(C)C] | |

TABLE 1-continued
Structure and ¹HNMR data of Compound I
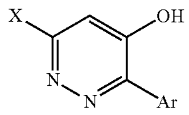
I
| No. | X | Ar | ¹HNMR |
| --- | --- | --- | --- |
| 333 | $CF_3$ | 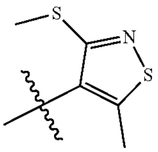 [SMILES: *c1c(SC)nsc1C] | |
| 334 | $CF_3$ | 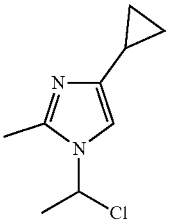 | |
| 335 | $CF_3$ | 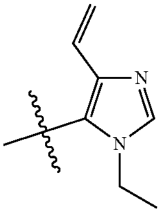 [SMILES: *c1c(C=C)ncn1CC] | |
TABLE 2
Structure of group M in the derivative Compound I-1
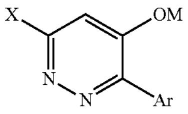
I-1
| No. | M |
| --- | --- |
| M-1 | 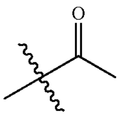 [SMILES: *C(C)=O] |
| M-2 | 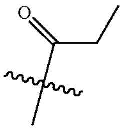 [SMILES: *C(=O)CC] |
| M-3 | 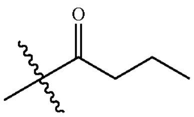 [SMILES: *C(=O)CCC] |
TABLE 2-continued
Structure of group M in the derivative Compound I-1
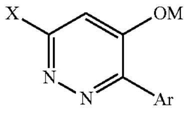
I-1
| No. | M |
| --- | --- |
| M-4 | 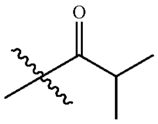 [SMILES: *C(=O)C(C)C] |
| M-5 | 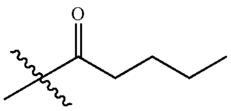 [SMILES: *C(=O)CCCC] |
| M-6 | 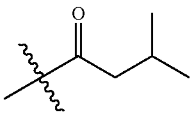 [SMILES: *C(=O)CC(C)C] |

TABLE 2-continued
Structure of group M in the derivative Compound I-1
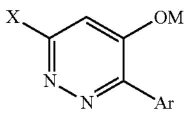
I-1
| No. | M |
|---|---|
| M-7 | 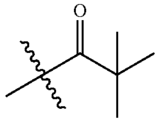 [SMILES: *C(=O)C(C)(C)C] |
| M-8 | 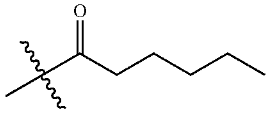 [SMILES: *C(=O)CCCCC] |
| M-9 | 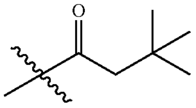 [SMILES: *C(=O)CC(C)(C)C] |
| M-10 | 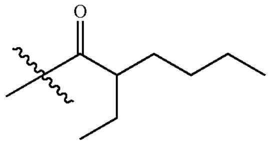 [SMILES: *C(=O)C(CC)CCCC] |
| M-11 | 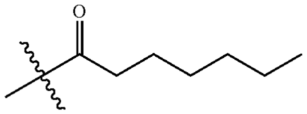 [SMILES: *C(=O)CCCCCC] |
| M-12 | 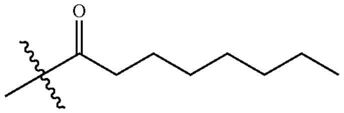 [SMILES: *C(=O)CCCCCCC] |
| M-13 | 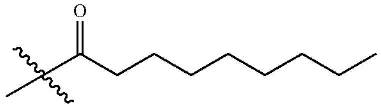 [SMILES: *C(=O)CCCCCCCC] |
| M-14 | 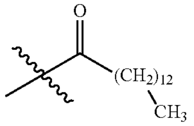 |
| M-15 | 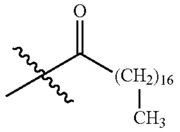 |
| M-16 | 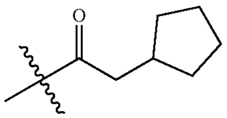 [SMILES: *C(=O)CC1CCCC1] |
TABLE 2-continued
Structure of group M in the derivative Compound I-1
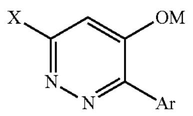
I-1
| No. | M |
|---|---|
| M-17 | 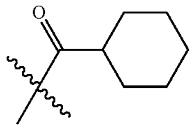 |
| M-18 | 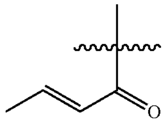 [SMILES: *C(=O)/C=C/C] |
| M-19 | 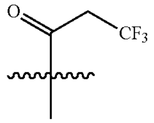 [SMILES: *C(=O)CC(F)(F)F] |
| M-20 | 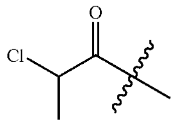 [SMILES: *C(=O)C(C)Cl] |
| M-21 | 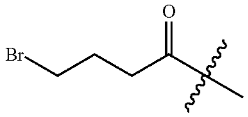 [SMILES: *C(=O)CCCBr] |
| M-22 | 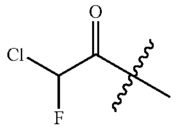 [SMILES: *C(=O)C(F)Cl] |
| M-23 | 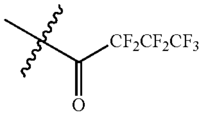 |
| M-24 | 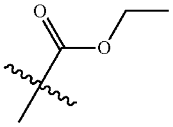 [SMILES: *C(=O)OCC] |
| M-25 | 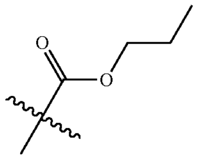 [SMILES: *C(=O)OCCC] |
| M-26 | 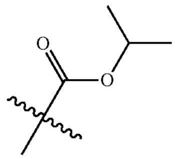 [SMILES: *C(=O)OC(C)C] |

TABLE 2-continued
Structure of group M in the derivative Compound I-1
I-1
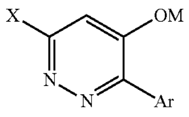
| No. | M |
|---|---|
| M-27 | 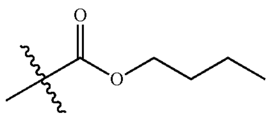 [SMILES: *C(=O)OCCCC] |
| M-28 | 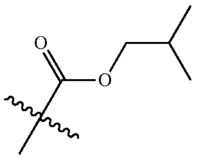 [SMILES: *C(=O)OCC(C)C] |
| M-29 | 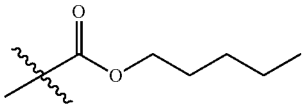 [SMILES: *C(=O)OCCCCC] |
| M-30 | 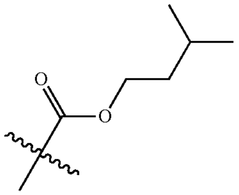 [SMILES: *C(=O)OCCC(C)C] |
| M-31 | 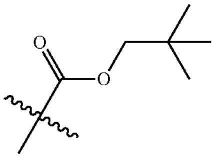 [SMILES: *C(=O)OCC(C)(C)C] |
| M-32 | 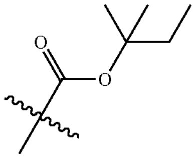 [SMILES: *C(=O)OC(C)(C)CC] |
| M-33 | 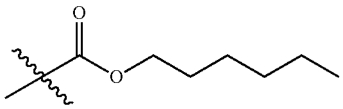 |
| M-34 | 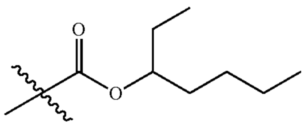 [SMILES: *C(=O)OC(CC)CCCC] |
| M-35 | 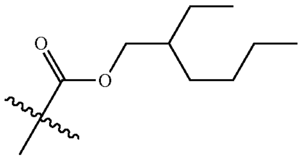 [SMILES: *C(=O)OCC(CC)CCCC] |
TABLE 2-continued
Structure of group M in the derivative Compound I-1
I-1
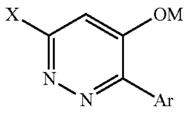
| No. | M |
|---|---|
| M-36 | 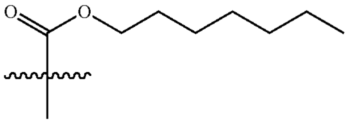 [SMILES: *C(=O)OCCCCCCC] |
| M-37 | 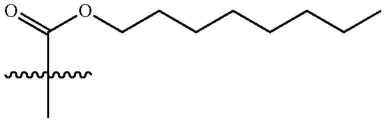 [SMILES: *C(=O)OCCCCCCCC] |
| M-38 | 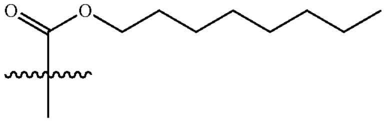 [SMILES: *C(=O)OCCCCCCCC] |
| M-39 | 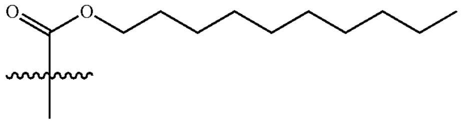 [SMILES: *C(=O)OCCCCCCCCCC] |
| M-40 | 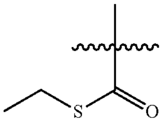 [SMILES: *C(=O)SCC] |
| M-41 | 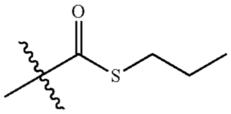 [SMILES: *C(=O)SCCC] |
| M-42 | 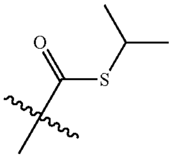 |
| M-43 | 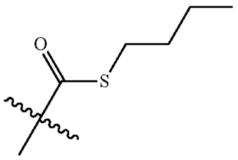 [SMILES: *C(=O)SCCCC] |
| M-44 | 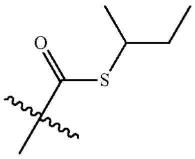 [SMILES: *C(=O)SC(C)CC] |

TABLE 2-continued
Structure of group M in the derivative Compound I-1
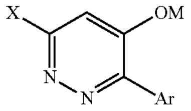
I-1
| No. | M |
|---|---|
| M-45 | 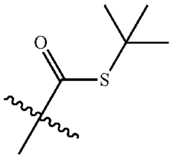 [SMILES: *C(=O)SC(C)(C)C] |
| M-46 | 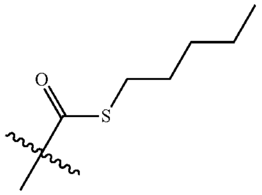 [SMILES: *C(=O)SCCCCC] |
| M-47 | 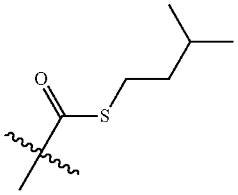 |
| M-48 | 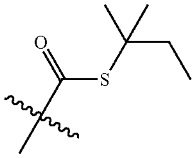 [SMILES: *C(=O)SC(C)(C)CC] |
| M-49 | 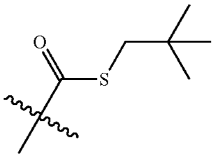 |
| M-50 | 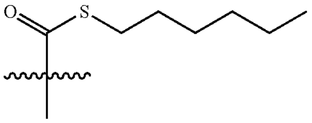 [SMILES: *C(=O)SCCCCCC] |
| M-51 | 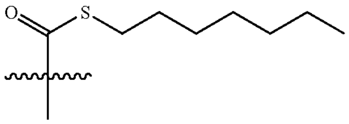 [SMILES: *C(=O)SCCCCCCC] |
| M-52 | 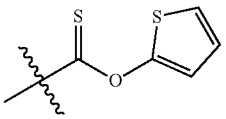 [SMILES: *C(=S)Oc1cccs1] |
TABLE 2-continued
Structure of group M in the derivative Compound I-1
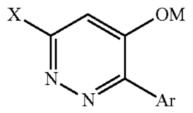
I-1
| No. | M |
|---|---|
| M-53 | 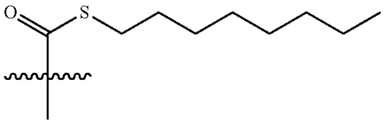 |
| M-54 | 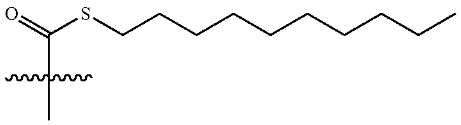 |
| M-55 | 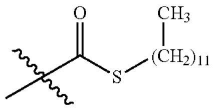 |
| M-56 | 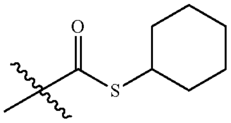 [SMILES: *C(=O)SC1CCCCC1] |
| M-57 | 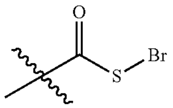 [SMILES: *C(=O)SBr] |
| M-58 | 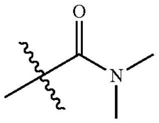 [SMILES: *C(=O)N(C)C] |
| M-59 | 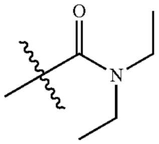 [SMILES: *C(=O)N(CC)CC] |
| M-60 | 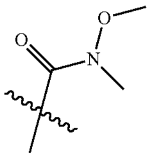 [SMILES: *C(=O)N(C)OC] |
| M-61 | 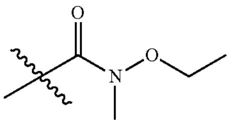 [SMILES: *C(=O)N(C)OCC] |
| M-62 | 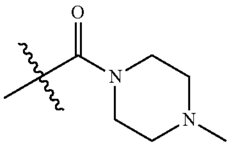 [SMILES: *C(=O)N1CCN(C)CC1] |

TABLE 2-continued
Structure of group M in the derivative Compound I-1
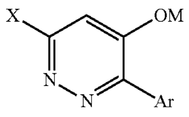
I-1
| No. | M |
|---|---|
| M-63 | 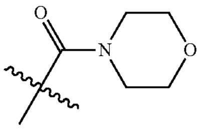 [SMILES: *C(=O)N1CCOCC1] |
| M-64 | 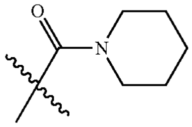 [SMILES: *C(=O)N1CCCCC1] |
| M-65 | 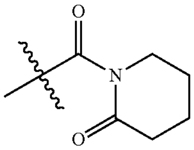 [SMILES: *C(=O)N1CCCCC1=O] |
| M-66 | 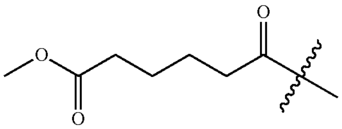 [SMILES: *C(=O)CCCCC(=O)OC] |
| M-67 | 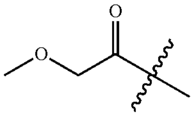 [SMILES: *C(=O)COC] |
| M-68 | 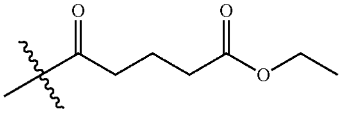 [SMILES: *C(=O)CCCC(=O)OCC] |
| M-69 | 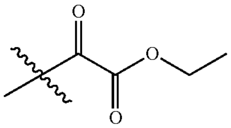 [SMILES: *C(=O)C(=O)OCC] |
| M-70 | 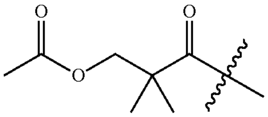 [SMILES: *C(=O)C(C)(C)COC(C)=O] |
| M-71 | 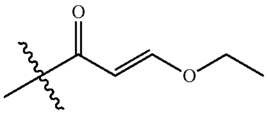 [SMILES: *C(=O)/C=C/OCC] |
| M-72 | 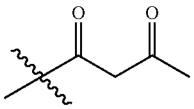 [SMILES: *C(=O)CC(C)=O] |
TABLE 2-continued
Structure of group M in the derivative Compound I-1
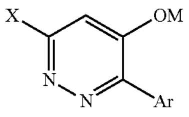
I-1
| No. | M |
|---|---|
| M-73 | 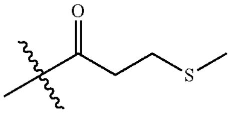 [SMILES: *C(=O)CCSC] |
| M-74 | 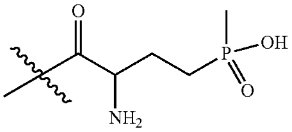 [SMILES: *C(=O)C(N)CCP(C)(=O)O] |
| M-75 | 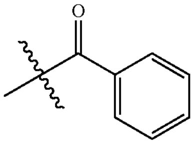 [SMILES: *C(=O)c1ccccc1] |
| M-76 | 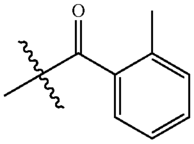 [SMILES: *C(=O)c1ccccc1C] |
| M-77 | 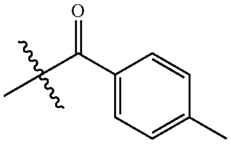 [SMILES: *C(=O)c1ccc(C)cc1] |
| M-78 | 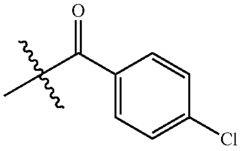 [SMILES: *C(=O)c1ccc(Cl)cc1] |
| M-79 | 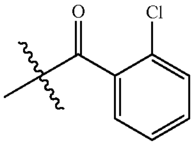 [SMILES: *C(=O)c1ccccc1Cl] |
| M-80 | 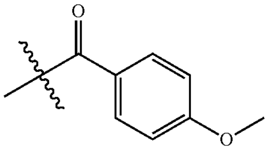 [SMILES: *C(=O)c1ccc(OC)cc1] |
| M-81 | 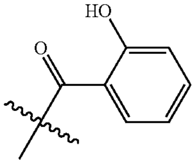 [SMILES: *C(=O)c1ccccc1O] |

TABLE 2-continued
Structure of group M in the derivative Compound I-1
I-1
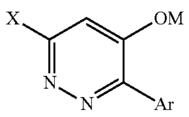
| No. | M |
|---|---|
| M-82 | 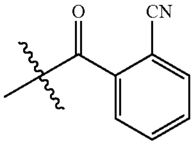 [SMILES: *C(=O)c1ccccc1C#N] |
| M-83 | 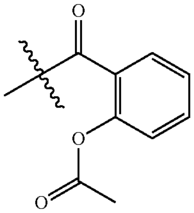 [SMILES: *C(=O)c1ccccc1OC(C)=O] |
| M-84 | 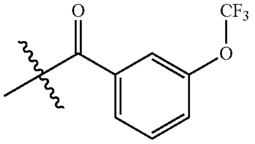 [SMILES: *C(=O)c1cccc(OC(F)(F)F)c1] |
| M-85 | 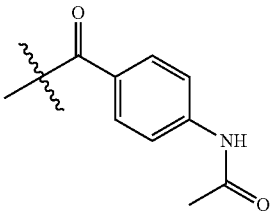 [SMILES: *C(=O)c1ccc(NC(C)=O)cc1] |
| M-86 | 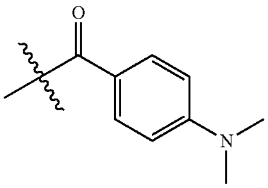 [SMILES: *C(=O)c1ccc(N(C)C)cc1] |
| M-87 | 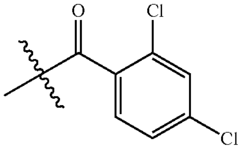 |
| M-88 | 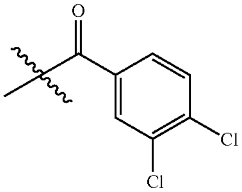 [SMILES: *C(=O)c1ccc(Cl)c(Cl)c1] |
TABLE 2-continued
Structure of group M in the derivative Compound I-1
I-1
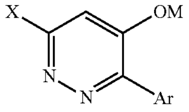
| No. | M |
|---|---|
| M-89 | 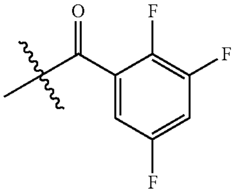 [SMILES: *C(=O)c1cc(F)cc(F)c1F] |
| M-90 | 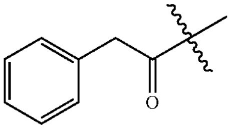 [SMILES: *C(=O)Cc1ccccc1] |
| M-91 | 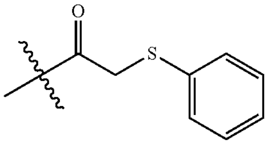 [SMILES: *C(=O)CSc1ccccc1] |
| M-92 | 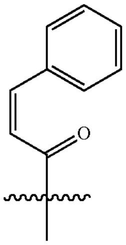 [SMILES: *C(=O)/C=C\c1ccccc1] |
| M-93 | 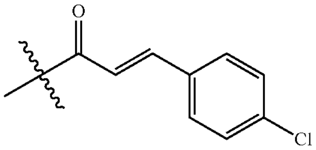 [SMILES: *C(=O)/C=C/c1ccc(Cl)cc1] |
| M-94 | 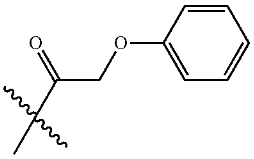 [SMILES: *C(=O)COc1ccccc1] |
| M-95 | 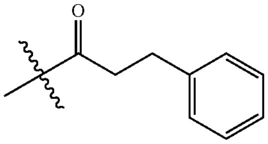 [SMILES: *C(=O)CCc1ccccc1] |
| M-96 | 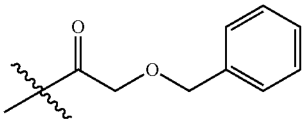 [SMILES: *C(=O)COCc1ccccc1] |

TABLE 2-continued
Structure of group M in the derivative Compound I-1
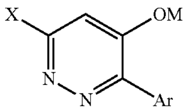
I-1
| No. | M |
|---|---|
| M-97 | 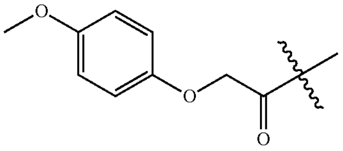 [SMILES: *C(=O)COc1ccc(OC)cc1] |
| M-98 | 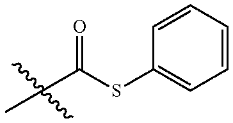 [SMILES: *C(=O)Sc1ccccc1] |
| M-99 | 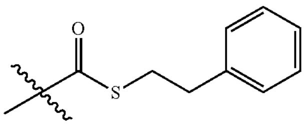 [SMILES: *C(=O)SCCc1ccccc1] |
| M-100 | 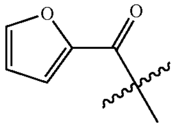 [SMILES: *C(=O)c1ccco1] |
| M-101 | 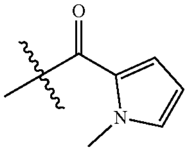 [SMILES: *C(=O)c1cccn1C] |
| M-102 | 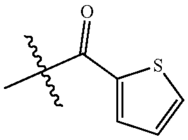 [SMILES: *C(=O)c1cccs1] |
| M-103 | 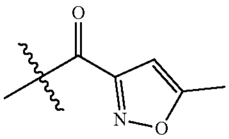 [SMILES: *C(=O)c1cc(C)on1] |
| M-104 | 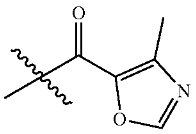 [SMILES: *C(=O)c1ocnc1C] |
| M-105 | 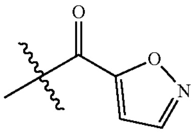 [SMILES: *C(=O)c1ccno1] |
TABLE 2-continued
Structure of group M in the derivative Compound I-1
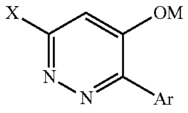
I-1
| No. | M |
|---|---|
| M-106 | 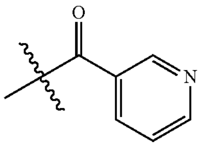 [SMILES: *C(=O)c1cccnc1] |
| M-107 | 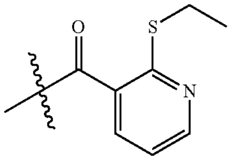 [SMILES: *C(=O)c1cccnc1SCC] |
| M-108 | 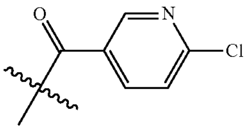 [SMILES: *C(=O)c1ccc(Cl)nc1] |
| M-109 | 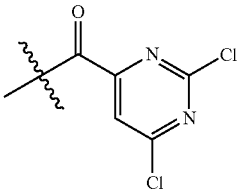 [SMILES: *C(=O)c1cc(Cl)nc(Cl)n1] |
| M-110 | 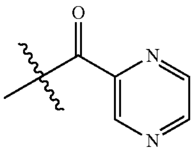 [SMILES: *C(=O)c1cnccn1] |
| M-111 | 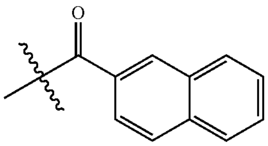 [SMILES: *C(=O)c1ccc2ccccc2c1] |
| M-112 | 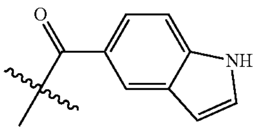 [SMILES: *C(=O)c1ccc2[nH]ccc2c1] |
| M-113 | 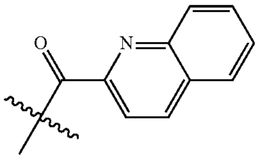 [SMILES: *C(=O)c1ccc2ccccc2n1] |

TABLE 2-continued
Structure of group M in the derivative Compound I-1
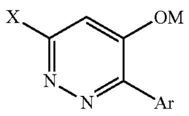
I-1
| No. | M |
|---|---|
| M-114 | 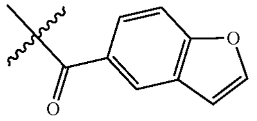 [SMILES: *C(=O)c1ccc2occc2c1] |
| M-115 | 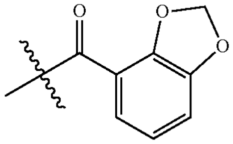 [SMILES: *C(=O)c1cccc2c1OCO2] |
| M-116 | 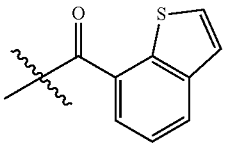 [SMILES: *C(=O)c1cccc2ccsc12] |
| M-117 | 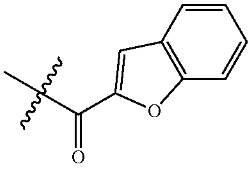 [SMILES: *C(=O)c1cc2ccccc2o1] |
| M-118 | 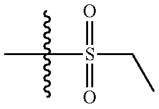 [SMILES: *S(=O)(=O)CC] |
| M-119 | 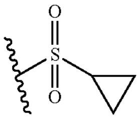 |
| M-120 | 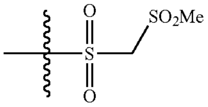 [SMILES: *S(=O)(=O)CS(C)(=O)=O] |
| M-121 | 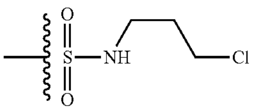 |
| M-122 | 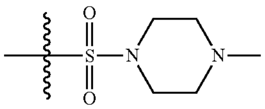 [SMILES: *S(=O)(=O)N1CCN(C)CC1] |
| M-123 | 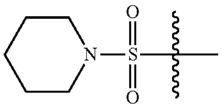 [SMILES: *S(=O)(=O)N1CCCCC1] |
TABLE 2-continued
Structure of group M in the derivative Compound I-1
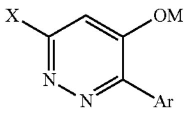
I-1
| No. | M |
|---|---|
| M-124 | 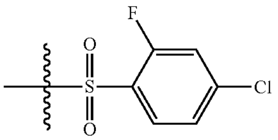 [SMILES: *S(=O)(=O)c1ccc(Cl)cc1F] |
| M-125 | 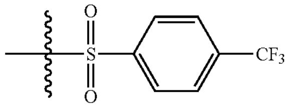 [SMILES: *S(=O)(=O)c1ccc(C(F)(F)F)cc1] |
| M-126 | 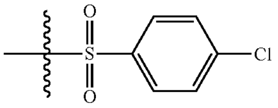 [SMILES: *S(=O)(=O)c1ccc(Cl)cc1] |
| M-127 | 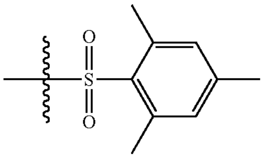 [SMILES: *S(=O)(=O)c1c(C)cc(C)cc1C] |
| M-128 | 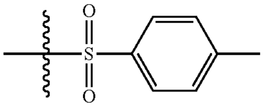 |
| M-129 | 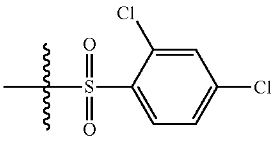 |
| M-130 | 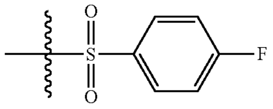 [SMILES: *S(=O)(=O)c1ccc(F)cc1] |
| M-131 | 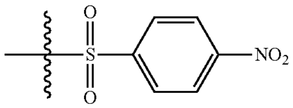 [SMILES: *S(=O)(=O)c1ccc([N+](=O)[O-])cc1] |
| M-132 | 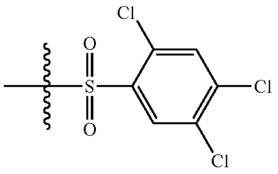 |
| M-133 | 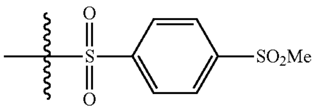 [SMILES: *S(=O)(=O)c1ccc(S(C)(=O)=O)cc1] |

TABLE 2-continued
Structure of group M in the derivative Compound I-1
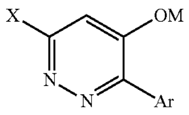
I-1
| No. | M |
|---|---|
| M-134 | 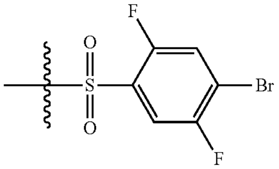 |
| M-135 | 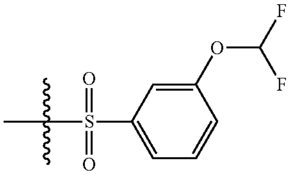 [SMILES: *S(=O)(=O)c1cccc(OC(F)F)c1] |
| M-136 | 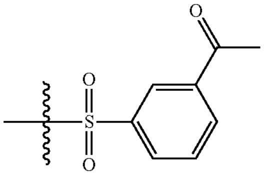 [SMILES: *S(=O)(=O)c1cccc(C(C)=O)c1] |
| M-137 | 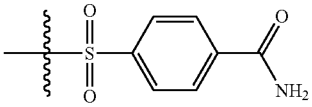 [SMILES: *S(=O)(=O)c1ccc(C(N)=O)cc1] |
| M-138 | 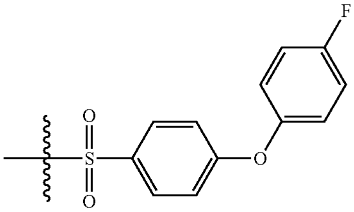 [SMILES: *S(=O)(=O)c1ccc(Oc2ccc(F)cc2)cc1] |
| M-139 | 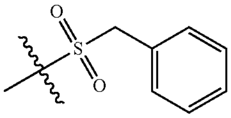 [SMILES: *S(=O)(=O)Cc1ccccc1] |
| M-140 | 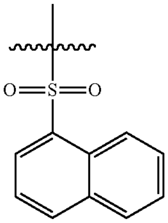 [SMILES: *S(=O)(=O)c1cccc2ccccc12] |
| M-141 | 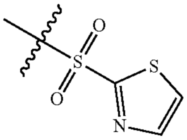 [SMILES: *S(=O)(=O)c1nccs1] |
TABLE 2-continued
Structure of group M in the derivative Compound I-1
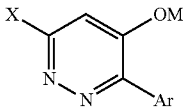
I-1
| No. | M |
|---|---|
| M-142 | 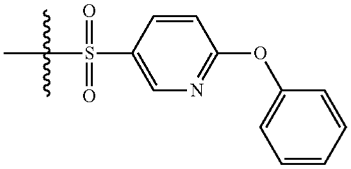 [SMILES: *S(=O)(=O)c1ccc(Oc2ccccc2)nc1] |
| M-143 | 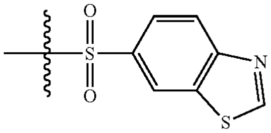 [SMILES: *S(=O)(=O)c1ccc2ncsc2c1] |
| M-144 | 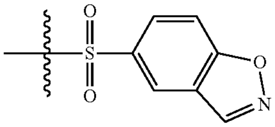 [SMILES: *S(=O)(=O)c1ccc2oncc2c1] |
| M-145 | 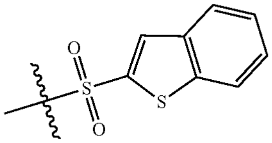 [SMILES: *S(=O)(=O)c1cc2ccccc2s1] |
| M-146 | 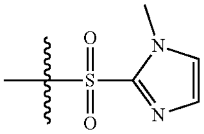 [SMILES: *S(=O)(=O)c1nccn1C] |
| M-147 | 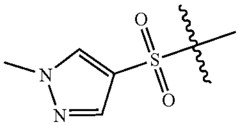 [SMILES: *S(=O)(=O)c1cnn(C)c1] |
| M-148 | 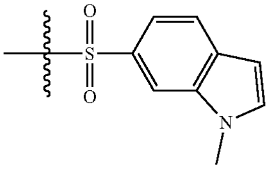 [SMILES: *S(=O)(=O)c1ccc2ccn(C)c2c1] |
| M-149 | 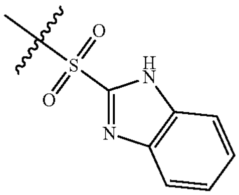 [SMILES: *S(=O)(=O)c1nc2ccccc2[nH]1] |

TABLE 2-continued
Structure of group M in the derivative Compound I-1
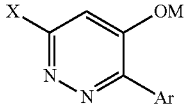
I-1
| No. | M |
|---|---|
| M-150 | 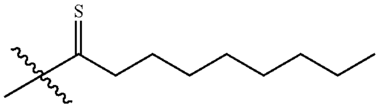 |
| M-151 | 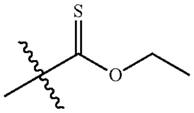 [SMILES: *C(=S)OCC] |
| M-152 | 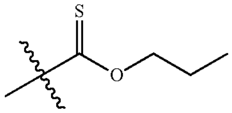 [SMILES: *C(=S)OCCC] |
| M-153 | 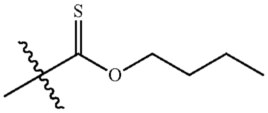 [SMILES: *C(=S)OCCCC] |
| M-154 | 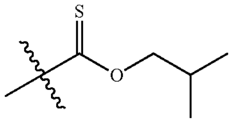 [SMILES: *C(=S)OCC(C)C] |
| M-155 | 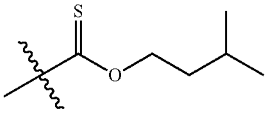 [SMILES: *C(=S)OCCC(C)C] |
| M-156 | 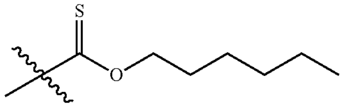 [SMILES: *C(=S)OCCCCCC] |
| M-157 | 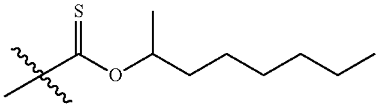 [SMILES: *C(=S)OC(C)CCCCCC] |
| M-158 | 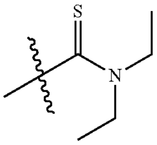 [SMILES: *C(=S)N(CC)CC] |
| M-159 | 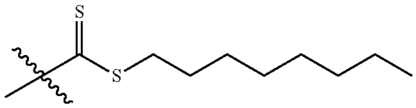 [SMILES: *C(=S)SCCCCCCCC] |
TABLE 2-continued
Structure of group M in the derivative Compound I-1
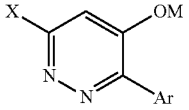
I-1
| No. | M |
|---|---|
| M-160 | 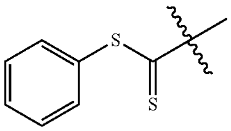 |
| M-161 | 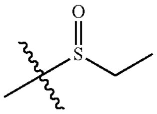 |
| M-162 | 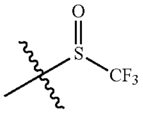 [SMILES: *S(=O)C(F)(F)F] |
| M-163 | 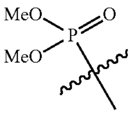 [SMILES: *P(=O)(OC)OC] |
| M-164 | 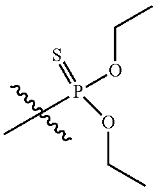 [SMILES: *P(=S)(OCC)OCC] |
| M-165 | 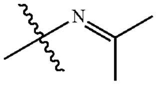 [SMILES: *N=C(C)C] |
| M-166 | 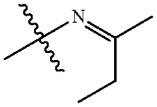 [SMILES: */N=C(/C)CC] |
| M-167 | 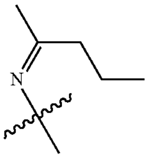 [SMILES: */N=C(/C)CCC] |
| M-168 | 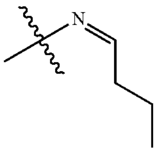 [SMILES: */N=C\CCC] |

TABLE 2-continued
Structure of group M in the derivative Compound I-1
I-1
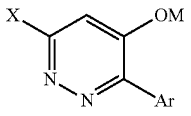
| No. | M |
| --- | --- |
| M-169 | 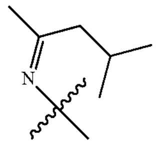 [SMILES: */N=C(/C)CC(C)C] |
| M-170 | 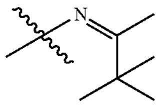 [SMILES: */N=C(/C)C(C)(C)C] |
| M-171 | 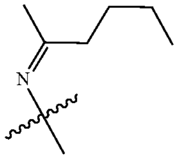 [SMILES: */N=C(/C)CCCC] |
| M-172 | 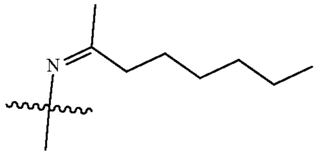 [SMILES: */N=C(/C)CCCCCC] |
| M-173 | 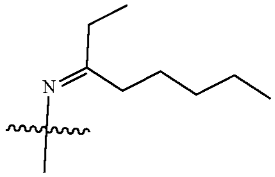 [SMILES: */N=C(/CC)CCCCC] |
| M-174 | 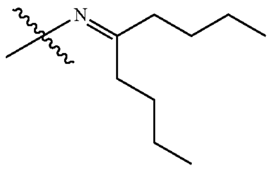 [SMILES: *N=C(CCCC)CCCC] |
| M-175 | 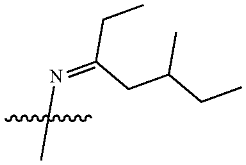 [SMILES: */N=C(/CC)CC(C)CC] |
| M-176 | 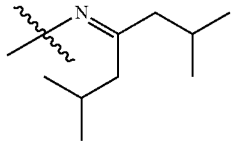 [SMILES: *N=C(CC(C)C)CC(C)C] |
TABLE 2-continued
Structure of group M in the derivative Compound I-1
I-1
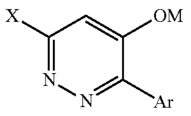
| No. | M |
| --- | --- |
| M-177 | 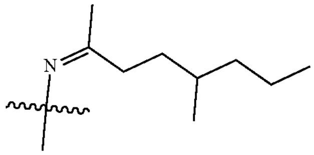 [SMILES: */N=C(/C)CCC(C)CCC] |
| M-178 | 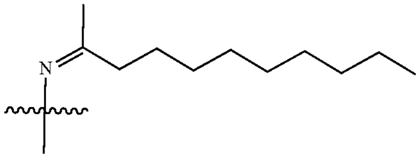 [SMILES: */N=C(/C)CCCCCCCCC] |
| M-179 | 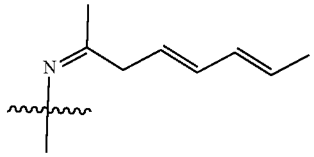 [SMILES: */N=C(/C)C/C=C/C=C/C] |
| M-180 | 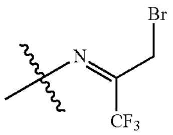 |
| M-181 | 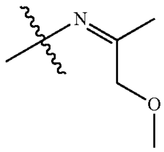 |
| M-182 | 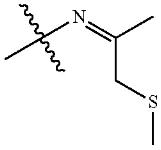 [SMILES: */N=C(/C)CSC] |
| M-183 | 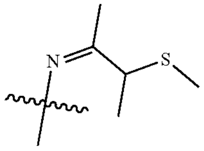 [SMILES: */N=C(/C)C(C)SC] |
| M-184 | 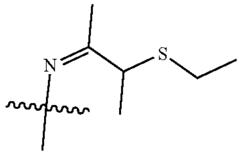 [SMILES: */N=C(/C)C(C)SCC] |

TABLE 2-continued
Structure of group M in the derivative Compound I-1
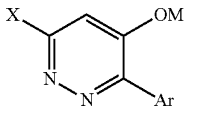
I-1
| No. | M |
|---|---|
| M-185 | 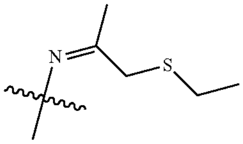 [SMILES: */N=C(/C)CSCC] |
| M-186 | 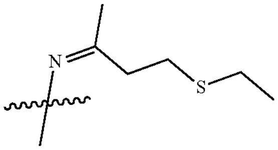 [SMILES: */N=C(/C)CCSCC] |
| M-187 | 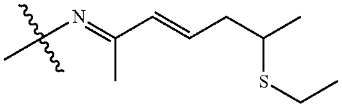 [SMILES: */N=C(C)/C=C/CC(C)SCC] |
| M-188 | 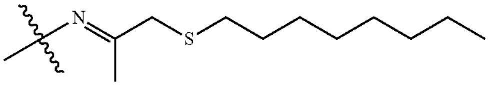 [SMILES: */N=C(\C)CSCCCCCCCC] |
| M-189 | 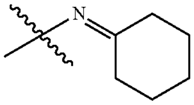 [SMILES: *N=C1CCCCC1] |
| M-190 | 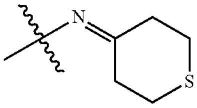 [SMILES: *N=C1CCSCC1] |
| M-191 | 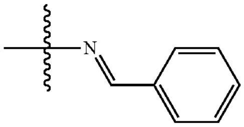 [SMILES: */N=C/c1ccccc1] |
| M-192 | 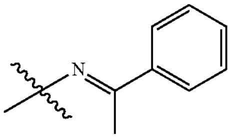 [SMILES: */N=C(\C)c1ccccc1] |
| M-193 | 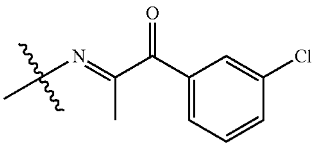 [SMILES: */N=C(\C)C(=O)c1cccc(Cl)c1] |
TABLE 2-continued
Structure of group M in the derivative Compound I-1
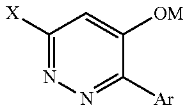
I-1
| No. | M |
|---|---|
| M-194 | 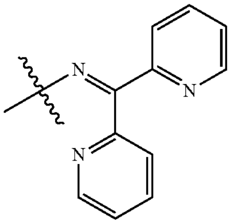 [SMILES: *N=C(c1ccccn1)c1ccccn1] |
| M-195 | 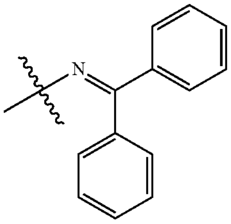 [SMILES: *N=C(c1ccccc1)c1ccccc1] |
| M-196 | 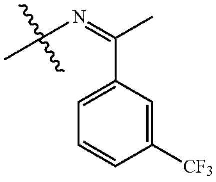 [SMILES: */N=C(/C)c1cccc(C(F)(F)F)c1] |
| M-197 | Me |
| M-198 | Et |
| M-199 | 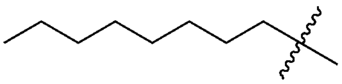 [SMILES: *CCCCCCCC] |
| M-200 | CN |
| M-201 | 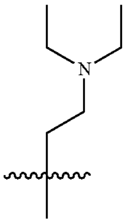 [SMILES: *CCN(CC)CC] |
| M-202 | 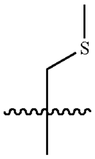 [SMILES: *CSC] |

TABLE 2-continued
Structure of group M in the derivative Compound I-1
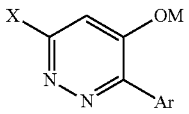
I-1
| No. | M |
|---|---|
| M-203 | 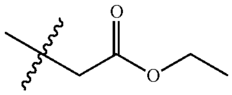 [SMILES: *CC(=O)OCC] |
| M-204 | 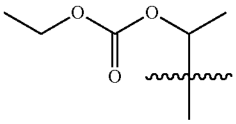 [SMILES: *C(C)OC(=O)OCC] |
| M-205 | 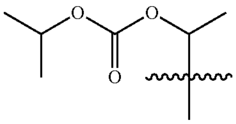 [SMILES: *C(C)OC(=O)OC(C)C] |
| M-206 | 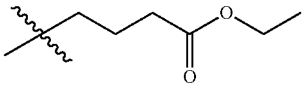 [SMILES: *CCCC(=O)OCC] |
| M-207 | 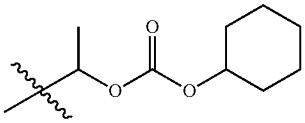 [SMILES: *C(C)OC(=O)OC1CCCCC1] |
| M-208 | 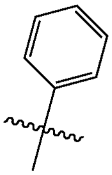 [SMILES: *c1ccccc1] |
| M-209 | 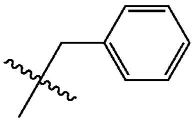 [SMILES: *Cc1ccccc1] |
TABLE 2-continued
Structure of group M in the derivative Compound I-1
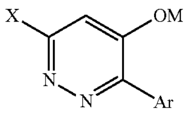
I-1
| No. | M |
|---|---|
| M-210 | 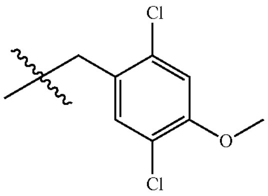 [SMILES: *Cc1cc(Cl)c(OC)cc1Cl] |
| M-211 | 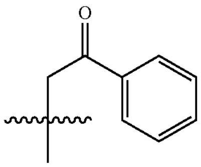 [SMILES: *CC(=O)c1ccccc1] |
| M-212 | 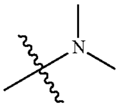 [SMILES: *N(C)C] |
| M-213 | 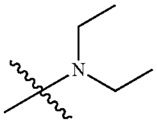 [SMILES: *N(CC)CC] |
| M-214 | 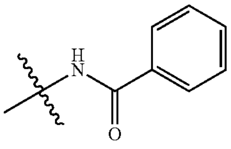 [SMILES: *NC(=O)c1ccccc1] |
| M-215 | 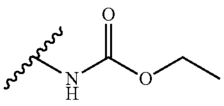 [SMILES: *NC(=O)OCC] |
| M-216 | 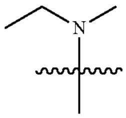 [SMILES: *N(C)CC] |

TABLE 3

Structure and $^1$HNMR data of the derivative Compound I-1

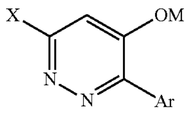

I-1

| No. | X | Ar | M | $^1$HNMR |
|---|---|---|---|---|
| 1-1 | Cl | 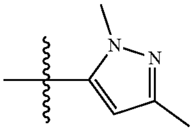 [SMILES: *c1cc(C)nn1C] | M-29 | $^1$H NMR (500 MHz, Chloroform-d) δ 7.46 (s, 1H), 6.47 (s, 1H), 4.23 (t, J = 7.5 Hz, 2H), 3.98 (s, 3H), 2.35 (s, 3H), 1.79-1.69 (m, 2H), 1.39-1.16 (m, 4H), 0.95 (t, J = 8.0 Hz, 3H). |
| 1-2 | Cl | 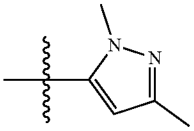 [SMILES: *c1cc(C)nn1C] | M-54 | $^1$H NMR (500 MHz, Chloroform-d) δ 7.43 (s, 1H), 6.49 (s, 1H), 3.98 (s, 3H), 2.85 (t, J = 8.0 Hz, 2H), 2.35 (s, 3H), 1.94-1.79 (m, 2H), 1.38-1.21 (m, 14H), 0.89 (t, J = 8.0 Hz, 3H). |
| 1-3 | Cl | 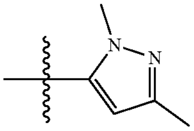 | M-79 | $^1$H NMR (500 MHz, Chloroform-d) δ 7.74 (dd, J = 7.5, 2.0 Hz, 1H), 7.63-7.55 (m, 2H), 7.53 (dd, J = 7.5, 2.0 Hz, 1H), 7.32-7.21 (m, 1H), 6.48 (s, 1H), 3.91 (s, 3H), 2.35 (s, 3H). |
| 1-4 | Cl | 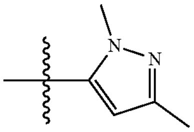 [SMILES: *c1cc(C)nn1C] | M-88 | $^1$H NMR (500 MHz, Chloroform-d) δ 8.25 (d, J = 2.0 Hz, 1H), 7.83 (dd, J = 7.5, 2.0 Hz, 1H), 7.57-7.50 (m, 2H), 6.49 (s, 1H), 4.00 (s, 3H), 2.35 (s, 3H). |
| 1-5 | Cl | 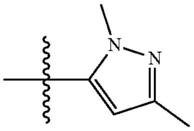 [SMILES: *c1cc(C)nn1C] | M-52 | $^1$H NMR (500 MHz, Chloroform-d) δ 7.50 (s, 1H), 7.30 (d, J = 2.5 Hz, 1H), 6.56 (s, 1H), 6.39 (dd, J = 2.5, 2.0 Hz, 1H), 5.51 (d, J = 2.0 Hz, 1H), 4.12 (s, 3H), 2.35 (s, 3H). |
| 1-6 | Cl | 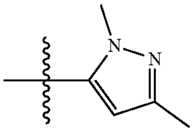 [SMILES: *c1cc(C)nn1C] | M-205 | $^1$H NMR (500 MHz, Chloroform-d) δ 7.56 (s, 1H), 7.00 (q, J = 6.5 Hz, 1H), 6.48 (s, 1H), 5.22 (hept, J = 6.5 Hz, 1H), 3.98 (s, 3H), 2.35 (s, 3H), 1.77 (d, J = 6.5 Hz, 3H), 1.29 (d, J = 6.5 Hz, 6H). |
| 1-7 | Cl | 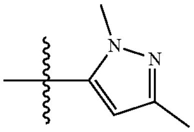 [SMILES: *c1cc(C)nn1C] | M-156 | $^1$H NMR (500 MHz, Chloroform-d) δ 7.52 (s, 1H), 6.41 (s, 1H), 4.03 (s, 3H), 3.60 (t, J = 7.5 Hz, 2H), 2.35 (s, 3H), 1.65-1.51 (m, 2H), 1.44-1.31 (m, 6H), 0.93 (t, J = 7.5 Hz, 3H). |
| 1-8 | Cl | 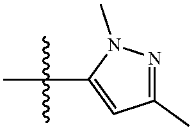 [SMILES: *c1cc(C)nn1C] | M-40 | $^1$H NMR (500 MHz, Chloroform-d) δ 7.41 (s, 1H), 6.33 (s, 1H), 3.97 (s, 3H), 2.91 (q, J = 6.5 Hz, 2H), 2.35 (s, 3H), 1.36 (t, J = 6.5 Hz, 3H). |
| 1-9 | Cl | 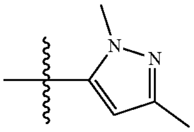 | M-63 | $^1$H NMR (500 MHz, Chloroform-d) δ 7.47 (s, 1H), 6.38 (s, 1H), 3.99 (s, 3H), 3.64-3.50 (m, 4H), 3.47-3.37 (m, 4H), 2.35 (s, 3H). |

TABLE 3-continued
Structure and $^1$HNMR data of the derivative Compound I-1
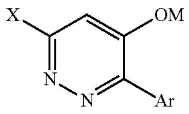
I-1
| No. | X | Ar | M | $^1$HNMR |
|---|---|---|---|---|
| 1-10 | Cl | 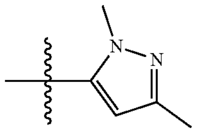 [SMILES: *c1cc(C)nn1C] | M-150 | $^1$H NMR (500 MHz, Chloroform-d) δ 7.43 (s, 1H), 6.50 (s, 1H), 3.97 (s, 3H), 2.35 (s, 3H), 2.16 (t, J = 7.5 Hz, 2H), 1.65-1.51 (m, 2H), 1.44-1.31 (m, 10H), 0.89 (t, J = 7.5 Hz, 3H). |
| 1-11 | Cl | 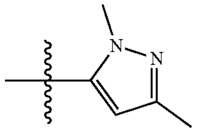 [SMILES: *c1cc(C)nn1C] | M-53 | $^1$H NMR (500 MHz, Chloroform-d) δ 7.43 (s, 1H), 6.49 (s, 1H), 3.98 (s, 3H), 2.85 (t, J = 8.0 Hz, 2H), 2.35 (s, 3H), 1.94-1.83 (m, 2H), 1.38-1.24 (m, 10H), 0.89 (t, J = 8.0 Hz, 3H). |
| 1-12 | CN | 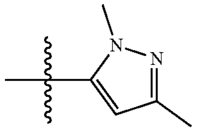 [SMILES: *c1cc(C)nn1C] | M-1 | |
| 1-13 | $NH_2$ | 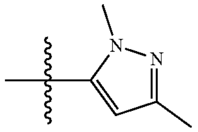 [SMILES: *c1cc(C)nn1C] | M-2 | |
| 1-14 | Ph | 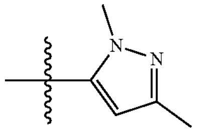 [SMILES: *c1cc(C)nn1C] | M-7 | |
| 1-15 | Br | 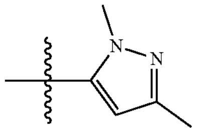 [SMILES: *c1cc(C)nn1C] | M-12 | |
| 1-16 | OH | 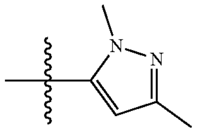 [SMILES: *c1cc(C)nn1C] | M-24 | |
| 1-17 | Cl | 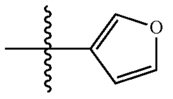 [SMILES: *c1ccoc1] | M-27 | $^1$H NMR (300 MHz, Chloroform-d) δ 7.65 (s, 1H), 7.51 (d, J = 2.4 Hz, 1H), 7.41 (s, 1H), 6.20 (d, J = 2.4 Hz, 1H), 4.23 (t, J = 7.3 Hz, 2H), 1.64-1.36 (m, 4H), 0.98 (t, J = 7.7 Hz, 3H). |
| 1-18 | $CONH_2$ | 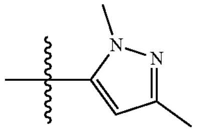 [SMILES: *c1cc(C)nn1C] | M-37 | |
| 1-19 | Cl | 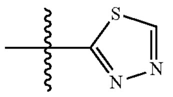 [SMILES: *c1nncs1] | M-58 | $^1$H NMR (300 MHz, Chloroform-d) δ 9.34 (s, 1H), 7.36 (s, 1H), 3.17 (s, 6H). |

TABLE 3-continued
Structure and $^1$HNMR data of the derivative Compound I-1
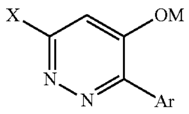
I-1
| No. | X | Ar | M | $^1$HNMR |
|---|---|---|---|---|
| 1-20 | Cl | 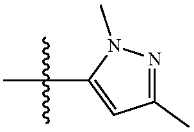 [SMILES: *c1cc(C)nn1C] | M-60 | |
| 1-21 | Cl | 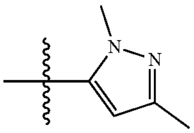 [SMILES: *c1cc(C)nn1C] | M-77 | |
| 1-22 | Cl | 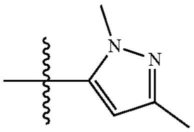 [SMILES: *c1cc(C)nn1C] | M-92 | |
| 1-23 | Cl | 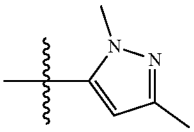 [SMILES: *c1cc(C)nn1C] | M-104 | |
| 1-24 | Cl | 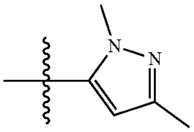 [SMILES: *c1cc(C)nn1C] | M-108 | |
| 1-25 | Cl | 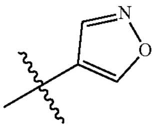 [SMILES: *c1cnoc1] | M-119 | $^1$H NMR (300 MHz, Chloroform-d) δ 8.09-7.99 (m, 2H), 7.91 (s, 1H), 1.72-1.62 (m, 1H), 1.07-0.89 (m, 2H), 0.72-0.63 (m, 2H). |
| 1-26 | Cl | 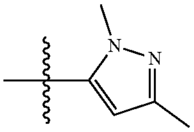 [SMILES: *c1cc(C)nn1C] | M-120 | |
| 1-27 | Cl | 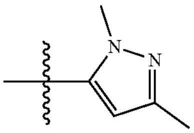 [SMILES: *c1cc(C)nn1C] | M-121 | |
| 1-28 | OEt | 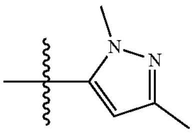 [SMILES: *c1cc(C)nn1C] | M-125 | |

TABLE 3-continued
Structure and $^1$HNMR data of the derivative Compound I-1
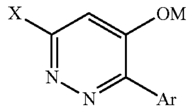
I-1
| No. | X | Ar | M | $^1$HNMR |
| --- | --- | --- | --- | --- |
| 1-29 | $OCF_3$ | 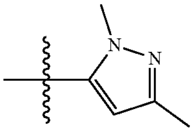 [SMILES: *c1cc(C)nn1C] | M-126 | |
| 1-30 | Cl | 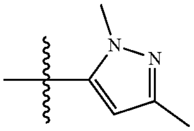 [SMILES: *c1cc(C)nn1C] | M-127 | |
| 1-31 | Cl | 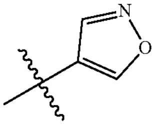 [SMILES: *c1cnoc1] | M-128 | $^1$H NMR (300 MHz, Chloroform-d) δ 8.17 (s, 1H), 8.10 (s, 1H), 7.92 (s, 1H), 7.78-7.68 (m, 2H), 7.51-7.41 (m, 2H), 2.42 (s, 3H). |
| 1-32 | Cl | 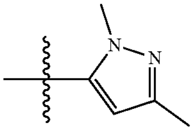 | M-131 | |
| 1-33 | Cl | 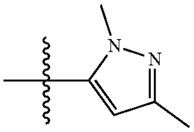 [SMILES: *c1cc(C)nn1C] | M-132 | |
| 1-34 | Cl | 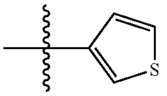 [SMILES: *c1ccsc1] | M-160 | $^1$H NMR (300 MHz, Chloroform-d) δ 7.53 (d, J = 2.4 Hz, 2H), 7.48-7.31 (m, 4H), 7.30-7.17 (m, 2H), 6.86 (d, J = 2.4 Hz, 1H). |
| 1-35 | $CHF_2$ | 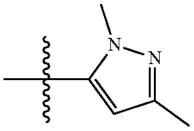 | M-162 | |
| 1-36 | Cl | 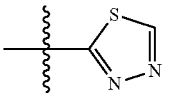 [SMILES: *c1nncs1] | M-165 | $^1$H NMR (300 MHz, Chloroform-d) δ 9.38 (s, 1H), 7.31 (s, 1H), 2.63 (s, 3H), 2.47 (s, 3H). |
| 1-37 | $CF_2CF_3$ | 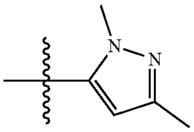 [SMILES: *c1cc(C)nn1C] | M-168 | |
| 1-38 | Cl | 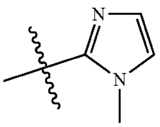 [SMILES: *c1nccn1C] | M-198 | $^1$H NMR (300 MHz, Chloroform-d) δ 7.57 (s, 1H), 7.35 (d, J = 2.5 Hz, 1H), 7.02 (d, J = 2.5 Hz, 1H), 4.34 (q, J = 8.1 Hz, 2H), 3.75 (s, 3H), 1.61 (t, J = 8.0 Hz, 3H). |

TABLE 3-continued
Structure and $^1$HNMR data of the derivative Compound I-1
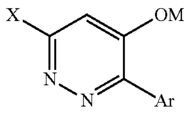
I-1
| No. | X | Ar | M | $^1$HNMR |
|---|---|---|---|---|
| 1-39 | Br | 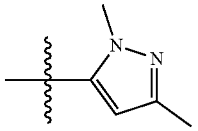 [SMILES: *c1cc(C)nn1C] | M-199 | |
| 1-40 | CN | 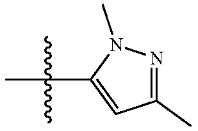 [SMILES: *c1cc(C)nn1C] | M-200 | |
| 1-41 | Me | 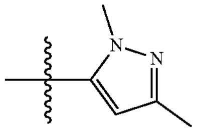 [SMILES: *c1cc(C)nn1C] | M-203 | |
| 1-42 | Cl | 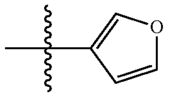 [SMILES: *c1ccoc1] | M-204 | $^1$H NMR (300 MHz, Chloroform-d) δ 7.73 (s, 1H), 7.60-7.47 (m, 2H), 6.71 (q, J = 6.8 Hz, 1H), 6.37 (d, J = 2.4 Hz, 1H), 4.79 (d, J = 8.0 Hz, 2H), 1.85 (d, J = 6.8 Hz, 3H), 1.32 (t, J = 8.0 Hz, 3H). |
| 1-43 | Cl | 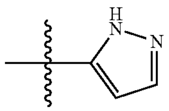 [SMILES: *c1ccn[nH]1] | M-207 | |
| 1-44 | Cl | 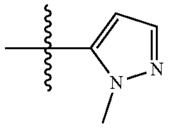 [SMILES: *c1ccnn1C] | M-208 | |
| 1-45 | Cl | 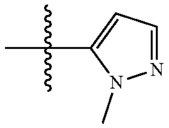 [SMILES: *c1ccnn1C] | M-209 | |
| 1-46 | OMe | 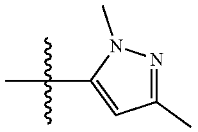 [SMILES: *c1cc(C)nn1C] | M-211 | |
| 1-47 | Cl | 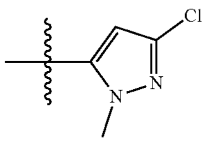 [SMILES: *c1cc(Cl)nn1C] | M-212 | $^1$H NMR (300 MHz, Chloroform-d) δ 7.34 (s, 1H), 6.76 (s, 1H), 4.02 (s, 3H), 2.47 (s, 6H). |
| 1-48 | Et | 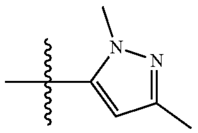 [SMILES: *c1cc(C)nn1C] | M-123 | |

TABLE 3-continued

Structure and $^1$HNMR data of the derivative Compound I-1

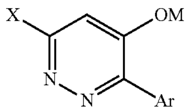

I-1

| No. | X | Ar | M | $^1$HNMR |
|---|---|---|---|---|
| 1-49 | F | 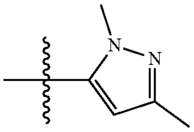 | M-216 | |
| 1-50 | Cl | 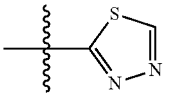 | M-40 | $^1$H NMR (300 MHz, Chloroform-d) δ 9.35 (s, 1H), 7.38 (s, 1H), 2.91 (q, J = 8.0 Hz, 2H), 1.37 (t, J = 8.0 Hz, 3H). |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route.

Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to beany limit of the reasonable scope thereof. Reagents of the following synthetic compound showed in the table can either be purchased from the market or easily prepared by those skilled in the art.

Examples of representative compounds are as follows:

1. Synthesis of Compound 1

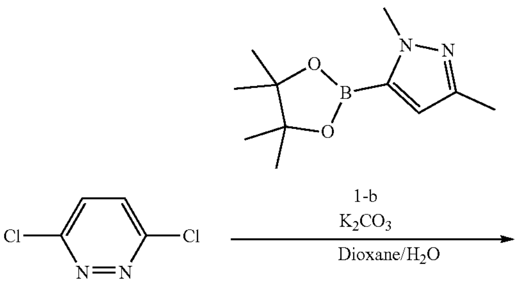

1-b 1-a

-continued

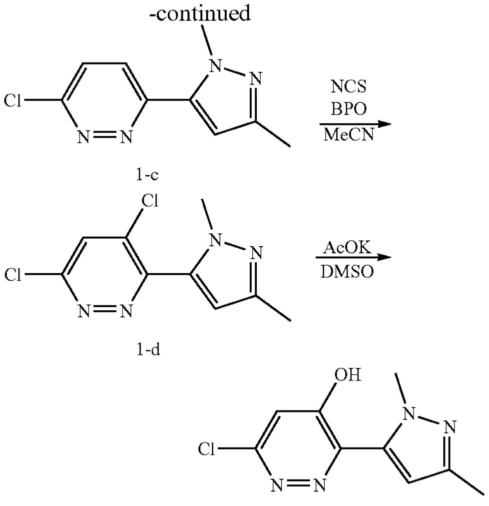

1-c 1-d

1

(1) To a three-necked round bottom flask, compound 1-a (10 g, 67 mmol), compound 1-b (14.9 g, 67 mmol) and potassium carbonate (27.8 g, 201 mmol) were charged, and nitrogen replacement was performed three times after the addition of 1,4-dioxane (100 mL)/water (20 mL). Pd(dppf)$Cl_2CH_2Cl_2$ (0.2 g) was added quickly under nitrogen protection and then nitrogen replacement was performed three times. The reaction solution was treated by nitrogen replacement for another three times and reacted at 100° C. for 16 h. After high performance liquid chromatography detection showed the completion of the reaction, the reaction system was concentrated and subjected to column chromatography separation to obtain 10 g (48 mmol, yield 71%) of compound 1-c (grey solid).

(2) To a three-necked round bottom flask, compound 1-c (10 g, 48 mmol), N-chloro succimide (6.4 g, 48 mmol), benzoyl peroxide (0.5 g, catalytic amount) and acetonitrile (100 mL) were charged and reacted at 80° C. for 16 h. A small amount of the raw material was detected to remain by high performance liquid chromatography. The reaction system was concentrated and subjected to column chromatography separation to obtain 5 g (21 mmol, yield 42%) of compound 1-d (white solid).

(3) To a three-necked round bottom flask, compound 1-d (1 g, 4 mmol), potassium acetate (2 g, 20 mmol) and 10 mL of DMSO were charged and reacted at 120° C. for 2 h. After high performance liquid chromatography detection showed the completion of the reaction, the reaction solution was cooled to 25° C. and added with 1M HCl in a dropwise manner with temperature control (no higher than 25° C.) till pH of the solution was around 5. Solid was precipitated out, which was collected by suction filtration, washed with a large quantity of water, purified by beating with methyl tert-butyl ether (20 mL) and a small amount of methanol (1 mL). After suction filtration, the solid was dried to obtain 300 mg (1.3 mmol, yield 32%) of compound 1 (off-white solid).

2. Synthesis of Compound 1-1

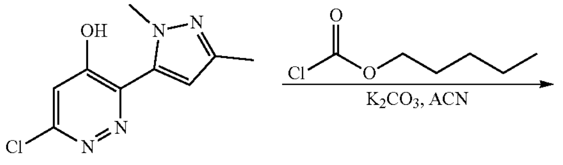

1

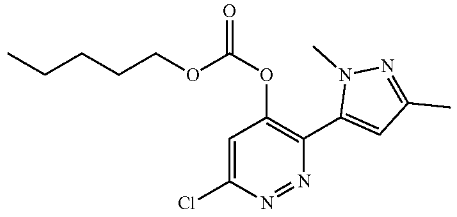

1-1

To a 50 mL eggplant-shaped flask, compound 1 (1 equiv.), potassium carbonate (3 equiv.) and acetonitrile (10V) were charged at room temperature, then added with

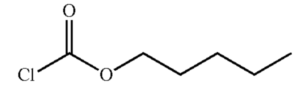

(1.2 equiv.) and stirred for 30 minutes after the addition. TLC detection showed the completion of the reaction. The reaction system was concentrated to remove acetonitrile, then dissolved with water (5V) and extracted with ethyl acetate (5V*3), then ethyl acetate was removed by vacuum distillation. The residue was separated through silica gel column chromatography (100 mesh to 200 mesh) to obtain the product with yield of 72%.

3. Synthesis of Compound 1-5

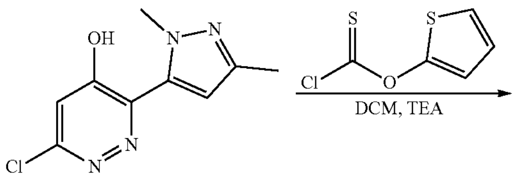

1

-continued

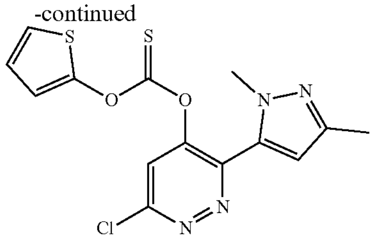

1-5

To a 50 mL eggplant-shaped flask, compound 1 (1 equiv.), triethyl amine (2 equiv.) and dichloromethane (5V) were charged in ice bath, and

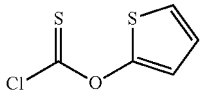

(1.2 equiv.) was added in ice bath and stirred for 30 minutes at room temperature. TLC detection showed the completion of the reaction. The reaction system was added with water and extracted with dichloromethane (5V*3), and then subjected to vacuum distillation to remove dichloromethane. The residue was separated through silica gel column chromatography (100 mesh to 200 mesh) to obtain the product with yield of 73%.

4. Synthesis of Compound 1-6

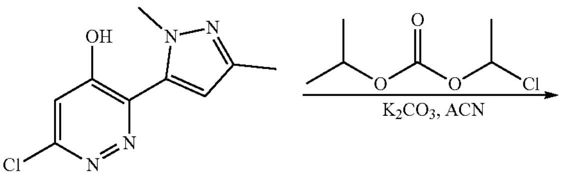

1

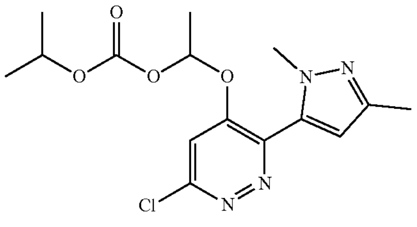

1-6

To a 50 mL eggplant-shaped flask, compound 1 (1 equiv.),

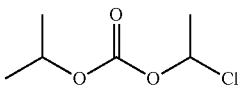

(1.2 equiv.), potassium carbonate (3 equiv.) and acetonitrile (10 V) were charged, then heated to 80° C. and stirred for 12 h. TLC detection showed the completion of the reaction. The reaction system was subjected to vacuum distillation to remove acetonitrile, then dissolved with water (5V) and extracted with ethyl acetate (5V*3), and then ethyl acetate was removed by vacuum distillation. The residue was separated through silica gel column chromatography (100 mesh to 200 mesh) to obtain the product with yield of 79%.

5. Synthesis of Compound 1-8

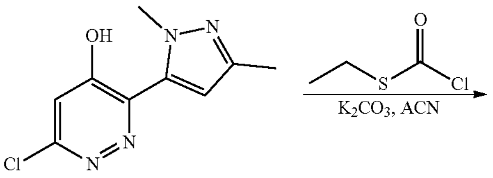

1

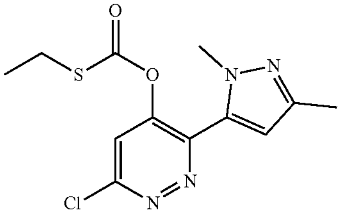

1-8

To a 50 mL eggplant-shaped flask, compound 1 (1 equiv.), potassium carbonate (3 equiv.) and acetonitrile (10 V) were charged, and

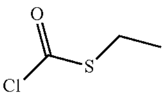

(1.2 equiv.) was added in a dropwise manner and stirred for 30 min at room temperature after the addition. TLC detection showed the completion of the reaction. The reaction system was subjected to vacuum distillation to remove acetonitrile, then dissolved with water (5V) and extracted with ethyl acetate (5V*3), and then ethyl acetate was removed by vacuum distillation. The residue was separated through silica gel column chromatography (100 mesh to 200 mesh) to obtain the product with yield of 72%.

6. Synthesis of Compound 1-9

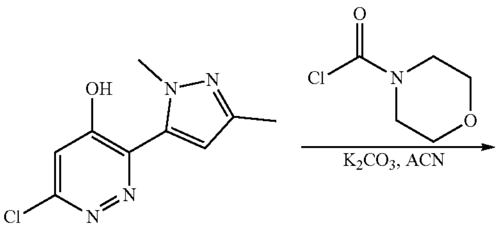

1

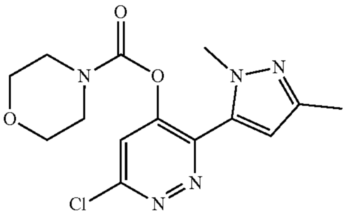

1-9

To a 50 mL eggplant-shaped flask, compound 1 (1 equiv.)

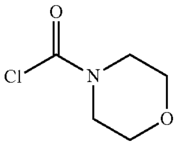

(1.2 equiv.), potassium carbonate (3 equiv.) and acetonitrile (10 V) were charged, then heated to 80° C. and stirred for 12 h. TLC detection showed the completion of the reaction. The reaction system was subjected to vacuum distillation to remove acetonitrile, then dissolved with water (5V) and extracted with ethyl acetate (5V*3), and then ethyl acetate was removed by vacuum distillation. The residue was separated through silica gel column chromatography (100 mesh to 200 mesh) to obtain the product with yield of 85%.

7. Synthesis of Compound 1-25

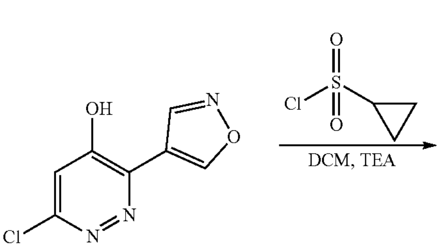

9

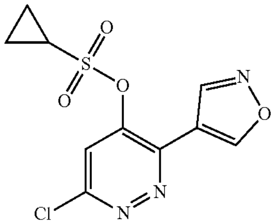

1-25

With reference to the preparation method of compound 1, compound 9 was prepared. Then to a 50 mL eggplant-shaped flask, compound 9 (1 equiv.), triethyl amine (3 equiv.) and dichloromethane (10 V) were charged in ice bath, and

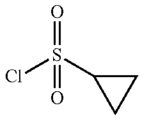

(1.2 equiv.) was added in dropwise manner in ice bath, and then stirred at room temperature for 30 min. TLC detection showed the completion of the reaction. The reaction system was added with water (5V) and extracted with dichloromethane (5V*3), and then subjected to vacuum distillation to remove dichloromethane. The residue was separated through silica gel column chromatography (100 mesh to 200 mesh) to obtain the product with yield of 81%.

8. Synthesis of Compound 1-36

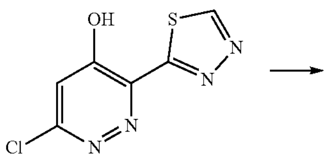

22

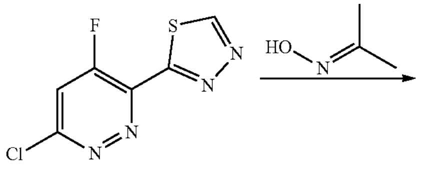

1-36-a

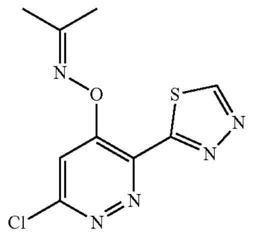

1-36

With reference to the preparation method of compound 1, compound 22 was prepared. Then to a 50 mL eggplant-shaped flask, compound 22 (1 equiv.), Phenofluor (1.5 equiv.), cesium fluoride (3 equiv.) and toluene (10 V) were charged, then heated to 80° C. and stirred for 18 h. TLC detection showed the completion of the reaction. Intermediate 1-36-a was obtained after work-up. To another 50 mL eggplant-shaped flask, compound 1-36-a (1 equiv.),

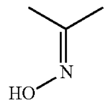

(1.2 equiv.), potassium carbonate (3 equiv.) and acetonitrile (10 V) were charged, then heated to 80° C. and stirred for 18 h. TLC detection showed the completion of the reaction. The reaction system was subjected to vacuum distillation to remove acetonitrile, then added with water (5V) and extracted with ethyl acetate (5V*3), and then ethyl acetate was removed by vacuum distillation. The residue was separated through silica gel column chromatography (100 mesh to 200 mesh) to obtain the product with yield of 65%.

9. Synthesis of Compound 1-47

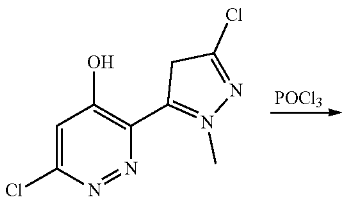

48

-continued

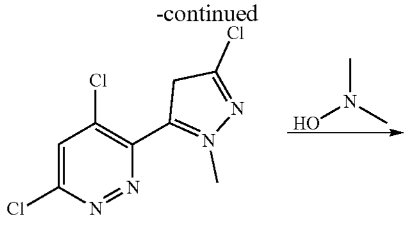

1-47-a

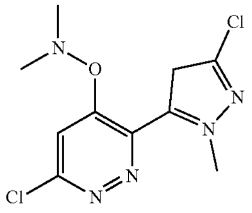

1-47

With reference to the preparation method of compound 1, compound 48 was prepared. Then to a 50 mL eggplant-shaped flask, compound 48 (1 equiv.), $POCl_3$ (1.5 equiv.), 1,2-dichloroethane (10 V) and 5% N,N-dimethylformamide were charged, then heated to 80° C. and stirred for 6 h. TLC detection showed the completion of the reaction. Water (5V) was added for dissolution and extracted with 1,2-dichloromethane (5V*3), and then 1,2-dichloroethane was removed by vacuum distillation to obtain compound 1-47a. To another 50 mL eggplant-shaped flask, compound 1-47-a (1 equiv.),

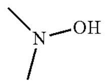

(1.2 equiv.), potassium hydroxide (3 equiv.) and N,N-dimethyl formamide (10 V) were charged, then heated to 100° C. and stirred for 18 h. TLC detection showed the completion of the reaction. The reaction system was diluted with water (5V) and extracted with ethyl acetate (5V*3), and then ethyl acetate was removed by vacuum distillation. The residue was separated through silica gel column chromatography (100 mesh to 200 mesh) to obtain the product with yield of 48%.

Evaluation of Biological Activity:

The activity level standard of harmful plant destruction (i.e. growth inhibition rate) is as follows:

Level 10: completely dead;

Level 9: above 90% growth inhibition rate;

Level 8: above 80% growth inhibition rate;

Level 7: above 70% growth inhibition rate;

Level 6: above 60% growth inhibition rate;

Level 5: above 50% growth inhibition rate;

Level 4: above 40% growth inhibition rate;

Level 3: above 30% growth inhibition rate;

Level 2: above 20% growth inhibition rate;

Level 1: below 20% growth inhibition rate;

Level 0: no effect.

The above described growth inhibition rates are fresh weight inhibition rates.

Experiment of post-emergence test: monocotyledonous and dicotyledonous weed seeds as well as main crop seeds (i.e., wheat, corn, rice, soybean, cotton, oilseed rape, millet and sorghum) were put into a plastic pot loaded with soil, then covered with 0.5-2 cm of soil, and the seeds were allowed to grow in good greenhouse environment. The test plants were treated at 4-5 leaf stage 2-3 weeks after sowing. The test compounds of the invention were dissolved in acetone respectively, then added with Tween-80 and diluted by a certain amount of water to give solutions with certain concentrations. The solution was sprayed to the plants with a sprayer. The plants were cultured for 3 weeks in the greenhouse. The experiment results of weed controlling effect after 3 weeks were listed in Table 3 and Table 4.

TABLE 3

Experiment on weed control effect of compounds of Formula I in Post-emergence stage

| Compound No. | Chenopodiaceae | *Rorippa indica* | *Amaranthus retroflexus* | *Veronica polita* | Dose |
|---|---|---|---|---|---|
| 1 | 10 | 10 | 10 | 10 | 3000 g/ha |
| 3 | 10 | 10 | 10 | 10 | 3000 g/ha |
| 4 | 10 | 10 | 10 | 10 | 3000 g/ha |
| 27 | 10 | 10 | 10 | 10 | 3000 g/ha |
| 29 | 10 | 10 | 10 | 10 | 3000 g/ha |
| 33 | 10 | 10 | 10 | 10 | 3000 g/ha |
| 44 | 10 | 10 | 10 | 10 | 3000 g/ha |
| 45 | 10 | 10 | 10 | 10 | 3000 g/ha |
| 48 | 10 | 10 | 10 | 10 | 3000 g/ha |
| 54 | 10 | 10 | 10 | 10 | 3000 g/ha |
| 56 | 10 | 10 | 10 | 10 | 3000 g/ha |
| 61 | 10 | 10 | 10 | 10 | 3000 g/ha |
| 71 | 10 | 10 | 10 | 10 | 3000 g/ha |
| 72 | 10 | 10 | 10 | 10 | 3000 g/ha |
| 73 | 10 | 10 | 10 | 10 | 3000 g/ha |
| 74 | 10 | 10 | 10 | 10 | 3000 g/ha |
| 75 | 10 | 10 | 10 | 10 | 3000 g/ha |
| 76 | 10 | 10 | 10 | 10 | 3000 g/ha |
| 77 | 10 | 10 | 10 | 10 | 3000 g/ha |
| 78 | 10 | 10 | 10 | 10 | 3000 g/ha |
| 79 | 10 | 10 | 10 | 10 | 3000 g/ha |
| 80 | 10 | 10 | 10 | 10 | 3000 g/ha |
| 81 | 10 | 10 | 10 | 10 | 3000 g/ha |
| 82 | 10 | 10 | 10 | 10 | 3000 g/ha |
| 95 | 10 | 10 | 10 | 10 | 3000 g/ha |
| 130 | 10 | 10 | 10 | 10 | 3000 g/ha |

TABLE 4

Experiment on weed control effect of derivatives of Formula I-1 in Post-emergence stage (2000 g/ha)

| Compound No. | *Amaranthus retroflexus* | Chenopodiaceae | *Setaria viridis* | *Veronica polita* |
|---|---|---|---|---|
| 1-1 | 10 | 10 | 10 | 10 |
| 1-2 | 10 | 10 | 10 | 10 |
| 1-3 | 10 | 10 | 10 | 10 |
| 1-4 | 10 | 10 | 10 | 10 |
| 1-5 | 10 | 10 | 10 | 10 |
| 1-6 | 10 | 10 | 10 | 10 |
| 1-7 | 10 | 10 | 10 | 10 |
| 1-8 | 10 | 10 | 10 | 10 |
| 1-9 | 10 | 10 | 10 | 10 |
| 1-10 | 10 | 10 | 10 | 10 |
| 1-11 | 10 | 10 | 10 | 10 |

Comparative Experiment

The post-emergence test conditions were the same as above, and the results are shown in Table 5.

Control Compound A:

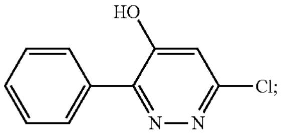 [SMILES: Oc1cc(Cl)nnc1-c1ccccc1]

Control Compound B:

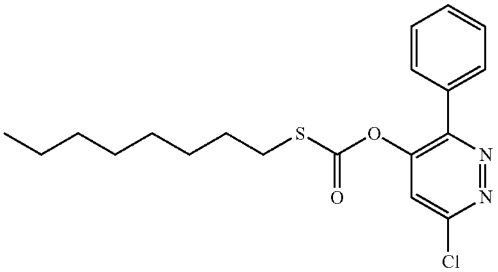 [SMILES: CCCCCCCCSC(=O)Oc1cc(Cl)nnc1-c1ccccc1]

TABLE 5

| Results of comparison experiment | | | | | | |
|---|---|---|---|---|---|---|
| Compound NO. | *Echinochloa crus-galli* | *Setaria viridis* | *Digitaria sanguinalis* | *Rorippa indica* | *Veronica polita* | Dose |
| 1 | 8 | 10 | 7 | 10 | 10 | 300 g/ha |
| 29 | 8 | 10 | 6 | 10 | 9 | 300 g/ha |
| 33 | N | N | N | 10 | 10 | 300 g/ha |
| 1-1 | 8 | 10 | 8 | 10 | 10 | 300 g/ha |
| 1-2 | 8 | 10 | 10 | 10 | 10 | 300 g/ha |
| 1-3 | 9 | 10 | 9 | 10 | 10 | 300 g/ha |
| 1-11 | 9 | 9 | 7 | 10 | 10 | 300 g/ha |
| Control Compound A | 0 | 2 | 0 | 2 | 5 | 300 g/ha |
| Control Compound B | 0 | 2 | 0 | 3 | 5 | 300 g/ha |

Note:
N means no data.

It can be seen from the above table, the compounds of the present invention have better herbicidal activity than the control compounds A and B.

Experiment of Pre-Emergence Test:

Seeds of monocotyledonous and dicotyledonous weeds and main crops (e.g. wheat, corn, rice, soybean, cotton, oilseed rape, millet and sorghum) were put into a plastic pot loaded with soil and covered with 0.5-2 cm of soil. The test compounds of the present invention was dissolved with acetone, then added with Tween-80, diluted by a certain amount of water to reach a certain concentration, and sprayed immediately after sowing. The obtained seeds were incubated for 4 weeks in the greenhouse after spraying. The test results were observed 3 weeks later. It was observed that the herbicides of the present invention mostly had excellent effect at dose of 250 g/ha, especially to weeds such as *Echinochloa crusgalli, Digitaria sanguinalis* and *Abutilon theophrasti*, etc., and many compounds had good selectivity for corn, wheat, rice, soybean, oilseed rape, etc.

It is found in the experiment that the compounds of the present invention generally have good weed control efficacy, especially for major weeds which are widely occurred in corn, rice and wheat fields, and have excellent commercial value. Above all, it is noted that the compound of the invention have extremely high activity to broadleaf weeds, which are resistant to ALS inhibitor.

Transplanted rice safety evaluation and weed control effect evaluation in rice field:

Rice field soil was loaded into a 1/1,000,000 ha pot. The seeds of *Echinochloa crusgalli, Scirpus juncoides, Bidens tripartite* and *Sagittaria trifolia* L. were sowed and gently covered with soil, then left to stand still in greenhouse in the state of 0.5-1 cm of water storage. The tuber of *Sagittaria trifolia* L. was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli, Scirpus juncoides* and *Bidens tripartite* reached 0.5 leaf stage and *Sagittaria trifolia* L. reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *Echinochloa crusgalli, Scirpus juncoides, Bidens tripartite* and *Sagittaria trifolia* L. 14 days after the treatment of the compound of the invention and the fertility condition of rice 21 days after the treatment of the compound of the invention respectively with the naked eye. Evaluate the weed control effect with 1-10 activity standard level. It has been found that many of the compounds of the present invention have excellent activity and selectivity, especially for *Sagittaria trifolia* L. and *Echinochloa crusgalli.*

Note: The seeds of *Echinochloa crusgalli, Scirpus juncoides, Sagittaria trifolia* L. and *Bidens tripartite* were collected from Heilongjiang Province of China. Tests indicated that the weeds were resistant to common rate of pyrazosulfuron-ethyl.

At the same time, it is found after several tests that the compound and the composition of the present invention have good selectivity to many gramineae grasses such as *Zoysia japonica*, bermuda grass, tall fescue, bluegrass, ryegrass and seashore paspalum etc, and are able to control many important grass weeds and broadleaf weeds. The compounds also show excellent selectivity and commercial value in the tests on wheat, corn, rice, sugarcane, soybean, cotton, oil sunflower, potato, orchards and vegetables in different herbicide application methods.

What is claimed is:

1. A five-membered ring-substituted pyridazinol compound of Formula I or a derivative thereof:

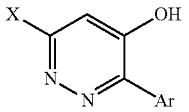

I wherein, X is halogen, alkyl, halogenated alkyl, alkoxy, halogenated alkoxy, $R_1R_2N—(C{=}O)—$, $R_1R_2N—$, hydroxy, or phenyl;

Ar is

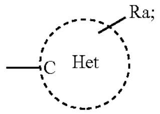

Het is a 5-membered unsaturated ring, comprising, besides the 1-C atom, 0 to 4 atoms or radicals as follows to form the ring: O, $NR_b$, S;

$R_a$ is one or more groups selected from: hydrogen, halogen, cyano, nitro, azido, a halogen-containing or not containing group selected from alkyl, alkenyl, alkynyl, cycloalkyl, cycloalkenyl, and cycloalkylalkyl, a group selected from aryl, arylalkyl, heteroaryl, and heteroarylalkyl, which is unsubstituted or substituted, $R-O-(CH_2)_n-$, $R-O-(CH_2)_p-O-(CH_2)_q-$, $R-O-(CH_2)_p-S-(CH_2)_q-$, $R-S-(CH_2)_n-$, $R-S-(CH_2)_p-O-(CH_2)_q-$, $R-S-(CH_2)_p-S-(CH_2)_q-$, $R-O-(CH_2)_n-(C{=}O)-(CH_2)_q-(O)_m-$, $R-S-(CH_2)_n-(C{=}S)-(CH_2)_q-(S)_m-$, $R-O-(CH_2)_n-(C{=}O)-(CH_2)_q-(S)_m-$, $R-O-(CH_2)_n-(C{=}S)-(CH_2)_q-(O)_m-$, $R-S-(CH_2)_n-(C{=}O)-(CH_2)_q-(O)_m-$, $R-O-(CH_2)_n-(C{=}S)-(CH_2)_q-(S)_m-$, $R-S-(CH_2)_n-(C{=}O)-(CH_2)_q-(S)_m-$, $R-S-(CH_2)_n-(C{=}S)-(CH_2)_q-(O)_m-$, $R-(C{=}O)-(CH_2)_n-$, $R-(C{=}S)-(CH_2)_n-$, $R-(C{=}O)-(CH_2)_n-O-(CH_2)_q-$, $R-(C{=}S)-(CH_2)_n-S-(CH_2)_q-$, $R-(C{=}O)-(CH_2)_n-S-(CH_2)_q-$, $R-(C{=}S)-(CH_2)_n-O-(CH_2)_q-$, $R-SO-(CH_2)_n-(O)_m-$, $R-SO-(CH_2)_n-(S)_m-$, $R-SO-(CH_2)_n-(NR_3)_m-$, $R-SO_2-(CH_2)_n-(O)_m-$, $R-SO_2-(CH_2)_n-(S)_m-$, $R-SO_2-(CH_2)_n-(NR_3)_m-$, $R_1R_2N-(CH_2)_n-$, $R_1R_2N-(CH_2)_n-O-(CH_2)_q-(O)_m-$, $R_1R_2N-(CH_2)_n-O-(CH_2)_q-(S)_m-$, $R_1R_2N-(CH_2)_n-O-(CH_2)_q-(NR_3)_m-$, $R_1R_2N-(CH_2)_n-(C{=}O)-(CH_2)_q-(O)_m-$, $R_1R_2N-(CH_2)_n-(C{=}O)-(CH_2)_q-(S)_m-$, $R_1R_2N-(CH_2)-(C{=}O)-(CH_2)_q-(NR_3)_m-$, $R_1R_2N-(CH_2)_n-SO_2-(CH_2)_q-(O)_m-$, $R_1R_2N-(CH_2)_n-SO_2-(CH_2)_q-(S)_m-$, $R_1R_2N-(CH_2)_n-SO_2-(CH_2)_q-(NR_3)_m-$, $R_1R_2PO_3-(O)_m-(CH_2)_q-$, $R_1R_2R_3SiO-(CH_2)_q-$, $R_1R_2R_3Si-(CH{=}CH)_m-(CH_2)_q-$, $R_1R_2C{=}N-(O)_m-(CH_2)_n-$, and $R_1R_2C{=}N-NH-(CH_2)_n-$; or two adjacent $R_a$ form $-OCH_2O-$, $-CH_2CH_2O-$, $-OCH_2CH_2O-$, $-OCH(CH_3)O-$, $-OC(CH_3)_2O-$, $-OCF_2O-$, $-CF_2CF_2O-$, $-OCF_2CF_2O-$, or $-CH{=}CH-CH{=}CH-$;

m is 0 or 1, n and q are independently an integer from 0 to 8, p is an integer from 1 to 8;

R is hydrogen, a halogen-containing or not containing group selected from alkyl, alkenyl, alkynyl, cycloalkyl, cycloalkenyl, and cycloalkylalkyl, or a group selected from aryl, arylalkyl, heteroaryl, and heteroarylalkyl, which is unsubstituted or substituted;

$R_b$, $R_1$, $R_2$, $R_3$ are each independently hydrogen, nitro, hydroxy, amino, a halogen-containing or not containing group selected from alkyl, alkenyl, alkynyl, cycloalkyl, cycloalkenyl, cycloalkylalkyl, alkoxy, alkenyloxy, alkynyloxy, cycloalkyloxy, alkoxyalkyl, alkoxycarbonyl, alkylsulfanylcarbonyl, alkylsulfonyl, alkylsulfonylalkyl, alkylcarbonyl, alkylcarbonylalkyl, alkylcarbonyloxy, alkylamino, alkylaminocarbonyl, alkoxyaminocarbonyl, alkoxycarbonylalkyl, alkylaminocarbonylalkyl, trialkylsilyl, and dialkylphosphonyl, or a group selected from 6-membered heterocyclyl, aryl, arylalkyl, aryloxy, arylalkyloxy, aryloxyalkyl, arylcarbonyl, arylsulfonyl, heteroaryl, heteroarylalkyl, heteroaryloxy, heteroarylalkyloxy, heteroaryloxyalkyl, heteroarylcarbonyl, and heteroarylsulfonyl, which is unsubstituted or substituted; or $R_1R_2N$-forms a 6-membered heterocyclyl; or adjacent $R_a$ and $R_b$ form $-CH_2CH_2NR_3CH_2-$.

2. The five-membered ring-substituted pyridazinol compound or a derivative thereof according to claim 1, wherein, X is halogen, $C_{1-8}$alkyl, halogenated $C_{1-8}$alkyl, $C_{1-8}$alkoxy, halogenated $C_{1-8}$alkoxy, $R_1R_2N-(C{=}O)-$, $R_1R_2N-$, hydroxy, or phenyl;

Ar is

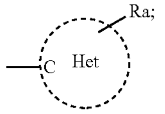

Het is a 5-membered unsaturated heterocycle, comprising, besides the 1-C atom, 1 to 4 atoms or radicals as follows to form the ring: O, $NR_b$, S;

$R_a$ is one or more substituents selected from: hydrogen, halogen, cyano, nitro, azido, a halogen-containing or not containing group selected from $C_{1-8}$alkyl, $C_{2-8}$alkenyl, $C_{2-8}$alkynyl, $C_{3-8}$cycloalkyl, $C_{5-8}$cycloalkenyl, and $C_{3-8}$cycloalkyl-$C_{1-8}$alkyl, aryl, aryl-$C_{1-8}$alkyl, heteroaryl, heteroaryl-$C_{1-8}$alkyl, each of said aryl, aryl-$C_{1-8}$alkyl, heteroaryl, or heteroaryl-$C_{1-8}$alkyl is unsubstituted or substituted with 1-5 groups independently selected from halogen, cyano, nitro, hydroxy, carboxyl, sulfhydryl, amino, and a halogen-containing or not containing group selected from $C_{1-8}$alkyl, $C_{3-8}$cycloalkyl, $C_{3-8}$cycloalkyl-$C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, $C_{1-8}$alkylsulfonyl, $C_{1-8}$alkylamino, and $C_{1-8}$alkylcarbonyloxy, $R-O-(CH_2)_n-$, $R-O-(CH_2)_p-O-(CH_2)_q-$, $R-O-(CH_2)_p-S-(CH_2)_q-$, $R-S-(CH_2)_n-$, $R-S-(CH_2)_p-O-(CH_2)_q-$, $R-S-(CH_2)_p-S-(CH_2)_q-$, $R-O-(CH_2)_n-(C{=}O)-(CH_2)_q-$, $R-S-(CH_2)_n-(C{=}S)-(CH_2)_q-$, $R-O-(CH_2)_n-(C{=}S)-(CH_2)_q-$, $R-S-(CH_2)_n-(C{=}O)-(CH_2)_q-$, $R-O-(C{=}O)-(CH_2)_q-(O)_m-$, $R-S-(C{=}S)-(CH_2)_q-(S)_m-$, $R-O-(C{=}O)-(CH_2)_q-(S)_m-$, $R-O-(C{=}S)-(CH_2)_q-(O)_m-$, $R-S-(C{=}O)-(CH_2)_q-(O)_m-$, $R-O-(C{=}S)-(CH_2)_q-(S)_m-$, $R-S-(C{=}O)-(CH_2)_q-(S)_m-$, $R-S-(C{=}S)-(CH_2)_q-(O)_m-$, $R-O-(CH_2)_n-(C{=}O)-(O)_m-$, $R-S-(CH_2)_n-(C{=}S)-(S)_m-$, $R-O-(CH_2)_n-(C{=}O)-(S)_m-$, $R-O-(CH_2)_n-(C{=}S)-(O)_m-$, $R-S-(CH_2)_n-(C{=}O)-(O)_m-$, $R-O-(CH_2)_n-(C{=}S)-(S)_m-$, $R-S-(CH_2)-(C{=}O)-(S)_m-$, $R-S-(CH_2)_n-(C{=}S)-(O)_m-$, $R-(C{=}O)-$, $R-(C{=}S)-$, $R-(C{=}O)-(CH_2)_n-O-$, $R-(C{=}S)-(CH_2)_n-S-$, $R-(C{=}O)-(CH_2)_n-S-$, $R-(C{=}S)-(CH_2)_n-O-$, $R-(C{=}O)-O-(CH_2)_q-$, $R-(C{=}S)-S-(CH_2)_q-$, $R-(C{=}O)-S-(CH_2)_q-$, $R-(C{=}S)-O-(CH_2)_q-$, $R-SO-(O)_m-$, $R-SO-(S)_m-$, $R-SO-(NR_3)_m-$, $R-SO_2-(O)_m-$, $R-SO_2-(S)_m-$, $R-SO_2-(NR_3)_m-$, $R-SO-(CH_2)_n-$, $R-SO_2-(CH_2)_n-$, $R_1R_2N-$, $R_1R_2N-(CH_2)_n-O-(CH_2)_q-$, $R_1R_2N-(CH_2)-(C{=}O)-(CH_2)_q-$, $R_1R_2N-(CH_2)_n-SO_2-(CH_2)_q-$, $R_1R_2N-(CH_2)_n-(C{=}O)-(O)_m-$, $R_1R_2N-(CH_2)_n-(C{=}O)-(S)_m-$, $R_1R_2N-(CH_2)_n-(C{=}O)-(NR_3)_m-$, $R_1R_2N-(CH_2)_n-SO_2-(O)_m-$, $R_1R_2N-(CH_2)_n-SO_2-(S)_m-$, $R_1R_2N-(CH_2)_n-SO_2-(NR_3)_m-$, $R_1R_2N-$ (C═O)—$(CH_2)_n$—$(O)_m$—, $R_1R_2N$—(C═O)—$(CH_2)_n$—$(S)_m$—, $R_1R_2N$—(C═O)—$(CH_2)_n$—$(NR_3)_m$—, $R_1R_2N$—$SO_2$—$(CH_2)_q$—$(O)_m$—, $R_1R_2N$—$SO_2$—$(CH_2)_q$—$(S)_m$—, $R_1R_2N$—$SO_2$—$(CH_2)_q$—$(NR_3)_m$—, $R_1R_2N$—$(CH_2)_n$—O—, $R_1R_2N$—O—$(CH_2)_q$—, $R_1R_2PO_3$—$(O)_m$—, $R_1R_2R_3SiO$—, $R_1R_2R_3Si$—(CH═CH)$_m$—, $R_1R_2C$═N—$(O)_m$—, and $R_1R_2C$═N—NH—; or two adjacent $R_a$ form —$OCH_2O$—, —$CH_2CH_2O$—, —$OCH_2CH_2O$—, —$OCH(CH_3)O$—, —$OC(CH_3)_2O$—, —$OCF_2O$—, —$CF_2CF_2O$—, —$OCF_2CF_2O$—, or —CH═CH—CH═CH—;

m is 0 or 1, n and q are independently an integer from 0 to 6, p is an integer from 1 to 6;

R is hydrogen, a halogen-containing or not containing group selected from $C_{1-8}$alkyl, $C_{2-8}$alkenyl, $C_{2-8}$alkynyl, $C_{3-8}$cycloalkyl, $C_{5-8}$cycloalkenyl, and $C_{3-8}$cycloalkyl-$C_{1-8}$alkyl, aryl, aryl-$C_{1-8}$alkyl, heteroaryl, or heteroaryl-$C_{1-8}$alkyl, each of said aryl, aryl-$C_{1-8}$alkyl, heteroaryl, or heteroaryl-$C_{1-8}$alkyl is unsubstituted or substituted with 1-5 groups substituents independently selected from halogen, cyano, nitro, hydroxy, carboxyl, sulfhydryl, amino, and a halogen-containing or not containing group selected from $C_{1-8}$alkyl, $C_{3-8}$cycloalkyl, $C_{3-8}$cycloalkyl-$C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, $C_{1-8}$alkylsulfonyl, $C_{1-8}$alkylamino, and $C_{1-8}$alkylcarbonyloxy;

$R_b$, $R_1$, $R_2$, $R_3$ are each independently hydrogen, nitro, hydroxy, amino, a halogen-containing or not containing group selected from $C_{1-8}$alkyl, $C_{2-8}$alkenyl, $C_{2-8}$alkynyl, $C_{3-8}$cycloalkyl, $C_{5-8}$cycloalkenyl, $C_{3-8}$cycloalkyl-$C_{1-8}$alkyl, $C_{1-8}$alkoxy, $C_{2-8}$alkenyloxy, $C_{2-8}$alkynyloxy, $C_{3-8}$cycloalkyloxy, $C_{1-8}$alkoxy-$C_{1-8}$alkyl, $C_{1-8}$alkoxycarbonyl, $C_{1-8}$alkylcarbonyl-$C_{1-8}$alkyl, $C_{1-8}$alkylsulfanylcarbonyl, $C_{1-8}$alkylsulfonyl, $C_{1-8}$alkylsulfonyl-$C_{1-8}$alkyl, $C_{1-8}$alkylcarbonyl, $C_{1-8}$alkylcarbonyloxy, $C_{1-8}$alkylamino, $C_{1-8}$alkylaminocarbonyl, $C_{1-8}$alkoxyaminocarbonyl, $C_{1-8}$alkoxycarbonyl-$C_{1-8}$alkyl, $C_{1-8}$alkylaminocarbonyl-$C_{1-8}$alkyl, tri$C_{1-8}$alkylsilyl, and di$C_{1-8}$alkylphosphonyl, 6-membered heterocyclyl, aryl, aryl-$C_{1-8}$alkyl, aryloxy, aryl-$C_{1-8}$alkyloxy, aryloxy-$C_{1-8}$alkyl, arylcarbonyl, arylsulfonyl, heteroaryl, heteroaryl-$C_{1-8}$alkyl, heteroaryloxy, heteroaryl-$C_{1-8}$alkyloxy, heteroaryloxy-$C_{1-8}$alkyl, heteroarylcarbonyl, or heteroarylsulfonyl, each of said 6-membered heterocyclyl, aryl, aryl-$C_{1-8}$alkyl, aryloxy, aryl-$C_{1-8}$alkyloxy, aryloxy-$C_{1-8}$alkyl, arylcarbonyl, arylsulfonyl, heteroaryl, heteroaryl-$C_{1-8}$alkyl, heteroaryloxy, heteroaryl-$C_{1-8}$alkyloxy, heteroaryloxy-$C_{1-8}$alkyl, heteroarylcarbonyl, or heteroarylsulfonyl is unsubstituted or substituted with 1-5 groups independently selected from halogen, cyano, nitro, hydroxy, carboxyl, sulfhydryl, amino, and a halogen-containing or not containing group selected from $C_{1-8}$alkyl, $C_{3-8}$cycloalkyl, $C_{3-8}$cycloalkyl-$C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, $C_{1-8}$alkylsulfonyl, $C_{1-8}$alkylamino, and $C_{1-8}$alkylcarbonyloxy; or $R_1R_2N$— forms a 6-membered heterocyclyl containing or not containing other hetero atoms; or adjacent $R_a$ and $R_b$ form —$CH_2CH_2NR_3CH_2$—;

the derivative refers to an agriculturally acceptable derivative of the 4-hydroxy of the pyridazine ring of Formula I.

3. The five-membered ring-substituted pyridazinol compound or a derivative thereof according to claim 1, wherein, X is fluorine, chlorine, bromine, iodine, $C_{1-6}$alkyl, halogenated $C_{1-6}$alkyl, $C_{1-6}$alkoxy, halogenated $C_{1-6}$alkoxy, $R_1R_2N$—(C═O)—, $R_1R_2N$—, hydroxy, or phenyl;

Ar is

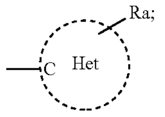

Het is a 5-membered unsaturated heterocycle, comprising, besides the 1-C atom, 2, 3, or 4 atoms or radicals as follows to form the ring: O, $NR_b$, S;

$R_a$ is one or more substituents selected from: hydrogen, fluorine, chlorine, bromine, cyano, nitro, azido, a fluoro-, chloro-, or bromo-containing or not containing group selected from $C_{1-6}$alkyl, $C_{2-6}$alkenyl, $C_{2-6}$alkynyl, $C_{3-6}$cycloalkyl, $C_{5-6}$cycloalkenyl, and $C_{3-6}$cycloalkyl-$C_{1-6}$alkyl, aryl, aryl-$C_{1-6}$alkyl, heteroaryl, heteroaryl-$C_{1-6}$alkyl, each of said aryl, aryl-$C_{1-6}$alkyl, heteroaryl, or heteroaryl-$C_{1-6}$alkyl is unsubstituted or substituted with 1-3 groups independently selected from fluorine, chlorine, bromine, cyano, nitro, hydroxy, carboxyl, sulfhydryl, amino, and a fluoro-, chloro-, or bromo-containing or not containing group selected from $C_{1-6}$alkyl, $C_{3-6}$cycloalkyl, $C_{3-6}$cycloalkyl-$C_{1-6}$alkyl, $C_{2-6}$alkenyl, $C_{2-6}$alkynyl, $C_{1-6}$alkoxy, $C_{1-6}$alkylcarbonyl, $C_{1-6}$alkoxycarbonyl, $C_{1-6}$alkylsulfonyl, $C_{1-6}$alkylamino, and $C_{1-6}$alkylcarbonyloxy, R—O—, R—O—$(CH_2)_p$—O—, R—O—$(CH_2)_p$—S—, R—S—, R—S—$(CH_2)_p$—O—, R—S—$(CH_2)_p$—S—, R—O—(C═O)—$(O)_m$—, R—S—(C═S)—$(S)_m$—, R—O—(C═O)—$(S)_m$—, R—O—(C═S)—$(O)_m$—, R—S—(C═O)—$(O)_m$—, R—O—(C═S)—$(S)_m$—, R—S—(C═O)—$(S)_m$—, R—S—(C═S)—$(O)_m$—, R—O—(C═O)—$(CH_2)_q$—, R—S—(C═S)—$(CH_2)_q$—, R—O—(C═S)—$(CH_2)_q$—, R—S—(C═O)—$(CH_2)_q$—, R—O—$(CH_2)_n$—(C═O)—, R—S—$(CH_2)_n$—(C═S)—, R—O—$(CH_2)_n$—(C═S)—, R—S—$(CH_2)_n$—(C═O)—, R—(C═O)—, R—(C═S)—, R—(C═O)—O—, R—(C═S)—S—, R—(C═O)—S—, R—(C═S)—O—, R—SO—, R—$SO_2$—, $R_1R_2N$—, $R_1R_2N$—O—, $R_1R_2N$—(C═O)—$(CH_2)_p$—, $R_1R_2N$—(C═O)—$(O)_m$—, $R_1R_2N$—(C═O)—$(S)_m$—, $R_1R_2N$—(C═O)—$(NR_3)_m$—, $R_1R_2N$—$SO_2$—$(CH_2)_p$—, $R_1R_2N$—$SO_2$—, $R_1R_2N$—$(CH_2)_p$—(C═O)—, $R_1R_2N$—$(CH_2)_p$—$SO_2$—, $R_1R_2N$—$(CH_2)_p$—O—, $R_1R_2N$—O—$(CH_2)_p$—, $R_1R_2PO_3$—, $R_1R_2R_3SiO$—, $R_1R_2R_3Si$—, $R_1R_2R_3Si$—CH═CH—, $R_1R_2C$═N—, $R_1R_2C$═N—O—, and $R_1R_2C$═N—NH—; or two adjacent $R_a$ form —CH═CH—CH═CH—;

m is 0 or 1, n and q are each independently 0, 1, 2, 3 or 4, p is 1, 2, 3 or 4;

R is hydrogen, a fluoro-, chloro-, or bromo-containing or not containing group selected from $C_{1-6}$alkyl, $C_{2-6}$alkenyl, $C_{2-6}$alkynyl, $C_{3-6}$cycloalkyl, $C_{5-6}$cycloalkenyl, and $C_{3-6}$cycloalkyl-$C_{1-6}$alkyl, aryl, aryl-$C_{1-6}$alkyl, heteroaryl, or heteroaryl-$C_{1-6}$alkyl, each of said aryl, aryl-$C_{1-6}$alkyl, heteroaryl, or heteroaryl-$C_{1-6}$alkyl is unsubstituted or substituted with 1-3 substituents independently selected from fluorine, chlorine, bromine, cyano, nitro, hydroxy, carboxyl, sulfhydryl, amino, and a fluoro-, chloro-, or bromo-containing or not containing group selected from $C_{1-6}$alkyl, $C_{3-6}$cycloalkyl, $C_{3-6}$cycloalkyl-$C_{1-6}$alkyl, $C_{2-6}$alkenyl, $C_{2-6}$alkynyl, $C_{1-6}$alkoxy, $C_{1-6}$alkylcarbonyl, $C_{1-6}$alkoxycarbonyl, $C_{1-6}$alkylsulfonyl, $C_{1-6}$alkylamino, and $C_{1-6}$alkylcarbonyloxy;

$R_b$, $R_1$, $R_2$, $R_3$ are each independently hydrogen, nitro, hydroxy, amino, a fluoro-, chloro-, or bromo-containing or not containing group selected from $C_{1-6}$alkyl, $C_{2-6}$alkenyl, $C_{2-6}$alkynyl, $C_{3-6}$cycloalkyl, $C_{5-6}$cycloalkenyl, $C_{3-6}$cycloalkyl-$C_{1-6}$alkyl, $C_{1-6}$alkoxy, $C_{2-6}$ alkenyloxy, $C_{2-6}$ alkynyloxy, $C_{3-6}$ cycloalkyloxy, $C_{1-6}$ alkoxy-$C_{1-6}$ alkyl, $C_{1-6}$ alkoxycarbonyl, $C_{1-6}$ alkylsulfanylcarbonyl, $C_{1-6}$ alkylsulfonyl, $C_{1-6}$ alkylsulfonyl-$C_{1-6}$ alkyl, $C_{1-6}$ alkylcarbonyl, $C_{1-6}$ alkylcarbonyl-$C_{1-6}$ alkyl, $C_{1-6}$ alkylcarbonyloxy, $C_{1-6}$ alkylamino, $C_{1-6}$ alkylaminocarbonyl, $C_{1-6}$ alkoxyaminocarbonyl, $C_{1-6}$ alkoxycarbonyl-$C_{1-6}$ alkyl, $C_{1-6}$ alkylaminocarbonyl-$C_{1-6}$ alkyl, tri$C_{1-6}$ alkylsilyl, and di$C_{1-6}$ alkylphosphonyl,

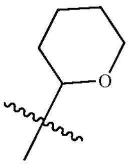,
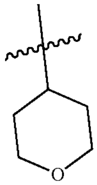,
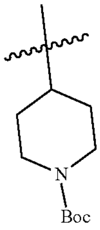, aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl, each of said

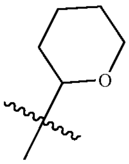,
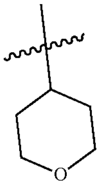,
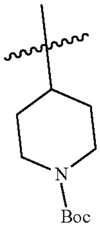, aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl is unsubstituted or substituted with 1-3 groups independently selected from fluorine, chlorine, bromine, cyano, nitro, hydroxy, carboxyl, sulfhydryl, amino, and a fluoro-, chloro-, or bromo-containing or not containing group selected from $C_{1-6}$ alkyl, $C_{3-6}$ cycloalkyl, $C_{3-6}$ cycloalkyl-$C_{1-6}$ alkyl, $C_{2-6}$ alkenyl, $C_{2-6}$ alkynyl, $C_{1-6}$ alkoxy, $C_{1-6}$ alkylcarbonyl, $C_{1-6}$ alkoxycarbonyl, $C_{1-6}$ alkylsulfonyl, $C_{1-6}$ alkylamino, and $C_{1-6}$ alkylcarbonyloxy; or $R_1R_2N$— is

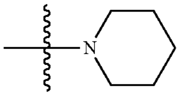,
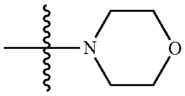, or

-continued

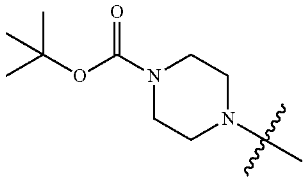;

or adjacent $R_a$ and $R_b$ form —$CH_2CH_2N(Boc)CH_2$—; the aryl is selected from

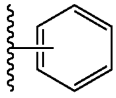,
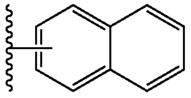,
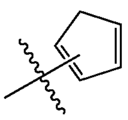,
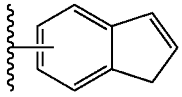,
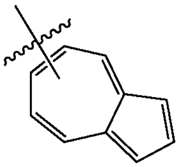,
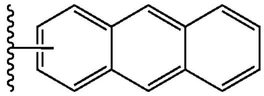,
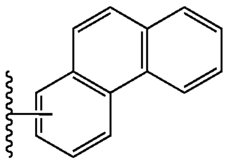, and
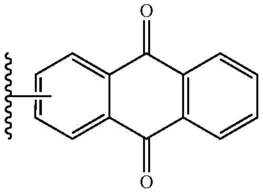;

he heteroaryl is selected from

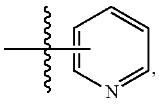,
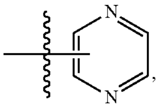,
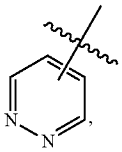,
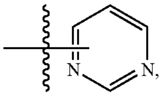,
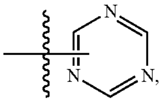,
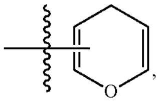,
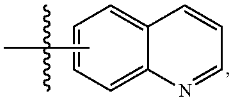,
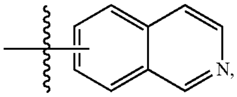,
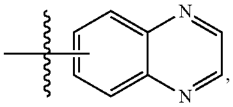,
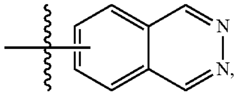,
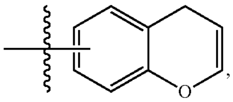,
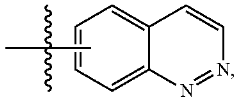, -continued
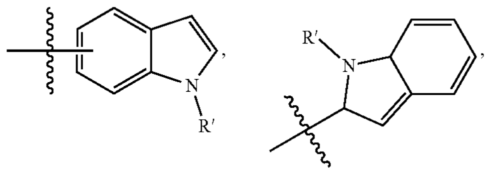
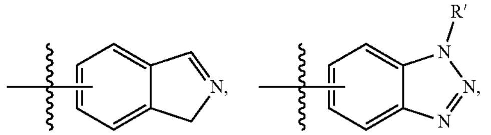
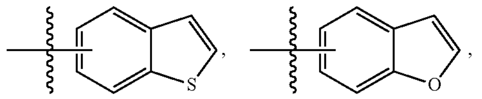
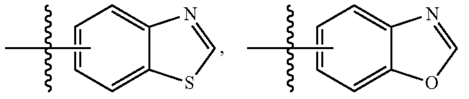
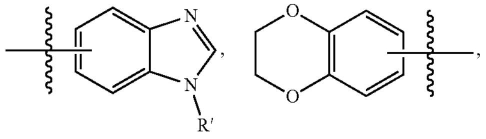
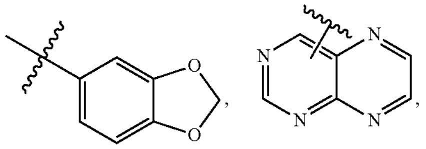
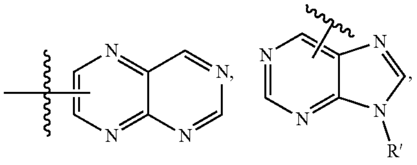
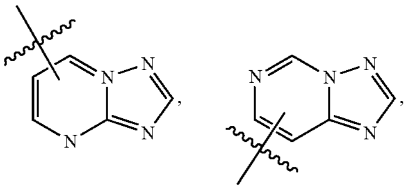
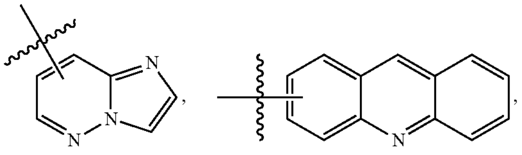
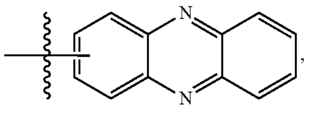
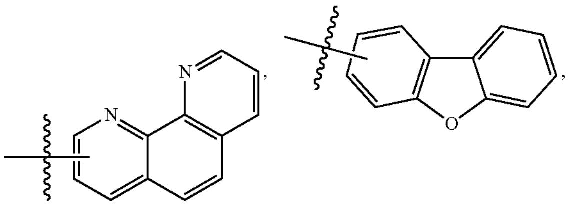
-continued
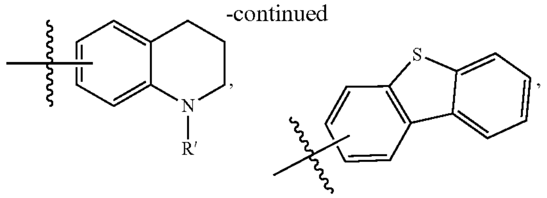
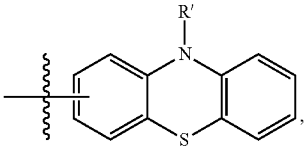
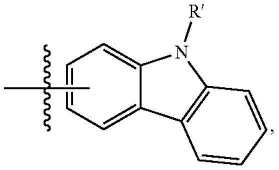
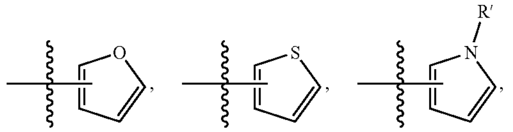
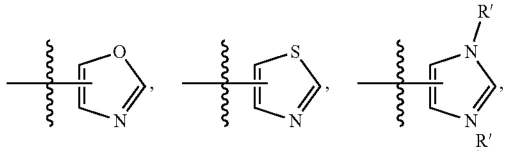
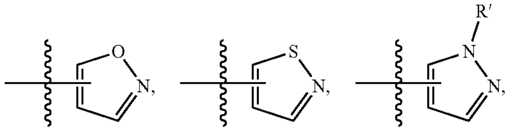
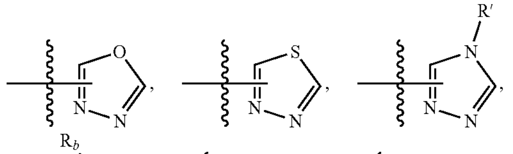
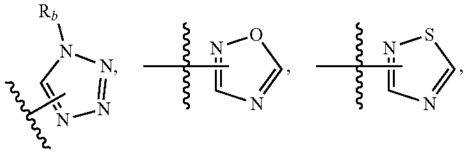
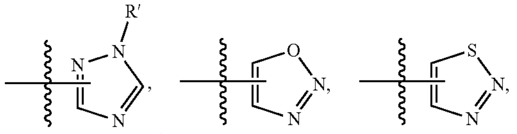
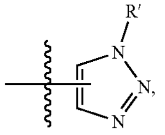
and
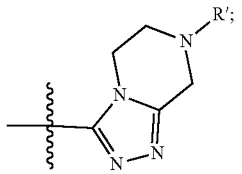
R' is hydrogen, nitro, hydroxy, amino, a fluoro-, chloro-, or bromo-containing or not containing group selected from $C_{1-6}$ alkyl, $C_{2-6}$ alkenyl, $C_{2-6}$ alkynyl, $C_{3-6}$ cycloalkyl, $C_{5-6}$ cycloalkenyl, $C_{3-6}$ cycloalkyl-$C_{1-6}$ alkyl, $C_{1-6}$ alkoxy, $C_{2-6}$ alkenyloxy, $C_{2-6}$ alkynyloxy, $C_{3-6}$ cycloalkyloxy, $C_{1-6}$ alkoxy-$C_{1-6}$ alkyl, $C_{1-6}$ alkoxycarbonyl, $C_{1-6}$ alkylsulfanylcarbonyl, $C_{1-6}$ alkylsulfonyl, $C_{1-6}$ alkylsulfonyl-$C_{1-6}$ alkyl, $C_{1-6}$ alkylcarbonyl, $C_{1-6}$ alkylcarbonyl-$C_{1-6}$ alkyl, $C_{1-6}$ alkylcarbonyloxy, $C_{1-6}$ alkylamino, $C_{1-6}$ alkylaminocarbonyl, $C_{1-6}$ alkoxyaminocarbonyl, $C_{1-6}$ alkoxycarbonyl-$C_{1-6}$ alkyl, $C_{1-6}$ alkylaminocarbonyl-$C_{1-6}$ alkyl, tri$C_{1-6}$ alkylsilyl, and di$C_{1-6}$ alkylphosphonyl,

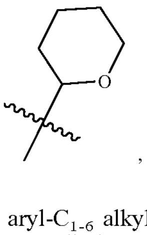, 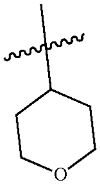, 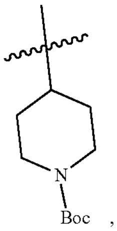, aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl, each of said

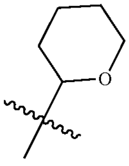, 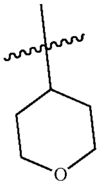, 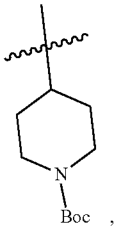, aryl, aryl-$C_{1-6}$ alkyl, aryloxy, aryl-$C_{1-6}$ alkyloxy, aryloxy-$C_{1-6}$ alkyl, arylcarbonyl, arylsulfonyl, heteroaryl, heteroaryl-$C_{1-6}$ alkyl, heteroaryloxy, heteroaryl-$C_{1-6}$ alkyloxy, heteroaryloxy-$C_{1-6}$ alkyl, heteroarylcarbonyl, or heteroarylsulfonyl is unsubstituted or substituted with 1-3 groups independently selected from fluorine, chlorine, bromine, cyano, nitro, hydroxy, carboxyl, sulfhydryl, amino, and a fluoro-, chloro-, or bromo-containing or not containing group selected from $C_{1-6}$ alkyl, $C_{3-6}$ cycloalkyl, $C_{3-6}$ cycloalkyl-$C_{1-6}$ alkyl, $C_{2-6}$ alkenyl, $C_{2-6}$ alkynyl, $C_{1-6}$ alkoxy, $C_{1-6}$ alkylcarbonyl, $C_{1-6}$ alkoxycarbonyl, $C_{1-6}$ alkylsulfonyl, $C_{1-6}$ alkylamino, and $C_{1-6}$ alkylcarbonyloxy;

the derivative refers to an agriculturally acceptable derivative of the 4-hydroxy of the pyridazine ring of Formula I, including a salt, an ester, a hydrazine, a hydroxylamine, and an ether thereof.

4. The five-membered ring-substituted pyridazinol compound or a derivative thereof according to claim 1, wherein, X represents fluorine, chlorine, bromine, iodine, methyl, ethyl, trifluoromethyl, pentafluoroethyl, difluoromethyl, monofluoromethyl, methoxy, ethoxy, trifluoromethoxy, or pentafluoroethoxy;

Het is

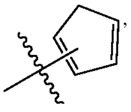, 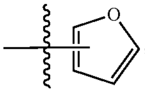, 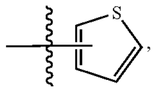,

-continued

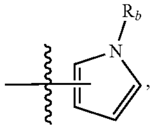, 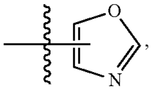, 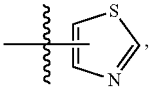,

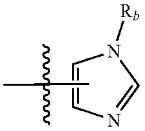, 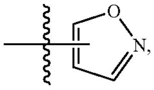 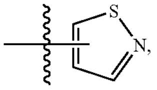

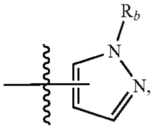 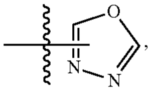, 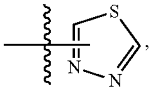,

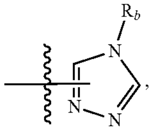, 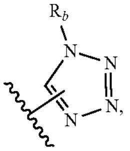 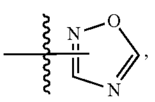,

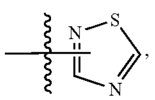, 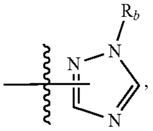, 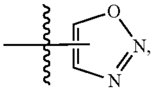

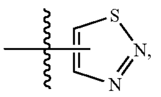 or 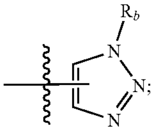

bonded at 1-C atom;

$R_a$ is selected from one or more of the following groups: hydrogen, methyl, ethyl, cyano, cyclopropyl, phenyl, fluorine, chlorine, bromine, iodine, cyano, nitro, difluoromethyl, 2,2,2,-trifluoroethyl, trifluoromethyl, methoxy, ethoxy, benzyloxy, —COOEt, amino, methylamino, dimethylamino, acetyl amino,

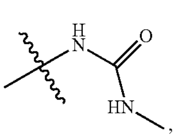, 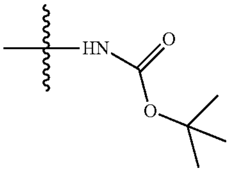,

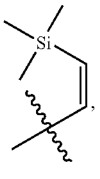, 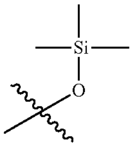, 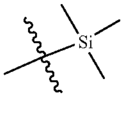, 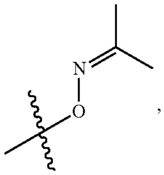,

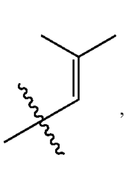, and 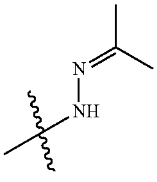;

or Ar is

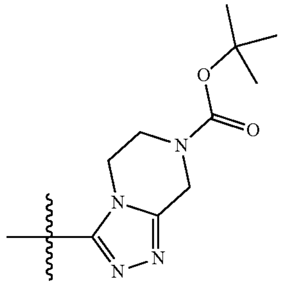 , 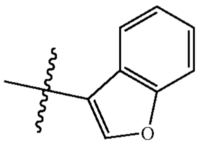 ,

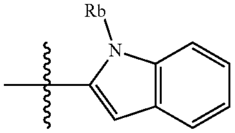 , 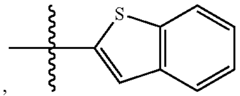 , or

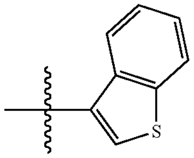 ;

$R_b$ represents hydrogen, methyl, ethyl, n-propyl, isopropyl, difluoromethyl, 2,2,2-trifluoroethyl, acetyl, phenyl, benzyl,

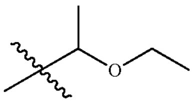 , 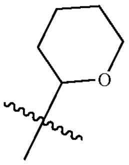 , 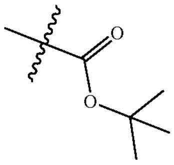 ,

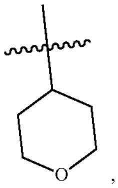 , 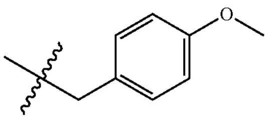 ,

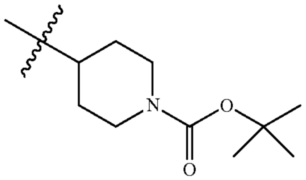 , 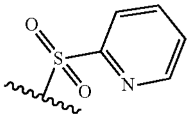 , or triphenylmethyl;

the derivative refers to an agriculturally acceptable derivative of the 4-hydroxy of the pyridazine ring of Formula I, including a salt, an ester, a hydrazine, a hydroxylamine, and an ether thereof.

5. A herbicidal composition, comprising at least one compound selected from the five-membered ring-substituted pyridazinol compound of Formula I or the derivative thereof according to claim 1.

6. The herbicidal composition according to claim 5, further comprising at least one additional herbicide and/or safener.

7. The herbicidal composition according to claim 6, further comprising at least one agriculturally acceptable formulation auxiliary.

8. The herbicidal composition according to claim 6, wherein the at least one additional herbicide is selected from an HPPD inhibitor, a hormone herbicide, and a PDS inhibitor.

9. The herbicidal composition according to claim 8, wherein the HPPD inhibitor is selected from Sulcotrione, Mesotrione, Topramezone, Tembotrione, Bicyclopyrone, Tefuryltrione, Benzobicyclon, Lancotrione, Shuangzuocaotong, Huanbifucaotong, Sanzuohuangcaotong, Benzuofucaotong, Pyrasulfotole, Pyrazolate, Benzofenap, Tolpyralate, Fenquinotrione, and Isoxaflutole; the hormone herbicide is selected from Fluroxypyr, Halauxifen-methyl, Florpyrauxifen-benzyl, Quinclorac, Quinmerac, 2-methyl-4-chlorophenoxy acetic acid, 2-methyl-4-chlorophenoxypropionic acid, MCPB, 2,4-D, Dichlorprop, 2,4-DB, Dicamba, Picloram, Trichlopyr, Clopyralid, Triclopyr, and derivatives thereof, and the PDS inhibitor is selected from Flurochloridone, Flurtamone, Diflufenican, Picolinafen, Beflubutamid, Norflurazon, and Fluridone.

10. A method for controlling weeds, comprising applying a herbicidally effective amount of at least one compound selected from the five-membered ring-substituted pyridazinol compound and the derivative thereof according to claim 1 to the weeds or an area with the weeds.

11. A method for controlling a weeds in a useful crop, comprising applying a herbicidally effective amount of at least one compound selected from the five-membered ring-substituted pyridazinol compound and the derivative thereof according to claim 1 to the weeds or an area with the weeds in a useful crop, wherein the useful crop is a genetically modified crop or a crop treated by genome editing technique.

12. A five-membered ring-substituted pyridazinol compound of Formula I, or a derivative thereof, wherein:

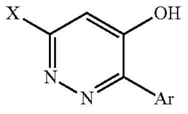

I

| No. | X | Ar |
|---|---|---|
| 1 | Cl | 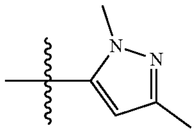 [SMILES: *c1cc(C)nn1C] |
| 2 | Cl | 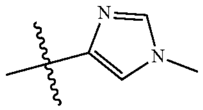 [SMILES: *c1cn(C)cn1] |
| 3 | Cl | 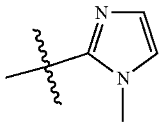 [SMILES: *c1nccn1C] |
| 4 | Cl | 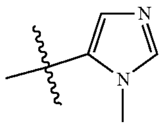 [SMILES: *c1cncn1C] |

-continued
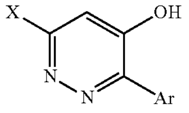
I
| No. | X | Ar |
| --- | --- | --- |
| 5 | Cl | 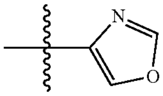 [SMILES: *c1cocn1] |
| 6 | Cl | 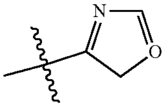 |
| 7 | Cl | 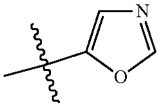 [SMILES: *c1cnco1] |
| 8 | Cl | 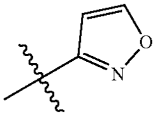 [SMILES: *c1ccon1] |
| 9 | Cl | 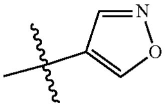 [SMILES: *c1cnoc1] |
| 10 | Cl | 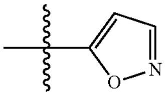 |
| 11 | Cl | 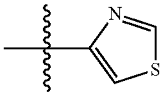 [SMILES: *c1cscn1] |
| 12 | Cl | 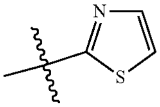 [SMILES: *c1nccs1] |
| 13 | Cl | 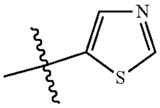 [SMILES: *c1cncs1] |
| 14 | Cl | 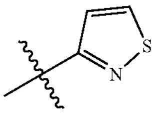 [SMILES: *c1ccsn1] |
| 15 | O | 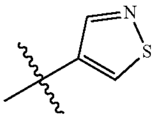 [SMILES: *c1cnsc1] |
-continued
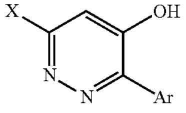
I
| No. | X | Ar |
| --- | --- | --- |
| 16 | Cl | 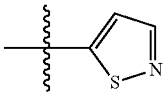 |
| 17 | Cl | 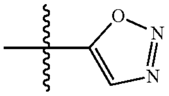 [SMILES: *c1cnno1] |
| 18 | Cl | 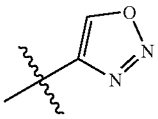 [SMILES: *c1conn1] |
| 19 | O | 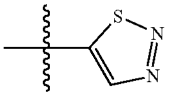 |
| 20 | Cl | 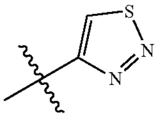 [SMILES: *c1csnn1] |
| 21 | Cl | 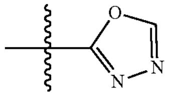 [SMILES: *c1nnco1] |
| 22 | Cl | 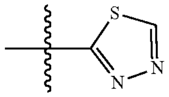 |
| 23 | Cl | 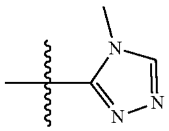 [SMILES: *c1nncn1C] |
| 24 | Cl | 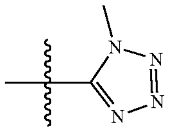 [SMILES: *c1nnnn1C] |
| 25 | Cl | 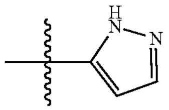 [SMILES: *c1ccn[nH]1] |

-continued
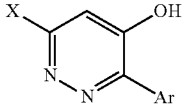
I
| No. | X | Ar |
|---|---|---|
| 26 | O | 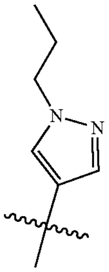 [SMILES: *c1cnn(CCC)c1] |
| 27 | Cl | 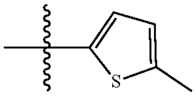 [SMILES: *c1ccc(C)s1] |
| 28 | Cl | 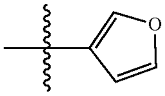 [SMILES: *c1ccoc1] |
| 29 | Cl | 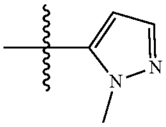 [SMILES: *c1ccnn1C] |
| 30 | O | 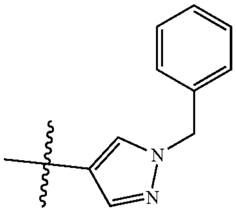 [SMILES: *c1cnn(Cc2ccccc2)c1] |
| 31 | O | 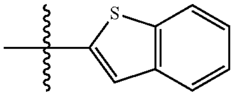 [SMILES: *c1cc2ccccc2s1] |
| 32 | Cl | 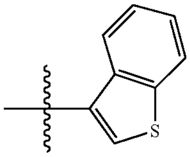 [SMILES: *c1csc2ccccc12] |
| 33 | O | 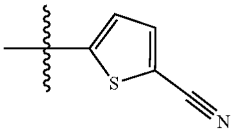 [SMILES: *c1ccc(C#N)s1] |
| 34 | Cl | 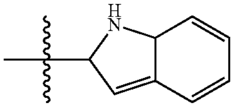 [SMILES: *C1C=C2C=CC=CC2N1] |
-continued
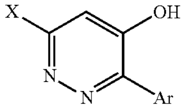
I
| No. | X | Ar |
|---|---|---|
| 35 | O | 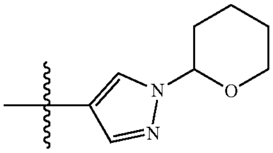 [SMILES: *c1cnn(C2CCCCO2)c1] |
| 36 | Cl | 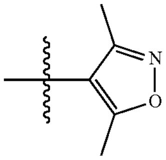 [SMILES: *c1c(C)noc1C] |
| 37 | Br | 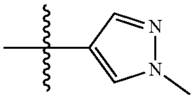 |
| 38 | CN | 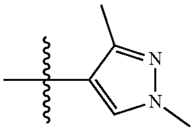 [SMILES: *c1cn(C)nc1C] |
| 39 | Me | 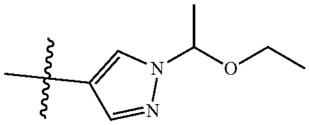 [SMILES: *c1cnn(C(C)OCC)c1] |
| 40 | OMe | 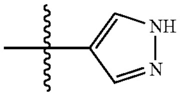 [SMILES: *c1cn[nH]c1] |
| 41 | Et | 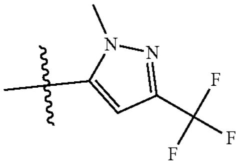 [SMILES: *c1cc(C(F)(F)F)nn1C] |
| 42 | F | 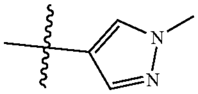 [SMILES: *c1cnn(C)c1] |
| 43 | Cl | 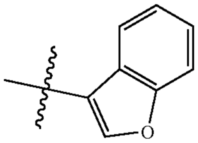 [SMILES: *c1coc2ccccc12] |

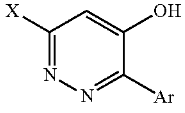
I
| No. | X | Ar |
|---|---|---|
| 44 | O | 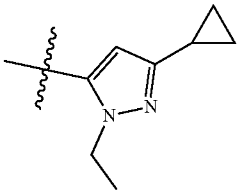 [SMILES: *c1cc(C2CC2)nn1CC] |
| 45 | $CF_2CF_3$ | 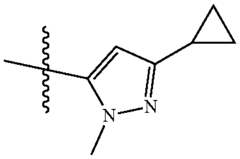 [SMILES: *c1cc(C2CC2)nn1C] |
| 46 | $CHF_2$ | 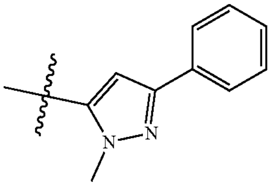 [SMILES: *c1cc(-c2ccccc2)nn1C] |
| 47 | $CH_2F$ | 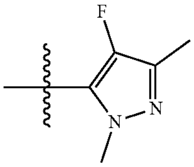 [SMILES: *c1c(F)c(C)nn1C] |
| 48 | Cl | 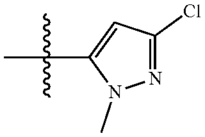 |
| 49 | OEt | 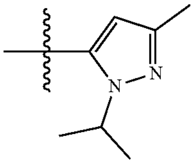 [SMILES: *c1cc(C)nn1C(C)C] |
| 50 | $OCF_3$ | 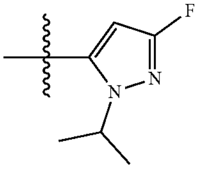 [SMILES: *c1cc(F)nn1C(C)C] |
| 51 | $OCF_2CF_3$ | 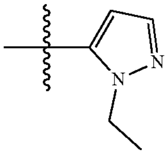 [SMILES: *c1ccnn1CC] |
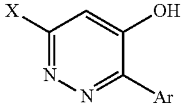
I
| No. | X | Ar |
|---|---|---|
| 52 | Cl | 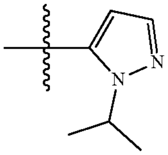 [SMILES: *c1ccnn1C(C)C] |
| 53 | Cl | 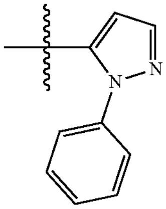 [SMILES: *c1ccnn1-c1ccccc1] |
| 54 | Cl | 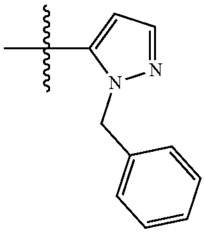 [SMILES: *c1ccnn1Cc1ccccc1] |
| 55 | Cl | 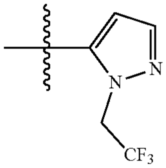 |
| 56 | Cl | 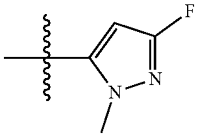 [SMILES: *c1cc(F)nn1C] |
| 57 | Cl | 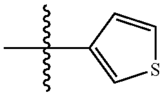 [SMILES: *c1ccsc1] |
| 58 | Cl | 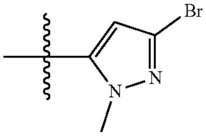 [SMILES: *c1cc(Br)nn1C] |
| 59 | Cl | 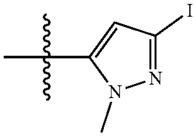 [SMILES: *c1cc(I)nn1C] |

-continued
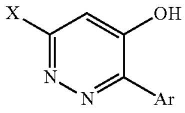
I
| No. | X | Ar |
|---|---|---|
| 60 | Cl | 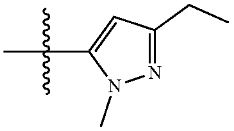 |
| 61 | Cl | 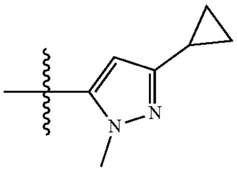 [SMILES: *c1cc(C2CC2)nn1C] |
| 62 | Cl | 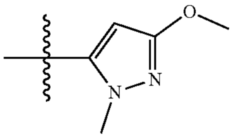 [SMILES: *c1cc(OC)nn1C] |
| 63 | Cl | 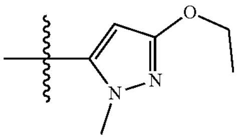 [SMILES: *c1cc(OCC)nn1C] |
| 64 | Cl | 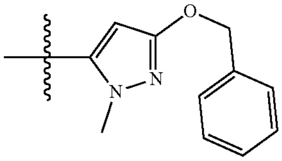 [SMILES: *c1cc(OCc2ccccc2)nn1C] |
| 65 | Cl | 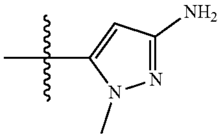 [SMILES: *c1cc(N)nn1C] |
| 66 | Cl | 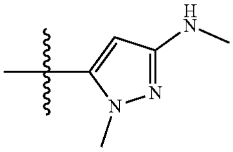 [SMILES: *c1cc(NC)nn1C] |
| 67 | Cl | 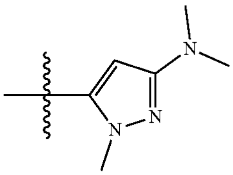 [SMILES: *c1cc(N(C)C)nn1C] |
-continued
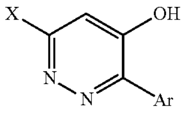
I
| No. | X | Ar |
|---|---|---|
| 68 | Cl | 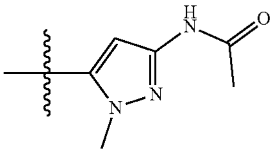 [SMILES: *c1cc(NC(C)=O)nn1C] |
| 69 | Cl | 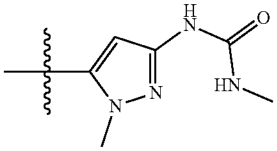 [SMILES: *c1cc(NC(=O)NC)nn1C] |
| 70 | Cl | 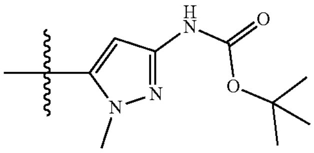 [SMILES: *c1cc(NC(=O)OC(C)(C)C)nn1C] |
| 71 | Cl | 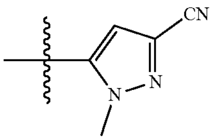 [SMILES: *c1cc(C#N)nn1C] |
| 72 | Cl | 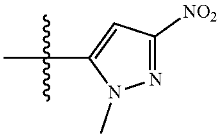 [SMILES: *c1cc([N+](=O)[O-])nn1C] |
| 73 | Cl | 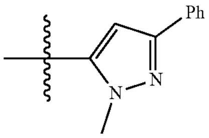 [SMILES: *c1cc(-c2ccccc2)nn1C] |
| 74 | Cl | 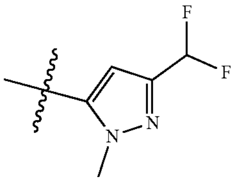 [SMILES: *c1cc(C(F)F)nn1C] |
| 75 | Cl | 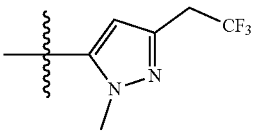 [SMILES: *c1cc(CC(F)(F)F)nn1C] |
| 76 | Cl | 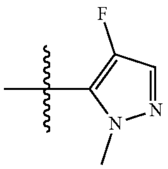 |

-continued
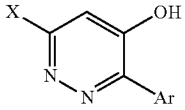
I
| No. | X | Ar |
|---|---|---|
| 77 | Cl | 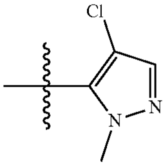 [SMILES: *c1c(Cl)cnn1C] |
| 78 | Cl | 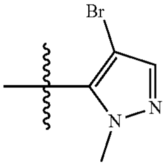 |
| 79 | Cl | 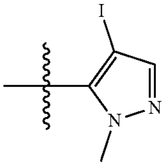 [SMILES: *c1c(I)cnn1C] |
| 80 | Cl | 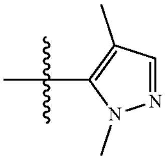 [SMILES: *c1c(C)cnn1C] |
| 81 | Cl | 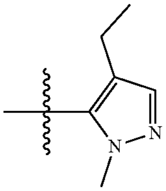 [SMILES: *c1c(CC)cnn1C] |
| 82 | Cl | 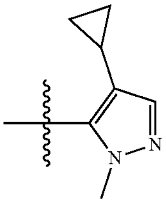 [SMILES: *c1c(C2CC2)cnn1C] |
| 83 | Cl | 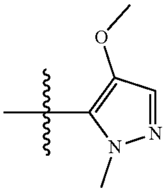 [SMILES: *c1c(OC)cnn1C] |
-continued
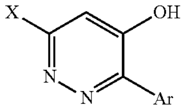
I
| No. | X | Ar |
|---|---|---|
| 84 | Cl | 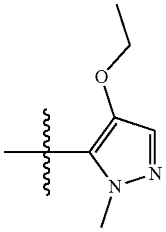 [SMILES: *c1c(OCC)cnn1C] |
| 85 | Cl | 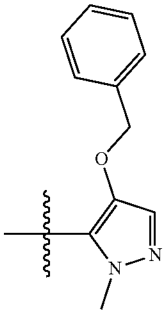 [SMILES: *c1c(OCc2ccccc2)cnn1C] |
| 86 | Cl | 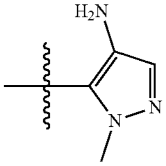 |
| 87 | $CF_2CF_3$ | 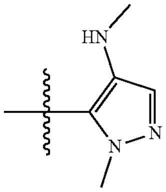 [SMILES: *c1c(NC)cnn1C] |
| 88 | I | 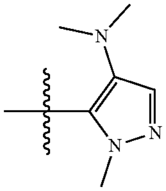 [SMILES: *c1c(N(C)C)cnn1C] |
| 89 | Cl | 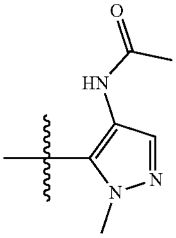 [SMILES: *c1c(NC(C)=O)cnn1C] |

-continued
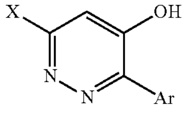
I
| No. | X | Ar |
|---|---|---|
| 90 | Cl | 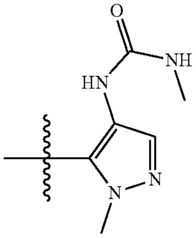 [SMILES: *c1c(NC(=O)NC)cnn1C] |
| 91 | Cl | 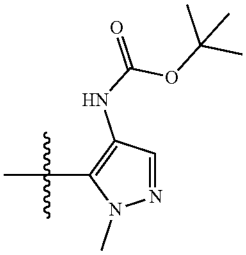 [SMILES: *c1c(NC(=O)OC(C)(C)C)cnn1C] |
| 92 | Cl | 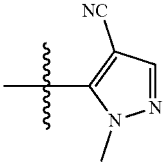 [SMILES: *c1c(C#N)cnn1C] |
| 93 | Cl | 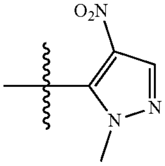 |
| 94 | Cl | 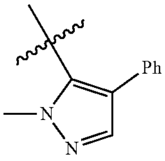 [SMILES: *c1c(-c2ccccc2)cnn1C] |
| 95 | Br | 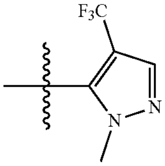 |
| 96 | O | 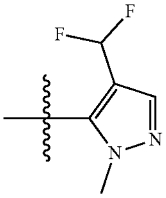 [SMILES: *c1c(C(F)F)cnn1C] |
-continued
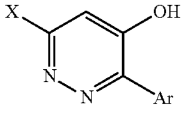
I
| No. | X | Ar |
|---|---|---|
| 97 | Cl | 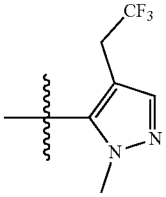 [SMILES: *c1c(CC(F)(F)F)cnn1C] |
| 98 | O | 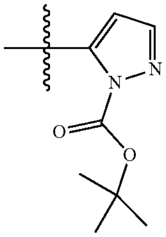 [SMILES: *c1ccnn1C(=O)OC(C)(C)C] |
| 99 | Cl | 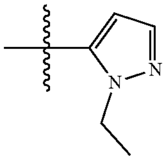 [SMILES: *c1ccnn1CC] |
| 100 | O | 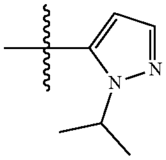 [SMILES: *c1ccnn1C(C)C] |
| 101 | O | 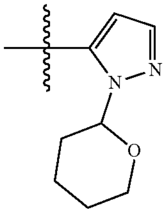 [SMILES: *c1ccnn1C1CCCCO1] |
| 102 | Cl | 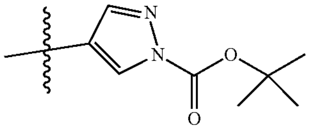 [SMILES: *c1cnn(C(=O)OC(C)(C)C)c1] |
| 103 | O | 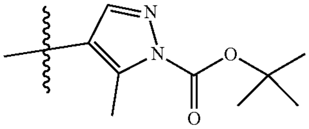 [SMILES: *c1cnn(C(=O)OC(C)(C)C)c1C] |
| 104 | Cl | 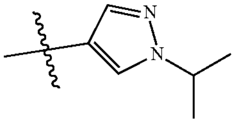 [SMILES: *c1cnn(C(C)C)c1] |

-continued
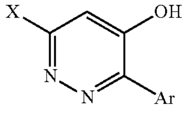
I
| No. | X | Ar |
|---|---|---|
| 105 | O | 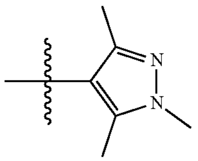 [SMILES: *c1c(C)nn(C)c1C] |
| 106 | O | 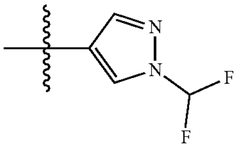 [SMILES: *c1cnn(C(F)F)c1] |
| 107 | O | 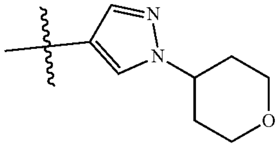 [SMILES: *c1cnn(C2CCOCC2)c1] |
| 108 | Cl | 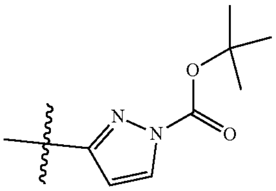 [SMILES: *c1ccn(C(=O)OC(C)(C)C)n1] |
| 109 | Cl | 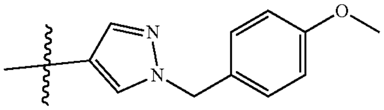 [SMILES: *c1cnn(Cc2ccc(OC)cc2)c1] |
| 110 | O | 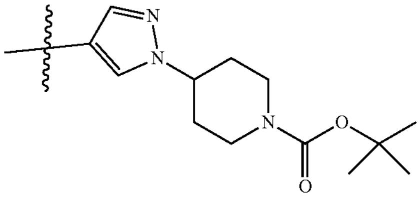 [SMILES: *c1cnn(C2CCN(C(=O)OC(C)(C)C)CC2)c1] |
| 111 | Cl | 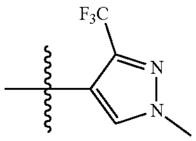 [SMILES: *c1cn(C)nc1C(F)(F)F] |
| 112 | Cl | 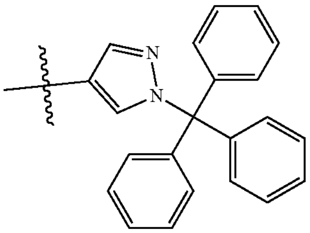 [SMILES: *c1cnn(C(c2ccccc2)(c2ccccc2)c2ccccc2)c1] |
-continued
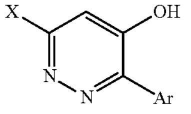
I
| No. | X | Ar |
|---|---|---|
| 113 | Cl | 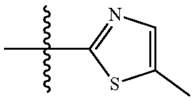 [SMILES: *c1ncc(C)s1] |
| 114 | O | 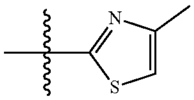 [SMILES: *c1nc(C)cs1] |
| 115 | O | 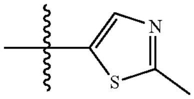 [SMILES: *c1cnc(C)s1] |
| 116 | O | 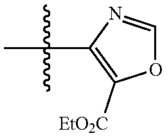 |
| 117 | Q | 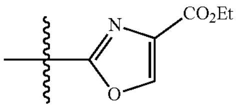 [SMILES: *c1nc(C(=O)OCC)co1] |
| 118 | Cl | 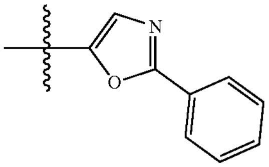 [SMILES: *c1cnc(-c2ccccc2)o1] |
| 119 | Cl | 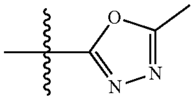 |
| 120 | Cl | 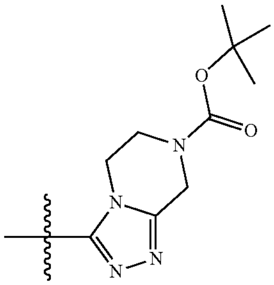 [SMILES: *c1nnc2n1CCN(C(=O)OC(C)(C)C)C2] |
| 121 | Cl | 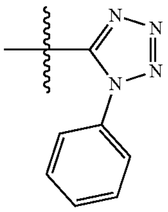 [SMILES: *c1nnnn1-c1ccccc1] |

-continued
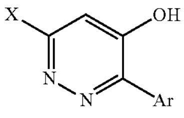
I
| No. | X | Ar |
|---|---|---|
| 122 | Cl | 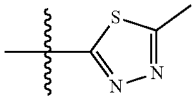 |
| 123 | Cl | 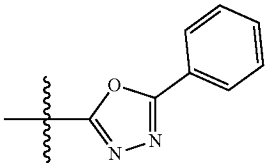 [SMILES: *c1nnc(-c2ccccc2)o1] |
| 124 | Cl | 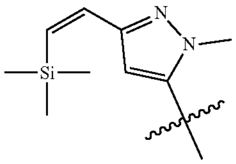 |
| 125 | Cl | 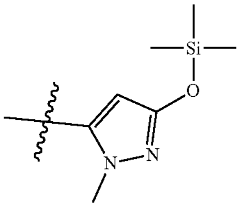 [SMILES: *c1cc(O[Si](C)(C)C)nn1C] |
| 126 | Cl | 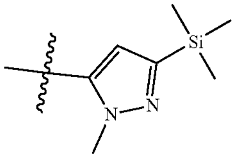 [SMILES: *c1cc([Si](C)(C)C)nn1C] |
| 127 | Cl | 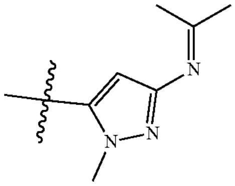 [SMILES: *c1cc(N=C(C)C)nn1C] |
| 128 | Cl | 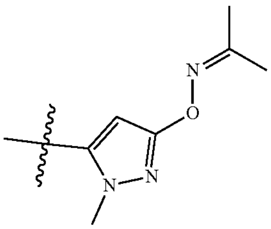 [SMILES: *c1cc(ON=C(C)C)nn1C] |
-continued
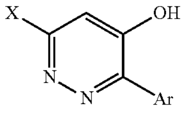
I
| No. | X | Ar |
|---|---|---|
| 129 | Cl | 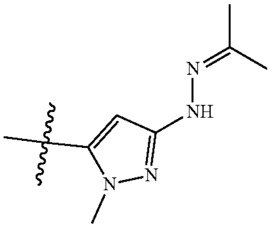 [SMILES: *c1cc(NN=C(C)C)nn1C] |
| 130 | Cl | 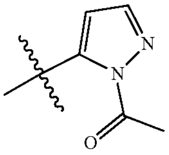 [SMILES: *c1ccnn1C(C)=O] |
| 131 | Cl | 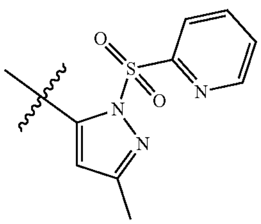 [SMILES: *c1cc(C)nn1S(=O)(=O)c1ccccn1] |
| 132 | Cl | 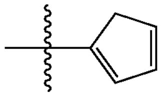 [SMILES: *C1=CC=CC1] |
| 133 | CN | 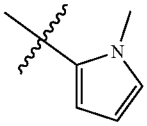 [SMILES: *c1cccn1C] |
| 134 | $NH_2$ | 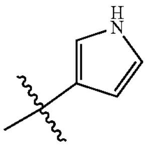 [SMILES: *c1cc[nH]c1] |
| 135 | Ph | 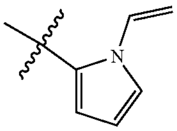 [SMILES: *c1cccn1C=C] |
| 136 | Br | 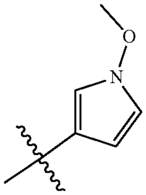 [SMILES: *c1ccn(OC)c1] |

-continued
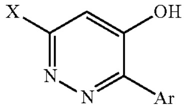
I
| No. | X | Ar |
|---|---|---|
| 137 | Cl | 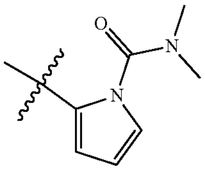 [SMILES: *c1cccn1C(=O)N(C)C] |
| 138 | Cl | 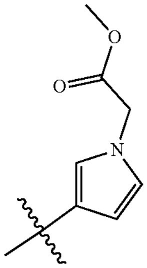 [SMILES: *c1ccn(CC(=O)OC)c1] |
| 139 | OF | 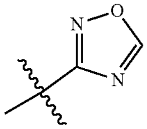 [SMILES: *c1ncon1] |
| 140 | Cl | 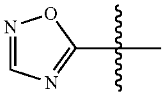 [SMILES: *c1ncno1] |
| 141 | Cl | 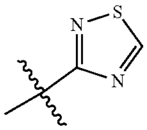 [SMILES: *c1ncsn1] |
| 142 | Cl | 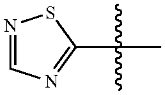 |
| 143 | $CONH_2$ | 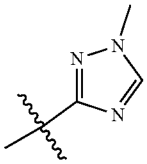 [SMILES: *c1ncn(C)n1] |
| 144 | Cl | 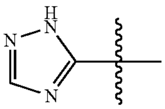 [SMILES: *c1ncn[nH]1] |
| 145 | Cl | 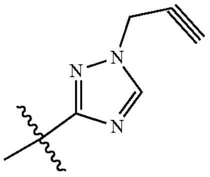 [SMILES: *c1ncn(CC#C)n1] |
-continued
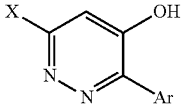
I
| No. | X | Ar |
|---|---|---|
| 146 | Cl | 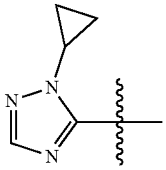 [SMILES: *c1ncnn1C1CC1] |
| 147 | Cl | 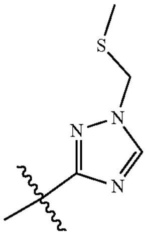 [SMILES: *c1ncn(CSC)n1] |
| 148 | $CH_2F$ | 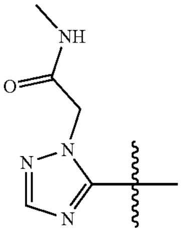 [SMILES: *c1ncnn1CC(=O)NC] |
| 149 | Cl | 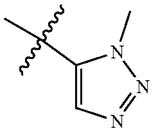 [SMILES: *c1cnnn1C] |
| 150 | Cl | 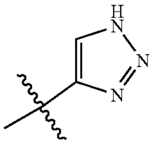 [SMILES: *c1c[nH]nn1] |
| 151 | Cl | 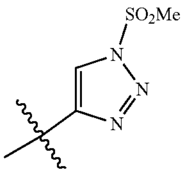 [SMILES: *c1cn(S(C)(=O)=O)nn1] |
| 152 | Cl | 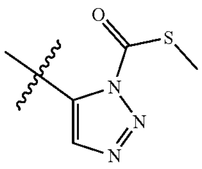 [SMILES: *c1cnnn1C(=O)SC] |

-continued
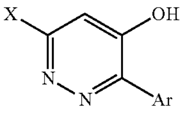
I
| No. | X | Ar |
|---|---|---|
| 153 | Cl | 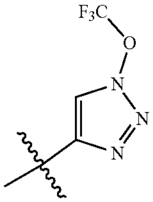 [SMILES: *c1cn(OC(F)(F)F)nn1] |
| 154 | Cl | 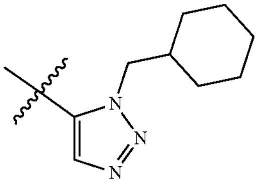 [SMILES: *c1cnnn1CC1CCCCC1] |
| 155 | Cl | 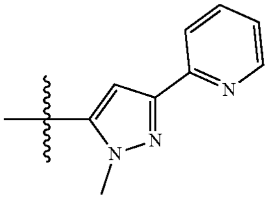 |
| 156 | Cl | 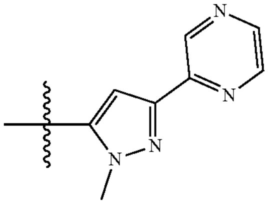 [SMILES: *c1cc(-c2cnccn2)nn1C] |
| 157 | Cl | 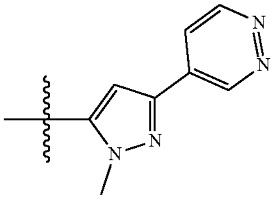 [SMILES: *c1cc(-c2ccnnc2)nn1C] |
| 158 | Cl | 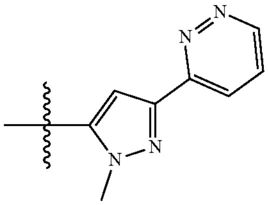 |
-continued
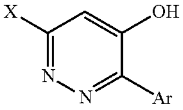
I
| No. | X | Ar |
|---|---|---|
| 159 | Cl | 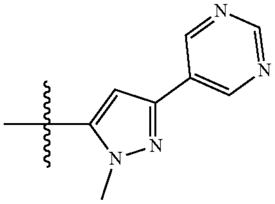 [SMILES: *c1cc(-c2cncnc2)nn1C] |
| 160 | Cl | 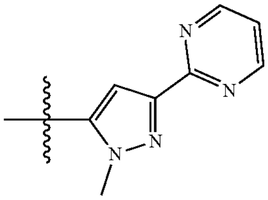 [SMILES: *c1cc(-c2ncccn2)nn1C] |
| 161 | Cl | 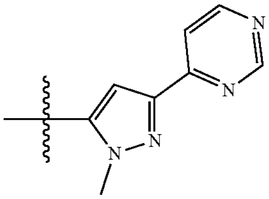 [SMILES: *c1cc(-c2ccncn2)nn1C] |
| 162 | Cl | 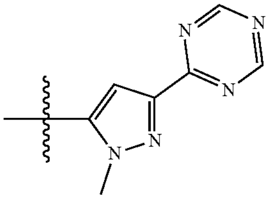 [SMILES: *c1cc(-c2ncncn2)nn1C] |
| 163 | Cl | 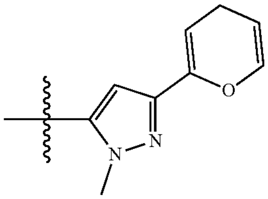 [SMILES: *c1cc(C2=CCC=CO2)nn1C] |
| 164 | Cl | 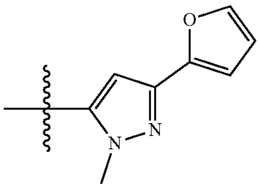 [SMILES: *c1cc(-c2ccco2)nn1C] |
| 165 | Cl | 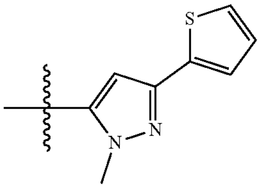 [SMILES: *c1cc(-c2cccs2)nn1C] |

-continued
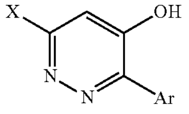
I
| No. | X | Ar |
|---|---|---|
| 166 | Cl | 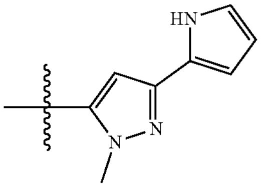 [SMILES: *c1cc(-c2ccc[nH]2)nn1C] |
| 167 | Cl | 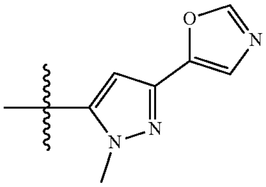 [SMILES: *c1cc(-c2cnco2)nn1C] |
| 168 | Cl | 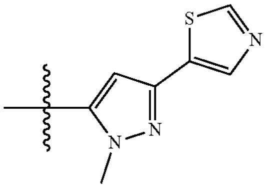 [SMILES: *c1cc(-c2cncs2)nn1C] |
| 169 | Cl | 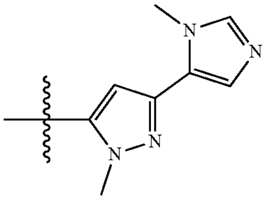 [SMILES: *c1cc(-c2cncn2C)nn1C] |
| 170 | Cl | 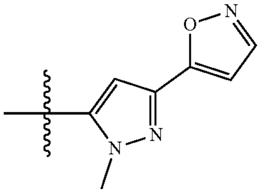 [SMILES: *c1cc(-c2ccno2)nn1C] |
| 171 | Cl | 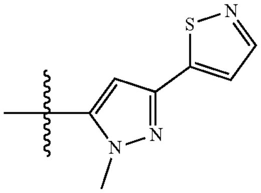 [SMILES: *c1cc(-c2ccns2)nn1C] |
| 172 | Cl | 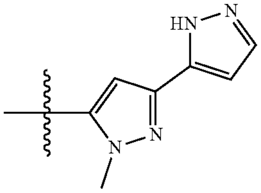 [SMILES: *c1cc(-c2ccn[nH]2)nn1C] |
-continued
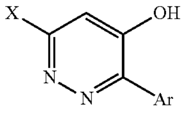
I
| No. | X | Ar |
|---|---|---|
| 173 | Cl | 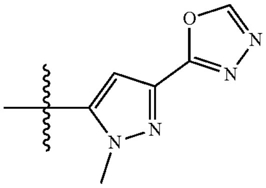 |
| 174 | Cl | 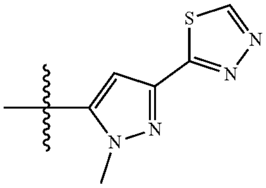 |
| 175 | Cl | 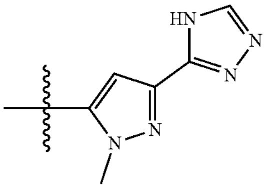 |
| 176 | Cl | 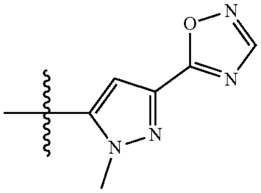 [SMILES: *c1cc(-c2ncno2)nn1C] |
| 177 | Cl | 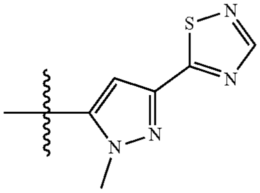 [SMILES: *c1cc(-c2ncns2)nn1C] |
| 178 | Cl | 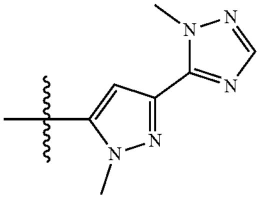 [SMILES: *c1cc(-c2ncnn2C)nn1C] |
| 179 | Cl | 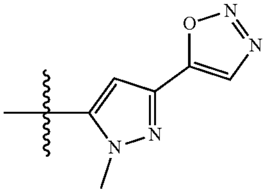 [SMILES: *c1cc(-c2cnno2)nn1C] |

-continued
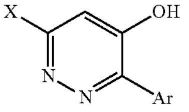
I
| No. | X | Ar |
| --- | --- | --- |
| 180 | Cl | 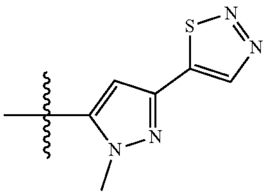 |
| 181 | Cl | 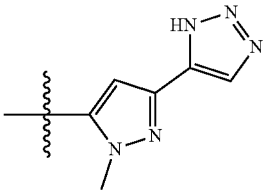 [SMILES: *c1cc(-c2cnn[nH]2)nn1C] |
| 182 | Cl | 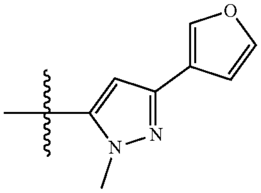 [SMILES: *c1cc(-c2ccoc2)nn1C] |
| 183 | Cl | 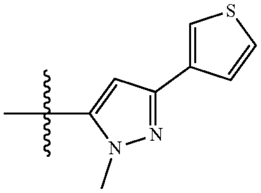 |
| 184 | Cl | 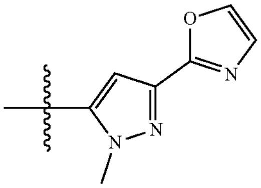 [SMILES: *c1cc(-c2ncco2)nn1C] |
| 185 | Cl | 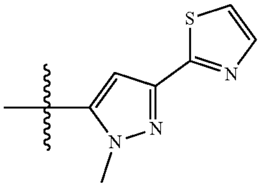 [SMILES: *c1cc(-c2nccs2)nn1C] |
| 186 | Cl | 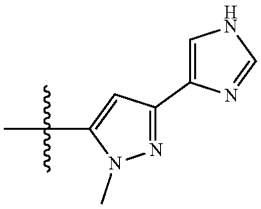 [SMILES: *c1cc(-c2c[nH]cn2)nn1C] |
-continued
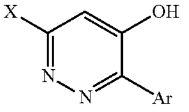
I
| No. | X | Ar |
| --- | --- | --- |
| 187 | Cl | 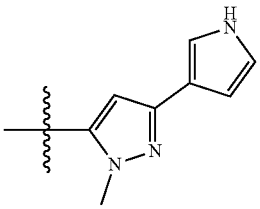 [SMILES: *c1cc(-c2cc[nH]c2)nn1C] |
| 188 | Cl | 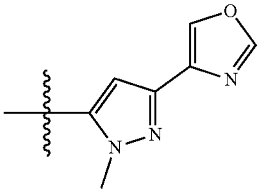 [SMILES: *c1cc(-c2cocn2)nn1C] |
| 189 | Cl | 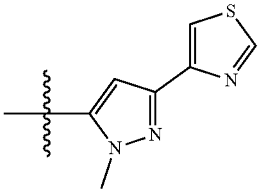 [SMILES: *c1cc(-c2cscn2)nn1C] |
| 190 | Cl | 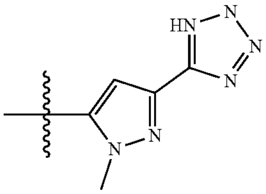 [SMILES: *c1cc(-c2nn[nH]n2)nn1C] |
| 191 | Cl | 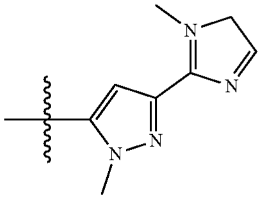 |
| 192 | Cl | 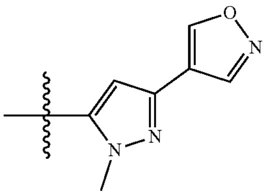 [SMILES: *c1cc(-c2cnoc2)nn1C] |
| 193 | Cl | 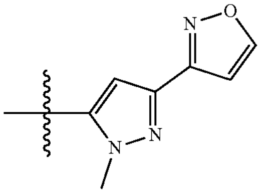 [SMILES: *c1cc(-c2ccon2)nn1C] |

-continued
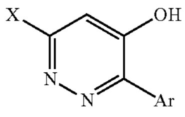
I
| No. | X | Ar |
|---|---|---|
| 194 | Cl | 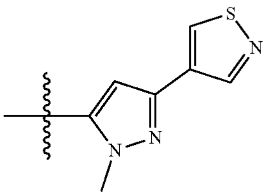 |
| 195 | Cl | 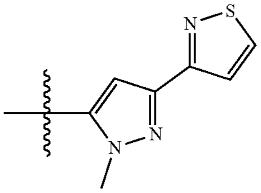 [SMILES: *c1cc(-c2ccsn2)nn1C] |
| 196 | Cl | 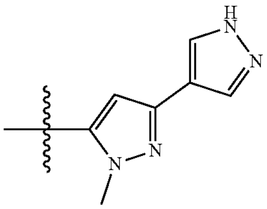 [SMILES: *c1cc(-c2cn[nH]c2)nn1C] |
| 197 | Cl | 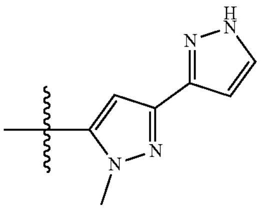 [SMILES: *c1cc(-c2cc[nH]n2)nn1C] |
| 198 | Cl | 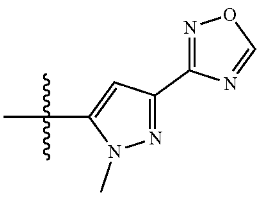 [SMILES: *c1cc(-c2ncon2)nn1C] |
| 199 | Cl | 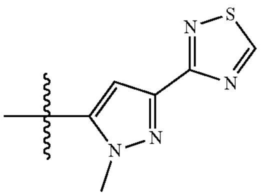 [SMILES: *c1cc(-c2ncsn2)nn1C] |
-continued
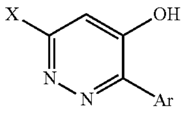
I
| No. | X | Ar |
|---|---|---|
| 200 | Cl | 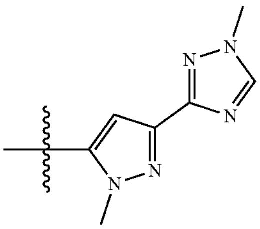 [SMILES: *c1cc(-c2ncn(C)n2)nn1C] |
| 201 | Cl | 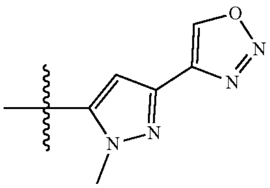 [SMILES: *c1cc(-c2conn2)nn1C] |
| 202 | Cl | 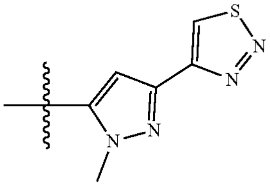 [SMILES: *c1cc(-c2csnn2)nn1C] |
| 203 | Cl | 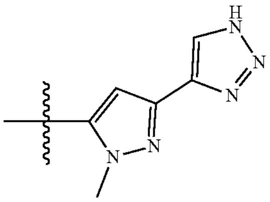 [SMILES: *c1cc(-c2c[nH]nn2)nn1C] |
| 204 | Cl | 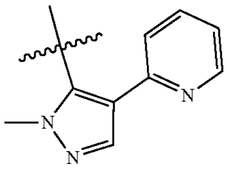 [SMILES: *c1c(-c2ccccn2)cnn1C] |
| 205 | Cl | 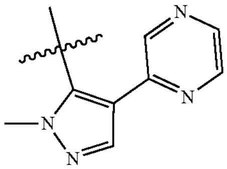 [SMILES: *c1c(-c2cnccn2)cnn1C] |
| 206 | Cl | 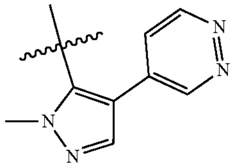 [SMILES: *c1c(-c2ccnnc2)cnn1C] |

-continued
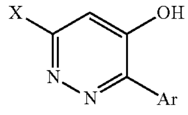
I
| No. | X | Ar |
|---|---|---|
| 207 | Cl | 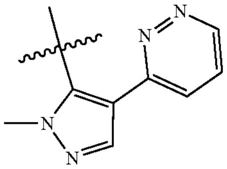 [SMILES: *c1c(-c2cccnn2)cnn1C] |
| 208 | Cl | 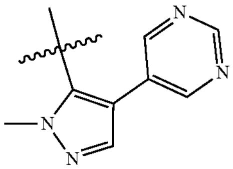 [SMILES: *c1c(-c2cncnc2)cnn1C] |
| 209 | Cl | 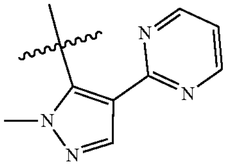 [SMILES: *c1c(-c2ncccn2)cnn1C] |
| 210 | Cl | 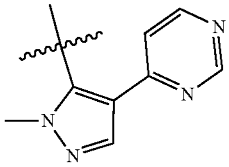 [SMILES: *c1c(-c2ccncn2)cnn1C] |
| 211 | Cl | 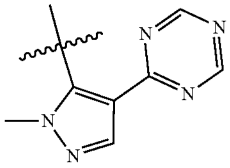 [SMILES: *c1c(-c2ncncn2)cnn1C] |
| 212 | Cl | 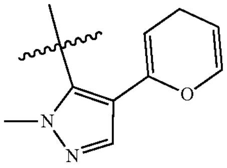 [SMILES: *c1c(C2=CCC=CO2)cnn1C] |
| 213 | Cl | 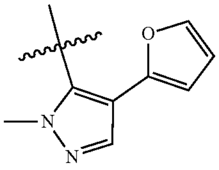 |
| 214 | Cl | 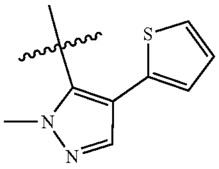 [SMILES: *c1c(-c2cccs2)cnn1C] |
-continued
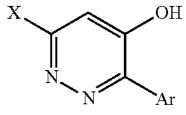
I
| No. | X | Ar |
|---|---|---|
| 215 | Cl | 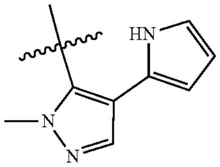 [SMILES: *c1c(-c2ccc[nH]2)cnn1C] |
| 216 | Cl | 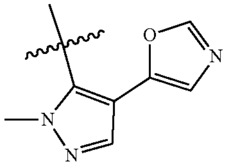 [SMILES: *c1c(-c2cnco2)cnn1C] |
| 217 | Cl | 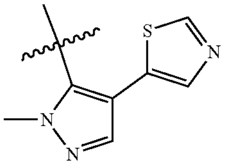 [SMILES: *c1c(-c2cncs2)cnn1C] |
| 218 | Cl | 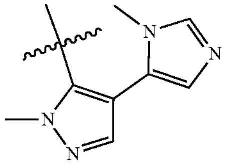 [SMILES: *c1c(-c2cncn2C)cnn1C] |
| 219 | Cl | 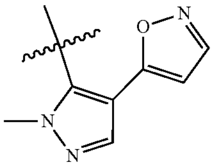 [SMILES: *c1c(-c2ccno2)cnn1C] |
| 220 | Cl | 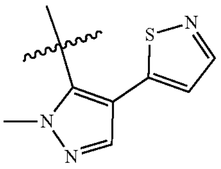 [SMILES: *c1c(-c2ccns2)cnn1C] |
| 221 | Cl | 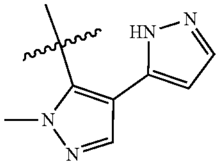 [SMILES: *c1c(-c2ccn[nH]2)cnn1C] |
| 222 | Cl | 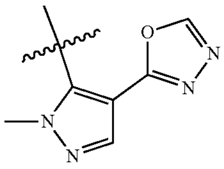 [SMILES: *c1c(-c2nnco2)cnn1C] |

-continued
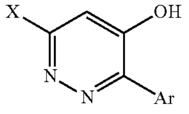
I
| No. | X | Ar |
|---|---|---|
| 223 | Cl | 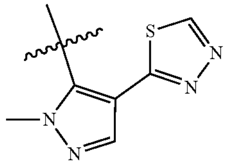 [SMILES: *c1c(-c2nncs2)cnn1C] |
| 224 | Cl | 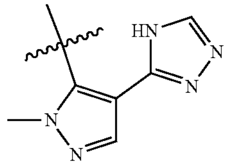 [SMILES: *c1c(-c2nnc[nH]2)cnn1C] |
| 225 | Cl | 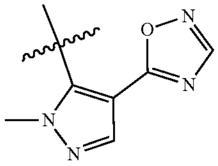 [SMILES: *c1c(-c2ncno2)cnn1C] |
| 226 | Cl | 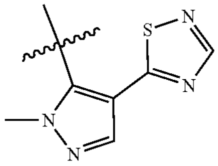 |
| 227 | Cl | 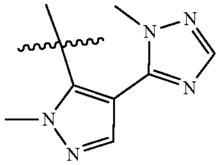 [SMILES: *c1c(-c2ncnn2C)cnn1C] |
| 228 | Cl | 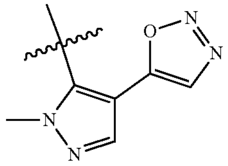 [SMILES: *c1c(-c2cnno2)cnn1C] |
| 229 | Cl | 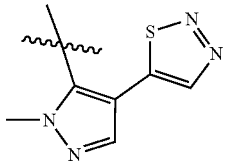 [SMILES: *c1c(-c2cnns2)cnn1C] |
| 230 | Cl | 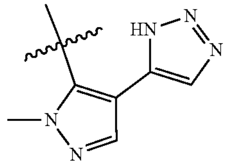 [SMILES: *c1c(-c2cnn[nH]2)cnn1C] |
-continued
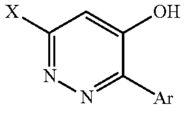
I
| No. | X | Ar |
|---|---|---|
| 231 | Cl | 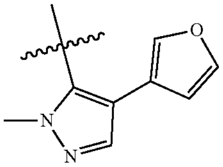 [SMILES: *c1c(-c2ccoc2)cnn1C] |
| 232 | Cl | 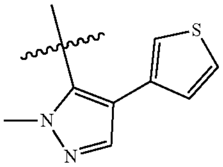 [SMILES: *c1c(-c2ccsc2)cnn1C] |
| 233 | Cl | 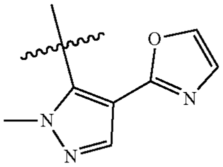 [SMILES: *c1c(-c2ncco2)cnn1C] |
| 234 | Cl | 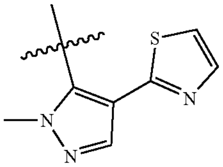 [SMILES: *c1c(-c2nccs2)cnn1C] |
| 235 | Cl | 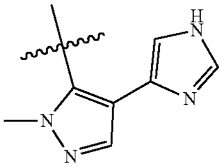 [SMILES: *c1c(-c2c[nH]cn2)cnn1C] |
| 236 | Cl | 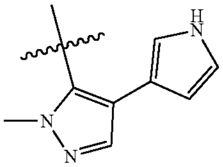 [SMILES: *c1c(-c2cc[nH]c2)cnn1C] |
| 237 | Cl | 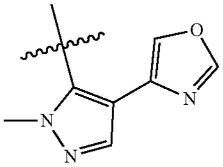 |
| 238 | Cl | 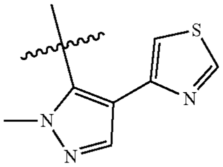 [SMILES: *c1c(-c2cscn2)cnn1C] |

-continued
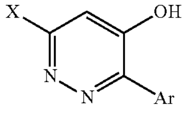
I
| No. | X | Ar |
|---|---|---|
| 239 | Cl | 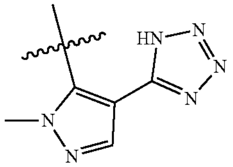 [SMILES: *c1c(-c2nnn[nH]2)cnn1C] |
| 240 | Cl | 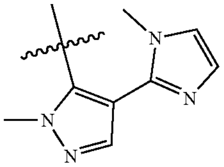 [SMILES: *c1c(-c2nccn2C)cnn1C] |
| 241 | Cl | 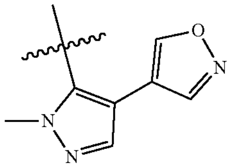 |
| 242 | Cl | 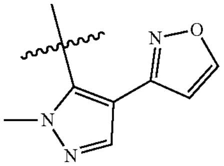 [SMILES: *c1c(-c2ccon2)cnn1C] |
| 243 | Cl | 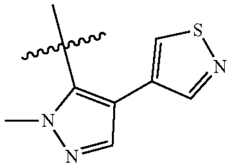 [SMILES: *c1c(-c2cnsc2)cnn1C] |
| 244 | Cl | 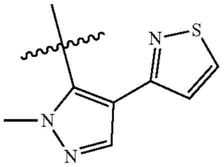 [SMILES: *c1c(-c2ccsn2)cnn1C] |
| 245 | Cl | 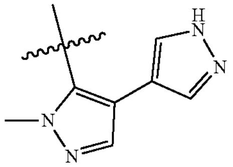 [SMILES: *c1c(-c2cn[nH]c2)cnn1C] |
| 246 | Cl | 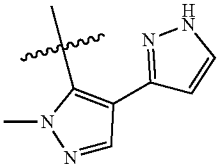 [SMILES: *c1c(-c2cc[nH]n2)cnn1C] |
-continued
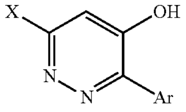
I
| No. | X | Ar |
|---|---|---|
| 247 | Cl | 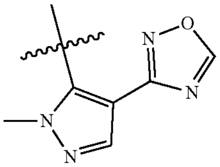 [SMILES: *c1c(-c2ncon2)cnn1C] |
| 248 | Cl | 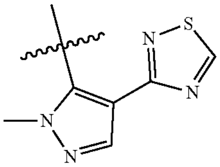 [SMILES: *c1c(-c2ncsn2)cnn1C] |
| 249 | Cl | 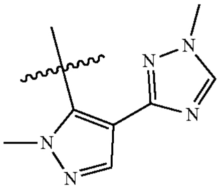 [SMILES: *c1c(-c2ncn(C)n2)cnn1C] |
| 250 | Cl | 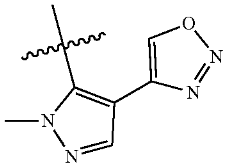 [SMILES: *c1c(-c2conn2)cnn1C] |
| 251 | Cl | 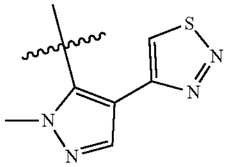 [SMILES: *c1c(-c2csnn2)cnn1C] |
| 252 | Cl | 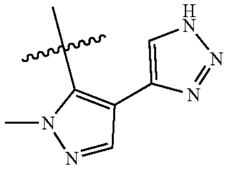 [SMILES: *c1c(-c2c[nH]nn2)cnn1C] |
| 253 | Cl | 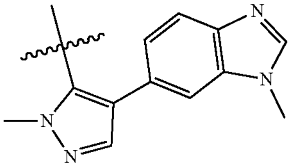 [SMILES: *c1c(-c2ccc3ncn(C)c3c2)cnn1C] |

-continued
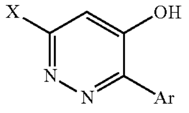
I
| No. | X | Ar |
|---|---|---|
| 254 | Cl | 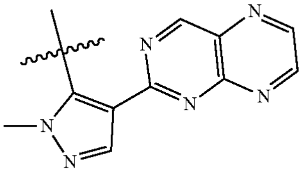 [SMILES: *c1c(-c2ncc3nccnc3n2)cnn1C] |
| 255 | Cl | 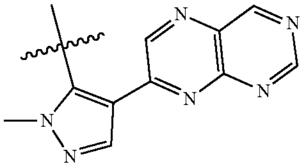 [SMILES: *c1c(-c2cnc3cncnc3n2)cnn1C] |
| 256 | Cl | 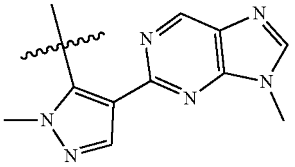 [SMILES: *c1c(-c2ncc3ncn(C)c3n2)cnn1C] |
| 257 | Cl | 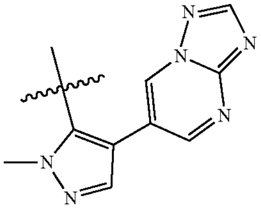 [SMILES: *c1c(-c2cnc3ncnn3c2)cnn1C] |
| 258 | Cl | 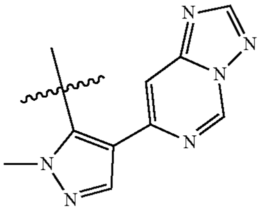 [SMILES: *c1c(-c2cc3ncnn3cn2)cnn1C] |
| 259 | Cl | 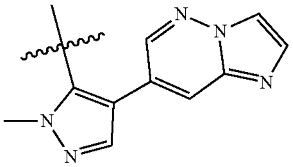 [SMILES: *c1c(-c2cnn3ccnc3c2)cnn1C] |
| 260 | Cl | 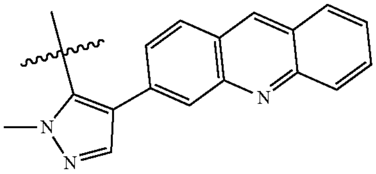 [SMILES: *c1c(-c2ccc3cc4ccccc4nc3c2)cnn1C] |
-continued
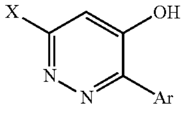
I
| No. | X | Ar |
|---|---|---|
| 261 | Cl | 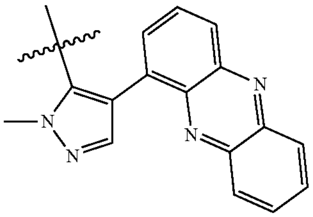 [SMILES: *c1c(-c2cccc3nc4ccccc4nc23)cnn1C] |
| 262 | Cl | 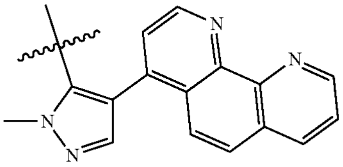 [SMILES: *c1c(-c2ccnc3c2ccc2cccnc23)cnn1C] |
| 263 | Cl | 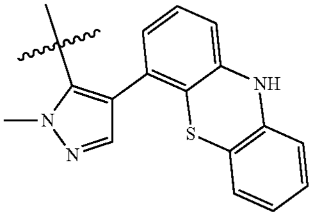 [SMILES: *c1c(-c2cccc3c2Sc2ccccc2N3)cnn1C] |
| 264 | Cl | 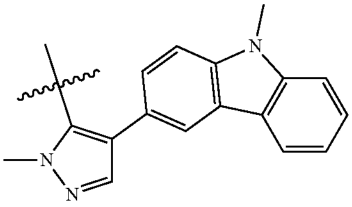 [SMILES: *c1c(-c2ccc3c(c2)c2ccccc2n3C)cnn1C] |
| 265 | Cl | 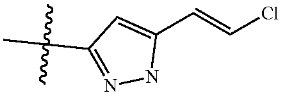 [SMILES: *c1cc(/C=C/Cl)[nH]n1] |
| 266 | Cl | 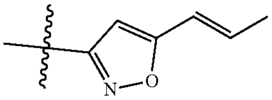 |
| 267 | Cl | 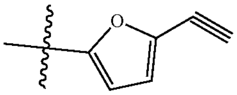 [SMILES: *c1ccc(C#C)o1] |
| 268 | Cl | 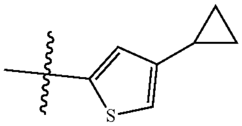 [SMILES: *c1cc(C2CC2)cs1] |

-continued
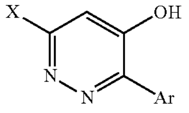
I
| No. | X | Ar |
|---|---|---|
| 269 | Cl | 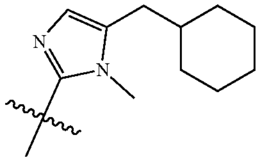 [SMILES: *c1ncc(CC2CCCCC2)n1C] |
| 270 | Cl | 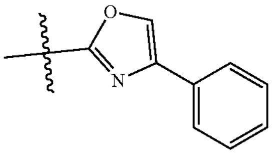 [SMILES: *c1nc(-c2ccccc2)co1] |
| 271 | Cl | 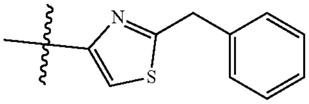 [SMILES: *c1csc(Cc2ccccc2)n1] |
| 272 | Cl | 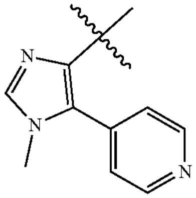 [SMILES: *c1ncn(C)c1-c1ccncc1] |
| 273 | Cl | 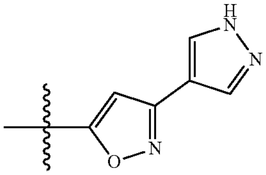 [SMILES: *c1cc(-c2cn[nH]c2)no1] |
| 274 | Cl | 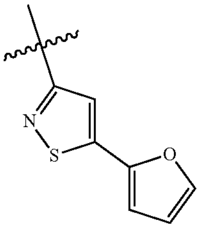 [SMILES: *c1cc(-c2ccco2)sn1] |
| 275 | Cl | 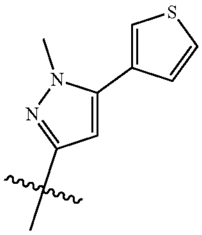 [SMILES: *c1cc(-c2ccsc2)n(C)n1] |
-continued
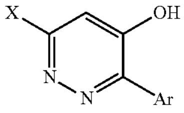
I
| No. | X | Ar |
|---|---|---|
| 276 | Cl | 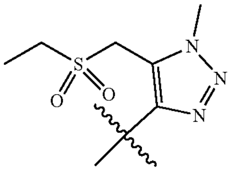 [SMILES: *c1nnn(C)c1CS(=O)(=O)CC] |
| 277 | Cl | 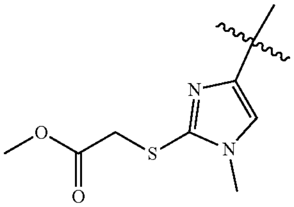 [SMILES: *c1cn(C)c(SCC(=O)OC)n1] |
| 278 | Cl | 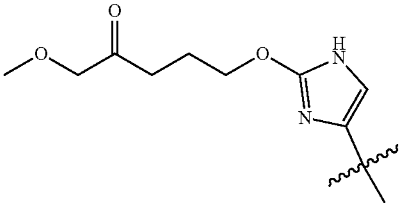 [SMILES: *c1c[nH]c(OCCCC(=O)COC)n1] |
| 279 | Cl | 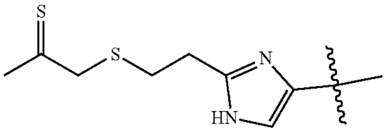 [SMILES: *c1c[nH]c(CCSCC(C)=S)n1] |
| 280 | Cl | 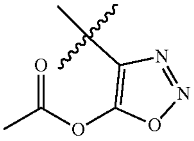 [SMILES: *c1nnoc1OC(C)=O] |
| 281 | Cl | 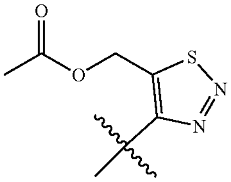 [SMILES: *c1nnsc1COC(C)=O] |
| 282 | Cl | 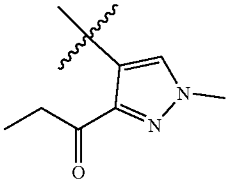 [SMILES: *c1cn(C)nc1C(=O)CC] |
| 283 | Cl | 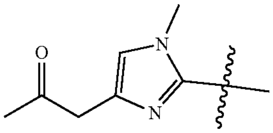 [SMILES: *c1nc(CC(C)=O)cn1C] |

-continued
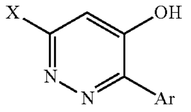
I
| No. | X | Ar |
|---|---|---|
| 284 | Cl | 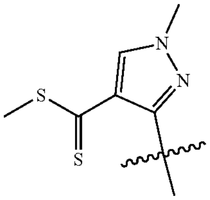 [SMILES: *c1nn(C)cc1C(=S)SC] |
| 285 | Cl | 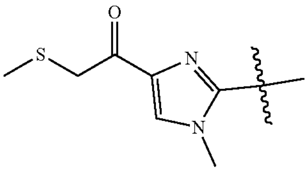 [SMILES: *c1nc(C(=O)CSC)cn1C] |
| 286 | Cl | 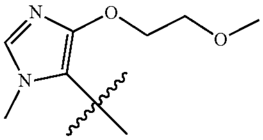 [SMILES: *c1c(OCCOC)ncn1C] |
| 287 | Cl | 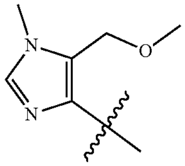 [SMILES: *c1ncn(C)c1COC] |
| 288 | Cl | 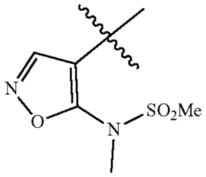 [SMILES: *c1cnoc1N(C)S(C)(=O)=O] |
| 289 | Cl | 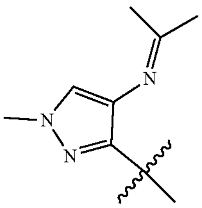 [SMILES: *c1nn(C)cc1N=C(C)C] |
| 290 | Cl | 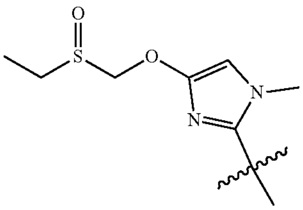 [SMILES: *c1nc(OCS(=O)CC)cn1C] |
-continued
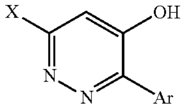
I
| No. | X | Ar |
|---|---|---|
| 291 | Cl | 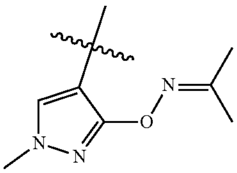 [SMILES: *c1cn(C)nc1ON=C(C)C] |
| 292 | Cl | 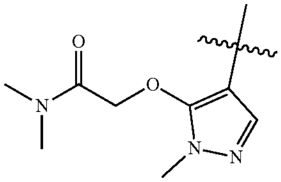 [SMILES: *c1cnn(C)c1OCC(=O)N(C)C] |
| 293 | Cl | 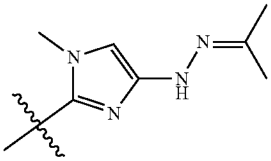 [SMILES: *c1nc(NN=C(C)C)cn1C] |
| 294 | Cl | 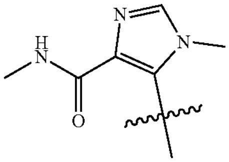 |
| 295 | Cl | 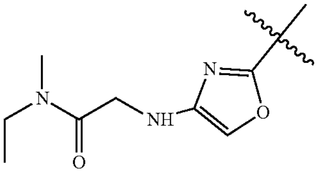 [SMILES: *c1nc(NCC(=O)N(C)CC)co1] |
| 296 | Cl | 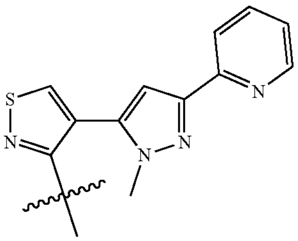 [SMILES: *c1nscc1-c1cc(-c2ccccn2)nn1C] |
| 297 | Cl | 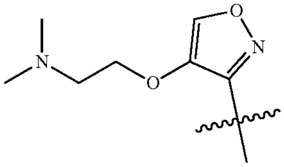 [SMILES: *c1nocc1OCCN(C)C] |

-continued
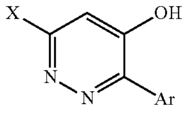
I
| No. | X | Ar |
|---|---|---|
| 298 | Cl | 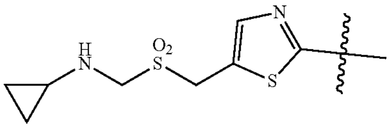 [SMILES: *c1ncc(CS(=O)(=O)CNC2CC2)s1] |
| 299 | Cl | 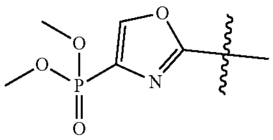 [SMILES: *c1nc(P(=O)(OC)OC)co1] |
| 300 | Cl | 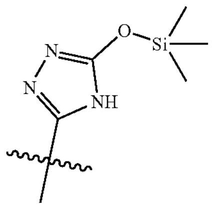 [SMILES: *c1nnc(O[Si](C)(C)C)[nH]1] |
| 301 | Cl | 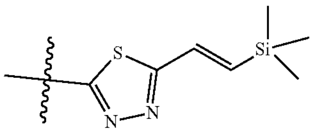 [SMILES: *c1nnc(/C=C/[Si](C)(C)C)s1] |
| 302 | Cl | 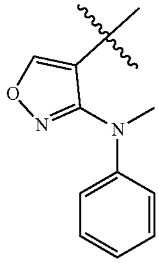 [SMILES: *c1conc1N(C)c1ccccc1] |
| 303 | Cl | 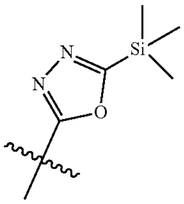 [SMILES: *c1nnc([Si](C)(C)C)o1] |
| 304 | Cl | 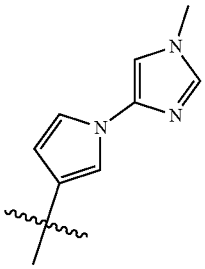 [SMILES: *c1ccn(-c2cn(C)cn2)c1] |
-continued
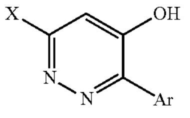
I
| No. | X | Ar |
|---|---|---|
| 305 | Cl | 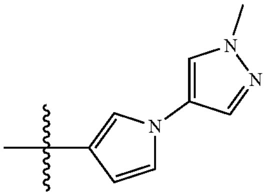 [SMILES: *c1ccn(-c2cnn(C)c2)c1] |
| 306 | Cl | 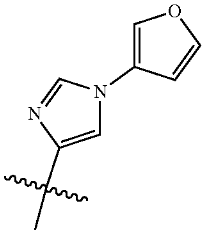 [SMILES: *c1cn(-c2ccoc2)cn1] |
| 307 | Cl | 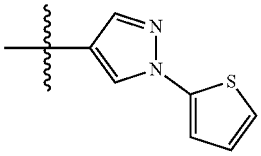 [SMILES: *c1cnn(-c2cccs2)c1] |
| 308 | Cl | 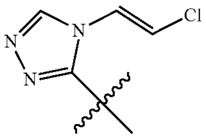 [SMILES: *c1nncn1/C=C/Cl] |
| 309 | Cl | 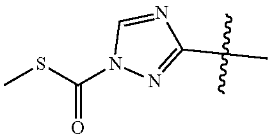 [SMILES: *c1ncn(C(=O)SC)n1] |
| 310 | Cl | 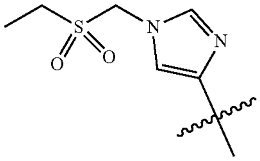 [SMILES: *c1cn(CS(=O)(=O)CC)cn1] |
| 311 | Cl | 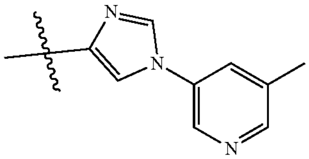 [SMILES: *c1cn(-c2cncc(C)c2)cn1] |
| 312 | Cl | 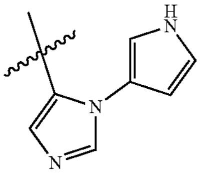 [SMILES: *c1cncn1-c1cc[nH]c1] |

-continued
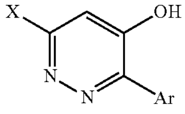
I
| No. | X | Ar |
|---|---|---|
| 313 | Cl | 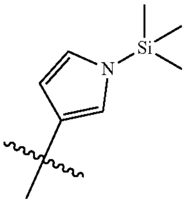 [SMILES: *c1ccn([Si](C)(C)C)c1] |
| 314 | Cl | 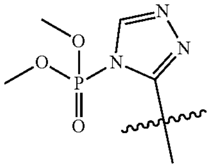 [SMILES: *c1nncn1P(=O)(OC)OC] |
| 315 | Cl | 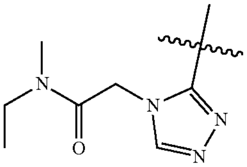 [SMILES: *c1nncn1CC(=O)N(C)CC] |
| 316 | Cl | 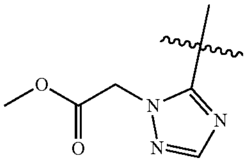 [SMILES: *c1ncnn1CC(=O)OC] |
| 317 | Cl | 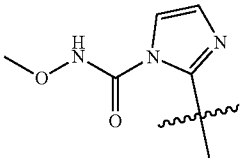 [SMILES: *c1nccn1C(=O)NOC] |
| 318 | Cl | 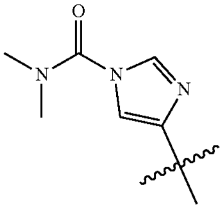 [SMILES: *c1cn(C(=O)N(C)C)cn1] |
| 319 | Cl | 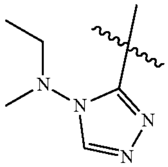 [SMILES: *c1nncn1N(C)CC] |
| 320 | Cl | 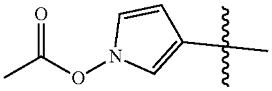 [SMILES: *c1ccn(OC(C)=O)c1] |
-continued
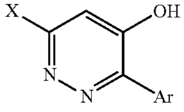
I
| No. | X | Ar |
|---|---|---|
| 321 | Cl | 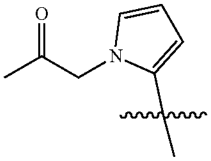 [SMILES: *c1cccn1CC(C)=O] |
| 322 | Cl | 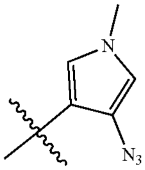 [SMILES: *c1cn(C)cc1N=[N+]=[N-]] |
| 323 | $CF_3$ | 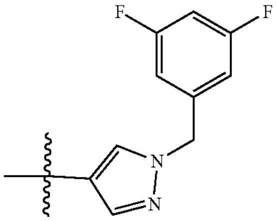 [SMILES: *c1cnn(Cc2cc(F)cc(F)c2)c1] |
| 324 | $CF_3$ | 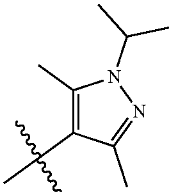 [SMILES: *c1c(C)nn(C(C)C)c1C] |
| 325 | $CF_3$ | 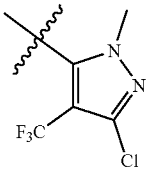 [SMILES: *c1c(C(F)(F)F)c(Cl)nn1C] |
| 326 | $CF_3$ | 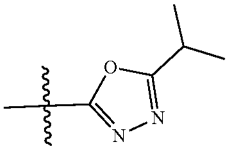 [SMILES: *c1nnc(C(C)C)o1] |
| 327 | $CF_3$ | 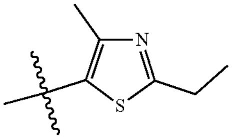 [SMILES: *c1sc(CC)nc1C] |

-continued

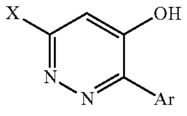

I

| No. | X | Ar |
|---|---|---|
| 328 | $CF_3$ | 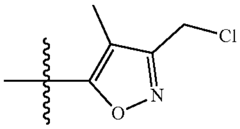 [SMILES: *c1onc(CCl)c1C] |
| 329 | $CF_3$ | 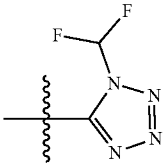 [SMILES: *c1nnnn1C(F)F] |
| 330 | $CF_3$ | 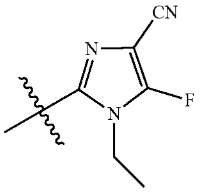 [SMILES: *c1nc(C#N)c(F)n1CC] |
| 331 | $CF_3$ | 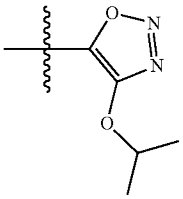 [SMILES: *c1onnc1OC(C)C] |
| 332 | $CF_3$ | 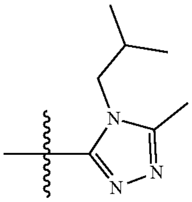 [SMILES: *c1nnc(C)n1CC(C)C] |
| 333 | $CF_3$ | 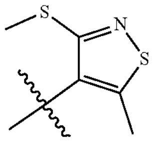 [SMILES: *c1c(SC)nsc1C] |
| 334 | $CF_3$ | 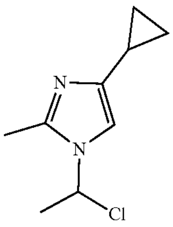 |

-continued

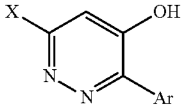

I

| No. | X | Ar |
|---|---|---|
| 335 | $CF_3$ | 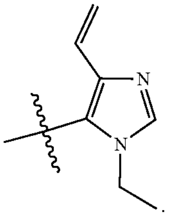 [SMILES: *c1c(C=C)ncn1CC] |

13. A derivative of the five-membered ring-substituted pyridazinol compound according to claim 1, which has a structure as shown in Formula I-1:

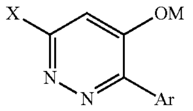

I-1 wherein M is (thio)formyl, C1-C18 alkyl(thio)carbonyl, further wherein said (thio)formyl or C1-C18 alkyl(thio) carbonyl is unsubstituted or substituted with a substituent independently selected from halogen, amino, C3-C8 cycloalkyl, C1-C8 alkoxy, C1-C8 alkylsulfanyl, C1-C8 alkoxycarbonyl, C1-C8 alkylcarbonyloxy, C1-C8 alkylcarbonyl, hydroxy(methyl)phosphinyl, phenyl, phenylsulfanyl, phenyloxy and benzyloxy, wherein said phenyl, phenylsulfanyl, phenyloxy or benzyloxy is unsubstituted or substituted with 1-3 substituents selected from halogen and C1-C8 alkoxy;

an unsubstituted or phenyl substituted group of C1-C18 alkoxy(thio)carbonyl or C1-C18 alkylsulfanyl(thio) carbonyl;

C3-C8 cycloalkylsulfanyl(thio)carbonyl;

phenyl-C1-C8 alkylsulfanyl(thio)carbonyl;

5- or 6-membered heterocyclyloxy(thio)carbonyl;

5- or 6-membered heterocyclylsulfanyl(thio)carbonyl;

C2-C8 alkenyl(thio)carbonyl, wherein said C2-C8 alkenyl(thio)carbonyl is unsubstituted or substituted with a substituent selected from C1-C8 alkoxy, phenyl and phenyl substituted with 1-3 substituents selected from halogen;

(thio)benzoyl, wherein said (thio)benzoyl is unsubstituted or substituted with 1-3 substituents selected from halogen, hydroxy, C1-C8 alkyl, C1-C8 alkoxy, cyano, C1-C8 alkoxy substituted with 1-3 substituents selected from halogen, C1-C8 alkylcarbonyloxy, C1-C8 alkylcarbonylamino, amino and amino substituted with 1 or 2 substituents selected from C1-C8 alkyl;

halogenated sulfhydryl formyl;

3- to 8-membered heterocyclyl(thio)carbonyl, wherein said 3- to 8-membered heterocyclyl(thio)carbonyl is unsubstituted or substituted with 1-3 substituents selected from C1-C8 alkyl, halogen and C1-C8 alkylsulfanyl;

fused 5- to 14-membered bicyclic or tricyclic heterocyclyl (thio)carbonyl;

amino(thio)formyl, wherein said amino(thio)formyl is unsubstituted or substituted with 1-3 substituents selected from C1-C8 alkyl and C1-C8 alkoxy;

an unsubstituted or halogen or C1-C8 alkylsulfonyl substituted group selected from C1-C8 alkylsulfoxide, C1-C8 alkylsulfonyl and C3-C8 cycloalkylsulfonyl;

phenylsulfonyl, benzylsulfonyl, naphthylsulfonyl, wherein each of said phenylsulfonyl, benzylsulfonyl and naphthylsulfonyl is unsubstituted or substituted with 1-3 substituents independently selected from halogen, nitro, C1-C8 alkyl, halogenated C1-C8 alkyl, halogenated C1-C8 alkoxy, C1-C8 alkylcarbonyl, C1-C8 alkylsulfonyl, aminoformyl, phenoxy and phenoxy substituted with 1-3 substituents selected from halogen;

5- to 10-membered heteroarylsulfonyl, wherein said 5- to 10-membered heteroarylsulfonyl is unsubstituted or substituted with 1-3 substituents selected from C1-C8 alkyl and phenoxy;

C1-C8 alkylaminosulfonyl that is unsubstituted or substituted with halogen;

di(C1-C8 alkyl) phosphoryl;

di(C1-C8 alkyl)thiophosphoryl;

C1-18 alkyl, wherein said C1-18 alkyl is unsubstituted or substituted with a substituent independently selected from C1-C8 alkylsulfanyl, di(C1-C8 alkyl)amino, C1-C8 alkoxycarbonyl and C1-C8 alkoxycarbonyloxy;

phenyl, benzyl, benzoyl-C1-C8 alkyl, wherein said phenyl, benzyl or benzoyl-C1-C8 alkyl is unsubstituted or substituted with 1-3 substituents selected from halogen and C1-C8 alkoxy;

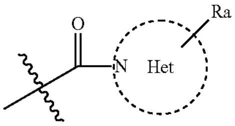
;

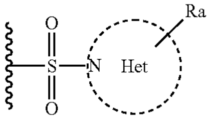
;

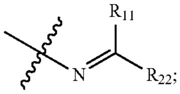
or

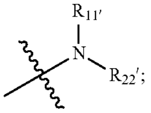

wherein, $R_{11}$ and $R_{22}$ are independently selected from hydrogen, C1-C18 alkyl, C2-C18 alkenyl, wherein said C1-C18 alkyl or C2-C18 alkenyl is unsubstituted or substituted with a substituent selected from halogen, C1-C8 alkoxy and C1-C8 alkylsulfanyl, phenyl, phenylcarbonyl and 5- to 6-membered heteroaryl, wherein said phenyl, phenylcarbonyl or 5- to 6-membered heteroaryl is unsubstituted or substituted with 1-3 substituents selected from halogen and C1-C8 alkyl; or $R_{11}$ and $R_{12}$ forms a 5- to 6-membered saturated carbocyclic ring or a 5- to 6-membered saturated heterocyclic ring;

$R_{11}$' and $R_{22}$' independently are hydrogen, C1-C18 alkyl, C1-C18 alkoxycarbonyl or benzoyl;

Het is selected from

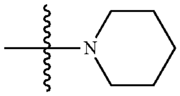
,

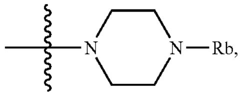

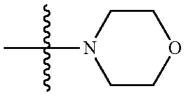
and

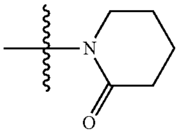
, $R_a$ and $R_b$ independently are hydrogen or C1-C6 alkyl.

14. The derivative of the five-membered ring-substituted pyridazinol compound according to claim 13, wherein M is selected from the following groups:

| No. | M |
|---|---|
| M-1 | 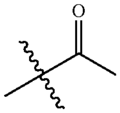 [SMILES: *C(C)=O] |
| M-2 | 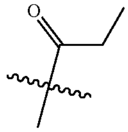 [SMILES: *C(=O)CC] |
| M-3 | 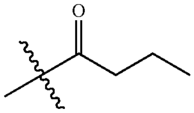 [SMILES: *C(=O)CCC] |
| M-4 | 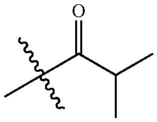 [SMILES: *C(=O)C(C)C] |
| M-5 | 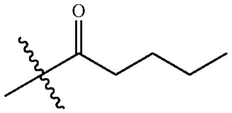 [SMILES: *C(=O)CCCC] |
| M-6 | 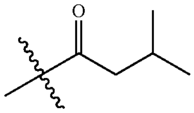 |
| M-7 | 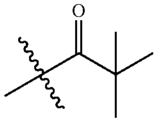 [SMILES: *C(=O)C(C)(C)C] |

-continued
| No. | M |
| --- | --- |
| M-8 | 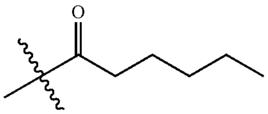 [SMILES: *C(=O)CCCCC] |
| M-9 | 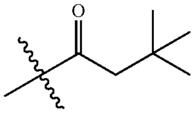 [SMILES: *C(=O)CC(C)(C)C] |
| M-10 | 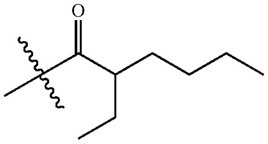 [SMILES: *C(=O)C(CC)CCCC] |
| M-11 | 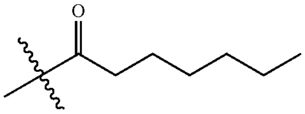 [SMILES: *C(=O)CCCCCC] |
| M-12 | 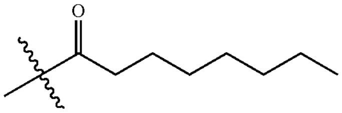 [SMILES: *C(=O)CCCCCCC] |
| M-13 | 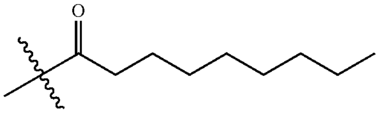 |
| M-14 | 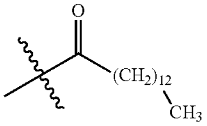 |
| M-15 | 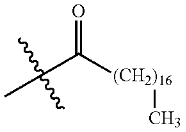 |
| M-16 | 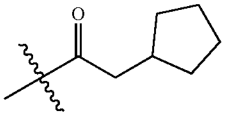 [SMILES: *C(=O)CC1CCCC1] |
| M-17 | 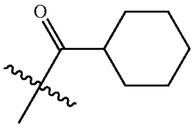 [SMILES: *C(=O)C1CCCCC1] |
| M-18 | 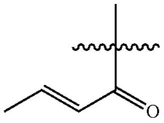 [SMILES: *C(=O)/C=C/C] |
-continued
| No. | M |
| --- | --- |
| M-19 | 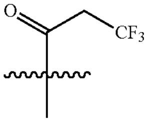 [SMILES: *C(=O)CC(F)(F)F] |
| M-20 | 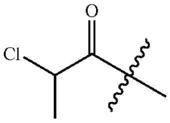 [SMILES: *C(=O)C(C)Cl] |
| M-21 | 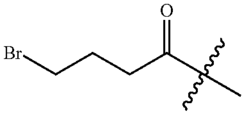 [SMILES: *C(=O)CCCBr] |
| M-22 | 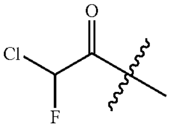 [SMILES: *C(=O)C(F)Cl] |
| M-23 | 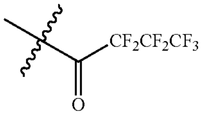 |
| M-24 | 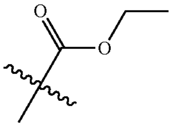 |
| M-25 | 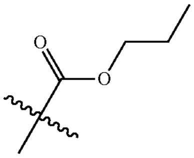 [SMILES: *C(=O)OCCC] |
| M-26 | 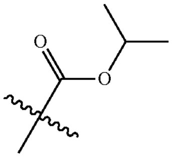 [SMILES: *C(=O)OC(C)C] |
| M-27 | 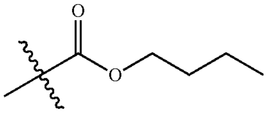 [SMILES: *C(=O)OCCCC] |
| M-28 | 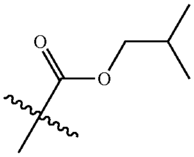 [SMILES: *C(=O)OCC(C)C] |
| M-29 | 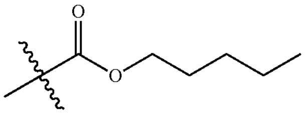 [SMILES: *C(=O)OCCCCC] |

-continued
| No. | M |
| --- | --- |
| M-30 | 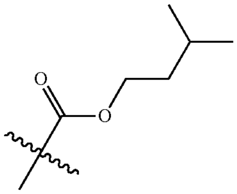 |
| M-31 | 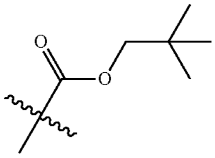 [SMILES: *C(=O)OCC(C)(C)C] |
| M-32 | 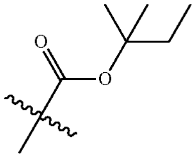 [SMILES: *C(=O)OC(C)(C)CC] |
| M-33 | 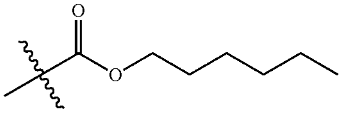 |
| M-34 | 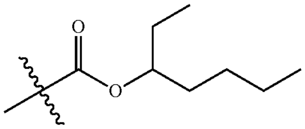 [SMILES: *C(=O)OC(CC)CCCC] |
| M-35 | 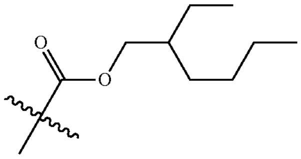 [SMILES: *C(=O)OCC(CC)CCCC] |
| M-36 | 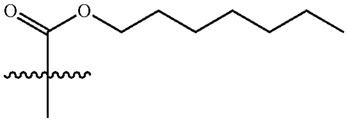 |
| M-37 | 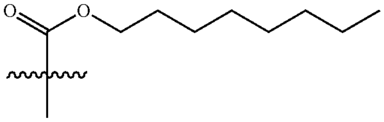 [SMILES: *C(=O)OCCCCCCCC] |
| M-38 | 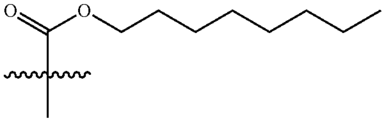 [SMILES: *C(=O)OCCCCCCCC] |
| M-39 | 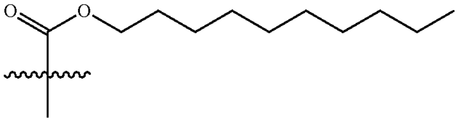 [SMILES: *C(=O)OCCCCCCCCCC] |
-continued
| No. | M |
| --- | --- |
| M-40 | 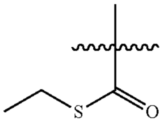 [SMILES: *C(=O)SCC] |
| M-41 | 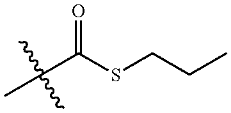 [SMILES: *C(=O)SCCC] |
| M-42 | 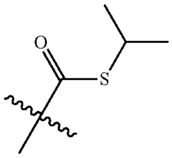 [SMILES: *C(=O)SC(C)C] |
| M-43 | 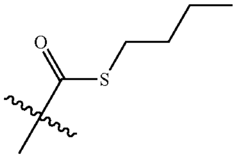 [SMILES: *C(=O)SCCCC] |
| M-44 | 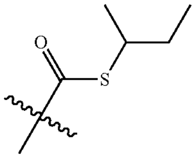 [SMILES: *C(=O)SC(C)CC] |
| M-45 | 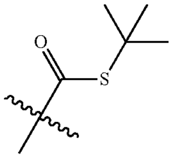 [SMILES: *C(=O)SC(C)(C)C] |
| M-46 | 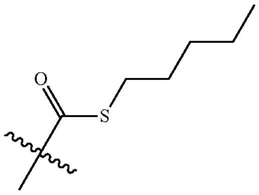 [SMILES: *C(=O)SCCCCC] |
| M-47 | 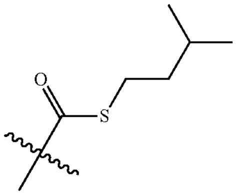 [SMILES: *C(=O)SCCC(C)C] |
| M-48 | 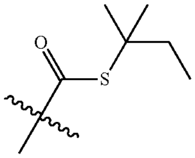 [SMILES: *C(=O)SC(C)(C)CC] |

-continued
| No. | M |
|---|---|
| M-49 | 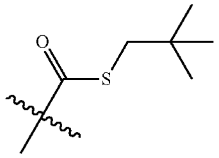 |
| M-50 | 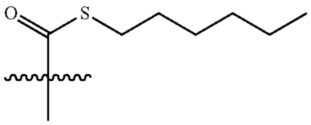 [SMILES: *C(=O)SCCCCCC] |
| M-51 | 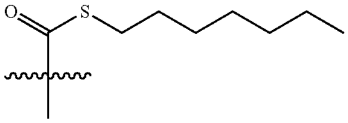 [SMILES: *C(=O)SCCCCCCC] |
| M-52 | 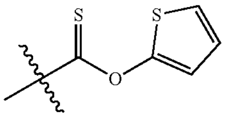 [SMILES: *C(=S)Oc1cccs1] |
| M-53 | 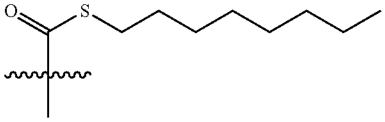 [SMILES: *C(=O)SCCCCCCCC] |
| M-54 | 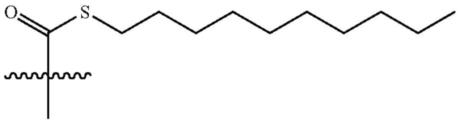 |
| M-55 | 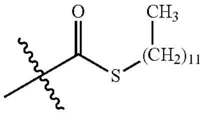 |
| M-56 | 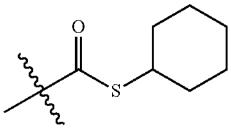 [SMILES: *C(=O)SC1CCCCC1] |
| M-57 | 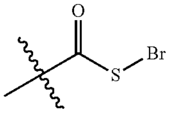 [SMILES: *C(=O)SBr] |
| M-58 | 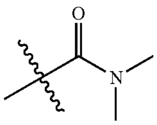 [SMILES: *C(=O)N(C)C] |
| M-59 | 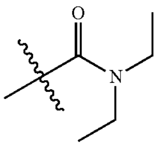 [SMILES: *C(=O)N(CC)CC] |
-continued
| No. | M |
|---|---|
| M-60 | 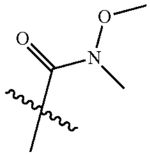 [SMILES: *C(=O)N(C)OC] |
| M-61 | 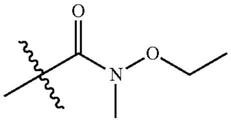 [SMILES: *C(=O)N(C)OCC] |
| M-62 | 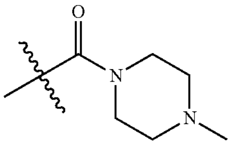 [SMILES: *C(=O)N1CCN(C)CC1] |
| M-63 | 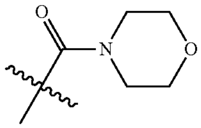 [SMILES: *C(=O)N1CCOCC1] |
| M-64 | 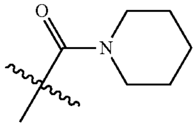 [SMILES: *C(=O)N1CCCCC1] |
| M-65 | 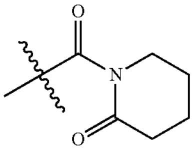 [SMILES: *C(=O)N1CCCCC1=O] |
| M-66 | 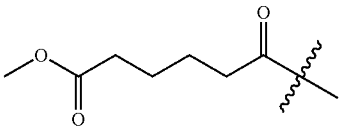 [SMILES: *C(=O)CCCCC(=O)OC] |
| M-67 | 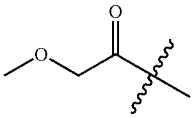 [SMILES: *C(=O)COC] |
| M-68 | 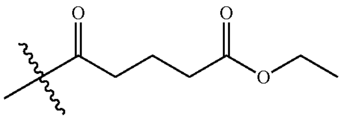 [SMILES: *C(=O)CCCC(=O)OCC] |
| M-69 | 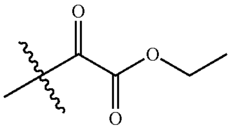 [SMILES: *C(=O)C(=O)OCC] |
| M-70 | 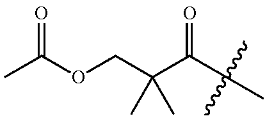 [SMILES: *C(=O)C(C)(C)COC(C)=O] |

-continued
| No. | M |
| --- | --- |
| M-71 | 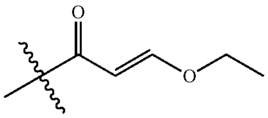 [SMILES: *C(=O)/C=C/OCC] |
| M-72 | 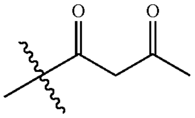 [SMILES: *C(=O)CC(C)=O] |
| M-73 | 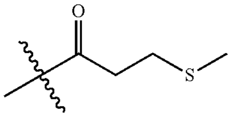 [SMILES: *C(=O)CCSC] |
| M-74 | 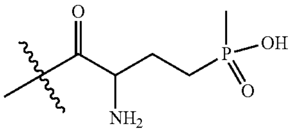 [SMILES: *C(=O)C(N)CCP(C)(=O)O] |
| M-75 | 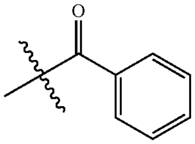 [SMILES: *C(=O)c1ccccc1] |
| M-76 | 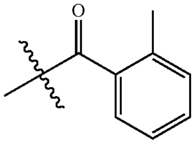 [SMILES: *C(=O)c1ccccc1C] |
| M-77 | 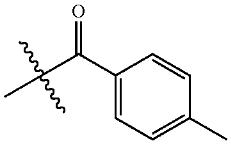 [SMILES: *C(=O)c1ccc(C)cc1] |
| M-78 | 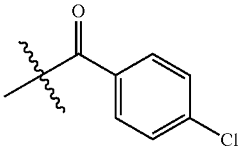 [SMILES: *C(=O)c1ccc(Cl)cc1] |
| M-79 | 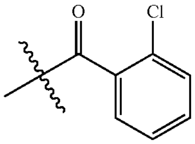 [SMILES: *C(=O)c1ccccc1Cl] |
| M-80 | 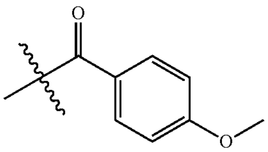 [SMILES: *C(=O)c1ccc(OC)cc1] |
-continued
| No. | M |
| --- | --- |
| M-81 | 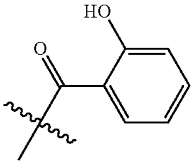 [SMILES: *C(=O)c1ccccc1O] |
| M-82 | 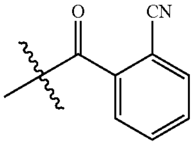 [SMILES: *C(=O)c1ccccc1C#N] |
| M-83 | 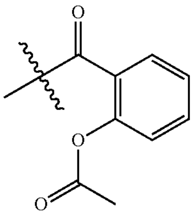 [SMILES: *C(=O)c1ccccc1OC(C)=O] |
| M-84 | 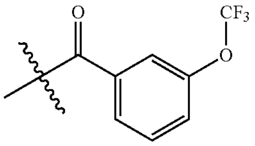 [SMILES: *C(=O)c1cccc(OC(F)(F)F)c1] |
| M-85 | 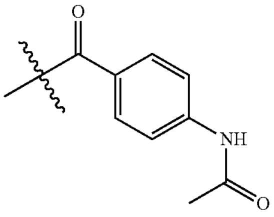 [SMILES: *C(=O)c1ccc(NC(C)=O)cc1] |
| M-86 | 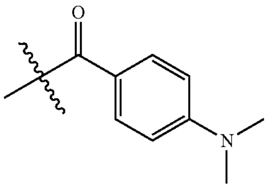 [SMILES: *C(=O)c1ccc(N(C)C)cc1] |
| M-87 | 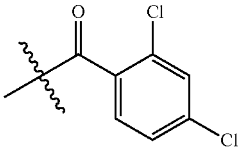 [SMILES: *C(=O)c1ccc(Cl)cc1Cl] |
| M-88 | 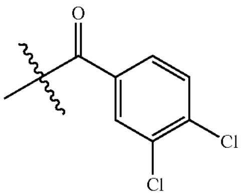 [SMILES: *C(=O)c1ccc(Cl)c(Cl)c1] |

-continued
| No. | M |
|---|---|
| M-89 | 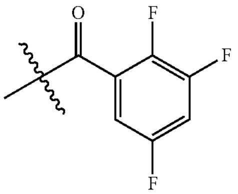 [SMILES: *C(=O)c1cc(F)cc(F)c1F] |
| M-90 | 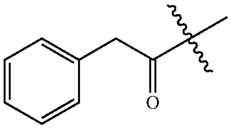 [SMILES: *C(=O)Cc1ccccc1] |
| M-91 | 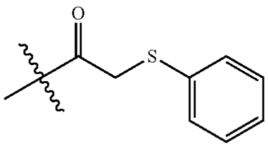 [SMILES: *C(=O)CSc1ccccc1] |
| M-92 | 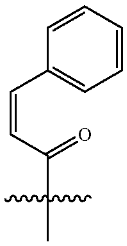 [SMILES: *C(=O)/C=C\c1ccccc1] |
| M-93 | 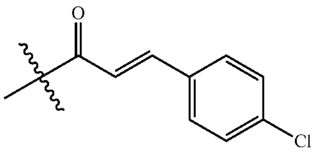 [SMILES: *C(=O)/C=C/c1ccc(Cl)cc1] |
| M-94 | 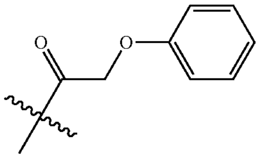 [SMILES: *C(=O)COc1ccccc1] |
| M-95 | 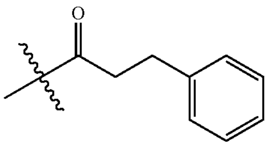 [SMILES: *C(=O)CCc1ccccc1] |
| M-96 | 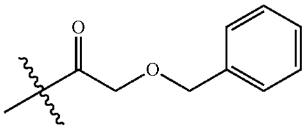 [SMILES: *C(=O)COCc1ccccc1] |
| M-97 | 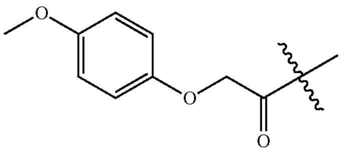 [SMILES: *C(=O)COc1ccc(OC)cc1] |
-continued
| No. | M |
|---|---|
| M-98 | 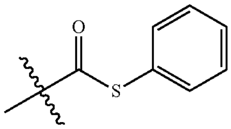 [SMILES: *C(=O)Sc1ccccc1] |
| M-99 | 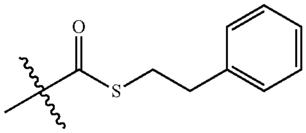 [SMILES: *C(=O)SCCc1ccccc1] |
| M-100 | 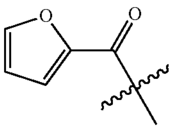 |
| M-101 | 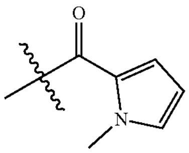 [SMILES: *C(=O)c1cccn1C] |
| M-102 | 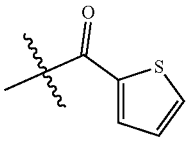 [SMILES: *C(=O)c1cccs1] |
| M-103 | 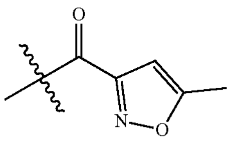 [SMILES: *C(=O)c1cc(C)on1] |
| M-104 | 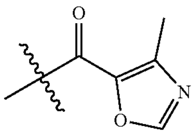 [SMILES: *C(=O)c1ocnc1C] |
| M-105 | 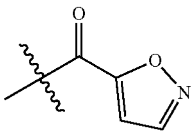 [SMILES: *C(=O)c1ccno1] |
| M-106 | 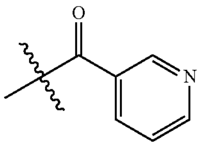 [SMILES: *C(=O)c1cccnc1] |
| M-107 | 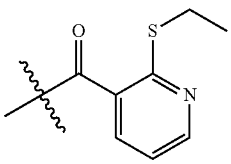 [SMILES: *C(=O)c1cccnc1SCC] |

-continued
| No. | M |
|---|---|
| M-108 | 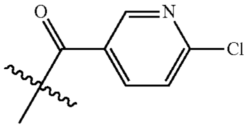 [SMILES: *C(=O)c1ccc(Cl)nc1] |
| M-109 | 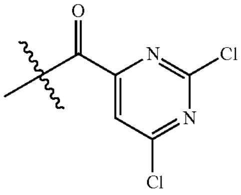 [SMILES: *C(=O)c1cc(Cl)nc(Cl)n1] |
| M-110 | 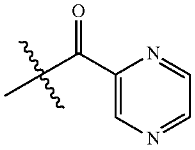 [SMILES: *C(=O)c1cnccn1] |
| M-111 | 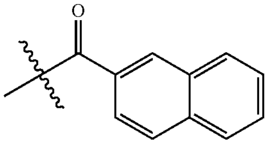 [SMILES: *C(=O)c1ccc2ccccc2c1] |
| M-112 | 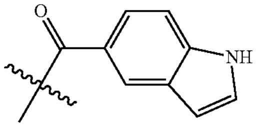 [SMILES: *C(=O)c1ccc2[nH]ccc2c1] |
| M-113 | 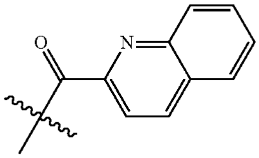 [SMILES: *C(=O)c1ccc2ccccc2n1] |
| M-114 | 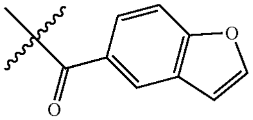 [SMILES: *C(=O)c1ccc2occc2c1] |
| M-115 | 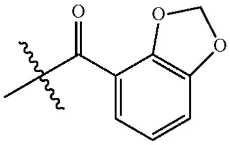 [SMILES: *C(=O)c1cccc2c1OCO2] |
| M-116 | 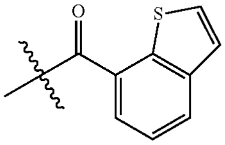 [SMILES: *C(=O)c1cccc2ccsc12] |
| M-117 | 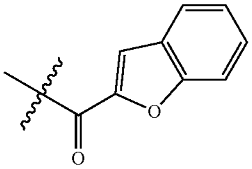 [SMILES: *C(=O)c1cc2ccccc2o1] |
-continued
| No. | M |
|---|---|
| M-118 | 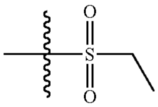 |
| M-119 | 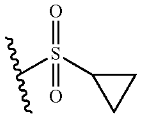 |
| M-120 | 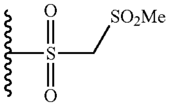 |
| M-121 | 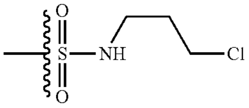 |
| M-122 | 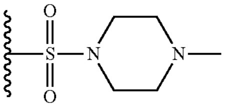 |
| M-123 | 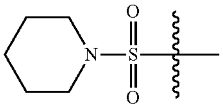 [SMILES: *S(=O)(=O)N1CCCCC1] |
| M-124 | 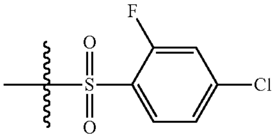 [SMILES: *S(=O)(=O)c1ccc(Cl)cc1F] |
| M-125 | 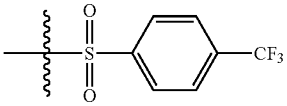 [SMILES: *S(=O)(=O)c1ccc(C(F)(F)F)cc1] |
| M-126 | 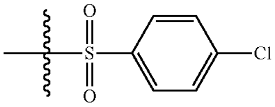 [SMILES: *S(=O)(=O)c1ccc(Cl)cc1] |
| M-127 | 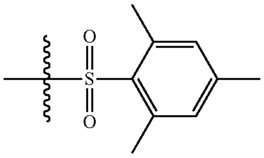 [SMILES: *S(=O)(=O)c1c(C)cc(C)cc1C] |
| M-128 | 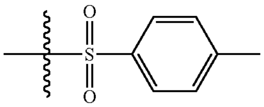 [SMILES: *S(=O)(=O)c1ccc(C)cc1] |
| M-129 | 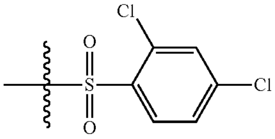 [SMILES: *S(=O)(=O)c1ccc(Cl)cc1Cl] |

-continued
| No. | M |
|---|---|
| M-130 | 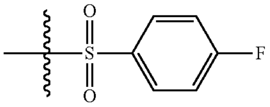 [SMILES: *S(=O)(=O)c1ccc(F)cc1] |
| M-131 | 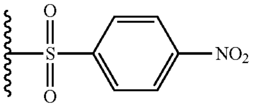 |
| M-132 | 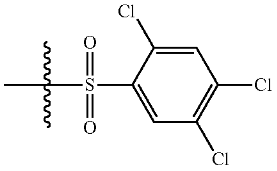 [SMILES: *S(=O)(=O)c1cc(Cl)c(Cl)cc1Cl] |
| M-133 | 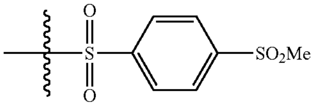 [SMILES: *S(=O)(=O)c1ccc(S(C)(=O)=O)cc1] |
| M-134 | 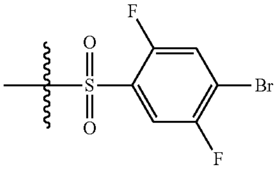 [SMILES: *S(=O)(=O)c1cc(F)c(Br)cc1F] |
| M-135 | 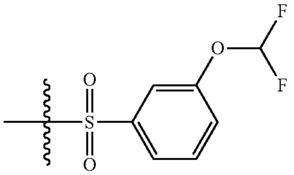 [SMILES: *S(=O)(=O)c1cccc(OC(F)F)c1] |
| M-136 | 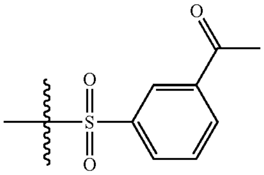 [SMILES: *S(=O)(=O)c1cccc(C(C)=O)c1] |
| M-137 | 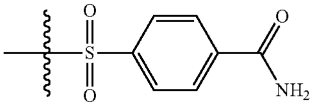 [SMILES: *S(=O)(=O)c1ccc(C(N)=O)cc1] |
| M-138 | 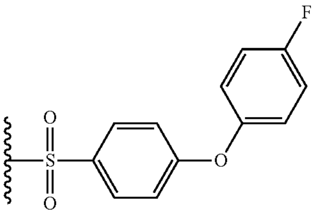 [SMILES: *S(=O)(=O)c1ccc(Oc2ccc(F)cc2)cc1] |
| M-139 | 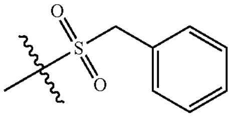 [SMILES: *S(=O)(=O)Cc1ccccc1] |
-continued
| No. | M |
|---|---|
| M-140 | 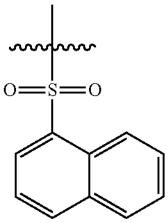 [SMILES: *S(=O)(=O)c1cccc2ccccc12] |
| M-141 | 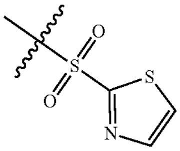 [SMILES: *S(=O)(=O)c1nccs1] |
| M-142 | 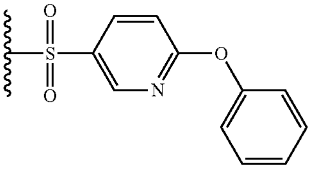 [SMILES: *S(=O)(=O)c1ccc(Oc2ccccc2)nc1] |
| M-143 | 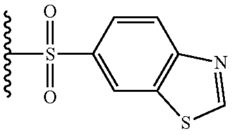 [SMILES: *S(=O)(=O)c1ccc2ncsc2c1] |
| M-144 | 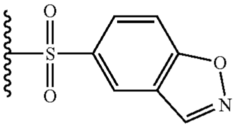 [SMILES: *S(=O)(=O)c1ccc2oncc2c1] |
| M-145 | 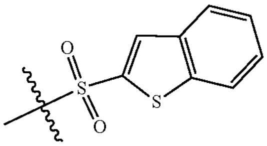 [SMILES: *S(=O)(=O)c1cc2ccccc2s1] |
| M-146 | 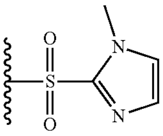 |
| M-147 | 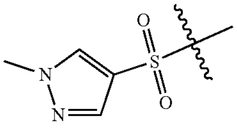 [SMILES: *S(=O)(=O)c1cnn(C)c1] |
| M-148 | 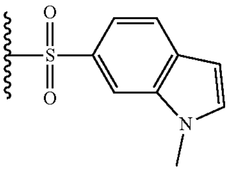 [SMILES: *S(=O)(=O)c1ccc2ccn(C)c2c1] |

-continued
| No. | M |
|---|---|
| M-149 | 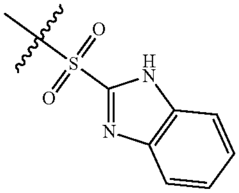 [SMILES: *S(=O)(=O)c1nc2ccccc2[nH]1] |
| M-150 | 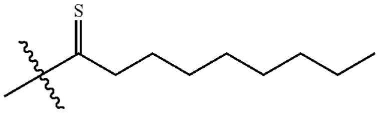 [SMILES: *C(=S)CCCCCCCC] |
| M-151 | 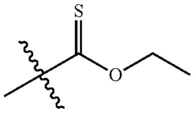 [SMILES: *C(=S)OCC] |
| M-152 | 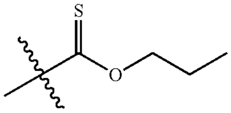 [SMILES: *C(=S)OCCC] |
| M-153 | 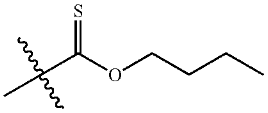 [SMILES: *C(=S)OCCCC] |
| M-154 | 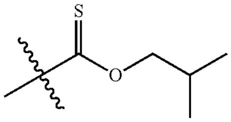 [SMILES: *C(=S)OCC(C)C] |
| M-155 | 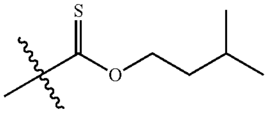 [SMILES: *C(=S)OCCC(C)C] |
| M-156 | 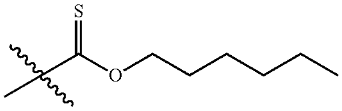 [SMILES: *C(=S)OCCCCCC] |
| M-157 | 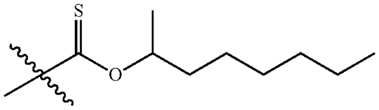 [SMILES: *C(=S)OC(C)CCCCCC] |
| M-158 | 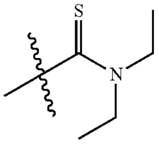 [SMILES: *C(=S)N(CC)CC] |
| M-159 | 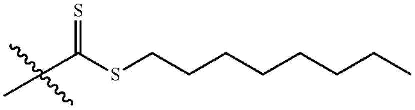 [SMILES: *C(=S)SCCCCCCCC] |
| M-160 | 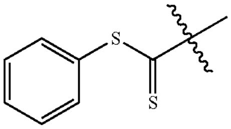 |
| M-161 | 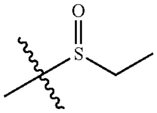 [SMILES: *S(=O)CC] |
| M-162 | 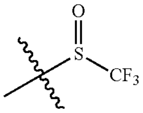 [SMILES: *S(=O)C(F)(F)F] |
| M-163 | 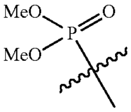 |
| M-164 | 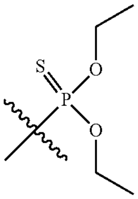 [SMILES: *P(=S)(OCC)OCC] |
| M-165 | 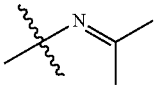 [SMILES: *N=C(C)C] |
| M-166 | 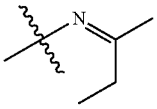 [SMILES: */N=C(/C)CC] |
| M-167 | 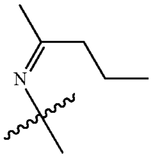 [SMILES: */N=C(/C)CCC] |
| M-168 | 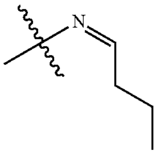 [SMILES: */N=C\CCC] |
| M-169 | 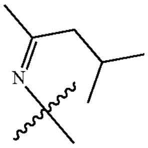 [SMILES: */N=C(/C)CC(C)C] |
| M-170 | 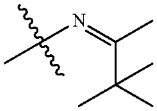 [SMILES: */N=C(/C)C(C)(C)C] |

-continued
| No. | M |
|---|---|
| M-171 | 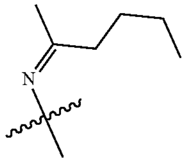 [SMILES: */N=C(/C)CCCC] |
| M-172 | 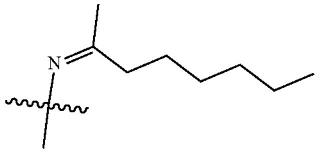 [SMILES: */N=C(/C)CCCCCC] |
| M-173 | 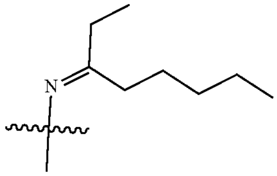 [SMILES: */N=C(/CC)CCCCC] |
| M-174 | 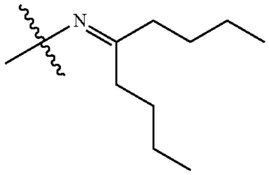 [SMILES: *N=C(CCCC)CCCC] |
| M-175 | 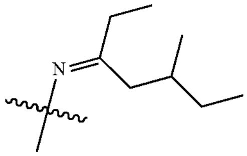 [SMILES: */N=C(/CC)CC(C)CC] |
| M-176 | 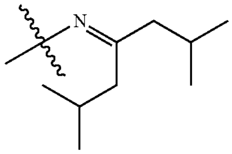 [SMILES: *N=C(CC(C)C)CC(C)C] |
| M-177 | 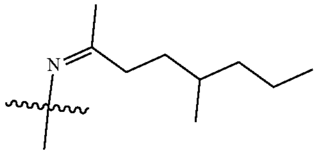 [SMILES: */N=C(/C)CCC(C)CCC] |
| M-178 | 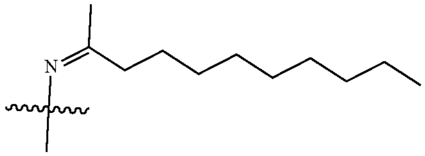 [SMILES: */N=C(/C)CCCCCCCCC] |
| M-179 | 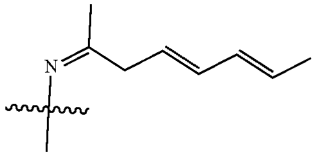 [SMILES: */N=C(/C)C/C=C/C=C/C] |
-continued
| No. | M |
|---|---|
| M-180 | 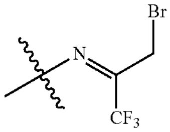 [SMILES: */N=C(/CBr)C(F)(F)F] |
| M-181 | 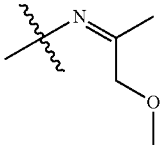 [SMILES: */N=C(/C)COC] |
| M-182 | 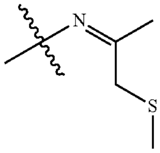 [SMILES: */N=C(/C)CSC] |
| M-183 | 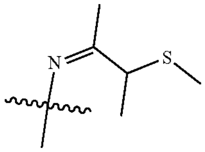 [SMILES: */N=C(/C)C(C)SC] |
| M-184 | 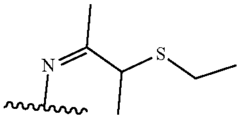 [SMILES: */N=C(/C)C(C)SCC] |
| M-185 | 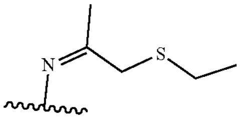 [SMILES: */N=C(/C)CSCC] |
| M-186 | 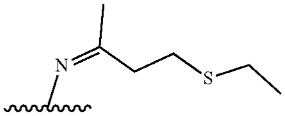 [SMILES: */N=C(/C)CCSCC] |
| M-187 | 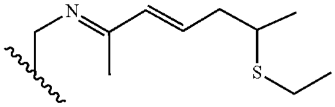 [SMILES: *C/N=C(C)/C=C/CC(C)SCC] |
| M-188 | 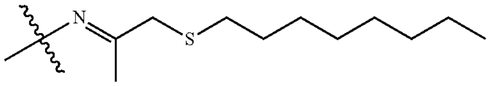 [SMILES: */N=C(\C)CSCCCCCCCC] |
| M-189 | 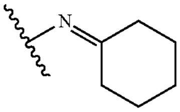 [SMILES: *N=C1CCCCC1] |
| M-190 | 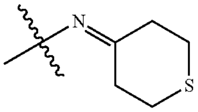 [SMILES: *N=C1CCSCC1] |

-continued
| No. | M |
|---|---|
| M-191 | 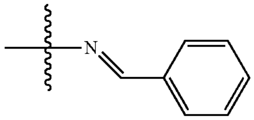 [SMILES: */N=C/c1ccccc1] |
| M-192 | 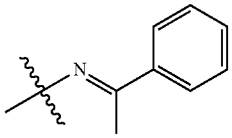 [SMILES: */N=C(\C)c1ccccc1] |
| M-193 | 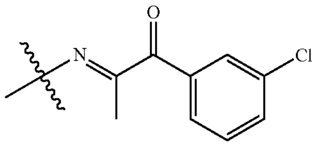 [SMILES: */N=C(\C)C(=O)c1cccc(Cl)c1] |
| M-194 | 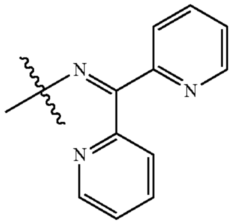 [SMILES: *N=C(c1ccccn1)c1ccccn1] |
| M-195 | 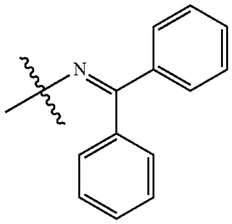 [SMILES: *N=C(c1ccccc1)c1ccccc1] |
| M-196 | 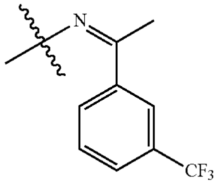 [SMILES: */N=C(/C)c1cccc(C(F)(F)F)c1] |
| M-197 | Me |
| M-198 | Et |
| M-199 | 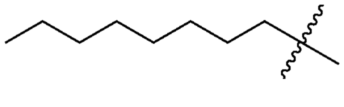 [SMILES: *CCCCCCCC] |
| M-200 | CN |
| M-201 | 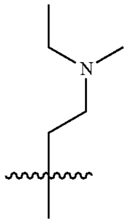 |
-continued
| No. | M |
|---|---|
| M-202 | 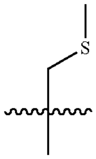 [SMILES: *CSC] |
| M-203 | 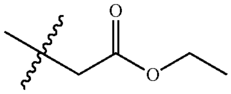 [SMILES: *CC(=O)OCC] |
| M-204 | 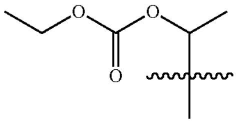 [SMILES: *C(C)OC(=O)OCC] |
| M-205 | 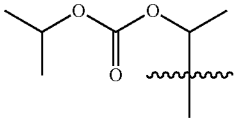 |
| M-206 | 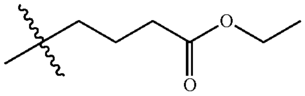 [SMILES: *CCCC(=O)OCC] |
| M-207 | 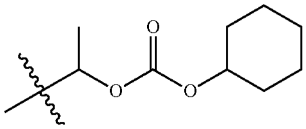 [SMILES: *C(C)OC(=O)OC1CCCCC1] |
| M-208 | 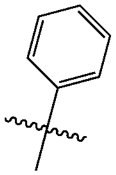 [SMILES: *c1ccccc1] |
| M-209 | 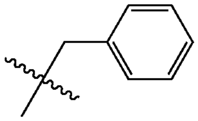 [SMILES: *Cc1ccccc1] |
| M-210 | 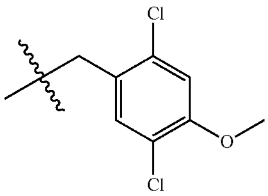 [SMILES: *Cc1cc(Cl)c(OC)cc1Cl] |
| M-211 | 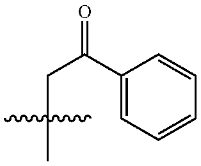 [SMILES: *CC(=O)c1ccccc1] |

-continued
| No. | M |
|---|---|
| M-212 | 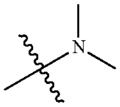 [SMILES: *N(C)C] |
| M-213 | 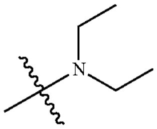 [SMILES: *N(CC)CC] |
| M-214 | 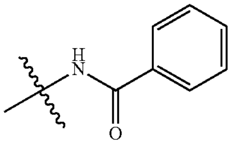 [SMILES: *NC(=O)c1ccccc1] |
-continued
| No. | M |
|---|---|
| M-215 | 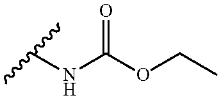 [SMILES: *NC(=O)OCC] |
| M-216 | 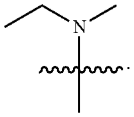 |
15. A compound of Formula I-1 or a derivative thereof,
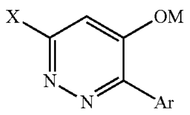
I-1
wherein:
| No. | X | Ar | M |
|---|---|---|---|
| 1-1 | Cl | 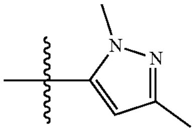 [SMILES: *c1cc(C)nn1C] | M-29 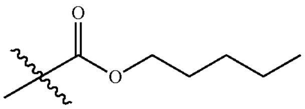 [SMILES: *C(=O)OCCCCC] |
| 1-2 | Cl | 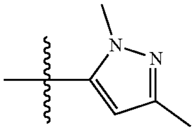 [SMILES: *c1cc(C)nn1C] | M-54 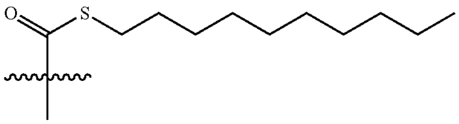 |
| 1-3 | Cl | 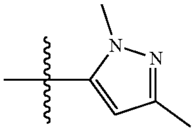 [SMILES: *c1cc(C)nn1C] | M-79 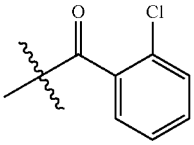 |
| 1-4 | Cl | 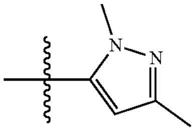 [SMILES: *c1cc(C)nn1C] | M-88 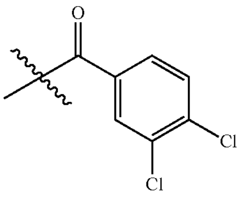 [SMILES: *C(=O)c1ccc(Cl)c(Cl)c1] |
| 1-5 | Cl | 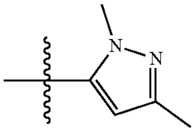 | M-52 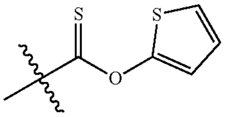 [SMILES: *C(=S)Oc1cccs1] |
| 1-6 | Cl | 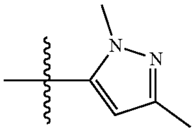 [SMILES: *c1cc(C)nn1C] | M-205 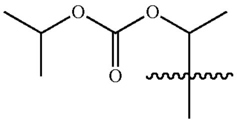 [SMILES: *C(C)OC(=O)OC(C)C] |

-continued
| No. | X | Ar | M |
|---|---|---|---|
| 1-7 | Cl | 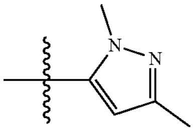 [SMILES: *c1cc(C)nn1C] | M-156 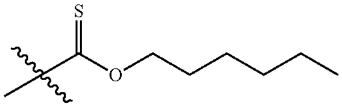 [SMILES: *C(=S)OCCCCCC] |
| 1-8 | Cl | 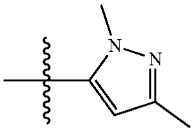 [SMILES: *c1cc(C)nn1C] | M-40 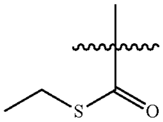 [SMILES: *C(=O)SCC] |
| 1-9 | Cl | 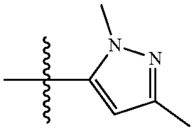 [SMILES: *c1cc(C)nn1C] | M-63 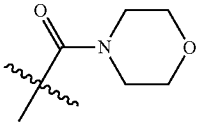 [SMILES: *C(=O)N1CCOCC1] |
| 1-10 | Cl | 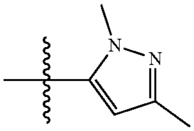 [SMILES: *c1cc(C)nn1C] | M-150 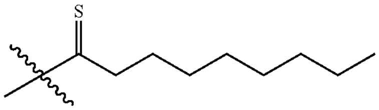 [SMILES: *C(=S)CCCCCCCC] |
| 1-11 | Cl | 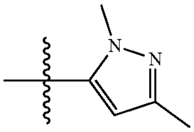 [SMILES: *c1cc(C)nn1C] | M-53 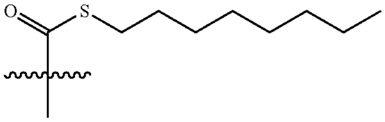 |
| 1-12 | CN | 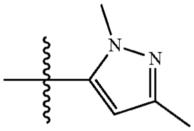 [SMILES: *c1cc(C)nn1C] | M-1 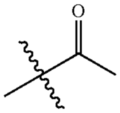 |
| 1-13 | $NH_2$ | 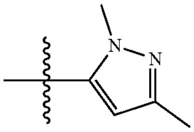 [SMILES: *c1cc(C)nn1C] | M-2 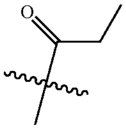 [SMILES: *C(=O)CC] |
| 1-14 | Ph | 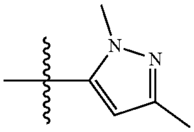 [SMILES: *c1cc(C)nn1C] | M-7 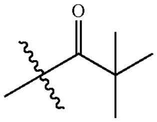 [SMILES: *C(=O)C(C)(C)C] |
| 1-15 | Br | 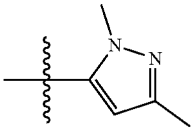 [SMILES: *c1cc(C)nn1C] | M-12 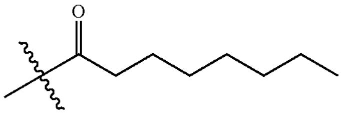 [SMILES: *C(=O)CCCCCCC] |
| 1-16 | OH | 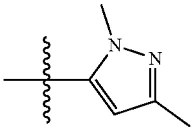 [SMILES: *c1cc(C)nn1C] | M-24 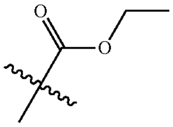 [SMILES: *C(=O)OCC] |
| 1-17 | Cl | 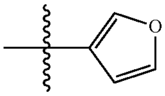 [SMILES: *c1ccoc1] | M-27 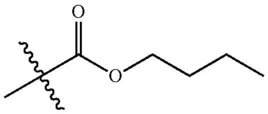 [SMILES: *C(=O)OCCCC] |

-continued
| No. | X | Ar | | M |
|---|---|---|---|---|
| 1-18 | $CONH_2$ | 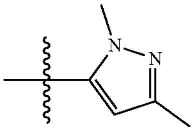 [SMILES: *c1cc(C)nn1C] | M-37 | 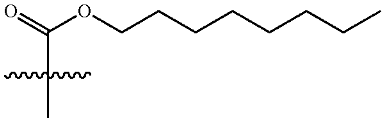 |
| 1-19 | Cl | 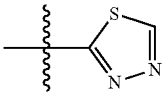 | M-58 | 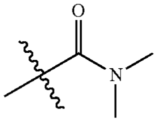 [SMILES: *C(=O)N(C)C] |
| 1-20 | Cl | 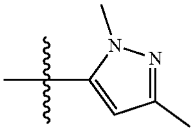 [SMILES: *c1cc(C)nn1C] | M-60 | 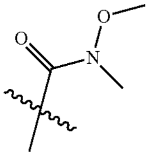 |
| 1-21 | Cl | 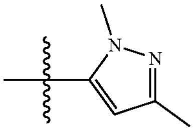 [SMILES: *c1cc(C)nn1C] | M-77 | 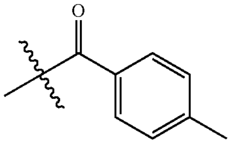 [SMILES: *C(=O)c1ccc(C)cc1] |
| 1-22 | Cl | 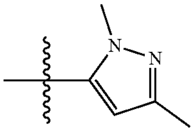 [SMILES: *c1cc(C)nn1C] | M-92 | 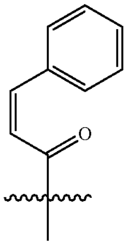 [SMILES: *C(=O)/C=C\c1ccccc1] |
| 1-23 | Cl | 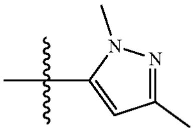 [SMILES: *c1cc(C)nn1C] | M-104 | 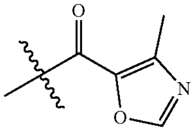 [SMILES: *C(=O)c1ocnc1C] |
| 1-24 | Cl | 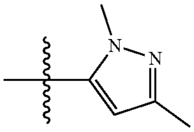 | M-108 | 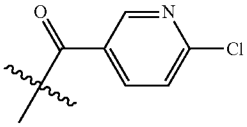 |
| 1-25 | Cl | 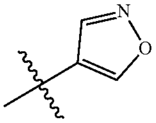 [SMILES: *c1cnoc1] | M-119 | 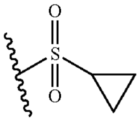 [SMILES: *S(=O)(=O)C1CC1] |
| 1-26 | Cl | 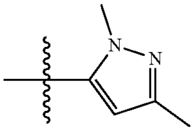 [SMILES: *c1cc(C)nn1C] | M-120 | 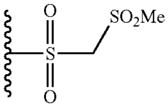 [SMILES: *S(=O)(=O)CS(C)(=O)=O] |
| 1-27 | Cl | 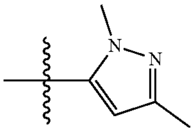 [SMILES: *c1cc(C)nn1C] | M-121 | 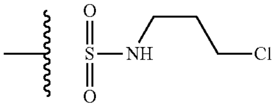 |

-continued
| No. | X | Ar | M |
|---|---|---|---|
| 1-28 | OEt | 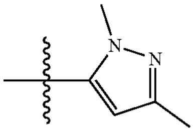 [SMILES: *c1cc(C)nn1C] | M-125 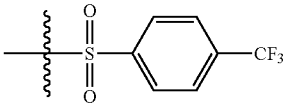 |
| 1-29 | $OCF_3$ | 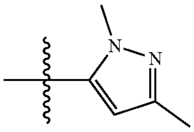 [SMILES: *c1cc(C)nn1C] | M-126 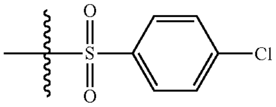 [SMILES: *S(=O)(=O)c1ccc(Cl)cc1] |
| 1-30 | Cl | 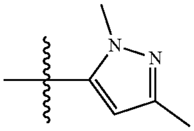 [SMILES: *c1cc(C)nn1C] | M-127 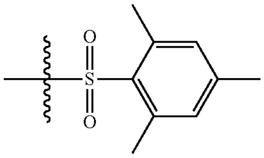 [SMILES: *S(=O)(=O)c1c(C)cc(C)cc1C] |
| 1-31 | Cl | 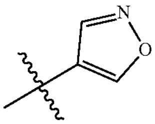 [SMILES: *c1cnoc1] | M-128 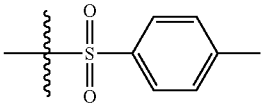 |
| 1-32 | Cl | 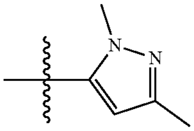 [SMILES: *c1cc(C)nn1C] | M-131 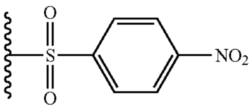 [SMILES: *S(=O)(=O)c1ccc([N+](=O)[O-])cc1] |
| 1-33 | Cl | 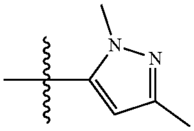 [SMILES: *c1cc(C)nn1C] | M-132 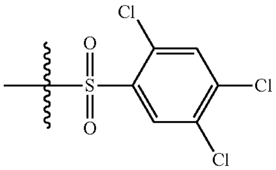 [SMILES: *S(=O)(=O)c1cc(Cl)c(Cl)cc1Cl] |
| 1-34 | Cl | 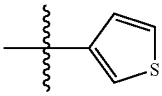 [SMILES: *c1ccsc1] | M-160 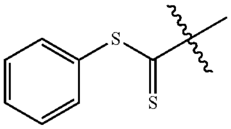 [SMILES: *C(=S)Sc1ccccc1] |
| 1-35 | $CHF_2$ | 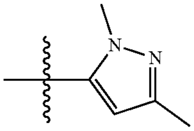 [SMILES: *c1cc(C)nn1C] | M-162 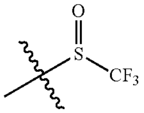 [SMILES: *S(=O)C(F)(F)F] |
| 1-36 | Cl | 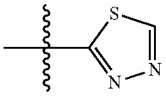 | M-165 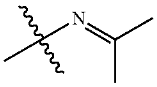 [SMILES: *N=C(C)C] |
| 1-37 | $CF_2CF_3$ | 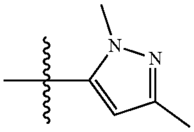 [SMILES: *c1cc(C)nn1C] | M-168 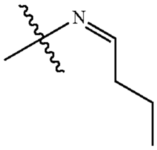 [SMILES: */N=C\CCC] |

-continued
| No. | X | Ar | | M |
|---|---|---|---|---|
| 1-38 | Cl | 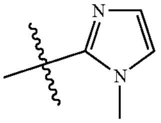 [SMILES: *c1nccn1C] | M-198 | Et |
| 1-39 | Br | 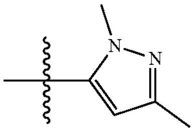 [SMILES: *c1cc(C)nn1C] | M-199 | 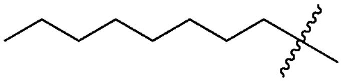 [SMILES: *CCCCCCCC] |
| 1-40 | CN | 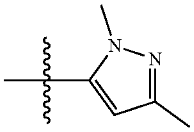 [SMILES: *c1cc(C)nn1C] | M-200 | CN |
| 1-41 | Me | 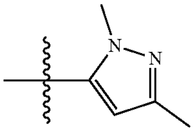 [SMILES: *c1cc(C)nn1C] | M-203 | 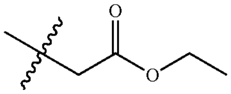 [SMILES: *CC(=O)OCC] |
| 1-42 | Cl | 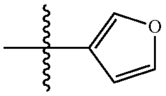 | M-204 | 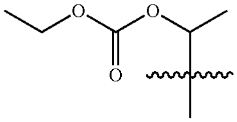 [SMILES: *C(C)OC(=O)OCC] |
| 1-43 | Cl | 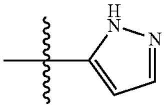 | M-207 | 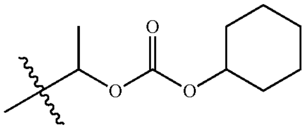 [SMILES: *C(C)OC(=O)OC1CCCCC1] |
| 1-44 | Cl | 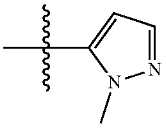 [SMILES: *c1ccnn1C] | M-208 | 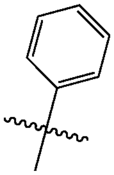 [SMILES: *c1ccccc1] |
| 1-45 | Cl | 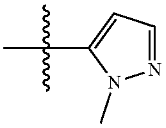 [SMILES: *c1ccnn1C] | M-209 | 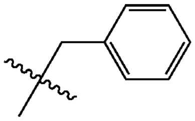 [SMILES: *Cc1ccccc1] |
| 1-46 | OMe | 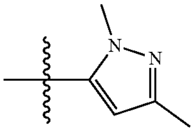 [SMILES: *c1cc(C)nn1C] | M-211 | 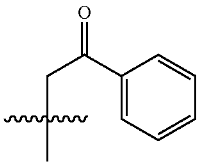 [SMILES: *CC(=O)c1ccccc1] |
| 1-47 | Cl | 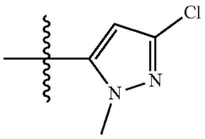 [SMILES: *c1cc(Cl)nn1C] | M-212 | 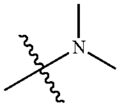 [SMILES: *N(C)C] |

-continued
| No. | X | Ar | | M |
|---|---|---|---|---|
| 1-48 | Et | 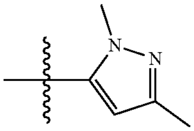 [SMILES: *c1cc(C)nn1C] | M-123 | 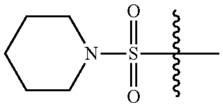 [SMILES: *S(=O)(=O)N1CCCCC1] |
| 1-49 | F | 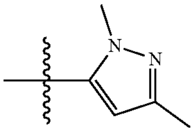 [SMILES: *c1cc(C)nn1C] | M-216 | 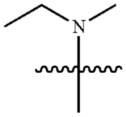 [SMILES: *N(C)CC] |
| 1-50 | Cl | 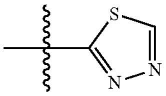 | M-40 | 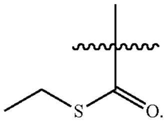 |
* * * * *

UNITED STATES PATENT AND TRADEMARK OFFICE

CERTIFICATE OF CORRECTION

PATENT NO. : 12,024,500 B2
APPLICATION NO. : 16/966704
DATED : July 2, 2024
INVENTOR(S) : Lei Lian et al.

It is certified that error appears in the above-identified patent and that said Letters Patent is hereby corrected as shown below:

In the Claims

In Claim 2, Column 174, Line 62, "$R_1R_2N—(CH_2)—(C{=}O)—(CH_2)_q—$," should read --$R_1R_2N—(CH_2)_n—(C{=}O)—(CH_2)_q—$,--.

In Claim 3, Column 178, Line 43, "he heteroaryl is selected from" should read --the heteroaryl is selected from--.

In Claim 12, Column 185, formula no. 15, in column X, "O" should read --Cl--.

In Claim 12, Column 186, formula no. 19, in column X, "O" should read --Cl--.

In Claim 12, Column 187, formula no. 30, in column X, "O" should read --Cl--.

In Claim 12, Column 187, formula no. 31, in column X, "O" should read --Cl--.

In Claim 12, Column 187, formula no. 33, in column X, "O" should read --Cl--.

In Claim 12, Column 189, formula no. 44, in column X, "O" should read --Cl--.

In Claim 12, Column 195, formula no. 96, in column X, "O" should read --Cl--.

In Claim 12, Column 196, formula no. 98, in column X, "O" should read --Cl--.

In Claim 12, Column 196, formula no. 100, in column X, "O" should read --Cl--.

In Claim 12, Column 196, formula no. 101, in column X, "O" should read --Cl--.

In Claim 12, Column 196, formula no. 103, in column X, "O" should read --Cl--.

Signed and Sealed this
First Day of October, 2024

Katherine Kelly Vidal

Katherine Kelly Vidal
*Director of the United States Patent and Trademark Office*

In Claim 12, Column 197, formula no. 105, in column X, "O" should read --Cl--.

In Claim 12, Column 197, formula no. 106, in column X, "O" should read --Cl--.

In Claim 12, Column 197, formula no. 107, in column X, "O" should read --Cl--.

In Claim 12, Column 197, formula no. 110, in column X, "O" should read --Cl--.

In Claim 12, Column 198, formula no. 114, in column X, "O" should read --Cl--.

In Claim 12, Column 198, formula no. 115, in column X, "O" should read --Cl--.

In Claim 12, Column 198, formula no. 116, in column X, "O" should read --Cl--.

In Claim 12, Column 198, formula no. 114, in column X, "O" should read --Cl--.

In Claim 12, Column 201, formula no. 139, in column X, "OF" should read --OH--.

In Claim 14, Column 248, formula no. M-187, " 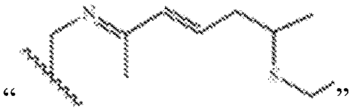 " should read as -- 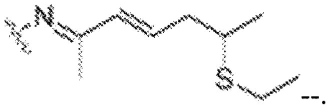 --.

In Claim 14, Column 249, formula no. M-201, " 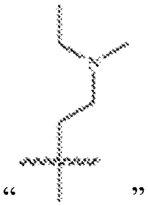 " should read as -- 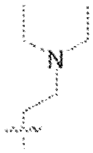 --.